US008193315B2

(12) United States Patent

Lipton et al.

(10) Patent No.: US 8,193,315 B2

(45) Date of Patent: Jun. 5, 2012

(54) EXCITATORY GLYCINE RECEPTORS AND METHODS

(75) Inventors: Stuart A. Lipton, Rancho Santa Fe, CA (US); Dongxian Zhang, San Diego, CA (US); Jon E. Chatterton, San Diego, CA (US); Kevin A. Sevarino, Cheshire, CT (US); Marc Awobuluyi, San Francisco, CA (US)

(73) Assignees: Sanford-Burnham Medical Research Institute, La Jolla, CA (US); Yale University, New Haven, CT (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 12/842,974

(22) Filed: Jul. 23, 2010

(65) Prior Publication Data

US 2011/0045098 A1 Feb. 24, 2011

Related U.S. Application Data

(63) Continuation of application No. 10/222,772, filed on Aug. 16, 2002, now Pat. No. 7,790,404.

(60) Provisional application No. 60/453,707, filed on Aug. 20, 2001.

(51) Int. Cl.
*C07K 14/705* (2006.01)

(52) U.S. Cl. ........................................................ 530/350

(58) Field of Classification Search ........................ None
See application file for complete search history.

(56) References Cited

U.S. PATENT DOCUMENTS 6,083,941 A 7/2000 Farb
2002/0077466 A1* 6/2002 Spaderna et al. ............ 536/23.5

FOREIGN PATENT DOCUMENTS

WO WO 01/44473 6/2001
WO WO 02/40538 5/2002

OTHER PUBLICATIONS

Abdrachmanova et al., "Molecular and functional properties of synaptically activated NMDA receptors in neonatal motoneurons in rat spinal cord slices," *Eur. J. Neurosci.* 12(3):955-63 (2000).

Alexander et al., "Altering the antigenicity of proteins," *Proc. Natl. Acad. Sci. U. S. A.* 89(8):3352-3356 (1992).

Andersson et al., "Nucleotide sequence, genomic organization, and chromosomal localization of genes encoding the human NMDA receptor subunits NR3A and NR3B," *Genomics* 78:178-184 (2001).

Barth et al., "Glycine-induced neurotoxicity in organotypic hippocampal slice cultures," *Exp. Brain Res.* 161(3):351-357 (2005).

Bendel et al., "Cloning and expression of the human NMDA receptor subunit NR3B in the adult human hippocampus," *Neurosci. Lett.* 377(1):31-36 (2005).

Bowie et al., "Deciphering the message in protein sequences: tolerance to amino acid substitutions," *Science* 247(4948):1306-1310 (1990).

Chatterton et al., "Excitatory glycine receptors containing the NR3 family of NMDA receptor subunits," *Nature* 415:793-798 (2002).

Ciaberra et al., "Cloning and characterization of $_{\chi}$-1: A developmentally regulated member of a novel class of the ionotropic glutamate receptor family," *J. Neurosci.* 15:6498-6508 (1995).

Cull-Candy et al., "NMDA receptor subunits: diversity, development and disease," *Curr. Opin. Neurobiol.* 11:327-335 (2001).

Das et al., "Increased NMDA current and spine density in mice lacking the NMDA receptor subunit NR3A," *Nature* 393:377-381 (1998).

Ehrlich et al., "Shift from depolarizing to hyperpolarizing glycine action in rat auditory neurones is due to age-dependent Cl-regulation," *J. Physiol.* 520 (Pt 1):121-137 (1999).

Goebel and Poosch, "NMDA receptor subunit gene expression in the rat brain: a quantitative analysis of endogenous mRNA levels of NR1 com, NR2A, NR2B, NR2C, NR2D, and DR3A," *Mol. Bran Res.* 69:164-170 (1999).

Guo et al., "Protein tolerance to random amino acid change," *Proc. Natl. Acad. Sci. U.S.A.* 101 (25):9205-9210 (2004).

Leuschner and Hoch, "Subtype-specific assembly of α-amino-3-hydroxy-5-methyl-4-isoxazole propionic acid receptor subunits is mediated by their N-terminal domains," *J. Biol. Chem.* 274:16907-16916 (1999).

Li et al., "In vitro selection of peptides acting at a new site of NMDA_glutamate receptors," *Nat. Biotechnol.* 14:986-991 (1996).

Lipton and Rosenburg, "Excitatory amino acids as a final common pathway for neurologic disorders," *N. Engl. J. Med.* 330(9):613-622 (1994).

Matsuda et al., "Specific assembly with the NMDA receptor 3B subunit controls surface expression and calcium permeability of NMDA receptors," *J. Neurosci.* 23(31):10064-10073 (2003).

Meddows et al., "Identification of molecular determinants that are important in the assembly of N-Methyl-D-aspartate receptors," *J. Biol. Chem.* 276 (22):18795-18803. (2001).

Nakanishi et al., "Glutamate receptors: brain function and signal transduction," *Brain Res. Reviews* 26:230-235 (1998).

Nishi et al., "Motoneuron-specific expression of NR3B, a novel NMDA-type glutamate receptor subunit that works in a dominant-negative manner," *J. Neurosci.* 21:1-6 (2001). Ozawa et al., "Glutamate receptors in the mammalian central nervous system," *Progress in Neurobiology* 54:581-618 (1998).

Perez-Otano et al., "Assembly with the NR1 subunit is required for surface expression of NR3A—containing NMDA receptors," *J. Neurosceince* 21(4):1228-1237 (2001).

Planells-Cases et al., "Molecular cloning, functional expressio, and pharmacological characterization of an N-methyl-D-aspartate receptor subunit from human brain," *Proc. Natl. Acad. Sci. USA* 90:5057-5061 (1993).

Rajendra et al., "The glycine receptor," *Pharmacol. Ther.* 73(2):121-146 (1997).

Reggiani et al., "The neuroprotective activity of the glycine receptor antagonist GV150526: an in vivo study by magnetic resonance imaging," *European J. Pharmacology* 419:147-153 (2001).

Reichling et al., "Mechanisms of GABA and glycine depolarization-induced calcium transients in rat dorsal horn neurons," *J. Physiol.* 476(3):411-421 (1994).

Seeburg et al, "RNA editing of brain glutamate receptor channels: mechanism and physiology," *Brain Research Reviews* 26:217-229 (1998).

Sheng et al, "Ligand-gated ion channel interactions with cytoskeletal and signaling proteins," *Annu. Rev. Physiol.* 62:755-778 (2000).

Souverbie et al, "Pharmacological characterization of [3H]MK-801 binding in the rat spinal cord," *Eur. J. Pharmacology* 307:347-353 (1996).

(Continued)

*Primary Examiner* — John Ulm

(74) *Attorney, Agent, or Firm* — Jones Day

(57) ABSTRACT

The invention provides isolated N-methyl-D-aspartate type 3B (NR3B) polypeptides, functional fragments and peptides, encoding nucleic acid molecules and polynucleotides, and specific antibodies. Also provided are excitatory glycine receptors, containing either NR3B or NR3A polypeptides. Further provided are methods for detecting excitatory glycine receptor ligands, agonists and antagonists. The invention also provides related diagnostic and therapeutic methods.

7 Claims, 17 Drawing Sheets

OTHER PUBLICATIONS

Sucher et al., "Developmental and regional expression pattern of a novel NMDA receptor-like subunit (NMDAR-L) in the rodent brain," *J. Neuroscience* 15:6509-3520.
Sucher et al., "NMDA receptors: from genes to channels," *TIPS* 17:348-355 (1996).
Villmann et al., "Investigation by ion channel domain transplantation of rat glutamate receptor subunits, orphan receptors and putative NMDA receptor," *Eur. J. Neurosci.* 11:1765-1778 (1999).
Wang et al., "Developmental loss of GABA- and glycine-induced depolarization and Ca2+ transients in embryonic rat dorsal horn neurons in culture," *Eur. J. Neurosci.* 6(8):1275-1280 (1984).
Wei et al., "Pharmacological characterization of N-methyl-D-aspartate receptors in spinal cord of rats with a chronic peripheral mononeuropathy," *Neuropharmacology* 36: 1561-1569 (1997).
Yamakura and Shimoji, "Subunit- and site-specific pharmacology of the NMDA receptor channel," *Prog. in Neurobiology* 59:279-298 (1999).
Zimmer et al., "Cloning and structure of the gene encoding the human N-methyl-D-aspartate receptor (NMDAR1)," *Gene* 159:219-223 (1995).
Genbank Accession No. AAB42494 (Feb. 8, 2001).
GenBank Accession No. AAC12680.
GenBank Accession No. AAH05494.
GenBank Accession No. AC004528.
GenBank Accession No. AC006531.
GenBank Accession No. AC007218.
GenBank Accession No. AC007535.
GenBank Accession No. AC008403.
GenBank Accession No. AC011527.
GenBank Accession No. AC087114.
GenBank Accession No. AF001423.
GenBank Accession No. AF061945.
GenBank Accession No. AF073379.
GenBank Accession No. AL359651.
GenBank Accession No. AL359933.
GenBank Accession No. BC005494.
GenBank Accession No. D10217.
GenBank Accession No. D10651.
GenBank Accession No. D10694.
GenBank Accession No. D12822.
GenBank Accession No. D13211.
GenBank Accession No. D13212.
GenBank Accession No. D13213.
GenBank Accession No. L31611.
GenBank Accession No. L31612.
GenBank Accession No. L34938.
GenBank Accession No. L76224.
GenBank Accession No. M91561.
GenBank Accession No. M91562.
GenBank Accession No. M91563.
GenBank Accession No. NM000833.
GenBank Accession No. NM000834.
GenBank Accession No. NM000835.
GenBank Accession No. NM000836.
GenBank Accession No. NM008170.
GenBank Accession No. NM008171.
GenBank Accession No. NM008172.
GenBank Accession No. NM010350.
GenBank Accession No. NM012573.
GenBank Accession No. NM012574.
GenBank Accession No. NM012575.
GenBank Accession No. NM022797.
GenBank Accession No. NT025809.
GenBank Accession No. U08259.
GenBank Accession No. U08260.
GenBank Accession No. U09002.
GenBank Accession No. U11287.
GenBank Accession No. U11419.
GenBank Accession No. U29873.
GenBank Accession No. U77782.
GenBank Accession No. U77783.
GenBank Accession No. U88963.
GenBank Accession No. U90277.
GenBank Accession No. U90278.
GenBank Accession No. XM006636.
GenBank Accession No. XM007911.
GenBank Accession No. XM009108.
GenBank Accession No. XM012596.
GenBank Accession No. XM016282.
GenBank Accession No. XM030214.
GenBank Accession No. XM030215.
GenBank Accession No. XM042404.
GenBank Accession No. XM042405.
GenBank Accession No. XM042406.
GenBank Accession No. XM042803.
GenBank Accession No. XM046949.

* cited by examiner

```
                    S1                                        S2
         ^  ^              ^       ^^              ^     ^
—— A D G K F G —— A P L T I N N E R A Q —— A T V K Q S S V D —— NR1
—— T N G K H G —— G S L T I N E E R S E —— G T V P N G S T E —— NR2A
—— T N G K H G —— G S L T I N E E R S E —— G T V P N G S T E —— NR2B
—— T N G K H G —— G S L T I N E E R S E —— G T V P N G S T E —— NR2C
—— T N G K H G —— G S L T I N E E R S E —— G T V P N G S T E —— NR2D
—— G D G K Y G —— T S F S I N T A R S Q —— G T V R E S S A E —— NR3A
—— G D G K Y G —— T S F S I N S A R S Q —— G T V W E S S A E —— NR3B
—— G D G K Y G —— A P L T I T L V R E E —— G T L D S G S T K —— GluR2
    *  * *         *         * *           * *     *   *

  □
```

Note: A=Acc65I; Ap=Apa; B=BamHI; E=EcoRI; K=KPN I; RV=EcoRV; H=HindIII; S=SacI; Sp=SpeI; X=XbaI; Xh=Xh

```
                          SEQUENCE LISTING


<160> NUMBER OF SEQ ID NOS: 63

<210> SEQ ID NO 1
<211> LENGTH: 3133
<212> TYPE: DNA
<213> ORGANISM: Rattus sp.
<220> FEATURE:
<221> NAME/KEY: CDS
<222> LOCATION: (76)...(3036)

<400> SEQUENCE: 1

gcacgagggg acaagagcgg gtctggctgg ggtgtctcct tcccttcgca cagcacagtg      60

gtaacttctt tcggg atg gag agt gtg cgg acg ctg tgg ctc agc gtg gcc      111
                 Met Glu Ser Val Arg Thr Leu Trp Leu Ser Val Ala
                  1               5                  10

ctg gcg ctg gcg gtg ggg tcc cga gtg gtg cgc ggt cac cct cag ccc      159
Leu Ala Leu Ala Val Gly Ser Arg Val Val Arg Gly His Pro Gln Pro
         15                  20                  25

tgc cgg gtt ccc acg cgc gct ggg gcc tcc gtg cgc ctg gcg gcg ctc      207
Cys Arg Val Pro Thr Arg Ala Gly Ala Ser Val Arg Leu Ala Ala Leu
     30                  35                  40

ctg ccc cgg gcg ccc gcc gcc cgc gcc cgc gtc cta gct gcc ctg gcc      255
Leu Pro Arg Ala Pro Ala Ala Arg Ala Arg Val Leu Ala Ala Leu Ala
 45                  50                  55                  60

acc cct gcg ccg cgg ctg ccg cac aac ctg agt ctg gaa ctg gtg gcc      303
Thr Pro Ala Pro Arg Leu Pro His Asn Leu Ser Leu Glu Leu Val Ala
                 65                  70                  75

gtc gcg tcc ccg acc cgg gac ccc gcg tcg cta gct cga ggt ctg tgc      351
Val Ala Ser Pro Thr Arg Asp Pro Ala Ser Leu Ala Arg Gly Leu Cys
             80                  85                  90

cag gtt ctg gca ccg cct ggc gtg gtg gcc tct ata gcc ttt ccc gag      399
Gln Val Leu Ala Pro Pro Gly Val Val Ala Ser Ile Ala Phe Pro Glu
         95                 100                 105

gcg cgg ccc gag ctg cgg cta ctg cag ttc ctg gca gcc gcc aca gag      447
Ala Arg Pro Glu Leu Arg Leu Leu Gln Phe Leu Ala Ala Ala Thr Glu
    110                 115                 120

acc cca gtg act ccg ttc cat ctg cag ctg gac tgg gct agt ccc ctg      495
Thr Pro Val Thr Pro Phe His Leu Gln Leu Asp Trp Ala Ser Pro Leu
125                 130                 135                 140

gag acc ata ctg gat gtg ctg gtg tcc ctg gta cgg gca cat gcc tgg      543
Glu Thr Ile Leu Asp Val Leu Val Ser Leu Val Arg Ala His Ala Trp
                145                 150                 155

gag gac att gct cta gta ctc tgc cgt gtc cgg gac cct ggc agc ctg      591
Glu Asp Ile Ala Leu Val Leu Cys Arg Val Arg Asp Pro Gly Ser Leu
            160                 165                 170

gtg aca ctc tgg act aac cat gct agc cag gct cca aag ttt gtg ctg      639
Val Thr Leu Trp Thr Asn His Ala Ser Gln Ala Pro Lys Phe Val Leu
```

-continued

```
        175                 180                 185

gac ctg agc cgg ctg gac agc agg aat gac agc ctt cgg gct gga ctg       687
Asp Leu Ser Arg Leu Asp Ser Arg Asn Asp Ser Leu Arg Ala Gly Leu
    190                 195                 200

gcc ctg ttg ggg gcg ctg gaa gga ggg gga acc cca gtg cct gca gca       735
Ala Leu Leu Gly Ala Leu Glu Gly Gly Gly Thr Pro Val Pro Ala Ala
205                 210                 215                 220

gtc ctc cta ggc tgc agc act gcc cgt gca cat gag gtc cta gag gct       783
Val Leu Leu Gly Cys Ser Thr Ala Arg Ala His Glu Val Leu Glu Ala
                225                 230                 235

gca cca ccg ggt ccc cag tgg ttg ctg ggc aca cca ttg ccc gct gag       831
Ala Pro Pro Gly Pro Gln Trp Leu Leu Gly Thr Pro Leu Pro Ala Glu
            240                 245                 250

gca ctg ccc acg act ggt ctg cca cct ggc gtg ctg gcg ctg ggg gaa       879
Ala Leu Pro Thr Thr Gly Leu Pro Pro Gly Val Leu Ala Leu Gly Glu
        255                 260                 265

acc gaa caa cac tct ctg gaa gct gtc gtc cac gac atg gtg gag ctt       927
Thr Glu Gln His Ser Leu Glu Ala Val Val His Asp Met Val Glu Leu
    270                 275                 280

gtg gct cag gca ctc agt agc atg gcc ctt gta cac cca gag cgg gca       975
Val Ala Gln Ala Leu Ser Ser Met Ala Leu Val His Pro Glu Arg Ala
285                 290                 295                 300

ctg ctt cca gct gtg gtg aac tgt gat gac ctg aaa aca ggc gga tct      1023
Leu Leu Pro Ala Val Val Asn Cys Asp Asp Leu Lys Thr Gly Gly Ser
                305                 310                 315

gag gca aca ggg cgc acc ttg gct cgg ttt ctc ggc aac acc tca ttt      1071
Glu Ala Thr Gly Arg Thr Leu Ala Arg Phe Leu Gly Asn Thr Ser Phe
            320                 325                 330

cag ggc cga aca ggg gcc gtg tgg gtg aca ggc tcc tct cag gtg cat      1119
Gln Gly Arg Thr Gly Ala Val Trp Val Thr Gly Ser Ser Gln Val His
        335                 340                 345

gtg tct cgg cat ttc aag gta tgg agc ctg cgc cgg gat ccg ctg ggt      1167
Val Ser Arg His Phe Lys Val Trp Ser Leu Arg Arg Asp Pro Leu Gly
    350                 355                 360

gcc cca gcc tgg gca acc gtg ggc agc tgg cag gat gga cag ctg gac      1215
Ala Pro Ala Trp Ala Thr Val Gly Ser Trp Gln Asp Gly Gln Leu Asp
365                 370                 375                 380

ttc cag cca ggg gca gcc gct ctc cga gtc cca tct ccg tct ggc acc      1263
Phe Gln Pro Gly Ala Ala Ala Leu Arg Val Pro Ser Pro Ser Gly Thr
                385                 390                 395

cag gcc cga cca aag ctg cgt gtg gta acc ctg gtg gaa cac ccg ttt      1311
Gln Ala Arg Pro Lys Leu Arg Val Val Thr Leu Val Glu His Pro Phe
            400                 405                 410

gtg ttc acc agg gaa tct gat gaa gac gga cag tgc cca gct ggg cag      1359
Val Phe Thr Arg Glu Ser Asp Glu Asp Gly Gln Cys Pro Ala Gly Gln
        415                 420                 425

ctg tgt ctg gac cca ggc acc aat gac tca gcc agg ctg gat gcc ctc      1407
Leu Cys Leu Asp Pro Gly Thr Asn Asp Ser Ala Arg Leu Asp Ala Leu
    430                 435                 440

ttt gct gca ctg gtg aat ggc tca gta cct cga acg ctg aga aga tgc      1455
Phe Ala Ala Leu Val Asn Gly Ser Val Pro Arg Thr Leu Arg Arg Cys
445                 450                 455                 460

tgc tat ggc tac tgc atc gac ctg ctg gag cgg ctg gcc gag gac ctg      1503
Cys Tyr Gly Tyr Cys Ile Asp Leu Leu Glu Arg Leu Ala Glu Asp Leu
                465                 470                 475

gcc ttt gac ttt gag ctc tat att gtg ggg gat ggc aag tac ggg gcc      1551
Ala Phe Asp Phe Glu Leu Tyr Ile Val Gly Asp Gly Lys Tyr Gly Ala
            480                 485                 490

ctg cgt gat ggg cgc tgg acg ggc ctg gtg ggt gac ctg ctg gct ggc      1599
Leu Arg Asp Gly Arg Trp Thr Gly Leu Val Gly Asp Leu Leu Ala Gly
```

```
        495                 500                 505

cgg gca cac atg gct gtg acc agc ttc agc atc aac tca gct cgc tct      1647
Arg Ala His Met Ala Val Thr Ser Phe Ser Ile Asn Ser Ala Arg Ser
    510                 515                 520

cag gtg gtg gat ttc acc agc cct ttc ttc tcc acc agc ctg ggg att      1695
Gln Val Val Asp Phe Thr Ser Pro Phe Phe Ser Thr Ser Leu Gly Ile
525                 530                 535                 540

atg gtg cgc acg aga gac acg gcc tcg ccc atc ggg gct ttc atg tgg      1743
Met Val Arg Thr Arg Asp Thr Ala Ser Pro Ile Gly Ala Phe Met Trp
                545                 550                 555

ccc ctg cac tgg tcc atg tgg gtg ggc gtg ttt gct gct ctg cac ctc      1791
Pro Leu His Trp Ser Met Trp Val Gly Val Phe Ala Ala Leu His Leu
            560                 565                 570

aca gcg ctc ttt ctc acc ctg tac gaa tgg cga agt ccc tac ggg ctc      1839
Thr Ala Leu Phe Leu Thr Leu Tyr Glu Trp Arg Ser Pro Tyr Gly Leu
        575                 580                 585

acg ccg cgc ggc cgc aac cgt ggc act gtc ttc tct tac tcc tcc gcg      1887
Thr Pro Arg Gly Arg Asn Arg Gly Thr Val Phe Ser Tyr Ser Ser Ala
    590                 595                 600

ctc aac ctg tgc tat gcc att ctc ttt gga cgc act gtc tcc agt aag      1935
Leu Asn Leu Cys Tyr Ala Ile Leu Phe Gly Arg Thr Val Ser Ser Lys
605                 610                 615                 620

acg ccc aag tgc cct act gga cgc ttc ctc atg aac ctc tgg gca atc      1983
Thr Pro Lys Cys Pro Thr Gly Arg Phe Leu Met Asn Leu Trp Ala Ile
                625                 630                 635

ttc tgc ctg ctg gtg ctt tcc agt tac acg gcc aac ctg gct gct gtc      2031
Phe Cys Leu Leu Val Leu Ser Ser Tyr Thr Ala Asn Leu Ala Ala Val
            640                 645                 650

atg gtt ggg gac aaa acc ttt gag gag ctg tct gga atc cat gat ccc      2079
Met Val Gly Asp Lys Thr Phe Glu Glu Leu Ser Gly Ile His Asp Pro
        655                 660                 665

aag ctg cac cac cct tcc caa ggc ttt cgc ttt ggc acc gta tgg gag      2127
Lys Leu His His Pro Ser Gln Gly Phe Arg Phe Gly Thr Val Trp Glu
    670                 675                 680

agc agc gcg gag gcc tac atc aag gca agc ttc cct gag atg cac gca      2175
Ser Ser Ala Glu Ala Tyr Ile Lys Ala Ser Phe Pro Glu Met His Ala
685                 690                 695                 700

cac atg cgt cgg cac agc gca ccc acc act cca cat ggg gtg gcc atg      2223
His Met Arg Arg His Ser Ala Pro Thr Thr Pro His Gly Val Ala Met
                705                 710                 715

ctc acg agc gac ccg ccc aag ctc aac gcc ttc atc atg gat aaa tca      2271
Leu Thr Ser Asp Pro Pro Lys Leu Asn Ala Phe Ile Met Asp Lys Ser
            720                 725                 730

cta ctg gac tat gag gtg tcc ata gat gcg gac tgc aag ctg ctc acc      2319
Leu Leu Asp Tyr Glu Val Ser Ile Asp Ala Asp Cys Lys Leu Leu Thr
        735                 740                 745

gtt ggc aaa ccc ttt gct atc gag ggc tac ggc ata ggg cta ccc caa      2367
Val Gly Lys Pro Phe Ala Ile Glu Gly Tyr Gly Ile Gly Leu Pro Gln
    750                 755                 760

aac tcg ccg ctc acc tcc aac ctg tcg gag ttc atc agt agg tac aag      2415
Asn Ser Pro Leu Thr Ser Asn Leu Ser Glu Phe Ile Ser Arg Tyr Lys
765                 770                 775                 780

tct tca ggc ttc att gat ctg ctc cat gac aag tgg tac aag atg gtg      2463
Ser Ser Gly Phe Ile Asp Leu Leu His Asp Lys Trp Tyr Lys Met Val
                785                 790                 795

cct tgc ggg aag cgg gtg ttc gcc gtg acg gag acg ctg cag atg ggg      2511
Pro Cys Gly Lys Arg Val Phe Ala Val Thr Glu Thr Leu Gln Met Gly
            800                 805                 810

gtc tac cac ttc tca gga ttg ttt gtc ctg ctg tgc ctc ggg ctg ggc      2559
Val Tyr His Phe Ser Gly Leu Phe Val Leu Leu Cys Leu Gly Leu Gly
```

```
        815                 820                 825

agc gcg ctt ctc acc tct ctg ggt gag cat gtc ttc tac cgc ctg gtg     2607
Ser Ala Leu Leu Thr Ser Leu Gly Glu His Val Phe Tyr Arg Leu Val
    830                 835                 840

ctg ccg cgc atc cgc agg ggt aat aag ctg cag tat tgg ctt cac acg     2655
Leu Pro Arg Ile Arg Arg Gly Asn Lys Leu Gln Tyr Trp Leu His Thr
845                 850                 855                 860

agc cag aag atc cac cga gcc ctc aat aca gga cca ccc gag ggg caa     2703
Ser Gln Lys Ile His Arg Ala Leu Asn Thr Gly Pro Pro Glu Gly Gln
                865                 870                 875

cag gag agg gca gag cag gag cgc agc ggc ccc aag gac gag ctg cct     2751
Gln Glu Arg Ala Glu Gln Glu Arg Ser Gly Pro Lys Asp Glu Leu Pro
            880                 885                 890

gcc acc gat ggt gca ggg cgc tgg agg cgg gtg cgc cgg gct gtg gaa     2799
Ala Thr Asp Gly Ala Gly Arg Trp Arg Arg Val Arg Arg Ala Val Glu
        895                 900                 905

cgg gag cga cgc gtg cgt ttc ctg ctg gaa cct ggg gag gct ggc gga     2847
Arg Glu Arg Arg Val Arg Phe Leu Leu Glu Pro Gly Glu Ala Gly Gly
    910                 915                 920

gac cgc ccg tgg ctc tgc tcc aac ggg ccc ggg ctg caa gcg gag ctg     2895
Asp Arg Pro Trp Leu Cys Ser Asn Gly Pro Gly Leu Gln Ala Glu Leu
925                 930                 935                 940

cgg gag ctg gag ctg cgc att gag gct gca cgg gag cag ctg cgc agt     2943
Arg Glu Leu Glu Leu Arg Ile Glu Ala Ala Arg Glu Gln Leu Arg Ser
                945                 950                 955

gcg ctg ttg cgg cgc ggg gag ctg cgg gcc ctg ctt ggg gat ggc acc     2991
Ala Leu Leu Arg Arg Gly Glu Leu Arg Ala Leu Leu Gly Asp Gly Thr
            960                 965                 970

cgg ctc agg cca ctg cgc ctg ttg cat gcg gcg cct gct gag agc         3036
Arg Leu Arg Pro Leu Arg Leu Leu His Ala Ala Pro Ala Glu Ser
        975                 980                 985

tgaggaacca caaggccgca ctgtccacga cagtttattc tatatacaaa cacgactctg   3096

tacactgcaa ttaaatagcg tggaacgtga aaaaaaa                            3133


<210> SEQ ID NO 2
<211> LENGTH: 987
<212> TYPE: PRT
<213> ORGANISM: Rattus sp.

<400> SEQUENCE: 2

Met Glu Ser Val Arg Thr Leu Trp Leu Ser Val Ala Leu Ala Leu Ala
 1               5                  10                  15

Val Gly Ser Arg Val Val Arg Gly His Pro Gln Pro Cys Arg Val Pro
            20                  25                  30

Thr Arg Ala Gly Ala Ser Val Arg Leu Ala Ala Leu Leu Pro Arg Ala
        35                  40                  45

Pro Ala Ala Arg Ala Arg Val Leu Ala Ala Leu Ala Thr Pro Ala Pro
     50                  55                  60

Arg Leu Pro His Asn Leu Ser Leu Glu Leu Val Ala Val Ala Ser Pro
 65                  70                  75                  80

Thr Arg Asp Pro Ala Ser Leu Ala Arg Gly Leu Cys Gln Val Leu Ala
                85                  90                  95

Pro Pro Gly Val Val Ala Ser Ile Ala Phe Pro Glu Ala Arg Pro Glu
            100                 105                 110

Leu Arg Leu Leu Gln Phe Leu Ala Ala Ala Thr Glu Thr Pro Val Thr
        115                 120                 125

Pro Phe His Leu Gln Leu Asp Trp Ala Ser Pro Leu Glu Thr Ile Leu
    130                 135                 140
```

-continued

```
Asp Val Leu Val Ser Leu Val Arg Ala His Ala Trp Glu Asp Ile Ala
145                 150                 155                 160

Leu Val Leu Cys Arg Val Arg Asp Pro Gly Ser Leu Val Thr Leu Trp
                165                 170                 175

Thr Asn His Ala Ser Gln Ala Pro Lys Phe Val Leu Asp Leu Ser Arg
            180                 185                 190

Leu Asp Ser Arg Asn Asp Ser Leu Arg Ala Gly Leu Ala Leu Leu Gly
        195                 200                 205

Ala Leu Glu Gly Gly Gly Thr Pro Val Pro Ala Ala Val Leu Leu Gly
    210                 215                 220

Cys Ser Thr Ala Arg Ala His Glu Val Leu Glu Ala Ala Pro Pro Gly
225                 230                 235                 240

Pro Gln Trp Leu Leu Gly Thr Pro Leu Pro Ala Glu Ala Leu Pro Thr
                245                 250                 255

Thr Gly Leu Pro Pro Gly Val Leu Ala Leu Gly Glu Thr Glu Gln His
            260                 265                 270

Ser Leu Glu Ala Val Val His Asp Met Val Glu Leu Val Ala Gln Ala
        275                 280                 285

Leu Ser Ser Met Ala Leu Val His Pro Glu Arg Ala Leu Leu Pro Ala
    290                 295                 300

Val Val Asn Cys Asp Asp Leu Lys Thr Gly Gly Ser Glu Ala Thr Gly
305                 310                 315                 320

Arg Thr Leu Ala Arg Phe Leu Gly Asn Thr Ser Phe Gln Gly Arg Thr
                325                 330                 335

Gly Ala Val Trp Val Thr Gly Ser Ser Gln Val His Val Ser Arg His
            340                 345                 350

Phe Lys Val Trp Ser Leu Arg Arg Asp Pro Leu Gly Ala Pro Ala Trp
        355                 360                 365

Ala Thr Val Gly Ser Trp Gln Asp Gly Gln Leu Asp Phe Gln Pro Gly
    370                 375                 380

Ala Ala Ala Leu Arg Val Pro Ser Pro Ser Gly Thr Gln Ala Arg Pro
385                 390                 395                 400

Lys Leu Arg Val Val Thr Leu Val Glu His Pro Phe Val Phe Thr Arg
                405                 410                 415

Glu Ser Asp Glu Asp Gly Gln Cys Pro Ala Gly Gln Leu Cys Leu Asp
            420                 425                 430

Pro Gly Thr Asn Asp Ser Ala Arg Leu Asp Ala Leu Phe Ala Ala Leu
        435                 440                 445

Val Asn Gly Ser Val Pro Arg Thr Leu Arg Arg Cys Cys Tyr Gly Tyr
    450                 455                 460

Cys Ile Asp Leu Leu Glu Arg Leu Ala Glu Asp Leu Ala Phe Asp Phe
465                 470                 475                 480

Glu Leu Tyr Ile Val Gly Asp Gly Lys Tyr Gly Ala Leu Arg Asp Gly
                485                 490                 495

Arg Trp Thr Gly Leu Val Gly Asp Leu Leu Ala Gly Arg Ala His Met
            500                 505                 510

Ala Val Thr Ser Phe Ser Ile Asn Ser Ala Arg Ser Gln Val Val Asp
        515                 520                 525

Phe Thr Ser Pro Phe Phe Ser Thr Ser Leu Gly Ile Met Val Arg Thr
    530                 535                 540

Arg Asp Thr Ala Ser Pro Ile Gly Ala Phe Met Trp Pro Leu His Trp
545                 550                 555                 560

Ser Met Trp Val Gly Val Phe Ala Ala Leu His Leu Thr Ala Leu Phe
```

-continued

```
                565                 570                 575

Leu Thr Leu Tyr Glu Trp Arg Ser Pro Tyr Gly Leu Thr Pro Arg Gly
            580                 585                 590

Arg Asn Arg Gly Thr Val Phe Ser Tyr Ser Ser Ala Leu Asn Leu Cys
        595                 600                 605

Tyr Ala Ile Leu Phe Gly Arg Thr Val Ser Ser Lys Thr Pro Lys Cys
    610                 615                 620

Pro Thr Gly Arg Phe Leu Met Asn Leu Trp Ala Ile Phe Cys Leu Leu
625                 630                 635                 640

Val Leu Ser Ser Tyr Thr Ala Asn Leu Ala Ala Val Met Val Gly Asp
                645                 650                 655

Lys Thr Phe Glu Glu Leu Ser Gly Ile His Asp Pro Lys Leu His His
            660                 665                 670

Pro Ser Gln Gly Phe Arg Phe Gly Thr Val Trp Glu Ser Ser Ala Glu
        675                 680                 685

Ala Tyr Ile Lys Ala Ser Phe Pro Glu Met His Ala His Met Arg Arg
    690                 695                 700

His Ser Ala Pro Thr Thr Pro His Gly Val Ala Met Leu Thr Ser Asp
705                 710                 715                 720

Pro Pro Lys Leu Asn Ala Phe Ile Met Asp Lys Ser Leu Leu Asp Tyr
                725                 730                 735

Glu Val Ser Ile Asp Ala Asp Cys Lys Leu Leu Thr Val Gly Lys Pro
            740                 745                 750

Phe Ala Ile Glu Gly Tyr Gly Ile Gly Leu Pro Gln Asn Ser Pro Leu
        755                 760                 765

Thr Ser Asn Leu Ser Glu Phe Ile Ser Arg Tyr Lys Ser Ser Gly Phe
    770                 775                 780

Ile Asp Leu Leu His Asp Lys Trp Tyr Lys Met Val Pro Cys Gly Lys
785                 790                 795                 800

Arg Val Phe Ala Val Thr Glu Thr Leu Gln Met Gly Val Tyr His Phe
                805                 810                 815

Ser Gly Leu Phe Val Leu Leu Cys Leu Gly Leu Gly Ser Ala Leu Leu
            820                 825                 830

Thr Ser Leu Gly Glu His Val Phe Tyr Arg Leu Val Leu Pro Arg Ile
        835                 840                 845

Arg Arg Gly Asn Lys Leu Gln Tyr Trp Leu His Thr Ser Gln Lys Ile
    850                 855                 860

His Arg Ala Leu Asn Thr Gly Pro Pro Glu Gly Gln Gln Glu Arg Ala
865                 870                 875                 880

Glu Gln Glu Arg Ser Gly Pro Lys Asp Glu Leu Pro Ala Thr Asp Gly
                885                 890                 895

Ala Gly Arg Trp Arg Arg Val Arg Arg Ala Val Glu Arg Glu Arg Arg
            900                 905                 910

Val Arg Phe Leu Leu Glu Pro Gly Glu Ala Gly Gly Asp Arg Pro Trp
        915                 920                 925

Leu Cys Ser Asn Gly Pro Gly Leu Gln Ala Glu Leu Arg Glu Leu Glu
    930                 935                 940

Leu Arg Ile Glu Ala Ala Arg Glu Gln Leu Arg Ser Ala Leu Leu Arg
945                 950                 955                 960

Arg Gly Glu Leu Arg Ala Leu Leu Gly Asp Gly Thr Arg Leu Arg Pro
                965                 970                 975

Leu Arg Leu Leu His Ala Ala Pro Ala Glu Ser
            980                 985
```

<210> SEQ ID NO 3
<211> LENGTH: 3178
<212> TYPE: DNA
<213> ORGANISM: Rattus sp.
<220> FEATURE:
<221> NAME/KEY: CDS
<222> LOCATION: (76)...(3081)

<400> SEQUENCE: 3

```
gcacgagggg acaagagcgg gtctggctgg ggtgtctcct tcccttcgca cagcacagtg      60

gtaacttctt tcggg atg gag agt gtg cgg acg ctg tgg ctc agc gtg gcc     111
                 Met Glu Ser Val Arg Thr Leu Trp Leu Ser Val Ala
                  1               5                  10

ctg gcg ctg gcg gtg ggg tcc cga gtg gtg cgc ggt cac cct cag ccc      159
Leu Ala Leu Ala Val Gly Ser Arg Val Val Arg Gly His Pro Gln Pro
        15                  20                  25

tgc cgg gtt ccc acg cgc gct ggg gcc tcc gtg cgc ctg gcg gcg ctc      207
Cys Arg Val Pro Thr Arg Ala Gly Ala Ser Val Arg Leu Ala Ala Leu
    30                  35                  40

ctg ccc cgg gcg ccc gcc gcc cgc gcc cgc gtc cta gct gcc ctg gcc      255
Leu Pro Arg Ala Pro Ala Ala Arg Ala Arg Val Leu Ala Ala Leu Ala
 45                  50                  55                  60

acc cct gcg ccg cgg ctg ccg cac aac ctg agt ctg gaa ctg gtg gcc      303
Thr Pro Ala Pro Arg Leu Pro His Asn Leu Ser Leu Glu Leu Val Ala
                65                  70                  75

gtc gcg tcc ccg acc cgg gac ccc gcg tcg cta gct cga ggt ctg tgc      351
Val Ala Ser Pro Thr Arg Asp Pro Ala Ser Leu Ala Arg Gly Leu Cys
            80                  85                  90

cag gtt ctg gca ccg cct ggc gtg gtg gcc tct ata gcc ttt ccc gag      399
Gln Val Leu Ala Pro Pro Gly Val Val Ala Ser Ile Ala Phe Pro Glu
        95                 100                 105

gcg cgg ccc gag ctg cgg cta ctg cag ttc ctg gca gcc gcc aca gag      447
Ala Arg Pro Glu Leu Arg Leu Leu Gln Phe Leu Ala Ala Ala Thr Glu
    110                 115                 120

acc cca gtg gtg agc gtc ctg cgg agg gag gtg cgc acg gcc ctc gga      495
Thr Pro Val Val Ser Val Leu Arg Arg Glu Val Arg Thr Ala Leu Gly
125                 130                 135                 140

gcc ccg act ccg ttc cat ctg cag ctg gac tgg gct agt ccc ctg gag      543
Ala Pro Thr Pro Phe His Leu Gln Leu Asp Trp Ala Ser Pro Leu Glu
                145                 150                 155

acc ata ctg gat gtg ctg gtg tcc ctg gta cgg gca cat gcc tgg gag      591
Thr Ile Leu Asp Val Leu Val Ser Leu Val Arg Ala His Ala Trp Glu
            160                 165                 170

gac att gct cta gta ctc tgc cgt gtc cgg gac cct ggc agc ctg gtg      639
Asp Ile Ala Leu Val Leu Cys Arg Val Arg Asp Pro Gly Ser Leu Val
        175                 180                 185

aca ctc tgg act aac cat gct agc cag gct cca aag ttt gtg ctg gac      687
Thr Leu Trp Thr Asn His Ala Ser Gln Ala Pro Lys Phe Val Leu Asp
    190                 195                 200

ctg agc cgg ctg gac agc agg aat gac agc ctt cgg gct gga ctg gcc      735
Leu Ser Arg Leu Asp Ser Arg Asn Asp Ser Leu Arg Ala Gly Leu Ala
205                 210                 215                 220

ctg ttg ggg gcg ctg gaa gga ggg gga acc cca gtg cct gca gca gtc      783
Leu Leu Gly Ala Leu Glu Gly Gly Gly Thr Pro Val Pro Ala Ala Val
                225                 230                 235

ctc cta ggc tgc agc act gcc cgt gca cat gag gtc cta gag gct gca      831
Leu Leu Gly Cys Ser Thr Ala Arg Ala His Glu Val Leu Glu Ala Ala
            240                 245                 250

cca ccg ggt ccc cag tgg ttg ctg ggc aca cca ttg ccc gct gag gca      879
Pro Pro Gly Pro Gln Trp Leu Leu Gly Thr Pro Leu Pro Ala Glu Ala
        255                 260                 265
```

-continued

```
ctg ccc acg act ggt ctg cca cct ggc gtg ctg gcg ctg ggg gaa acc      927
Leu Pro Thr Thr Gly Leu Pro Pro Gly Val Leu Ala Leu Gly Glu Thr
    270                 275                 280

gaa caa cac tct ctg gaa gct gtc gtc cac gac atg gtg gag ctt gtg      975
Glu Gln His Ser Leu Glu Ala Val Val His Asp Met Val Glu Leu Val
285                 290                 295                 300

gct cag gca ctc agt agc atg gcc ctt gta cac cca gag cgg gca ctg     1023
Ala Gln Ala Leu Ser Ser Met Ala Leu Val His Pro Glu Arg Ala Leu
                305                 310                 315

ctt cca gct gtg gtg aac tgt gat gac ctg aaa aca ggc gga tct gag     1071
Leu Pro Ala Val Val Asn Cys Asp Asp Leu Lys Thr Gly Gly Ser Glu
            320                 325                 330

gca aca ggg cgc acc ttg gct cgg ttt ctc ggc aac acc tca ttt cag     1119
Ala Thr Gly Arg Thr Leu Ala Arg Phe Leu Gly Asn Thr Ser Phe Gln
        335                 340                 345

ggc cga aca ggg gcc gtg tgg gtg aca ggc tcc tct cag gtg cat gtg     1167
Gly Arg Thr Gly Ala Val Trp Val Thr Gly Ser Ser Gln Val His Val
    350                 355                 360

tct cgg cat ttc aag gta tgg agc ctg cgc cgg gat ccg ctg ggt gcc     1215
Ser Arg His Phe Lys Val Trp Ser Leu Arg Arg Asp Pro Leu Gly Ala
365                 370                 375                 380

cca gcc tgg gca acc gtg ggc agc tgg cag gat gga cag ctg gac ttc     1263
Pro Ala Trp Ala Thr Val Gly Ser Trp Gln Asp Gly Gln Leu Asp Phe
                385                 390                 395

cag cca ggg gca gcc gct ctc cga gtc cca tct ccg tct ggc acc cag     1311
Gln Pro Gly Ala Ala Ala Leu Arg Val Pro Ser Pro Ser Gly Thr Gln
            400                 405                 410

gcc cga cca aag ctg cgt gtg gta acc ctg gtg gaa cac ccg ttt gtg     1359
Ala Arg Pro Lys Leu Arg Val Val Thr Leu Val Glu His Pro Phe Val
        415                 420                 425

ttc acc agg gaa tct gat gaa gac gga cag tgc cca gct ggg cag ctg     1407
Phe Thr Arg Glu Ser Asp Glu Asp Gly Gln Cys Pro Ala Gly Gln Leu
    430                 435                 440

tgt ctg gac cca ggc acc aat gac tca gcc agg ctg gat gcc ctc ttt     1455
Cys Leu Asp Pro Gly Thr Asn Asp Ser Ala Arg Leu Asp Ala Leu Phe
445                 450                 455                 460

gct gca ctg gtg aat ggc tca gta cct cga acg ctg aga aga tgc tgc     1503
Ala Ala Leu Val Asn Gly Ser Val Pro Arg Thr Leu Arg Arg Cys Cys
                465                 470                 475

tat ggc tac tgc atc gac ctg ctg gag cgg ctg gcc gag gac ctg gcc     1551
Tyr Gly Tyr Cys Ile Asp Leu Leu Glu Arg Leu Ala Glu Asp Leu Ala
            480                 485                 490

ttt gac ttt gag ctc tat att gtg ggg gat ggc aag tac ggg gcc ctg     1599
Phe Asp Phe Glu Leu Tyr Ile Val Gly Asp Gly Lys Tyr Gly Ala Leu
        495                 500                 505

cgt gat ggg cgc tgg acg ggc ctg gtg ggt gac ctg ctg gct ggc cgg     1647
Arg Asp Gly Arg Trp Thr Gly Leu Val Gly Asp Leu Leu Ala Gly Arg
    510                 515                 520

gca cac atg gct gtg acc agc ttc agc atc aac tca gct cgc tct cag     1695
Ala His Met Ala Val Thr Ser Phe Ser Ile Asn Ser Ala Arg Ser Gln
525                 530                 535                 540

gtg gtg gat ttc acc agc cct ttc ttc tcc acc agc ctg ggg att atg     1743
Val Val Asp Phe Thr Ser Pro Phe Phe Ser Thr Ser Leu Gly Ile Met
                545                 550                 555

gtg cgc acg aga gac acg gcc tcg ccc atc ggg gct ttc atg tgg ccc     1791
Val Arg Thr Arg Asp Thr Ala Ser Pro Ile Gly Ala Phe Met Trp Pro
            560                 565                 570

ctg cac tgg tcc atg tgg gtg ggc gtg ttt gct gct ctg cac ctc aca     1839
Leu His Trp Ser Met Trp Val Gly Val Phe Ala Ala Leu His Leu Thr
        575                 580                 585
```

```
gcg ctc ttt ctc acc ctg tac gaa tgg cga agt ccc tac ggg ctc acg      1887
Ala Leu Phe Leu Thr Leu Tyr Glu Trp Arg Ser Pro Tyr Gly Leu Thr
    590                 595                 600

ccg cgc ggc cgc aac cgt ggc act gtc ttc tct tac tcc tcc gcg ctc      1935
Pro Arg Gly Arg Asn Arg Gly Thr Val Phe Ser Tyr Ser Ser Ala Leu
605                 610                 615                 620

aac ctg tgc tat gcc att ctc ttt gga cgc act gtc tcc agt aag acg      1983
Asn Leu Cys Tyr Ala Ile Leu Phe Gly Arg Thr Val Ser Ser Lys Thr
                625                 630                 635

ccc aag tgc cct act gga cgc ttc ctc atg aac ctc tgg gca atc ttc      2031
Pro Lys Cys Pro Thr Gly Arg Phe Leu Met Asn Leu Trp Ala Ile Phe
            640                 645                 650

tgc ctg ctg gtg ctt tcc agt tac acg gcc aac ctg gct gct gtc atg      2079
Cys Leu Leu Val Leu Ser Ser Tyr Thr Ala Asn Leu Ala Ala Val Met
        655                 660                 665

gtt ggg gac aaa acc ttt gag gag ctg tct gga atc cat gat ccc aag      2127
Val Gly Asp Lys Thr Phe Glu Glu Leu Ser Gly Ile His Asp Pro Lys
    670                 675                 680

ctg cac cac cct tcc caa ggc ttt cgc ttt ggc acc gta tgg gag agc      2175
Leu His His Pro Ser Gln Gly Phe Arg Phe Gly Thr Val Trp Glu Ser
685                 690                 695                 700

agc gcg gag gcc tac atc aag gca agc ttc cct gag atg cac gca cac      2223
Ser Ala Glu Ala Tyr Ile Lys Ala Ser Phe Pro Glu Met His Ala His
                705                 710                 715

atg cgt cgg cac agc gca ccc acc act cca cat ggg gtg gcc atg ctc      2271
Met Arg Arg His Ser Ala Pro Thr Thr Pro His Gly Val Ala Met Leu
            720                 725                 730

acg agc gac ccg ccc aag ctc aac gcc ttc atc atg gat aaa tca cta      2319
Thr Ser Asp Pro Pro Lys Leu Asn Ala Phe Ile Met Asp Lys Ser Leu
        735                 740                 745

ctg gac tat gag gtg tcc ata gat gcg gac tgc aag ctg ctc acc gtt      2367
Leu Asp Tyr Glu Val Ser Ile Asp Ala Asp Cys Lys Leu Leu Thr Val
    750                 755                 760

ggc aaa ccc ttt gct atc gag ggc tac ggc ata ggg cta ccc caa aac      2415
Gly Lys Pro Phe Ala Ile Glu Gly Tyr Gly Ile Gly Leu Pro Gln Asn
765                 770                 775                 780

tcg ccg ctc acc tcc aac ctg tcg gag ttc atc agt agg tac aag tct      2463
Ser Pro Leu Thr Ser Asn Leu Ser Glu Phe Ile Ser Arg Tyr Lys Ser
                785                 790                 795

tca ggc ttc att gat ctg ctc cat gac aag tgg tac aag atg gtg cct      2511
Ser Gly Phe Ile Asp Leu Leu His Asp Lys Trp Tyr Lys Met Val Pro
            800                 805                 810

tgc ggg aag cgg gtg ttc gcc gtg acg gag acg ctg cag atg ggg gtc      2559
Cys Gly Lys Arg Val Phe Ala Val Thr Glu Thr Leu Gln Met Gly Val
        815                 820                 825

tac cac ttc tca gga ttg ttt gtc ctg ctg tgc ctc ggg ctg ggc agc      2607
Tyr His Phe Ser Gly Leu Phe Val Leu Leu Cys Leu Gly Leu Gly Ser
    830                 835                 840

gcg ctt ctc acc tct ctg ggt gag cat gtc ttc tac cgc ctg gtg ctg      2655
Ala Leu Leu Thr Ser Leu Gly Glu His Val Phe Tyr Arg Leu Val Leu
845                 850                 855                 860

ccg cgc atc cgc agg ggt aat aag ctg cag tat tgg ctt cac acg agc      2703
Pro Arg Ile Arg Arg Gly Asn Lys Leu Gln Tyr Trp Leu His Thr Ser
                865                 870                 875

cag aag atc cac cga gcc ctc aat aca gga cca ccc gag ggg caa cag      2751
Gln Lys Ile His Arg Ala Leu Asn Thr Gly Pro Pro Glu Gly Gln Gln
            880                 885                 890

gag agg gca gag cag gag cgc agc ggc ccc aag gac gag ctg cct gcc      2799
Glu Arg Ala Glu Gln Glu Arg Ser Gly Pro Lys Asp Glu Leu Pro Ala
        895                 900                 905
```

-continued

```
acc gat ggt gca ggg cgc tgg agg cgg gtg cgc cgg gct gtg gaa cgg      2847
Thr Asp Gly Ala Gly Arg Trp Arg Arg Val Arg Arg Ala Val Glu Arg
    910                 915                 920

gag cga cgc gtg cgt ttc ctg ctg gaa cct ggg gag gct ggc gga gac      2895
Glu Arg Arg Val Arg Phe Leu Leu Glu Pro Gly Glu Ala Gly Gly Asp
925                 930                 935                 940

cgc ccg tgg ctc tgc tcc aac ggg ccc ggg ctg caa gcg gag ctg cgg      2943
Arg Pro Trp Leu Cys Ser Asn Gly Pro Gly Leu Gln Ala Glu Leu Arg
                945                 950                 955

gag ctg gag ctg cgc att gag gct gca cgg gag cag ctg cgc agt gcg      2991
Glu Leu Glu Leu Arg Ile Glu Ala Ala Arg Glu Gln Leu Arg Ser Ala
            960                 965                 970

ctg ttg cgg cgc ggg gag ctg cgg gcc ctg ctt ggg gat ggc acc cgg      3039
Leu Leu Arg Arg Gly Glu Leu Arg Ala Leu Leu Gly Asp Gly Thr Arg
        975                 980                 985

ctc agg cca ctg cgc ctg ttg cat gcg gcg cct gct gag agc              3081
Leu Arg Pro Leu Arg Leu Leu His Ala Ala Pro Ala Glu Ser
     990                 995                1000

tgaggaacca caaggccgca ctgtccacga cagtttattc tatatacaaa cacgactctg   3141

tacactgcaa ttaaatagcg tggaacgtga aaaaaaa                            3178


<210> SEQ ID NO 4
<211> LENGTH: 1002
<212> TYPE: PRT
<213> ORGANISM: Rattus sp.

<400> SEQUENCE: 4

Met Glu Ser Val Arg Thr Leu Trp Leu Ser Val Ala Leu Ala Leu Ala
 1               5                  10                  15

Val Gly Ser Arg Val Val Arg Gly His Pro Gln Pro Cys Arg Val Pro
            20                  25                  30

Thr Arg Ala Gly Ala Ser Val Arg Leu Ala Ala Leu Leu Pro Arg Ala
        35                  40                  45

Pro Ala Ala Arg Ala Arg Val Leu Ala Ala Leu Ala Thr Pro Ala Pro
     50                  55                  60

Arg Leu Pro His Asn Leu Ser Leu Glu Leu Val Ala Val Ala Ser Pro
 65                  70                  75                  80

Thr Arg Asp Pro Ala Ser Leu Ala Arg Gly Leu Cys Gln Val Leu Ala
                 85                  90                  95

Pro Pro Gly Val Val Ala Ser Ile Ala Phe Pro Glu Ala Arg Pro Glu
            100                 105                 110

Leu Arg Leu Leu Gln Phe Leu Ala Ala Ala Thr Glu Thr Pro Val Val
        115                 120                 125

Ser Val Leu Arg Arg Glu Val Arg Thr Ala Leu Gly Ala Pro Thr Pro
    130                 135                 140

Phe His Leu Gln Leu Asp Trp Ala Ser Pro Leu Glu Thr Ile Leu Asp
145                 150                 155                 160

Val Leu Val Ser Leu Val Arg Ala His Ala Trp Glu Asp Ile Ala Leu
                165                 170                 175

Val Leu Cys Arg Val Arg Asp Pro Gly Ser Leu Val Thr Leu Trp Thr
            180                 185                 190

Asn His Ala Ser Gln Ala Pro Lys Phe Val Leu Asp Leu Ser Arg Leu
        195                 200                 205

Asp Ser Arg Asn Asp Ser Leu Arg Ala Gly Leu Ala Leu Leu Gly Ala
    210                 215                 220

Leu Glu Gly Gly Gly Thr Pro Val Pro Ala Ala Val Leu Leu Gly Cys
```

-continued

```
225                 230                 235                 240

Ser Thr Ala Arg Ala His Glu Val Leu Glu Ala Ala Pro Pro Gly Pro
                245                 250                 255

Gln Trp Leu Leu Gly Thr Pro Leu Pro Ala Glu Ala Leu Pro Thr Thr
            260                 265                 270

Gly Leu Pro Pro Gly Val Leu Ala Leu Gly Glu Thr Glu Gln His Ser
        275                 280                 285

Leu Glu Ala Val Val His Asp Met Val Glu Leu Val Ala Gln Ala Leu
    290                 295                 300

Ser Ser Met Ala Leu Val His Pro Glu Arg Ala Leu Leu Pro Ala Val
305                 310                 315                 320

Val Asn Cys Asp Asp Leu Lys Thr Gly Gly Ser Glu Ala Thr Gly Arg
                325                 330                 335

Thr Leu Ala Arg Phe Leu Gly Asn Thr Ser Phe Gln Gly Arg Thr Gly
            340                 345                 350

Ala Val Trp Val Thr Gly Ser Ser Gln Val His Val Ser Arg His Phe
        355                 360                 365

Lys Val Trp Ser Leu Arg Arg Asp Pro Leu Gly Ala Pro Ala Trp Ala
    370                 375                 380

Thr Val Gly Ser Trp Gln Asp Gly Gln Leu Asp Phe Gln Pro Gly Ala
385                 390                 395                 400

Ala Ala Leu Arg Val Pro Ser Pro Ser Gly Thr Gln Ala Arg Pro Lys
                405                 410                 415

Leu Arg Val Val Thr Leu Val Glu His Pro Phe Val Phe Thr Arg Glu
            420                 425                 430

Ser Asp Glu Asp Gly Gln Cys Pro Ala Gly Gln Leu Cys Leu Asp Pro
        435                 440                 445

Gly Thr Asn Asp Ser Ala Arg Leu Asp Ala Leu Phe Ala Ala Leu Val
    450                 455                 460

Asn Gly Ser Val Pro Arg Thr Leu Arg Arg Cys Cys Tyr Gly Tyr Cys
465                 470                 475                 480

Ile Asp Leu Leu Glu Arg Leu Ala Glu Asp Leu Ala Phe Asp Phe Glu
                485                 490                 495

Leu Tyr Ile Val Gly Asp Gly Lys Tyr Gly Ala Leu Arg Asp Gly Arg
            500                 505                 510

Trp Thr Gly Leu Val Gly Asp Leu Leu Ala Gly Arg Ala His Met Ala
        515                 520                 525

Val Thr Ser Phe Ser Ile Asn Ser Ala Arg Ser Gln Val Val Asp Phe
    530                 535                 540

Thr Ser Pro Phe Phe Ser Thr Ser Leu Gly Ile Met Val Arg Thr Arg
545                 550                 555                 560

Asp Thr Ala Ser Pro Ile Gly Ala Phe Met Trp Pro Leu His Trp Ser
                565                 570                 575

Met Trp Val Gly Val Phe Ala Ala Leu His Leu Thr Ala Leu Phe Leu
            580                 585                 590

Thr Leu Tyr Glu Trp Arg Ser Pro Tyr Gly Leu Thr Pro Arg Gly Arg
        595                 600                 605

Asn Arg Gly Thr Val Phe Ser Tyr Ser Ser Ala Leu Asn Leu Cys Tyr
    610                 615                 620

Ala Ile Leu Phe Gly Arg Thr Val Ser Ser Lys Thr Pro Lys Cys Pro
625                 630                 635                 640

Thr Gly Arg Phe Leu Met Asn Leu Trp Ala Ile Phe Cys Leu Leu Val
                645                 650                 655
```

-continued

```
Leu Ser Ser Tyr Thr Ala Asn Leu Ala Ala Val Met Val Gly Asp Lys
            660                 665                 670

Thr Phe Glu Glu Leu Ser Gly Ile His Asp Pro Lys Leu His His Pro
        675                 680                 685

Ser Gln Gly Phe Arg Phe Gly Thr Val Trp Glu Ser Ser Ala Glu Ala
    690                 695                 700

Tyr Ile Lys Ala Ser Phe Pro Glu Met His Ala His Met Arg Arg His
705                 710                 715                 720

Ser Ala Pro Thr Thr Pro His Gly Val Ala Met Leu Thr Ser Asp Pro
                725                 730                 735

Pro Lys Leu Asn Ala Phe Ile Met Asp Lys Ser Leu Leu Asp Tyr Glu
            740                 745                 750

Val Ser Ile Asp Ala Asp Cys Lys Leu Leu Thr Val Gly Lys Pro Phe
        755                 760                 765

Ala Ile Glu Gly Tyr Gly Ile Gly Leu Pro Gln Asn Ser Pro Leu Thr
    770                 775                 780

Ser Asn Leu Ser Glu Phe Ile Ser Arg Tyr Lys Ser Ser Gly Phe Ile
785                 790                 795                 800

Asp Leu Leu His Asp Lys Trp Tyr Lys Met Val Pro Cys Gly Lys Arg
                805                 810                 815

Val Phe Ala Val Thr Glu Thr Leu Gln Met Gly Val Tyr His Phe Ser
            820                 825                 830

Gly Leu Phe Val Leu Leu Cys Leu Gly Leu Gly Ser Ala Leu Leu Thr
        835                 840                 845

Ser Leu Gly Glu His Val Phe Tyr Arg Leu Val Leu Pro Arg Ile Arg
    850                 855                 860

Arg Gly Asn Lys Leu Gln Tyr Trp Leu His Thr Ser Gln Lys Ile His
865                 870                 875                 880

Arg Ala Leu Asn Thr Gly Pro Pro Glu Gly Gln Gln Glu Arg Ala Glu
                885                 890                 895

Gln Glu Arg Ser Gly Pro Lys Asp Glu Leu Pro Ala Thr Asp Gly Ala
            900                 905                 910

Gly Arg Trp Arg Arg Val Arg Arg Ala Val Glu Arg Glu Arg Arg Val
        915                 920                 925

Arg Phe Leu Leu Glu Pro Gly Glu Ala Gly Gly Asp Arg Pro Trp Leu
    930                 935                 940

Cys Ser Asn Gly Pro Gly Leu Gln Ala Glu Leu Arg Glu Leu Glu Leu
945                 950                 955                 960

Arg Ile Glu Ala Ala Arg Glu Gln Leu Arg Ser Ala Leu Leu Arg Arg
                965                 970                 975

Gly Glu Leu Arg Ala Leu Leu Gly Asp Gly Thr Arg Leu Arg Pro Leu
            980                 985                 990

Arg Leu Leu His Ala Ala Pro Ala Glu Ser
        995                 1000
```

<210> SEQ ID NO 5
<211> LENGTH: 3096
<212> TYPE: DNA
<213> ORGANISM: Homo sapiens
<220> FEATURE:
<221> NAME/KEY: CDS
<222> LOCATION: (1)...(3033)
<220> FEATURE:
<221> NAME/KEY: misc_feature
<222> LOCATION: 2692, 2693, 2694, 2695, 2696, 2697, 2698, 2699, 2700,
2701, 2702, 2703, 2704, 2705, 2706, 2707, 2708, 2709, 2710, 2711,
2712, 2713, 2714, 2715, 2716, 2717, 2718, 2719, 2720, 2721,
2722, 2723, 2724, 2725, 2726, 2727, 2728, 2729, 2730

<223> OTHER INFORMATION: n = A,T,C or G
<220> FEATURE:
<221> NAME/KEY: misc_feature
<222> LOCATION: 2791, 2792, 2793, 2794, 2795, 2796, 2797, 2798, 2799, 2800, 2801, 2802, 2803, 2804, 2805, 2806, 2807, 2808, 2809, 2810, 2811, 2812, 2813, 2814, 2827, 2828, 2829, 2830, 2831, 2832, 2833, 2834, 2835, 2836, 2837, 2838, 2839, 2840, 2841
<223> OTHER INFORMATION: n = A,T,C or G
<220> FEATURE:
<221> NAME/KEY: misc_feature
<222> LOCATION: 2842, 2843, 2844, 2845, 2846, 2847, 3037, 3038, 3039
<223> OTHER INFORMATION: n = A,T,C or G

<400> SEQUENCE: 5 atg gag ttt gtg cgg gcg ctg tgg ctg ggc ctg gcg ctg gcg ctg ggg 48
Met Glu Phe Val Arg Ala Leu Trp Leu Gly Leu Ala Leu Ala Leu Gly
1 5 10 15 ccg ggg tcc gcg ggg ggc cac cct cag ccg tgc ggc gtc ctg gcg cgc 96
Pro Gly Ser Ala Gly Gly His Pro Gln Pro Cys Gly Val Leu Ala Arg
20 25 30 ctc ggg ggc tcc gtg cgc ctg ggc gcc ctc ctg ccc cgc gcg cct ctc 144
Leu Gly Gly Ser Val Arg Leu Gly Ala Leu Leu Pro Arg Ala Pro Leu
35 40 45 gcc cgc gcc cgc gcc cgc gcc gcc ctg gcc cgg gcc gcc ctg gcg ccg 192
Ala Arg Ala Arg Ala Arg Ala Ala Leu Ala Arg Ala Ala Leu Ala Pro
50 55 60 cgg ctg ccg cac aac ctg agc ttg gag ctg gtg gtc gcc gcg ccc ccc 240
Arg Leu Pro His Asn Leu Ser Leu Glu Leu Val Val Ala Ala Pro Pro
65 70 75 80 gcc cgc gac ccc gcc tcg ctg acc cgc ggc ctg tgc cag gcg ctg gtg 288
Ala Arg Asp Pro Ala Ser Leu Thr Arg Gly Leu Cys Gln Ala Leu Val
85 90 95 cct ccg ggc gtg gcg gcc ctg ctc gcc ttt ccc gag gct cgg ccc gag 336
Pro Pro Gly Val Ala Ala Leu Leu Ala Phe Pro Glu Ala Arg Pro Glu
100 105 110 ctg ctg cag ctg cac ttc ctg gcg gcg gcc acc gag acc ccc gtg ctc 384
Leu Leu Gln Leu His Phe Leu Ala Ala Ala Thr Glu Thr Pro Val Leu
115 120 125 agc ctg ctg cgg cgg gag gcg cgc gcg ccc ctc gga gcc ccg aac cca 432
Ser Leu Leu Arg Arg Glu Ala Arg Ala Pro Leu Gly Ala Pro Asn Pro
130 135 140 ttc cac ctg cag ctg cac tgg gcc agc ccc ctg gag acg ctg ctg gat 480
Phe His Leu Gln Leu His Trp Ala Ser Pro Leu Glu Thr Leu Leu Asp
145 150 155 160 gtg ctg gtg gcg gtg ctg cag gcg cac gcc tgg gaa gac gtc ggc ctg 528
Val Leu Val Ala Val Leu Gln Ala His Ala Trp Glu Asp Val Gly Leu
165 170 175 gcc ctg tgc cgc act cag gac ccc ggc ggc ctg gtg gcc ctc tgg aca 576
Ala Leu Cys Arg Thr Gln Asp Pro Gly Gly Leu Val Ala Leu Trp Thr
180 185 190 agc cgg gct ggc cgg ccc cca cag ctg gtc ctg gac cta agc cgg cgg 624
Ser Arg Ala Gly Arg Pro Pro Gln Leu Val Leu Asp Leu Ser Arg Arg
195 200 205 gac acg gga gat gca gga ctg cgg gca cgc ctg gcc ccg atg gcg gcg 672
Asp Thr Gly Asp Ala Gly Leu Arg Ala Arg Leu Ala Pro Met Ala Ala
210 215 220 cca gtg ggg ggt gaa gca ccg gta ccc gcg gcg gtc ctc ctc ggc tgt 720
Pro Val Gly Gly Glu Ala Pro Val Pro Ala Ala Val Leu Leu Gly Cys
225 230 235 240 gac atc gcc cgt gcc cgt cgg gtg ctg gag gcc gta cct ccc ggc ccc 768
Asp Ile Ala Arg Ala Arg Arg Val Leu Glu Ala Val Pro Pro Gly Pro
245 250 255 cac tgg ctg ttg ggg aca cca ctg ccg ccc aag gcc ctg ccc acc gcg 816

-continued

```
His Trp Leu Leu Gly Thr Pro Leu Pro Pro Lys Ala Leu Pro Thr Ala
            260                 265                 270

ggg ctg cca cca ggg ctg ctg gcg ctg ggc gag gtg gca cga ccc ccg      864
Gly Leu Pro Pro Gly Leu Leu Ala Leu Gly Glu Val Ala Arg Pro Pro
        275                 280                 285

ctg gag gcc gcc atc cat gac att gtg caa ctg gtg gcc cgg gcg ctg      912
Leu Glu Ala Ala Ile His Asp Ile Val Gln Leu Val Ala Arg Ala Leu
    290                 295                 300

ggc agt gcg gcc cag gtg cag ccg aag cga gcc ctc ctc ccc gcc ccg      960
Gly Ser Ala Ala Gln Val Gln Pro Lys Arg Ala Leu Leu Pro Ala Pro
305                 310                 315                 320

gtc aac tgc ggg gac ctg cag ccg gcc ggg ccc gag tcc ccg ggg cgc     1008
Val Asn Cys Gly Asp Leu Gln Pro Ala Gly Pro Glu Ser Pro Gly Arg
            325                 330                 335

ttc ttg gcc aac acg tcc ttc cag ggc cgc acg ggc ccc gtg tgg gtg     1056
Phe Leu Ala Asn Thr Ser Phe Gln Gly Arg Thr Gly Pro Val Trp Val
            340                 345                 350

aca ggc agc tcc cag gta cac atg tct cgg cac ttt aag gtg tgg agc     1104
Thr Gly Ser Ser Gln Val His Met Ser Arg His Phe Lys Val Trp Ser
        355                 360                 365

ctt cgc cgg gac cca cgg ggc gcc ccg gcc tgg gcc acg gtg ggc agc     1152
Leu Arg Arg Asp Pro Arg Gly Ala Pro Ala Trp Ala Thr Val Gly Ser
    370                 375                 380

tgg cgg gac ggc cag ctg gac ttg gaa ccg gga ggt gcc tct gca cgg     1200
Trp Arg Asp Gly Gln Leu Asp Leu Glu Pro Gly Gly Ala Ser Ala Arg
385                 390                 395                 400

ccc ccg ccc cca cag ggt gcc cag gtc tgg ccc aag ctg cgt gtg gta     1248
Pro Pro Pro Pro Gln Gly Ala Gln Val Trp Pro Lys Leu Arg Val Val
                405                 410                 415

acg ctg ttg gaa cac cca ttt gtg ttt gcc cgt gat cca gac gaa gac     1296
Thr Leu Leu Glu His Pro Phe Val Phe Ala Arg Asp Pro Asp Glu Asp
            420                 425                 430

ggg cag tgc cca gcg ggg cag ctg tgc ctg gac cct ggc acc aac gac     1344
Gly Gln Cys Pro Ala Gly Gln Leu Cys Leu Asp Pro Gly Thr Asn Asp
        435                 440                 445

tcg gcc acc ctg gac gca ctg ttc gcc gcg ctg gcc aac ggc tca gcg     1392
Ser Ala Thr Leu Asp Ala Leu Phe Ala Ala Leu Ala Asn Gly Ser Ala
    450                 455                 460

ccc cgt gcc ctg cgc aag tgc tgc tac ggc tac tgc att gac ctg ctg     1440
Pro Arg Ala Leu Arg Lys Cys Cys Tyr Gly Tyr Cys Ile Asp Leu Leu
465                 470                 475                 480

gag cgg ctg gcg gag gac acg ccc ttc gac ttc gag ctg tac ctc gtg     1488
Glu Arg Leu Ala Glu Asp Thr Pro Phe Asp Phe Glu Leu Tyr Leu Val
                485                 490                 495

ggt gac ggc aag tac ggc gcc ctg cgg gac ggc cgc tgg acc ggc ctg     1536
Gly Asp Gly Lys Tyr Gly Ala Leu Arg Asp Gly Arg Trp Thr Gly Leu
            500                 505                 510

gtc ggg gac ctg ctg gcc ggc cgg gcc cac atg gcg gtc acc agc ttc     1584
Val Gly Asp Leu Leu Ala Gly Arg Ala His Met Ala Val Thr Ser Phe
        515                 520                 525

agt atc aac tcc gcc cgc tca cag gtg gtg gac ttc acc agc ccc ttc     1632
Ser Ile Asn Ser Ala Arg Ser Gln Val Val Asp Phe Thr Ser Pro Phe
    530                 535                 540

ttc tcc acc agc ctg ggc atc atg gtg cgg gca cgg gac acg gcc tca     1680
Phe Ser Thr Ser Leu Gly Ile Met Val Arg Ala Arg Asp Thr Ala Ser
545                 550                 555                 560

ccc atc ggt gcc ttt atg tgg ccc ctg cac tgg tcc acg tgg ctg ggc     1728
Pro Ile Gly Ala Phe Met Trp Pro Leu His Trp Ser Thr Trp Leu Gly
                565                 570                 575

gtc ttt gcg gcc ctg cac ctc acc gcg ctc ttc ctc acc gtg tac gag     1776
```

-continued

```
Val Phe Ala Ala Leu His Leu Thr Ala Leu Phe Leu Thr Val Tyr Glu
            580                 585                 590

tgg cgt agc ccc tac ggc ctc acg cca cgt ggc cgc aac cgc agc acc      1824
Trp Arg Ser Pro Tyr Gly Leu Thr Pro Arg Gly Arg Asn Arg Ser Thr
        595                 600                 605

gtc ttc tcc tac tcc tca gcc ctc aac ctg tgc tac gcc atc ctc ttc      1872
Val Phe Ser Tyr Ser Ser Ala Leu Asn Leu Cys Tyr Ala Ile Leu Phe
    610                 615                 620

aga cgc acc gtg tcc agc aag acg ccc aag tgc ccc acg ggc cgc ctg      1920
Arg Arg Thr Val Ser Ser Lys Thr Pro Lys Cys Pro Thr Gly Arg Leu
625                 630                 635                 640

ctc atg aac ctc tgg gcc atc ttc tgc ctg ctg gtg ctg tcc agc tac      1968
Leu Met Asn Leu Trp Ala Ile Phe Cys Leu Leu Val Leu Ser Ser Tyr
                645                 650                 655

acg gcc aac ctg gct gcc gtc atg gtc ggg gac aag acc ttc gag gag      2016
Thr Ala Asn Leu Ala Ala Val Met Val Gly Asp Lys Thr Phe Glu Glu
            660                 665                 670

ctg tcg ggg atc cac gac ccc aag ctg cac cac ccg gcg cag ggc ttc      2064
Leu Ser Gly Ile His Asp Pro Lys Leu His His Pro Ala Gln Gly Phe
        675                 680                 685

cgc ttc ggc acc gtg tgg gag agc agc gcc gag gcg tac atc aag aag      2112
Arg Phe Gly Thr Val Trp Glu Ser Ser Ala Glu Ala Tyr Ile Lys Lys
    690                 695                 700

agc ttc ccc gac atg cac gca cac atg cgg cgc cac agc gcg ccc acc      2160
Ser Phe Pro Asp Met His Ala His Met Arg Arg His Ser Ala Pro Thr
705                 710                 715                 720

acg ccc cgc ggc gtc gcc atg ctc acg agc gac ccc ccc aag ctc aac      2208
Thr Pro Arg Gly Val Ala Met Leu Thr Ser Asp Pro Pro Lys Leu Asn
                725                 730                 735

gcc ttc atc atg gac aag tcg ctc ctg gac tac gag gtc tcc atc gac      2256
Ala Phe Ile Met Asp Lys Ser Leu Leu Asp Tyr Glu Val Ser Ile Asp
            740                 745                 750

gcc gac tgc aaa ctg ctg acc gtg gga aag ccc ttc gcc att gag ggc      2304
Ala Asp Cys Lys Leu Leu Thr Val Gly Lys Pro Phe Ala Ile Glu Gly
        755                 760                 765

tat ggg atc gga ctg ccc cag aac tcg ccg ctc acc tcc aac ctg tcc      2352
Tyr Gly Ile Gly Leu Pro Gln Asn Ser Pro Leu Thr Ser Asn Leu Ser
    770                 775                 780

gag ttc atc agc cgc tac aag tcc tcc ggc ttc atc gac ctg ctc cac      2400
Glu Phe Ile Ser Arg Tyr Lys Ser Ser Gly Phe Ile Asp Leu Leu His
785                 790                 795                 800

gac aag tgg tac aag atg gtg cct tgc ggc aag cgg gtc ttt gcg gtt      2448
Asp Lys Trp Tyr Lys Met Val Pro Cys Gly Lys Arg Val Phe Ala Val
                805                 810                 815

aca gag acc ctg cag atg agc atc tac cac ttc gcg ggc ctc ttc gtg      2496
Thr Glu Thr Leu Gln Met Ser Ile Tyr His Phe Ala Gly Leu Phe Val
            820                 825                 830

ttg ctg tgc ctg ggc ctg ggc agc gct ctg ctc agc tcg ctg ggc gag      2544
Leu Leu Cys Leu Gly Leu Gly Ser Ala Leu Leu Ser Ser Leu Gly Glu
        835                 840                 845

cac gcc ttc ttc cgc ctg gcg ctg ccg cgc atc cgc aag ggg agc agg      2592
His Ala Phe Phe Arg Leu Ala Leu Pro Arg Ile Arg Lys Gly Ser Arg
    850                 855                 860

ctg cag tac tgg ctg cac acc agc cag aaa atc cac cgc gcc ctc aac      2640
Leu Gln Tyr Trp Leu His Thr Ser Gln Lys Ile His Arg Ala Leu Asn
865                 870                 875                 880

acg gag cca cca gag ggg tcg aag gag gag acg gca gag gcg gag ccc      2688
Thr Glu Pro Pro Glu Gly Ser Lys Glu Glu Thr Ala Glu Ala Glu Pro
                885                 890                 895

agg nnn nnn nnn nnn nnn nnn nnn nnn nnn nnn nnn nnn nnn tgg aaa      2736
```

```
Arg Xaa Xaa Xaa Xaa Xaa Xaa Xaa Xaa Xaa Xaa Xaa Xaa Xaa Trp Lys
            900                 905                 910

cgg gcg cgc cgg gcc gtg gac aag gag cgc cgc gtg cgc ttc ctg ctg      2784
Arg Ala Arg Arg Ala Val Asp Lys Glu Arg Arg Val Arg Phe Leu Leu
        915                 920                 925

gag ccc nnn nnn nnn nnn nnn nnn nnn nnn tgg ctg tgc tcc nnn nnn      2832
Glu Pro Xaa Xaa Xaa Xaa Xaa Xaa Xaa Xaa Trp Leu Cys Ser Xaa Xaa
    930                 935                 940

nnn nnn nnn nnn nnn gag ctg cag gag ctg gag cgc cgc atc gaa gtc      2880
Xaa Xaa Xaa Xaa Xaa Glu Leu Gln Glu Leu Glu Arg Arg Ile Glu Val
945                 950                 955                 960

gcg cgt gag cgg ctc cgc cag gcc ctg gtg cgg cgc ggc cag ctc ctg      2928
Ala Arg Glu Arg Leu Arg Gln Ala Leu Val Arg Arg Gly Gln Leu Leu
                965                 970                 975

gca cag ctc ggg gac agc gca cgt cac cgg cct cgg cgc ttg ctt cag      2976
Ala Gln Leu Gly Asp Ser Ala Arg His Arg Pro Arg Arg Leu Leu Gln
            980                 985                 990

gcc aga gcg gcc ccc gcg gag gcc cca cca cac tct ggc cga ccg ggg      3024
Ala Arg Ala Ala Pro Ala Glu Ala Pro Pro His Ser Gly Arg Pro Gly
        995                 1000                1005

agc cag gaa tgannngaca gtttattcta tatacaaaca caattttgta             3073
Ser Gln Glu
    1010

cactgcaatt aaatagaatg gaa                                            3096


<210> SEQ ID NO 6
<211> LENGTH: 1011
<212> TYPE: PRT
<213> ORGANISM: Homo sapiens
<220> FEATURE:
<221> NAME/KEY: VARIANT
<222> LOCATION: 898, 899, 900, 901, 902, 903, 904, 905, 906, 907, 908,
      909, 910, 931, 932, 933, 934, 935, 936, 937, 938, 943, 944, 945,
      946, 947, 948, 949
<223> OTHER INFORMATION: Xaa = Any Amino Acid

<400> SEQUENCE: 6

Met Glu Phe Val Arg Ala Leu Trp Leu Gly Leu Ala Leu Ala Leu Gly
 1              5                   10                  15

Pro Gly Ser Ala Gly Gly His Pro Gln Pro Cys Gly Val Leu Ala Arg
            20                  25                  30

Leu Gly Gly Ser Val Arg Leu Gly Ala Leu Leu Pro Arg Ala Pro Leu
        35                  40                  45

Ala Arg Ala Arg Ala Arg Ala Ala Leu Ala Arg Ala Ala Leu Ala Pro
    50                  55                  60

Arg Leu Pro His Asn Leu Ser Leu Glu Leu Val Val Ala Ala Pro Pro
65                  70                  75                  80

Ala Arg Asp Pro Ala Ser Leu Thr Arg Gly Leu Cys Gln Ala Leu Val
                85                  90                  95

Pro Pro Gly Val Ala Ala Leu Leu Ala Phe Pro Glu Ala Arg Pro Glu
            100                 105                 110

Leu Leu Gln Leu His Phe Leu Ala Ala Ala Thr Glu Thr Pro Val Leu
        115                 120                 125

Ser Leu Leu Arg Arg Glu Ala Arg Ala Pro Leu Gly Ala Pro Asn Pro
    130                 135                 140

Phe His Leu Gln Leu His Trp Ala Ser Pro Leu Glu Thr Leu Leu Asp
145                 150                 155                 160

Val Leu Val Ala Val Leu Gln Ala His Ala Trp Glu Asp Val Gly Leu
                165                 170                 175
```

-continued

```
Ala Leu Cys Arg Thr Gln Asp Pro Gly Gly Leu Val Ala Leu Trp Thr
            180                 185                 190

Ser Arg Ala Gly Arg Pro Pro Gln Leu Val Leu Asp Leu Ser Arg Arg
        195                 200                 205

Asp Thr Gly Asp Ala Gly Leu Arg Ala Arg Leu Ala Pro Met Ala Ala
    210                 215                 220

Pro Val Gly Gly Glu Ala Pro Val Pro Ala Ala Val Leu Leu Gly Cys
225                 230                 235                 240

Asp Ile Ala Arg Ala Arg Arg Val Leu Glu Ala Val Pro Pro Gly Pro
                245                 250                 255

His Trp Leu Leu Gly Thr Pro Leu Pro Pro Lys Ala Leu Pro Thr Ala
            260                 265                 270

Gly Leu Pro Pro Gly Leu Leu Ala Leu Gly Glu Val Ala Arg Pro Pro
        275                 280                 285

Leu Glu Ala Ala Ile His Asp Ile Val Gln Leu Val Ala Arg Ala Leu
    290                 295                 300

Gly Ser Ala Ala Gln Val Gln Pro Lys Arg Ala Leu Leu Pro Ala Pro
305                 310                 315                 320

Val Asn Cys Gly Asp Leu Gln Pro Ala Gly Pro Glu Ser Pro Gly Arg
                325                 330                 335

Phe Leu Ala Asn Thr Ser Phe Gln Gly Arg Thr Gly Pro Val Trp Val
            340                 345                 350

Thr Gly Ser Ser Gln Val His Met Ser Arg His Phe Lys Val Trp Ser
        355                 360                 365

Leu Arg Arg Asp Pro Arg Gly Ala Pro Ala Trp Ala Thr Val Gly Ser
    370                 375                 380

Trp Arg Asp Gly Gln Leu Asp Leu Glu Pro Gly Gly Ala Ser Ala Arg
385                 390                 395                 400

Pro Pro Pro Pro Gln Gly Ala Gln Val Trp Pro Lys Leu Arg Val Val
                405                 410                 415

Thr Leu Leu Glu His Pro Phe Val Phe Ala Arg Asp Pro Asp Glu Asp
            420                 425                 430

Gly Gln Cys Pro Ala Gly Gln Leu Cys Leu Asp Pro Gly Thr Asn Asp
        435                 440                 445

Ser Ala Thr Leu Asp Ala Leu Phe Ala Ala Leu Ala Asn Gly Ser Ala
    450                 455                 460

Pro Arg Ala Leu Arg Lys Cys Cys Tyr Gly Tyr Cys Ile Asp Leu Leu
465                 470                 475                 480

Glu Arg Leu Ala Glu Asp Thr Pro Phe Asp Phe Glu Leu Tyr Leu Val
                485                 490                 495

Gly Asp Gly Lys Tyr Gly Ala Leu Arg Asp Gly Arg Trp Thr Gly Leu
            500                 505                 510

Val Gly Asp Leu Leu Ala Gly Arg Ala His Met Ala Val Thr Ser Phe
        515                 520                 525

Ser Ile Asn Ser Ala Arg Ser Gln Val Val Asp Phe Thr Ser Pro Phe
    530                 535                 540

Phe Ser Thr Ser Leu Gly Ile Met Val Arg Ala Arg Asp Thr Ala Ser
545                 550                 555                 560

Pro Ile Gly Ala Phe Met Trp Pro Leu His Trp Ser Thr Trp Leu Gly
                565                 570                 575

Val Phe Ala Ala Leu His Leu Thr Ala Leu Phe Leu Thr Val Tyr Glu
            580                 585                 590

Trp Arg Ser Pro Tyr Gly Leu Thr Pro Arg Gly Arg Asn Arg Ser Thr
        595                 600                 605
```

-continued

```
Val Phe Ser Tyr Ser Ser Ala Leu Asn Leu Cys Tyr Ala Ile Leu Phe
    610                 615                 620

Arg Arg Thr Val Ser Ser Lys Thr Pro Lys Cys Pro Thr Gly Arg Leu
625                 630                 635                 640

Leu Met Asn Leu Trp Ala Ile Phe Cys Leu Leu Val Leu Ser Ser Tyr
                645                 650                 655

Thr Ala Asn Leu Ala Ala Val Met Val Gly Asp Lys Thr Phe Glu Glu
            660                 665                 670

Leu Ser Gly Ile His Asp Pro Lys Leu His His Pro Ala Gln Gly Phe
        675                 680                 685

Arg Phe Gly Thr Val Trp Glu Ser Ser Ala Glu Ala Tyr Ile Lys Lys
    690                 695                 700

Ser Phe Pro Asp Met His Ala His Met Arg Arg His Ser Ala Pro Thr
705                 710                 715                 720

Thr Pro Arg Gly Val Ala Met Leu Thr Ser Asp Pro Pro Lys Leu Asn
                725                 730                 735

Ala Phe Ile Met Asp Lys Ser Leu Leu Asp Tyr Glu Val Ser Ile Asp
            740                 745                 750

Ala Asp Cys Lys Leu Leu Thr Val Gly Lys Pro Phe Ala Ile Glu Gly
        755                 760                 765

Tyr Gly Ile Gly Leu Pro Gln Asn Ser Pro Leu Thr Ser Asn Leu Ser
    770                 775                 780

Glu Phe Ile Ser Arg Tyr Lys Ser Ser Gly Phe Ile Asp Leu Leu His
785                 790                 795                 800

Asp Lys Trp Tyr Lys Met Val Pro Cys Gly Lys Arg Val Phe Ala Val
                805                 810                 815

Thr Glu Thr Leu Gln Met Ser Ile Tyr His Phe Ala Gly Leu Phe Val
            820                 825                 830

Leu Leu Cys Leu Gly Leu Gly Ser Ala Leu Leu Ser Ser Leu Gly Glu
        835                 840                 845

His Ala Phe Phe Arg Leu Ala Leu Pro Arg Ile Arg Lys Gly Ser Arg
    850                 855                 860

Leu Gln Tyr Trp Leu His Thr Ser Gln Lys Ile His Arg Ala Leu Asn
865                 870                 875                 880

Thr Glu Pro Pro Glu Gly Ser Lys Glu Glu Thr Ala Glu Ala Glu Pro
                885                 890                 895

Arg Xaa Xaa Xaa Xaa Xaa Xaa Xaa Xaa Xaa Xaa Xaa Xaa Xaa Trp Lys
            900                 905                 910

Arg Ala Arg Arg Ala Val Asp Lys Glu Arg Arg Val Arg Phe Leu Leu
        915                 920                 925

Glu Pro Xaa Xaa Xaa Xaa Xaa Xaa Xaa Xaa Trp Leu Cys Ser Xaa Xaa
    930                 935                 940

Xaa Xaa Xaa Xaa Xaa Glu Leu Gln Glu Leu Glu Arg Arg Ile Glu Val
945                 950                 955                 960

Ala Arg Glu Arg Leu Arg Gln Ala Leu Val Arg Arg Gly Gln Leu Leu
                965                 970                 975

Ala Gln Leu Gly Asp Ser Ala Arg His Arg Pro Arg Arg Leu Leu Gln
            980                 985                 990

Ala Arg Ala Ala Pro Ala Glu Ala Pro Pro His Ser Gly Arg Pro Gly
        995                 1000                1005

Ser Gln Glu
    1010
```

```
<210> SEQ ID NO 7
<211> LENGTH: 3166
<212> TYPE: DNA
<213> ORGANISM: Mus musculus
<220> FEATURE:
<221> NAME/KEY: CDS
<222> LOCATION: (63)...(3077)

<400> SEQUENCE: 7

agagcggggc tggctgggat gtctccttac cctcgcacag cacagtggta acttccatcg      60

gg atg gag tgt gtg cag acg ctg tgg ctc agc ctg gcc ctg gcg ctg       107
   Met Glu Cys Val Gln Thr Leu Trp Leu Ser Leu Ala Leu Ala Leu
    1               5                  10                  15

gcg cga ggg tcc tgg gtg gtg cgc ggt cac cct cag ccc tgc ggg gtt      155
Ala Arg Gly Ser Trp Val Val Arg Gly His Pro Gln Pro Cys Gly Val
                20                  25                  30

ccc acg cgc gcc ggg gcc tcc gtg cgc ctg gct gcg ctc cta ccc cgg      203
Pro Thr Arg Ala Gly Ala Ser Val Arg Leu Ala Ala Leu Leu Pro Arg
            35                  40                  45

gcg ccc gcc gcc cgc gcc cgc gtc cta gcc gcc ctg gcc acc cct tcc      251
Ala Pro Ala Ala Arg Ala Arg Val Leu Ala Ala Leu Ala Thr Pro Ser
        50                  55                  60

ccg cgg ctg ccg cac aac ctg agt ctg gag cta gtg gcc gtc gcg tcc      299
Pro Arg Leu Pro His Asn Leu Ser Leu Glu Leu Val Ala Val Ala Ser
    65                  70                  75

cca acc cgg gac ccc gcg tcg ctg gcc cga ggt ctg tgc cag gtt ctg      347
Pro Thr Arg Asp Pro Ala Ser Leu Ala Arg Gly Leu Cys Gln Val Leu
 80                  85                  90                  95

gca ccg ccc ggc gtg gtg gcc tct ata acc ttt ccc gag gcg cgg cct      395
Ala Pro Pro Gly Val Val Ala Ser Ile Thr Phe Pro Glu Ala Arg Pro
                100                 105                 110

gag cta cgg cta ttg cag ttc ctg gca gct gcc aca gag acc ccg gtg      443
Glu Leu Arg Leu Leu Gln Phe Leu Ala Ala Ala Thr Glu Thr Pro Val
            115                 120                 125

ctg agc gtc cta cgg agg gag gtg cgc gcg ccc ctc gga gct cgg cgg      491
Leu Ser Val Leu Arg Arg Glu Val Arg Ala Pro Leu Gly Ala Arg Arg
        130                 135                 140

acc ccg ttc cac ctg cag ctg gac tgg gct agt ccc ctg gag acc atc      539
Thr Pro Phe His Leu Gln Leu Asp Trp Ala Ser Pro Leu Glu Thr Ile
    145                 150                 155

ctg gat gtg ctg gtg tcc ctg gta cgg gca cac gcc tgg gag gac att      587
Leu Asp Val Leu Val Ser Leu Val Arg Ala His Ala Trp Glu Asp Ile
160                 165                 170                 175

gct cta gtg ctc tgt cgt gtc cgg gac ccc agt ggc ctg gtg aca ctc      635
Ala Leu Val Leu Cys Arg Val Arg Asp Pro Ser Gly Leu Val Thr Leu
                180                 185                 190

tgg acc agc cgt gct agc cag gct cca aag ttt gtg ctg gac ctg agc      683
Trp Thr Ser Arg Ala Ser Gln Ala Pro Lys Phe Val Leu Asp Leu Ser
            195                 200                 205

cag ttg gac agc ggg aat gac agc ctt cgg gct aca ctg gcc ctg ctg      731
Gln Leu Asp Ser Gly Asn Asp Ser Leu Arg Ala Thr Leu Ala Leu Leu
        210                 215                 220

ggg acg ctg gaa gga ggg gga acc ccc gtg tct gca gcc gtc ctc ctg      779
Gly Thr Leu Glu Gly Gly Gly Thr Pro Val Ser Ala Ala Val Leu Leu
    225                 230                 235

ggc tgc agc act gcc cat gca cat gag gtc cta gag gca gca cca ccg      827
Gly Cys Ser Thr Ala His Ala His Glu Val Leu Glu Ala Ala Pro Pro
240                 245                 250                 255

ggt ccc cag tgg ctg ctg ggc aca cca ctg ccc gcc gag gca ctg ccc      875
Gly Pro Gln Trp Leu Leu Gly Thr Pro Leu Pro Ala Glu Ala Leu Pro
                260                 265                 270
```

-continued

```
aaa acc ggt ctg ccc cct ggg gtg ttg gtg ctg ggg gaa acc ggg cag       923
Lys Thr Gly Leu Pro Pro Gly Val Leu Val Leu Gly Glu Thr Gly Gln
            275                 280                 285

cct tcc ctg gaa gct gcc gtc cac gac atg gtg gag ctt gtg gct cgg       971
Pro Ser Leu Glu Ala Ala Val His Asp Met Val Glu Leu Val Ala Arg
        290                 295                 300

gca ctc agc agc atg gcc ctc atg cac cca gag cgg gcc ctg ctt cca      1019
Ala Leu Ser Ser Met Ala Leu Met His Pro Glu Arg Ala Leu Leu Pro
    305                 310                 315

gcg gca gta aat tgt gag gac ctg aaa acg ggc ggc tct gag tca aca      1067
Ala Ala Val Asn Cys Glu Asp Leu Lys Thr Gly Gly Ser Glu Ser Thr
320                 325                 330                 335

gca cgc acc ttg gct agg tgg ttt ctg agc aac acc tca ttt cag ggc      1115
Ala Arg Thr Leu Ala Arg Trp Phe Leu Ser Asn Thr Ser Phe Gln Gly
                340                 345                 350

cgc aca ggg gct gtg tgg gtg gca ggc tcc tct cag gtg cat gtg tct      1163
Arg Thr Gly Ala Val Trp Val Ala Gly Ser Ser Gln Val His Val Ser
            355                 360                 365

cgg cat ttc aag gta tgg agc tta cgc agg gac ccg ctg ggt gcc cca      1211
Arg His Phe Lys Val Trp Ser Leu Arg Arg Asp Pro Leu Gly Ala Pro
        370                 375                 380

gcc tgg gca aca gta ggc agc tgg cag gat gga cag ctg gac ttc cag      1259
Ala Trp Ala Thr Val Gly Ser Trp Gln Asp Gly Gln Leu Asp Phe Gln
    385                 390                 395

cca ggg gcg gct gct ctc cga gtt cca tct cca tct ggc acc cag gcc      1307
Pro Gly Ala Ala Ala Leu Arg Val Pro Ser Pro Ser Gly Thr Gln Ala
400                 405                 410                 415

cgg cca aag ctg cga gtg gta act ctg gtg gaa cac cca ttt gtg ttc      1355
Arg Pro Lys Leu Arg Val Val Thr Leu Val Glu His Pro Phe Val Phe
                420                 425                 430

acc agg gaa tct gat gaa gat ggg cag tgc ccg gct ggg cag ctg tgt      1403
Thr Arg Glu Ser Asp Glu Asp Gly Gln Cys Pro Ala Gly Gln Leu Cys
            435                 440                 445

cta gac cca ggc acc aat gac tcg gcc agg ctg gat gcg ctc ttc act      1451
Leu Asp Pro Gly Thr Asn Asp Ser Ala Arg Leu Asp Ala Leu Phe Thr
        450                 455                 460

gca ttg gag aat ggc tcc gtg cct cgc acc ctg aga aga tgc tgt tat      1499
Ala Leu Glu Asn Gly Ser Val Pro Arg Thr Leu Arg Arg Cys Cys Tyr
    465                 470                 475

ggc tac tgc att gac ctg ctg gag cgg ctg gcc gag gac ctg gcc ttt      1547
Gly Tyr Cys Ile Asp Leu Leu Glu Arg Leu Ala Glu Asp Leu Ala Phe
480                 485                 490                 495

gac ttt gag ctc tat att gtg ggg gat ggc aag tac ggg gcc ctg cgt      1595
Asp Phe Glu Leu Tyr Ile Val Gly Asp Gly Lys Tyr Gly Ala Leu Arg
                500                 505                 510

gat gga cgc tgg aca ggc ctg gtg ggt gac ctg ctg gcc ggt cgg gca      1643
Asp Gly Arg Trp Thr Gly Leu Val Gly Asp Leu Leu Ala Gly Arg Ala
            515                 520                 525

cac atg gcc gtg acc agc ttc agt atc aac tcg gct cgc tcc cag gtg      1691
His Met Ala Val Thr Ser Phe Ser Ile Asn Ser Ala Arg Ser Gln Val
        530                 535                 540

gtg gat ttc acc agc cct ttc ttc tcc acc agc ctg ggc atc atg gtg      1739
Val Asp Phe Thr Ser Pro Phe Phe Ser Thr Ser Leu Gly Ile Met Val
    545                 550                 555

cgc acg cga gat aca gcc tca ccc att ggg gct ttc atg tgg ccc ctg      1787
Arg Thr Arg Asp Thr Ala Ser Pro Ile Gly Ala Phe Met Trp Pro Leu
560                 565                 570                 575

cac tgg tcc atg tgg gtg ggt gtg ttt gct gcc ctg cac ctc aca gcg      1835
His Trp Ser Met Trp Val Gly Val Phe Ala Ala Leu His Leu Thr Ala
                580                 585                 590
```

-continued

```
ctc ttc ctt act ctg tac gaa tgg cgg agt ccc tac ggg ctc acg cca      1883
Leu Phe Leu Thr Leu Tyr Glu Trp Arg Ser Pro Tyr Gly Leu Thr Pro
            595                 600                 605

cgc ggc cgc aac cgt ggt acc gtc ttc tcc tac tcc tcc gct ctc aac      1931
Arg Gly Arg Asn Arg Gly Thr Val Phe Ser Tyr Ser Ser Ala Leu Asn
        610                 615                 620

ctc tgc tac gcc att ctc ttc gga cgc act gtc tcc agt aag aca ccc      1979
Leu Cys Tyr Ala Ile Leu Phe Gly Arg Thr Val Ser Ser Lys Thr Pro
    625                 630                 635

aag tgt cct acc gga cgc ttc ctc atg aat ctc tgg gca atc ttc tgc      2027
Lys Cys Pro Thr Gly Arg Phe Leu Met Asn Leu Trp Ala Ile Phe Cys
640                 645                 650                 655

ctg ctg gtg cta tcc agt tac aca gcc aac ctg gca gct gtc atg gtc      2075
Leu Leu Val Leu Ser Ser Tyr Thr Ala Asn Leu Ala Ala Val Met Val
                660                 665                 670

ggg gac aag aca ttt gag gag ctg tct gga atc cat gat ccc aag ctg      2123
Gly Asp Lys Thr Phe Glu Glu Leu Ser Gly Ile His Asp Pro Lys Leu
            675                 680                 685

cac cac cct tcc caa ggc ttc cgc ttt ggc acc gtg tgg gag agc agc      2171
His His Pro Ser Gln Gly Phe Arg Phe Gly Thr Val Trp Glu Ser Ser
        690                 695                 700

gcg gag gcc tac atc aag gcg agc ttc ccc gag atg cac gca cac atg      2219
Ala Glu Ala Tyr Ile Lys Ala Ser Phe Pro Glu Met His Ala His Met
    705                 710                 715

cgt cgc cac agc gca cct acc act cca cac gga gtg gcc atg ctc acg      2267
Arg Arg His Ser Ala Pro Thr Thr Pro His Gly Val Ala Met Leu Thr
720                 725                 730                 735

agc gac ccg ccc aag ctc aac gcc ttc atc atg gat aaa tca cta ctg      2315
Ser Asp Pro Pro Lys Leu Asn Ala Phe Ile Met Asp Lys Ser Leu Leu
                740                 745                 750

gat tat gag gtg tcc ata gat gcg gac tgc aag ctg ctc acc gtg ggc      2363
Asp Tyr Glu Val Ser Ile Asp Ala Asp Cys Lys Leu Leu Thr Val Gly
            755                 760                 765

aaa ccc ttt gcg atc gag ggc tac ggc ata ggg ctg ccc caa aat tcg      2411
Lys Pro Phe Ala Ile Glu Gly Tyr Gly Ile Gly Leu Pro Gln Asn Ser
        770                 775                 780

ccg ctc acc tcc aac ctg tca gag ttc atc agt agg tac aag tcc tca      2459
Pro Leu Thr Ser Asn Leu Ser Glu Phe Ile Ser Arg Tyr Lys Ser Ser
    785                 790                 795

ggc ttc att gat ctg ctc cat gac aag tgg tac aag atg gtg cct tgc      2507
Gly Phe Ile Asp Leu Leu His Asp Lys Trp Tyr Lys Met Val Pro Cys
800                 805                 810                 815

ggg aag cgg gtg ttc gcc gtg acg gag acg ctg cag atg ggg gtc tac      2555
Gly Lys Arg Val Phe Ala Val Thr Glu Thr Leu Gln Met Gly Val Tyr
                820                 825                 830

cac ttg tca ggg ttg ttt gtc ctg ctg tgc ctc ggg ctg ggc agt gca      2603
His Leu Ser Gly Leu Phe Val Leu Leu Cys Leu Gly Leu Gly Ser Ala
            835                 840                 845

ctt ctc acc tcg ctg ggt gag cac gtc ttc tac cgc ctg gtg ctg ccg      2651
Leu Leu Thr Ser Leu Gly Glu His Val Phe Tyr Arg Leu Val Leu Pro
        850                 855                 860

cgc atc cgc agg ggc aat aag ctg cag tat tgg ctt cac acg agc cag      2699
Arg Ile Arg Arg Gly Asn Lys Leu Gln Tyr Trp Leu His Thr Ser Gln
    865                 870                 875

gaa gat cca ccg agc cct caa cac agg gcc acc aga ggg gca aca gga      2747
Glu Asp Pro Pro Ser Pro Gln His Arg Ala Thr Arg Gly Ala Thr Gly
880                 885                 890                 895

gag ggc aga gca gga gtg cag ggc ccc aag gag gag caa cct gca gcc      2795
Glu Gly Arg Ala Gly Val Gln Gly Pro Lys Glu Glu Gln Pro Ala Ala
                900                 905                 910
```

```
gac ggt gcg ggg cgc tgg agg cgg gtg cgc cgg gcc gtg gtg gaa cgg      2843
Asp Gly Ala Gly Arg Trp Arg Arg Val Arg Arg Ala Val Val Glu Arg
            915                 920                 925

gaa cgg cgc gtg cgt ttc ctg ctg gaa cct ggg gag gct ggc ggg gac      2891
Glu Arg Arg Val Arg Phe Leu Leu Glu Pro Gly Glu Ala Gly Gly Asp
        930                 935                 940

cat ccg tgg ctc tgc tcc aat ggg ccc ggg gtg caa gca gaa ctg cgg      2939
His Pro Trp Leu Cys Ser Asn Gly Pro Gly Val Gln Ala Glu Leu Arg
    945                 950                 955

gag ctg gag ctg cgc att gag gct gca cgg gag cgg ctg cgt agt gcg      2987
Glu Leu Glu Leu Arg Ile Glu Ala Ala Arg Glu Arg Leu Arg Ser Ala
960                 965                 970                 975

ctg ctg cgg cga ggg gaa ctg cgg gcc cag ctt ggg gat ggc acc cgg      3035
Leu Leu Arg Arg Gly Glu Leu Arg Ala Gln Leu Gly Asp Gly Thr Arg
                980                 985                 990

ctc agg cca ctg cgc ctg ctg cat gcg gcg ccc gcc gag agc              3077
Leu Arg Pro Leu Arg Leu Leu His Ala Ala Pro Ala Glu Ser
            995                 1000                1005

tgaggaacta cacggccaca ctgtccacga cagtttattc tatatacaaa cacgactctg   3137

tacactgcaa ttaaatagcg tggaacgtg                                     3166


<210> SEQ ID NO 8
<211> LENGTH: 1005
<212> TYPE: PRT
<213> ORGANISM: Mus musculus

<400> SEQUENCE: 8

Met Glu Cys Val Gln Thr Leu Trp Leu Ser Leu Ala Leu Ala Leu Ala
 1               5                  10                  15

Arg Gly Ser Trp Val Val Arg Gly His Pro Gln Pro Cys Gly Val Pro
            20                  25                  30

Thr Arg Ala Gly Ala Ser Val Arg Leu Ala Ala Leu Leu Pro Arg Ala
        35                  40                  45

Pro Ala Ala Arg Ala Arg Val Leu Ala Ala Leu Ala Thr Pro Ser Pro
    50                  55                  60

Arg Leu Pro His Asn Leu Ser Leu Glu Leu Val Ala Val Ala Ser Pro
 65                  70                  75                  80

Thr Arg Asp Pro Ala Ser Leu Ala Arg Gly Leu Cys Gln Val Leu Ala
                85                  90                  95

Pro Pro Gly Val Val Ala Ser Ile Thr Phe Pro Glu Ala Arg Pro Glu
            100                 105                 110

Leu Arg Leu Leu Gln Phe Leu Ala Ala Ala Thr Glu Thr Pro Val Leu
        115                 120                 125

Ser Val Leu Arg Arg Glu Val Arg Ala Pro Leu Gly Ala Arg Arg Thr
    130                 135                 140

Pro Phe His Leu Gln Leu Asp Trp Ala Ser Pro Leu Glu Thr Ile Leu
145                 150                 155                 160

Asp Val Leu Val Ser Leu Val Arg Ala His Ala Trp Glu Asp Ile Ala
                165                 170                 175

Leu Val Leu Cys Arg Val Arg Asp Pro Ser Gly Leu Val Thr Leu Trp
            180                 185                 190

Thr Ser Arg Ala Ser Gln Ala Pro Lys Phe Val Leu Asp Leu Ser Gln
        195                 200                 205

Leu Asp Ser Gly Asn Asp Ser Leu Arg Ala Thr Leu Ala Leu Leu Gly
    210                 215                 220

Thr Leu Glu Gly Gly Gly Thr Pro Val Ser Ala Ala Val Leu Leu Gly
225                 230                 235                 240
```

-continued

```
Cys Ser Thr Ala His Ala His Glu Val Leu Glu Ala Ala Pro Pro Gly
                245                 250                 255

Pro Gln Trp Leu Leu Gly Thr Pro Leu Pro Ala Glu Ala Leu Pro Lys
            260                 265                 270

Thr Gly Leu Pro Pro Gly Val Leu Val Leu Gly Glu Thr Gly Gln Pro
        275                 280                 285

Ser Leu Glu Ala Ala Val His Asp Met Val Glu Leu Val Ala Arg Ala
    290                 295                 300

Leu Ser Ser Met Ala Leu Met His Pro Glu Arg Ala Leu Leu Pro Ala
305                 310                 315                 320

Ala Val Asn Cys Glu Asp Leu Lys Thr Gly Gly Ser Glu Ser Thr Ala
                325                 330                 335

Arg Thr Leu Ala Arg Trp Phe Leu Ser Asn Thr Ser Phe Gln Gly Arg
            340                 345                 350

Thr Gly Ala Val Trp Val Ala Gly Ser Ser Gln Val His Val Ser Arg
        355                 360                 365

His Phe Lys Val Trp Ser Leu Arg Arg Asp Pro Leu Gly Ala Pro Ala
    370                 375                 380

Trp Ala Thr Val Gly Ser Trp Gln Asp Gly Gln Leu Asp Phe Gln Pro
385                 390                 395                 400

Gly Ala Ala Ala Leu Arg Val Pro Ser Pro Ser Gly Thr Gln Ala Arg
                405                 410                 415

Pro Lys Leu Arg Val Val Thr Leu Val Glu His Pro Phe Val Phe Thr
            420                 425                 430

Arg Glu Ser Asp Glu Asp Gly Gln Cys Pro Ala Gly Gln Leu Cys Leu
        435                 440                 445

Asp Pro Gly Thr Asn Asp Ser Ala Arg Leu Asp Ala Leu Phe Thr Ala
    450                 455                 460

Leu Glu Asn Gly Ser Val Pro Arg Thr Leu Arg Arg Cys Cys Tyr Gly
465                 470                 475                 480

Tyr Cys Ile Asp Leu Leu Glu Arg Leu Ala Glu Asp Leu Ala Phe Asp
                485                 490                 495

Phe Glu Leu Tyr Ile Val Gly Asp Gly Lys Tyr Gly Ala Leu Arg Asp
            500                 505                 510

Gly Arg Trp Thr Gly Leu Val Gly Asp Leu Leu Ala Gly Arg Ala His
        515                 520                 525

Met Ala Val Thr Ser Phe Ser Ile Asn Ser Ala Arg Ser Gln Val Val
    530                 535                 540

Asp Phe Thr Ser Pro Phe Phe Ser Thr Ser Leu Gly Ile Met Val Arg
545                 550                 555                 560

Thr Arg Asp Thr Ala Ser Pro Ile Gly Ala Phe Met Trp Pro Leu His
                565                 570                 575

Trp Ser Met Trp Val Gly Val Phe Ala Ala Leu His Leu Thr Ala Leu
            580                 585                 590

Phe Leu Thr Leu Tyr Glu Trp Arg Ser Pro Tyr Gly Leu Thr Pro Arg
        595                 600                 605

Gly Arg Asn Arg Gly Thr Val Phe Ser Tyr Ser Ser Ala Leu Asn Leu
    610                 615                 620

Cys Tyr Ala Ile Leu Phe Gly Arg Thr Val Ser Ser Lys Thr Pro Lys
625                 630                 635                 640

Cys Pro Thr Gly Arg Phe Leu Met Asn Leu Trp Ala Ile Phe Cys Leu
                645                 650                 655

Leu Val Leu Ser Ser Tyr Thr Ala Asn Leu Ala Ala Val Met Val Gly
```

```
            660                 665                 670

Asp Lys Thr Phe Glu Glu Leu Ser Gly Ile His Asp Pro Lys Leu His
        675                 680                 685

His Pro Ser Gln Gly Phe Arg Phe Gly Thr Val Trp Glu Ser Ser Ala
    690                 695                 700

Glu Ala Tyr Ile Lys Ala Ser Phe Pro Glu Met His Ala His Met Arg
705                 710                 715                 720

Arg His Ser Ala Pro Thr Thr Pro His Gly Val Ala Met Leu Thr Ser
                725                 730                 735

Asp Pro Pro Lys Leu Asn Ala Phe Ile Met Asp Lys Ser Leu Leu Asp
            740                 745                 750

Tyr Glu Val Ser Ile Asp Ala Asp Cys Lys Leu Leu Thr Val Gly Lys
        755                 760                 765

Pro Phe Ala Ile Glu Gly Tyr Gly Ile Gly Leu Pro Gln Asn Ser Pro
    770                 775                 780

Leu Thr Ser Asn Leu Ser Glu Phe Ile Ser Arg Tyr Lys Ser Ser Gly
785                 790                 795                 800

Phe Ile Asp Leu Leu His Asp Lys Trp Tyr Lys Met Val Pro Cys Gly
                805                 810                 815

Lys Arg Val Phe Ala Val Thr Glu Thr Leu Gln Met Gly Val Tyr His
            820                 825                 830

Leu Ser Gly Leu Phe Val Leu Leu Cys Leu Gly Leu Gly Ser Ala Leu
        835                 840                 845

Leu Thr Ser Leu Gly Glu His Val Phe Tyr Arg Leu Val Leu Pro Arg
    850                 855                 860

Ile Arg Arg Gly Asn Lys Leu Gln Tyr Trp Leu His Thr Ser Gln Glu
865                 870                 875                 880

Asp Pro Pro Ser Pro Gln His Arg Ala Thr Arg Gly Ala Thr Gly Glu
                885                 890                 895

Gly Arg Ala Gly Val Gln Gly Pro Lys Glu Glu Gln Pro Ala Ala Asp
            900                 905                 910

Gly Ala Gly Arg Trp Arg Arg Val Arg Arg Ala Val Val Glu Arg Glu
        915                 920                 925

Arg Arg Val Arg Phe Leu Leu Glu Pro Gly Glu Ala Gly Gly Asp His
    930                 935                 940

Pro Trp Leu Cys Ser Asn Gly Pro Gly Val Gln Ala Glu Leu Arg Glu
945                 950                 955                 960

Leu Glu Leu Arg Ile Glu Ala Ala Arg Glu Arg Leu Arg Ser Ala Leu
                965                 970                 975

Leu Arg Arg Gly Glu Leu Arg Ala Gln Leu Gly Asp Gly Thr Arg Leu
            980                 985                 990

Arg Pro Leu Arg Leu Leu His Ala Ala Pro Ala Glu Ser
        995                 1000                1005


<210> SEQ ID NO 9
<211> LENGTH: 2691
<212> TYPE: DNA
<213> ORGANISM: Homo sapiens
<220> FEATURE:
<221> NAME/KEY: CDS
<222> LOCATION: (1)...(2691)

<400> SEQUENCE: 9

atg gag ttt gtg cgg gcg ctg tgg ctg ggc ctg gcg ctg gcg ctg ggg        48
Met Glu Phe Val Arg Ala Leu Trp Leu Gly Leu Ala Leu Ala Leu Gly
 1               5                  10                  15
```

-continued

```
ccg ggg tcc gcg ggg ggc cac cct cag ccg tgc ggc gtc ctg gcg cgc        96
Pro Gly Ser Ala Gly Gly His Pro Gln Pro Cys Gly Val Leu Ala Arg
            20                  25                  30

ctc ggg ggc tcc gtg cgc ctg ggc gcc ctc ctg ccc cgc gcg cct ctc       144
Leu Gly Gly Ser Val Arg Leu Gly Ala Leu Leu Pro Arg Ala Pro Leu
        35                  40                  45

gcc cgc gcc cgc gcc cgc gcc gcc ctg gcc cgg gcc gcc ctg gcg ccg       192
Ala Arg Ala Arg Ala Arg Ala Ala Leu Ala Arg Ala Ala Leu Ala Pro
    50                  55                  60

cgg ctg ccg cac aac ctg agc ttg gag ctg gtg gtc gcc gcg ccc ccc       240
Arg Leu Pro His Asn Leu Ser Leu Glu Leu Val Val Ala Ala Pro Pro
65                  70                  75                  80

gcc cgc gac ccc gcc tcg ctg acc cgc ggc ctg tgc cag gcg ctg gtg       288
Ala Arg Asp Pro Ala Ser Leu Thr Arg Gly Leu Cys Gln Ala Leu Val
                85                  90                  95

cct ccg ggc gtg gcg gcc ctg ctc gcc ttt ccc gag gct cgg ccc gag       336
Pro Pro Gly Val Ala Ala Leu Leu Ala Phe Pro Glu Ala Arg Pro Glu
            100                 105                 110

ctg ctg cag ctg cac ttc ctg gcg gcg gcc acc gag acc ccc gtg ctc       384
Leu Leu Gln Leu His Phe Leu Ala Ala Ala Thr Glu Thr Pro Val Leu
        115                 120                 125

agc ctg ctg cgg cgg gag gcg cgc gcg ccc ctc gga gcc ccg aac cca       432
Ser Leu Leu Arg Arg Glu Ala Arg Ala Pro Leu Gly Ala Pro Asn Pro
    130                 135                 140

ttc cac ctg cag ctg cac tgg gcc agc ccc ctg gag acg ctg ctg gat       480
Phe His Leu Gln Leu His Trp Ala Ser Pro Leu Glu Thr Leu Leu Asp
145                 150                 155                 160

gtg ctg gtg gcg gtg ctg cag gcg cac gcc tgg gaa gac gtc ggc ctg       528
Val Leu Val Ala Val Leu Gln Ala His Ala Trp Glu Asp Val Gly Leu
                165                 170                 175

gcc ctg tgc cgc act cag gac ccc ggc ggc ctg gtg gcc ctc tgg aca       576
Ala Leu Cys Arg Thr Gln Asp Pro Gly Gly Leu Val Ala Leu Trp Thr
            180                 185                 190

agc cgg gct ggc cgg ccc cca cag ctg gtc ctg gac cta agc cgg cgg       624
Ser Arg Ala Gly Arg Pro Pro Gln Leu Val Leu Asp Leu Ser Arg Arg
        195                 200                 205

gac acg gga gat gca gga ctg cgg gca cgc ctg gcc ccg atg gcg gcg       672
Asp Thr Gly Asp Ala Gly Leu Arg Ala Arg Leu Ala Pro Met Ala Ala
    210                 215                 220

cca gtg ggg ggt gaa gca ccg gta ccc gcg gcg gtc ctc ctc ggc tgt       720
Pro Val Gly Gly Glu Ala Pro Val Pro Ala Ala Val Leu Leu Gly Cys
225                 230                 235                 240

gac atc gcc cgt gcc cgt cgg gtg ctg gag gcc gta cct ccc ggc ccc       768
Asp Ile Ala Arg Ala Arg Arg Val Leu Glu Ala Val Pro Pro Gly Pro
                245                 250                 255

cac tgg ctg ttg ggg aca cca ctg ccg ccc aag gcc ctg ccc acc gcg       816
His Trp Leu Leu Gly Thr Pro Leu Pro Pro Lys Ala Leu Pro Thr Ala
            260                 265                 270

ggg ctg cca cca ggg ctg ctg gcg ctg ggc gag gtg gca cga ccc ccg       864
Gly Leu Pro Pro Gly Leu Leu Ala Leu Gly Glu Val Ala Arg Pro Pro
        275                 280                 285

ctg gag gcc gcc atc cat gac att gtg caa ctg gtg gcc cgg gcg ctg       912
Leu Glu Ala Ala Ile His Asp Ile Val Gln Leu Val Ala Arg Ala Leu
    290                 295                 300

ggc agt gcg gcc cag gtg cag ccg aag cga gcc ctc ctc ccc gcc ccg       960
Gly Ser Ala Ala Gln Val Gln Pro Lys Arg Ala Leu Leu Pro Ala Pro
305                 310                 315                 320

gtc aac tgc ggg gac ctg cag ccg gcc ggg ccc gag tcc ccg ggg cgc      1008
Val Asn Cys Gly Asp Leu Gln Pro Ala Gly Pro Glu Ser Pro Gly Arg
                325                 330                 335
```

-continued

```
ttc ttg gcc aac acg tcc ttc cag ggc cgc acg ggc ccc gtg tgg gtg      1056
Phe Leu Ala Asn Thr Ser Phe Gln Gly Arg Thr Gly Pro Val Trp Val
            340                 345                 350

aca ggc agc tcc cag gta cac atg tct cgg cac ttt aag gtg tgg agc      1104
Thr Gly Ser Ser Gln Val His Met Ser Arg His Phe Lys Val Trp Ser
        355                 360                 365

ctt cgc cgg gac cca cgg ggc gcc ccg gcc tgg gcc acg gtg ggc agc      1152
Leu Arg Arg Asp Pro Arg Gly Ala Pro Ala Trp Ala Thr Val Gly Ser
    370                 375                 380

tgg cgg gac ggc cag ctg gac ttg gaa ccg gga ggt gcc tct gca cgg      1200
Trp Arg Asp Gly Gln Leu Asp Leu Glu Pro Gly Gly Ala Ser Ala Arg
385                 390                 395                 400

ccc ccg ccc cca cag ggt gcc cag gtc tgg ccc aag ctg cgt gtg gta      1248
Pro Pro Pro Pro Gln Gly Ala Gln Val Trp Pro Lys Leu Arg Val Val
                405                 410                 415

acg ctg ttg gaa cac cca ttt gtg ttt gcc cgt gat cca gac gaa gac      1296
Thr Leu Leu Glu His Pro Phe Val Phe Ala Arg Asp Pro Asp Glu Asp
            420                 425                 430

ggg cag tgc cca gcg ggg cag ctg tgc ctg gac cct ggc acc aac gac      1344
Gly Gln Cys Pro Ala Gly Gln Leu Cys Leu Asp Pro Gly Thr Asn Asp
        435                 440                 445

tcg gcc acc ctg gac gca ctg ttc gcc gcg ctg gcc aac ggc tca gcg      1392
Ser Ala Thr Leu Asp Ala Leu Phe Ala Ala Leu Ala Asn Gly Ser Ala
    450                 455                 460

ccc cgt gcc ctg cgc aag tgc tgc tac ggc tac tgc att gac ctg ctg      1440
Pro Arg Ala Leu Arg Lys Cys Cys Tyr Gly Tyr Cys Ile Asp Leu Leu
465                 470                 475                 480

gag cgg ctg gcg gag gac acg ccc ttc gac ttc gag ctg tac ctc gtg      1488
Glu Arg Leu Ala Glu Asp Thr Pro Phe Asp Phe Glu Leu Tyr Leu Val
                485                 490                 495

ggt gac ggc aag tac ggc gcc ctg cgg gac ggc cgc tgg acc ggc ctg      1536
Gly Asp Gly Lys Tyr Gly Ala Leu Arg Asp Gly Arg Trp Thr Gly Leu
            500                 505                 510

gtc ggg gac ctg ctg gcc ggc cgg gcc cac atg gcg gtc acc agc ttc      1584
Val Gly Asp Leu Leu Ala Gly Arg Ala His Met Ala Val Thr Ser Phe
        515                 520                 525

agt atc aac tcc gcc cgc tca cag gtg gtg gac ttc acc agc ccc ttc      1632
Ser Ile Asn Ser Ala Arg Ser Gln Val Val Asp Phe Thr Ser Pro Phe
    530                 535                 540

ttc tcc acc agc ctg ggc atc atg gtg cgg gca cgg gac acg gcc tca      1680
Phe Ser Thr Ser Leu Gly Ile Met Val Arg Ala Arg Asp Thr Ala Ser
545                 550                 555                 560

ccc atc ggt gcc ttt atg tgg ccc ctg cac tgg tcc acg tgg ctg ggc      1728
Pro Ile Gly Ala Phe Met Trp Pro Leu His Trp Ser Thr Trp Leu Gly
                565                 570                 575

gtc ttt gcg gcc ctg cac ctc acc gcg ctc ttc ctc acc gtg tac gag      1776
Val Phe Ala Ala Leu His Leu Thr Ala Leu Phe Leu Thr Val Tyr Glu
            580                 585                 590

tgg cgt agc ccc tac ggc ctc acg cca cgt ggc cgc aac cgc agc acc      1824
Trp Arg Ser Pro Tyr Gly Leu Thr Pro Arg Gly Arg Asn Arg Ser Thr
        595                 600                 605

gtc ttc tcc tac tcc tca gcc ctc aac ctg tgc tac gcc atc ctc ttc      1872
Val Phe Ser Tyr Ser Ser Ala Leu Asn Leu Cys Tyr Ala Ile Leu Phe
    610                 615                 620

aga cgc acc gtg tcc agc aag acg ccc aag tgc ccc acg ggc cgc ctg      1920
Arg Arg Thr Val Ser Ser Lys Thr Pro Lys Cys Pro Thr Gly Arg Leu
625                 630                 635                 640

ctc atg aac ctc tgg gcc atc ttc tgc ctg ctg gtg ctg tcc agc tac      1968
Leu Met Asn Leu Trp Ala Ile Phe Cys Leu Leu Val Leu Ser Ser Tyr
                645                 650                 655
```

-continued

```
acg gcc aac ctg gct gcc gtc atg gtc ggg gac aag acc ttc gag gag      2016
Thr Ala Asn Leu Ala Ala Val Met Val Gly Asp Lys Thr Phe Glu Glu
            660                 665                 670

ctg tcg ggg atc cac gac ccc aag ctg cac cac ccg gcg cag ggc ttc      2064
Leu Ser Gly Ile His Asp Pro Lys Leu His His Pro Ala Gln Gly Phe
        675                 680                 685

cgc ttc ggc acc gtg tgg gag agc agc gcc gag gcg tac atc aag aag      2112
Arg Phe Gly Thr Val Trp Glu Ser Ser Ala Glu Ala Tyr Ile Lys Lys
    690                 695                 700

agc ttc ccc gac atg cac gca cac atg cgg cgc cac agc gcg ccc acc      2160
Ser Phe Pro Asp Met His Ala His Met Arg Arg His Ser Ala Pro Thr
705                 710                 715                 720

acg ccc cgc ggc gtc gcc atg ctc acg agc gac ccc ccc aag ctc aac      2208
Thr Pro Arg Gly Val Ala Met Leu Thr Ser Asp Pro Pro Lys Leu Asn
                725                 730                 735

gcc ttc atc atg gac aag tcg ctc ctg gac tac gag gtc tcc atc gac      2256
Ala Phe Ile Met Asp Lys Ser Leu Leu Asp Tyr Glu Val Ser Ile Asp
            740                 745                 750

gcc gac tgc aaa ctg ctg acc gtg gga aag ccc ttc gcc att gag ggc      2304
Ala Asp Cys Lys Leu Leu Thr Val Gly Lys Pro Phe Ala Ile Glu Gly
        755                 760                 765

tat ggg atc gga ctg ccc cag aac tcg ccg ctc acc tcc aac ctg tcc      2352
Tyr Gly Ile Gly Leu Pro Gln Asn Ser Pro Leu Thr Ser Asn Leu Ser
    770                 775                 780

gag ttc atc agc cgc tac aag tcc tcc ggc ttc atc gac ctg ctc cac      2400
Glu Phe Ile Ser Arg Tyr Lys Ser Ser Gly Phe Ile Asp Leu Leu His
785                 790                 795                 800

gac aag tgg tac aag atg gtg cct tgc ggc aag cgg gtc ttt gcg gtt      2448
Asp Lys Trp Tyr Lys Met Val Pro Cys Gly Lys Arg Val Phe Ala Val
                805                 810                 815

aca gag acc ctg cag atg agc atc tac cac ttc gcg ggc ctc ttc gtg      2496
Thr Glu Thr Leu Gln Met Ser Ile Tyr His Phe Ala Gly Leu Phe Val
            820                 825                 830

ttg ctg tgc ctg ggc ctg ggc agc gct ctg ctc agc tcg ctg ggc gag      2544
Leu Leu Cys Leu Gly Leu Gly Ser Ala Leu Leu Ser Ser Leu Gly Glu
        835                 840                 845

cac gcc ttc ttc cgc ctg gcg ctg ccg cgc atc cgc aag ggg agc agg      2592
His Ala Phe Phe Arg Leu Ala Leu Pro Arg Ile Arg Lys Gly Ser Arg
    850                 855                 860

ctg cag tac tgg ctg cac acc agc cag aaa atc cac cgc gcc ctc aac      2640
Leu Gln Tyr Trp Leu His Thr Ser Gln Lys Ile His Arg Ala Leu Asn
865                 870                 875                 880

acg gag cca cca gag ggg tcg aag gag gag acg gca gag gcg gag ccc      2688
Thr Glu Pro Pro Glu Gly Ser Lys Glu Glu Thr Ala Glu Ala Glu Pro
                885                 890                 895

agg                                                                  2691
Arg


<210> SEQ ID NO 10
<211> LENGTH: 897
<212> TYPE: PRT
<213> ORGANISM: Homo sapiens

<400> SEQUENCE: 10

Met Glu Phe Val Arg Ala Leu Trp Leu Gly Leu Ala Leu Ala Leu Gly
 1               5                  10                  15

Pro Gly Ser Ala Gly Gly His Pro Gln Pro Cys Gly Val Leu Ala Arg
            20                  25                  30

Leu Gly Gly Ser Val Arg Leu Gly Ala Leu Leu Pro Arg Ala Pro Leu
        35                  40                  45
```

-continued

```
Ala Arg Ala Arg Ala Arg Ala Ala Leu Ala Arg Ala Ala Leu Ala Pro
     50                  55                  60

Arg Leu Pro His Asn Leu Ser Leu Glu Leu Val Val Ala Ala Pro Pro
 65                  70                  75                  80

Ala Arg Asp Pro Ala Ser Leu Thr Arg Gly Leu Cys Gln Ala Leu Val
                 85                  90                  95

Pro Pro Gly Val Ala Ala Leu Leu Ala Phe Pro Glu Ala Arg Pro Glu
            100                 105                 110

Leu Leu Gln Leu His Phe Leu Ala Ala Ala Thr Glu Thr Pro Val Leu
        115                 120                 125

Ser Leu Leu Arg Arg Glu Ala Arg Ala Pro Leu Gly Ala Pro Asn Pro
    130                 135                 140

Phe His Leu Gln Leu His Trp Ala Ser Pro Leu Glu Thr Leu Leu Asp
145                 150                 155                 160

Val Leu Val Ala Val Leu Gln Ala His Ala Trp Glu Asp Val Gly Leu
                165                 170                 175

Ala Leu Cys Arg Thr Gln Asp Pro Gly Gly Leu Val Ala Leu Trp Thr
            180                 185                 190

Ser Arg Ala Gly Arg Pro Pro Gln Leu Val Leu Asp Leu Ser Arg Arg
        195                 200                 205

Asp Thr Gly Asp Ala Gly Leu Arg Ala Arg Leu Ala Pro Met Ala Ala
    210                 215                 220

Pro Val Gly Gly Glu Ala Pro Val Pro Ala Ala Val Leu Leu Gly Cys
225                 230                 235                 240

Asp Ile Ala Arg Ala Arg Arg Val Leu Glu Ala Val Pro Pro Gly Pro
                245                 250                 255

His Trp Leu Leu Gly Thr Pro Leu Pro Pro Lys Ala Leu Pro Thr Ala
            260                 265                 270

Gly Leu Pro Pro Gly Leu Leu Ala Leu Gly Glu Val Ala Arg Pro Pro
        275                 280                 285

Leu Glu Ala Ala Ile His Asp Ile Val Gln Leu Val Ala Arg Ala Leu
    290                 295                 300

Gly Ser Ala Ala Gln Val Gln Pro Lys Arg Ala Leu Leu Pro Ala Pro
305                 310                 315                 320

Val Asn Cys Gly Asp Leu Gln Pro Ala Gly Pro Glu Ser Pro Gly Arg
                325                 330                 335

Phe Leu Ala Asn Thr Ser Phe Gln Gly Arg Thr Gly Pro Val Trp Val
            340                 345                 350

Thr Gly Ser Ser Gln Val His Met Ser Arg His Phe Lys Val Trp Ser
        355                 360                 365

Leu Arg Arg Asp Pro Arg Gly Ala Pro Ala Trp Ala Thr Val Gly Ser
    370                 375                 380

Trp Arg Asp Gly Gln Leu Asp Leu Glu Pro Gly Gly Ala Ser Ala Arg
385                 390                 395                 400

Pro Pro Pro Pro Gln Gly Ala Gln Val Trp Pro Lys Leu Arg Val Val
                405                 410                 415

Thr Leu Leu Glu His Pro Phe Val Phe Ala Arg Asp Pro Asp Glu Asp
            420                 425                 430

Gly Gln Cys Pro Ala Gly Gln Leu Cys Leu Asp Pro Gly Thr Asn Asp
        435                 440                 445

Ser Ala Thr Leu Asp Ala Leu Phe Ala Ala Leu Ala Asn Gly Ser Ala
    450                 455                 460

Pro Arg Ala Leu Arg Lys Cys Cys Tyr Gly Tyr Cys Ile Asp Leu Leu
465                 470                 475                 480
```

-continued

```
Glu Arg Leu Ala Glu Asp Thr Pro Phe Asp Phe Glu Leu Tyr Leu Val
                485                 490                 495

Gly Asp Gly Lys Tyr Gly Ala Leu Arg Asp Gly Arg Trp Thr Gly Leu
            500                 505                 510

Val Gly Asp Leu Leu Ala Gly Arg Ala His Met Ala Val Thr Ser Phe
        515                 520                 525

Ser Ile Asn Ser Ala Arg Ser Gln Val Val Asp Phe Thr Ser Pro Phe
    530                 535                 540

Phe Ser Thr Ser Leu Gly Ile Met Val Arg Ala Arg Asp Thr Ala Ser
545                 550                 555                 560

Pro Ile Gly Ala Phe Met Trp Pro Leu His Trp Ser Thr Trp Leu Gly
                565                 570                 575

Val Phe Ala Ala Leu His Leu Thr Ala Leu Phe Leu Thr Val Tyr Glu
            580                 585                 590

Trp Arg Ser Pro Tyr Gly Leu Thr Pro Arg Gly Arg Asn Arg Ser Thr
        595                 600                 605

Val Phe Ser Tyr Ser Ser Ala Leu Asn Leu Cys Tyr Ala Ile Leu Phe
    610                 615                 620

Arg Arg Thr Val Ser Ser Lys Thr Pro Lys Cys Pro Thr Gly Arg Leu
625                 630                 635                 640

Leu Met Asn Leu Trp Ala Ile Phe Cys Leu Leu Val Leu Ser Ser Tyr
                645                 650                 655

Thr Ala Asn Leu Ala Ala Val Met Val Gly Asp Lys Thr Phe Glu Glu
            660                 665                 670

Leu Ser Gly Ile His Asp Pro Lys Leu His His Pro Ala Gln Gly Phe
        675                 680                 685

Arg Phe Gly Thr Val Trp Glu Ser Ser Ala Glu Ala Tyr Ile Lys Lys
    690                 695                 700

Ser Phe Pro Asp Met His Ala His Met Arg Arg His Ser Ala Pro Thr
705                 710                 715                 720

Thr Pro Arg Gly Val Ala Met Leu Thr Ser Asp Pro Pro Lys Leu Asn
                725                 730                 735

Ala Phe Ile Met Asp Lys Ser Leu Leu Asp Tyr Glu Val Ser Ile Asp
            740                 745                 750

Ala Asp Cys Lys Leu Leu Thr Val Gly Lys Pro Phe Ala Ile Glu Gly
        755                 760                 765

Tyr Gly Ile Gly Leu Pro Gln Asn Ser Pro Leu Thr Ser Asn Leu Ser
    770                 775                 780

Glu Phe Ile Ser Arg Tyr Lys Ser Ser Gly Phe Ile Asp Leu Leu His
785                 790                 795                 800

Asp Lys Trp Tyr Lys Met Val Pro Cys Gly Lys Arg Val Phe Ala Val
                805                 810                 815

Thr Glu Thr Leu Gln Met Ser Ile Tyr His Phe Ala Gly Leu Phe Val
            820                 825                 830

Leu Leu Cys Leu Gly Leu Gly Ser Ala Leu Leu Ser Ser Leu Gly Glu
        835                 840                 845

His Ala Phe Phe Arg Leu Ala Leu Pro Arg Ile Arg Lys Gly Ser Arg
    850                 855                 860

Leu Gln Tyr Trp Leu His Thr Ser Gln Lys Ile His Arg Ala Leu Asn
865                 870                 875                 880

Thr Glu Pro Pro Glu Gly Ser Lys Glu Glu Thr Ala Glu Ala Glu Pro
                885                 890                 895

Arg
```

<210> SEQ ID NO 11
<211> LENGTH: 1786
<212> TYPE: DNA
<213> ORGANISM: Mus musculus
<220> FEATURE:
<221> NAME/KEY: CDS
<222> LOCATION: (2)...(1444)

<400> SEQUENCE: 11

```
c atc aac tgc tta gag cat gtt cga gat cga tgg ccg cgg gag ggt gtc      49
  Ile Asn Cys Leu Glu His Val Arg Asp Arg Trp Pro Arg Glu Gly Val
   1               5                  10                  15

ctg cgg gtg gag gtg cgc cac aac tcg agc cgg gca ccg gtg atc ctg        97
Leu Arg Val Glu Val Arg His Asn Ser Ser Arg Ala Pro Val Ile Leu
            20                  25                  30

cag ttc tgt gat ggg ggc ctc ggt ggc ctg gag ctg gaa ccc ggg ggc       145
Gln Phe Cys Asp Gly Gly Leu Gly Gly Leu Glu Leu Glu Pro Gly Gly
        35                  40                  45

ctg gag ctg gag gag gag gag ctc aca gtg gag atg ttc acc aac agc       193
Leu Glu Leu Glu Glu Glu Glu Leu Thr Val Glu Met Phe Thr Asn Ser
    50                  55                  60

tcc atc aag ttt gag ctg gac att gag ccc aag gtg ttc aag cca cag       241
Ser Ile Lys Phe Glu Leu Asp Ile Glu Pro Lys Val Phe Lys Pro Gln
65                  70                  75                  80

agc ggt gca gat gcc ctg aac gac agc cag gac ttc cct ttt cct gag       289
Ser Gly Ala Asp Ala Leu Asn Asp Ser Gln Asp Phe Pro Phe Pro Glu
                85                  90                  95

acg cca gca aaa gtg tgg cca cag gat gag tac att gtg gag tac tca       337
Thr Pro Ala Lys Val Trp Pro Gln Asp Glu Tyr Ile Val Glu Tyr Ser
            100                 105                 110

ctg gaa tat ggc ttc ctg cgg cta tcc caa gcc aca cgc cag cgt ctg       385
Leu Glu Tyr Gly Phe Leu Arg Leu Ser Gln Ala Thr Arg Gln Arg Leu
        115                 120                 125

agc att cct gtc atg gtg gtc acc cta gac ccc acg cgg gac cag tgc       433
Ser Ile Pro Val Met Val Val Thr Leu Asp Pro Thr Arg Asp Gln Cys
    130                 135                 140

ttt ggg gac cgc ttc agc cgc cta ttg ctg gat gag ttc ctg ggc tat       481
Phe Gly Asp Arg Phe Ser Arg Leu Leu Leu Asp Glu Phe Leu Gly Tyr
145                 150                 155                 160

gat gac atc ctc atg tcc agt gta aag ggt ctg gca gag aac gag gag       529
Asp Asp Ile Leu Met Ser Ser Val Lys Gly Leu Ala Glu Asn Glu Glu
                165                 170                 175

aac aaa ggc ttc ttg agg aat gtg gtc tct ggg gag cac tac cgc ttt       577
Asn Lys Gly Phe Leu Arg Asn Val Val Ser Gly Glu His Tyr Arg Phe
            180                 185                 190

gtc agc atg tgg atg gcg cgc aca tcc tac ctg gcg gcc ttt gtc atc       625
Val Ser Met Trp Met Ala Arg Thr Ser Tyr Leu Ala Ala Phe Val Ile
        195                 200                 205

atg gtc atc ttt acc ctc agc gtg tcc atg ctg ttg cga tac tcg cac       673
Met Val Ile Phe Thr Leu Ser Val Ser Met Leu Leu Arg Tyr Ser His
    210                 215                 220

cac cag atc ttc gtc ttc atc gtg gac ctg ctg cag atg ctg gag atg       721
His Gln Ile Phe Val Phe Ile Val Asp Leu Leu Gln Met Leu Glu Met
225                 230                 235                 240

aac atg gcc atc gcc ttc ccc gca gcg ccc ttg ctg acc gtc atc ctg       769
Asn Met Ala Ile Ala Phe Pro Ala Ala Pro Leu Leu Thr Val Ile Leu
                245                 250                 255

gct ctc gtc ggg atg gaa gcc atc atg tct gag ttc ttc aat gat acc       817
Ala Leu Val Gly Met Glu Ala Ile Met Ser Glu Phe Phe Asn Asp Thr
            260                 265                 270
```

-continued

```
acc acg gcc ttc tac atc atc ctc act gtg tgg ctg gcc gac cag tat      865
Thr Thr Ala Phe Tyr Ile Ile Leu Thr Val Trp Leu Ala Asp Gln Tyr
        275                 280                 285

gat gcc atc tgc tgc cac acc aac acc agc aag cgg cac tgg ctg agg      913
Asp Ala Ile Cys Cys His Thr Asn Thr Ser Lys Arg His Trp Leu Arg
    290                 295                 300

ttc ttc tac ctc tac cac ttc gcc ttc tat gcc tac cac tac cgc ttt      961
Phe Phe Tyr Leu Tyr His Phe Ala Phe Tyr Ala Tyr His Tyr Arg Phe
305                 310                 315                 320

aac ggg cag tac agc agc ctg gcc ctg gtc acc tcc tgg ctc ttc atc     1009
Asn Gly Gln Tyr Ser Ser Leu Ala Leu Val Thr Ser Trp Leu Phe Ile
                325                 330                 335

cag cat tcc atg atc tac ttc ttc cac cac tat gag ttg ccc gcc atc     1057
Gln His Ser Met Ile Tyr Phe Phe His His Tyr Glu Leu Pro Ala Ile
            340                 345                 350

ctg cag cag atc cga atc cag gag atg ctg ctt cag acg cca ccg ctg     1105
Leu Gln Gln Ile Arg Ile Gln Glu Met Leu Leu Gln Thr Pro Pro Leu
        355                 360                 365

ggc ccc ggg acc ccc acg gcg ctg cct gac gac ctc aac aac aac tct     1153
Gly Pro Gly Thr Pro Thr Ala Leu Pro Asp Asp Leu Asn Asn Asn Ser
    370                 375                 380

ggc tcc cct gcc act ccg gat ccc agc cct ccc ctc gcg ctg ggc ccc     1201
Gly Ser Pro Ala Thr Pro Asp Pro Ser Pro Pro Leu Ala Leu Gly Pro
385                 390                 395                 400

agc tcc agc ccc gcg ccc act ggc ggg gca tct ggg cct ggc tca ctg     1249
Ser Ser Ser Pro Ala Pro Thr Gly Gly Ala Ser Gly Pro Gly Ser Leu
                405                 410                 415

ggc gct ggg gcc tca gta tcc ggc agt gac cta ggt tgg gtg gcc gag     1297
Gly Ala Gly Ala Ser Val Ser Gly Ser Asp Leu Gly Trp Val Ala Glu
            420                 425                 430

acc gcc gcc atc atc tct gac gca tcc ttc ctg tcg ggg ctg agc gcc     1345
Thr Ala Ala Ile Ile Ser Asp Ala Ser Phe Leu Ser Gly Leu Ser Ala
        435                 440                 445

tct ctc ctg gag cgg cgg cca aca gcc cct agt acc ccg gac agc tca     1393
Ser Leu Leu Glu Arg Arg Pro Thr Ala Pro Ser Thr Pro Asp Ser Ser
    450                 455                 460

cga cct gac cct ggg gtc cct ctg gag gac gca ccc gcc cct gcc ggg     1441
Arg Pro Asp Pro Gly Val Pro Leu Glu Asp Ala Pro Ala Pro Ala Gly
465                 470                 475                 480

tcc tgagaccggt gtcgtgcccg gctcccagtg gagccgcggc ccgagcccaa          1494
Ser

gagagctgtg gtctgcaggg agaggggctg gtggcgaagg ttctggaagc ggccgggaca   1554

gggcggcgat gggcacgagg ccatcggccg cctggtgctc cccagtgcct tccacacggc   1614

gcccgcacgg ggccgagcgc ccgggcccgg actagcaggt ggtggctcac gatgcggggc   1674

acacgttcca cgctatttaa ttgcagtgta cagagtcgtg tttgtatata gaataaactg   1734

tcgtggacag tgaaaaaaaa aaaaaaaaaa aaaaaaaaaa aaaaaaaaaa aa           1786


<210> SEQ ID NO 12
<211> LENGTH: 481
<212> TYPE: PRT
<213> ORGANISM: Mus musculus

<400> SEQUENCE: 12

Ile Asn Cys Leu Glu His Val Arg Asp Arg Trp Pro Arg Glu Gly Val
 1               5                  10                  15

Leu Arg Val Glu Val Arg His Asn Ser Ser Arg Ala Pro Val Ile Leu
             20                  25                  30

Gln Phe Cys Asp Gly Gly Leu Gly Gly Leu Glu Leu Glu Pro Gly Gly
```

```
        35                  40                  45

Leu Glu Leu Glu Glu Glu Glu Leu Thr Val Glu Met Phe Thr Asn Ser
    50                  55                  60

Ser Ile Lys Phe Glu Leu Asp Ile Glu Pro Lys Val Phe Lys Pro Gln
65                  70                  75                  80

Ser Gly Ala Asp Ala Leu Asn Asp Ser Gln Asp Phe Pro Phe Pro Glu
                85                  90                  95

Thr Pro Ala Lys Val Trp Pro Gln Asp Glu Tyr Ile Val Glu Tyr Ser
            100                 105                 110

Leu Glu Tyr Gly Phe Leu Arg Leu Ser Gln Ala Thr Arg Gln Arg Leu
        115                 120                 125

Ser Ile Pro Val Met Val Val Thr Leu Asp Pro Thr Arg Asp Gln Cys
    130                 135                 140

Phe Gly Asp Arg Phe Ser Arg Leu Leu Leu Asp Glu Phe Leu Gly Tyr
145                 150                 155                 160

Asp Asp Ile Leu Met Ser Ser Val Lys Gly Leu Ala Glu Asn Glu Glu
                165                 170                 175

Asn Lys Gly Phe Leu Arg Asn Val Val Ser Gly Glu His Tyr Arg Phe
            180                 185                 190

Val Ser Met Trp Met Ala Arg Thr Ser Tyr Leu Ala Ala Phe Val Ile
        195                 200                 205

Met Val Ile Phe Thr Leu Ser Val Ser Met Leu Leu Arg Tyr Ser His
    210                 215                 220

His Gln Ile Phe Val Phe Ile Val Asp Leu Leu Gln Met Leu Glu Met
225                 230                 235                 240

Asn Met Ala Ile Ala Phe Pro Ala Ala Pro Leu Leu Thr Val Ile Leu
                245                 250                 255

Ala Leu Val Gly Met Glu Ala Ile Met Ser Glu Phe Phe Asn Asp Thr
            260                 265                 270

Thr Thr Ala Phe Tyr Ile Ile Leu Thr Val Trp Leu Ala Asp Gln Tyr
        275                 280                 285

Asp Ala Ile Cys Cys His Thr Asn Thr Ser Lys Arg His Trp Leu Arg
    290                 295                 300

Phe Phe Tyr Leu Tyr His Phe Ala Phe Tyr Ala Tyr His Tyr Arg Phe
305                 310                 315                 320

Asn Gly Gln Tyr Ser Ser Leu Ala Leu Val Thr Ser Trp Leu Phe Ile
                325                 330                 335

Gln His Ser Met Ile Tyr Phe Phe His His Tyr Glu Leu Pro Ala Ile
            340                 345                 350

Leu Gln Gln Ile Arg Ile Gln Glu Met Leu Leu Gln Thr Pro Pro Leu
        355                 360                 365

Gly Pro Gly Thr Pro Thr Ala Leu Pro Asp Asp Leu Asn Asn Asn Ser
    370                 375                 380

Gly Ser Pro Ala Thr Pro Asp Pro Ser Pro Pro Leu Ala Leu Gly Pro
385                 390                 395                 400

Ser Ser Ser Pro Ala Pro Thr Gly Gly Ala Ser Gly Pro Gly Ser Leu
                405                 410                 415

Gly Ala Gly Ala Ser Val Ser Gly Ser Asp Leu Gly Trp Val Ala Glu
            420                 425                 430

Thr Ala Ala Ile Ile Ser Asp Ala Ser Phe Leu Ser Gly Leu Ser Ala
        435                 440                 445

Ser Leu Leu Glu Arg Arg Pro Thr Ala Pro Ser Thr Pro Asp Ser Ser
    450                 455                 460
```

Arg Pro Asp Pro Gly Val Pro Leu Glu Asp Ala Pro Ala Pro Ala Gly
465 470 475 480

Ser

<210> SEQ ID NO 13
<211> LENGTH: 579
<212> TYPE: DNA
<213> ORGANISM: Homo sapiens

<400> SEQUENCE: 13
ccacgcgtcc gatcttgtac cacttgtcgt ggagcaggtc gatgaagccg gaggacttgt 60
agcggctgat gaactcggac aggttggagg aggtccccag agaccccggc gccccgcctc 120
gcccaggtgc ctctcaccct caatggcgaa gggctttccc acggtcagca gtttgcagtc 180
ggcgtcgatg gagacctcgt agtccaggag cgacttgtcc atgatgaagg cgttgagctt 240
gggggggtcg ctcctgctgg ggccgggggc gggggtcagc catcgccccg cccaccccac 300
gccccgcccc cgcctcaccc cgcgcccggg ctcacgtgag catggcgacy ccgcggggcg 360
tggtgggcgc gctgtggcgc cgcatgtgtg cgtgcatgtc ggggaagctc ttcttgatgt 420
acgcctcggc gctgttctcc cacacggtgc cgaagcggaa gccctgcgcc gggtggtgca 480
gctgcgcggg ggaccccgtc agcgcctctg ctgcccctca ggacccctga ccattgaggg 540
gcgcgccgtt ctccggggtg gggccgtcct gggcacttg 579

<210> SEQ ID NO 14
<211> LENGTH: 938
<212> TYPE: PRT
<213> ORGANISM: Rattus sp.

<400> SEQUENCE: 14

Met Ser Thr Met His Leu Leu Thr Phe Ala Leu Leu Phe Ser Cys Ser
1 5 10 15

Phe Ala Arg Ala Ala Cys Asp Pro Lys Ile Val Asn Ile Gly Ala Val
20 25 30

Leu Ser Thr Arg Lys His Glu Gln Met Phe Arg Glu Ala Val Asn Gln
35 40 45

Ala Asn Lys Arg His Gly Ser Trp Lys Ile Gln Leu Asn Ala Thr Ser
50 55 60

Val Thr His Lys Pro Asn Ala Ile Gln Met Ala Leu Ser Val Cys Glu
65 70 75 80

Asp Leu Ile Ser Ser Gln Val Tyr Ala Ile Leu Val Ser His Pro Pro
85 90 95

Thr Pro Asn Asp His Phe Thr Pro Thr Pro Val Ser Tyr Thr Ala Gly
100 105 110

Phe Tyr Arg Ile Pro Val Leu Gly Leu Thr Thr Arg Met Ser Ile Tyr
115 120 125

Ser Asp Lys Ser Ile His Leu Ser Phe Leu Arg Thr Val Pro Pro Tyr
130 135 140

Ser His Gln Ser Ser Val Trp Phe Glu Met Met Arg Val Tyr Asn Trp
145 150 155 160

Asn His Ile Ile Leu Leu Val Ser Asp Asp His Glu Gly Arg Ala Ala
165 170 175

Gln Lys Arg Leu Glu Thr Leu Leu Glu Glu Arg Glu Ser Lys Ala Glu
180 185 190

Lys Val Leu Gln Phe Asp Pro Gly Thr Lys Asn Val Thr Ala Leu Leu
195 200 205

```
Met Glu Ala Arg Glu Leu Glu Ala Arg Val Ile Ile Leu Ser Ala Ser
    210                 215                 220

Glu Asp Asp Ala Ala Thr Val Tyr Arg Ala Ala Ala Met Leu Asn Met
225                 230                 235                 240

Thr Gly Ser Gly Tyr Val Trp Leu Val Gly Glu Arg Glu Ile Ser Gly
                245                 250                 255

Asn Ala Leu Arg Tyr Ala Pro Asp Gly Ile Ile Gly Leu Gln Leu Ile
            260                 265                 270

Asn Gly Lys Asn Glu Ser Ala His Ile Ser Asp Ala Val Gly Val Val
        275                 280                 285

Ala Gln Ala Val His Glu Leu Leu Glu Lys Glu Asn Ile Thr Asp Pro
    290                 295                 300

Pro Arg Gly Cys Val Gly Asn Thr Asn Ile Trp Lys Thr Gly Pro Leu
305                 310                 315                 320

Phe Lys Arg Val Leu Met Ser Ser Lys Tyr Ala Asp Gly Val Thr Gly
                325                 330                 335

Arg Val Glu Phe Asn Glu Asp Gly Asp Arg Lys Phe Ala Asn Tyr Ser
            340                 345                 350

Ile Met Asn Leu Gln Asn Arg Lys Leu Val Gln Val Gly Ile Tyr Asn
        355                 360                 365

Gly Thr His Val Ile Pro Asn Asp Arg Lys Ile Ile Trp Pro Gly Gly
    370                 375                 380

Glu Thr Glu Lys Pro Arg Gly Tyr Gln Met Ser Thr Arg Leu Lys Ile
385                 390                 395                 400

Val Thr Ile His Gln Glu Pro Phe Val Tyr Val Lys Pro Thr Met Ser
                405                 410                 415

Asp Gly Thr Cys Lys Glu Glu Phe Thr Val Asn Gly Asp Pro Val Lys
            420                 425                 430

Lys Val Ile Cys Thr Gly Pro Asn Asp Thr Ser Pro Gly Ser Pro Arg
        435                 440                 445

His Thr Val Pro Gln Cys Cys Tyr Gly Phe Cys Ile Asp Leu Leu Ile
    450                 455                 460

Lys Leu Ala Arg Thr Met Asn Phe Thr Tyr Glu Val His Leu Val Ala
465                 470                 475                 480

Asp Gly Lys Phe Gly Thr Gln Glu Arg Val Asn Asn Ser Asn Lys Lys
                485                 490                 495

Glu Trp Asn Gly Met Met Gly Glu Leu Leu Ser Gly Gln Ala Asp Met
            500                 505                 510

Ile Val Ala Pro Leu Thr Ile Asn Asn Glu Arg Ala Gln Tyr Ile Glu
        515                 520                 525

Phe Ser Lys Pro Phe Lys Tyr Gln Gly Leu Thr Ile Leu Val Lys Lys
    530                 535                 540

Glu Ile Pro Arg Ser Thr Leu Asp Ser Phe Met Gln Pro Phe Gln Ser
545                 550                 555                 560

Thr Leu Trp Leu Leu Val Gly Leu Ser Val His Val Val Ala Val Met
                565                 570                 575

Leu Tyr Leu Leu Asp Arg Phe Ser Pro Phe Gly Arg Phe Lys Val Asn
            580                 585                 590

Ser Glu Glu Glu Glu Glu Asp Ala Leu Thr Leu Ser Ser Ala Met Trp
        595                 600                 605

Phe Ser Trp Gly Val Leu Leu Asn Ser Gly Ile Gly Glu Gly Ala Pro
    610                 615                 620

Arg Ser Phe Ser Ala Arg Ile Leu Gly Met Val Trp Ala Gly Phe Ala
625                 630                 635                 640
```

-continued

```
Met Ile Ile Val Ala Ser Tyr Thr Ala Asn Leu Ala Ala Phe Leu Val
                645                 650                 655

Leu Asp Arg Pro Glu Glu Arg Ile Thr Gly Ile Asn Asp Pro Arg Leu
            660                 665                 670

Arg Asn Pro Ser Asp Lys Phe Ile Tyr Ala Thr Val Lys Gln Ser Ser
        675                 680                 685

Val Asp Ile Tyr Phe Arg Arg Gln Val Glu Leu Ser Thr Met Tyr Arg
    690                 695                 700

His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
            740                 745                 750

Phe Phe Arg Ser Gly Phe Gly Ile Gly Met Arg Lys Asp Ser Pro Trp
        755                 760                 765

Lys Gln Asn Val Ser Leu Ser Ile Leu Lys Ser His Glu Asn Gly Phe
    770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
            820                 825                 830

Ile Glu Ile Ala Tyr Lys Arg His Lys Asp Ala Arg Arg Lys Gln Met
        835                 840                 845

Gln Leu Ala Phe Ala Ala Val Asn Val Trp Arg Lys Asn Leu Gln Asp
    850                 855                 860

Arg Lys Ser Gly Arg Ala Glu Pro Asp Pro Lys Lys Lys Ala Thr Phe
865                 870                 875                 880

Arg Ala Ile Thr Ser Thr Leu Ala Ser Ser Phe Lys Arg Arg Arg Ser
                885                 890                 895

Ser Lys Asp Thr Ser Thr Gly Gly Gly Arg Gly Ala Leu Gln Asn Gln
            900                 905                 910

Lys Asp Thr Val Leu Pro Arg Arg Ala Ile Glu Arg Glu Glu Gly Gln
        915                 920                 925

Leu Gln Leu Cys Ser Arg His Arg Glu Ser
    930                 935
```

<210> SEQ ID NO 15
<211> LENGTH: 1464
<212> TYPE: PRT
<213> ORGANISM: Rattus sp.

<400> SEQUENCE: 15

```
Met Gly Arg Leu Gly Tyr Trp Thr Leu Leu Val Leu Pro Ala Leu Leu
 1               5                  10                  15

Val Trp Arg Asp Pro Ala Gln Asn Ala Ala Ala Glu Lys Gly Pro Pro
             20                  25                  30

Ala Leu Asn Ile Ala Val Leu Leu Gly His Ser His Asp Val Thr Glu
         35                  40                  45

Arg Glu Leu Arg Asn Leu Trp Gly Pro Glu Gln Ala Thr Gly Leu Pro
     50                  55                  60

Leu Asp Val Asn Val Val Ala Leu Leu Met Asn Arg Thr Asp Pro Lys
 65                  70                  75                  80
```

-continued

```
Ser Leu Ile Thr His Val Cys Asp Leu Met Ser Gly Ala Arg Ile His
                85                  90                  95

Gly Leu Val Phe Gly Asp Asp Thr Asp Gln Glu Ala Val Ala Gln Met
            100                 105                 110

Leu Asp Phe Ile Ser Ser Gln Thr Phe Ile Pro Ile Leu Gly Ile His
        115                 120                 125

Gly Gly Ala Ser Met Ile Met Ala Asp Lys Asp Pro Thr Ser Thr Phe
    130                 135                 140

Phe Gln Phe Gly Ala Ser Ile Gln Gln Gln Ala Thr Val Met Leu Lys
145                 150                 155                 160

Ile Met Gln Asp Tyr Asp Trp His Val Phe Ser Leu Val Thr Thr Ile
                165                 170                 175

Phe Pro Gly Tyr Arg Asp Phe Ile Ser Phe Ile Lys Thr Thr Val Asp
            180                 185                 190

Asn Ser Phe Val Gly Trp Asp Met Gln Asn Val Ile Thr Leu Asp Thr
        195                 200                 205

Ser Phe Glu Asp Ala Lys Thr Gln Val Gln Leu Lys Lys Ile His Ser
    210                 215                 220

Ser Val Ile Leu Leu Tyr Cys Ser Lys Asp Glu Ala Val Leu Ile Leu
225                 230                 235                 240

Ser Glu Ala Arg Ser Leu Gly Leu Thr Gly Tyr Asp Phe Phe Trp Ile
                245                 250                 255

Val Pro Ser Leu Val Ser Gly Asn Thr Glu Leu Ile Pro Lys Glu Phe
            260                 265                 270

Pro Ser Gly Leu Ile Ser Val Ser Tyr Asp Asp Trp Asp Tyr Ser Leu
        275                 280                 285

Glu Ala Arg Val Arg Asp Gly Leu Gly Ile Leu Thr Thr Ala Ala Ser
    290                 295                 300

Ser Met Leu Glu Lys Phe Ser Tyr Ile Pro Glu Ala Lys Ala Ser Cys
305                 310                 315                 320

Tyr Gly Gln Ala Glu Lys Pro Glu Thr Pro Leu His Thr Leu His Gln
                325                 330                 335

Phe Met Val Asn Val Thr Trp Asp Gly Lys Asp Leu Ser Phe Thr Glu
            340                 345                 350

Glu Gly Tyr Gln Val His Pro Arg Leu Val Val Ile Val Leu Asn Lys
        355                 360                 365

Asp Arg Glu Trp Glu Lys Val Gly Lys Trp Glu Asn Gln Thr Leu Ser
    370                 375                 380

Leu Arg His Ala Val Trp Pro Arg Tyr Lys Ser Phe Ser Asp Cys Glu
385                 390                 395                 400

Pro Asp Asp Asn His Leu Ser Ile Val Thr Leu Glu Glu Ala Pro Phe
                405                 410                 415

Val Ile Val Glu Asp Ile Asp Pro Leu Thr Glu Thr Cys Val Arg Asn
            420                 425                 430

Thr Val Pro Cys Arg Lys Phe Val Lys Ile Asn Asn Ser Thr Asn Glu
        435                 440                 445

Gly Met Asn Val Lys Lys Cys Cys Lys Gly Phe Cys Ile Asp Ile Leu
    450                 455                 460

Lys Lys Leu Ser Arg Thr Val Lys Phe Thr Tyr Asp Leu Tyr Leu Val
465                 470                 475                 480

Thr Asn Gly Lys His Gly Lys Lys Val Asn Asn Val Trp Asn Gly Met
                485                 490                 495

Ile Gly Glu Val Val Tyr Gln Arg Ala Val Met Ala Val Gly Ser Leu
```

```
            500                 505                 510

Thr Ile Asn Glu Glu Arg Ser Glu Val Val Asp Phe Ser Val Pro Phe
        515                 520                 525

Val Glu Thr Gly Ile Ser Val Met Val Ser Arg Ser Asn Gly Thr Val
    530                 535                 540

Ser Pro Ser Ala Phe Leu Glu Pro Phe Ser Ala Ser Val Trp Val Met
545                 550                 555                 560

Met Phe Val Met Leu Leu Ile Val Ser Ala Ile Ala Val Phe Val Phe
                565                 570                 575

Glu Tyr Phe Ser Pro Val Gly Tyr Asn Arg Asn Leu Ala Lys Gly Lys
            580                 585                 590

Ala Pro His Gly Pro Ser Phe Thr Ile Gly Lys Ala Ile Trp Leu Leu
        595                 600                 605

Trp Gly Leu Val Phe Asn Asn Ser Val Pro Val Gln Asn Pro Lys Gly
    610                 615                 620

Thr Thr Ser Lys Ile Met Val Ser Val Trp Ala Phe Phe Ala Val Ile
625                 630                 635                 640

Phe Leu Ala Ser Tyr Thr Ala Asn Leu Ala Ala Phe Met Ile Gln Glu
                645                 650                 655

Glu Phe Val Asp Gln Val Thr Gly Leu Ser Asp Lys Lys Phe Gln Arg
            660                 665                 670

Pro His Asp Tyr Ser Pro Pro Phe Arg Phe Gly Thr Val Pro Asn Gly
        675                 680                 685

Ser Thr Glu Arg Asn Ile Arg Asn Asn Tyr Pro Tyr Met His Gln Tyr
    690                 695                 700

Met Thr Arg Phe Asn Gln Arg Gly Val Glu Asp Ala Leu Val Ser Leu
705                 710                 715                 720

Lys Thr Gly Lys Leu Asp Ala Phe Ile Tyr Asp Ala Ala Val Leu Asn
                725                 730                 735

Tyr Lys Ala Gly Arg Asp Glu Gly Cys Lys Leu Val Thr Ile Gly Ser
            740                 745                 750

Gly Tyr Ile Phe Ala Thr Thr Gly Tyr Gly Ile Ala Leu Gln Lys Gly
        755                 760                 765

Ser Pro Trp Lys Arg Gln Ile Asp Leu Ala Leu Leu Gln Phe Val Gly
    770                 775                 780

Asp Gly Glu Met Glu Glu Leu Glu Thr Leu Trp Leu Thr Gly Ile Cys
785                 790                 795                 800

His Asn Glu Lys Asn Glu Val Met Ser Ser Gln Leu Asp Ile Asp Asn
                805                 810                 815

Met Ala Gly Val Phe Tyr Met Leu Ala Ala Ala Met Ala Leu Ser Leu
            820                 825                 830

Ile Thr Phe Ile Trp Glu His Leu Phe Tyr Trp Lys Leu Arg Phe Cys
        835                 840                 845

Phe Thr Gly Val Cys Ser Asp Arg Pro Gly Leu Leu Phe Ser Ile Ser
    850                 855                 860

Arg Gly Ile Tyr Ser Cys Ile His Gly Val His Ile Glu Glu Lys Lys
865                 870                 875                 880

Lys Ser Pro Asp Phe Asn Leu Thr Gly Ser Gln Ser Asn Met Leu Lys
                885                 890                 895

Leu Leu Arg Ser Ala Lys Asn Ile Ser Asn Met Ser Asn Met Asn Ser
            900                 905                 910

Ser Arg Met Asp Ser Pro Lys Arg Ala Thr Asp Phe Ile Gln Arg Gly
        915                 920                 925
```

-continued

```
Ser Leu Ile Val Asp Met Val Ser Asp Lys Gly Asn Leu Ile Tyr Ser
    930                 935                 940

Asp Asn Arg Ser Phe Gln Gly Lys Asp Ser Ile Phe Gly Asp Asn Met
945                 950                 955                 960

Asn Glu Leu Gln Thr Phe Val Ala Asn Arg His Lys Asp Asn Leu Ser
                965                 970                 975

Asn Tyr Val Phe Gln Gly Gln His Pro Leu Thr Leu Asn Asp Ser Asn
            980                 985                 990

Pro Asn Thr Val Glu Val Ala Val Ser Thr Glu Ser Lys Gly Asn Ser
        995                 1000                1005

Arg Pro Arg Gln Leu Trp Lys Lys Ser Met Glu Ser Leu Arg Gln Asp
    1010                1015                1020

Ser Leu Asn Gln Asn Pro Val Ser Gln Arg Asp Glu Lys Thr Ala Glu
1025                1030                1035                1040

Asn Arg Thr His Ser Leu Lys Ser Pro Arg Tyr Leu Pro Glu Glu Val
                1045                1050                1055

Ala His Ser Asp Ile Ser Glu Thr Ser Ser Arg Ala Thr Cys His Arg
            1060                1065                1070

Glu Pro Asp Asn Asn Lys Asn His Lys Thr Lys Asp Asn Phe Lys Arg
        1075                1080                1085

Ser Met Ala Ser Lys Tyr Pro Lys Asp Cys Ser Asp Val Asp Arg Thr
    1090                1095                1100

Tyr Met Lys Thr Lys Ala Ser Ser Pro Arg Asp Lys Ile Tyr Thr Ile
1105                1110                1115                1120

Asp Gly Glu Lys Glu Pro Ser Phe His Leu Asp Pro Pro Gln Phe Val
                1125                1130                1135

Glu Asn Ile Thr Leu Pro Glu Asn Val Gly Phe Pro Asp Thr Tyr Gln
            1140                1145                1150

Asp His Asn Glu Asn Phe Arg Lys Gly Asp Ser Thr Leu Pro Met Asn
        1155                1160                1165

Arg Asn Pro Leu His Asn Glu Asp Gly Leu Pro Asn Asn Asp Gln Tyr
    1170                1175                1180

Lys Leu Tyr Ala Lys His Phe Thr Leu Lys Asp Lys Gly Ser Pro His
1185                1190                1195                1200

Ser Glu Gly Ser Asp Arg Tyr Arg Gln Asn Ser Thr His Cys Arg Ser
                1205                1210                1215

Cys Leu Ser Asn Leu Pro Thr Tyr Ser Gly His Phe Thr Met Arg Ser
            1220                1225                1230

Pro Phe Lys Cys Asp Ala Cys Leu Arg Met Gly Asn Leu Tyr Asp Ile
        1235                1240                1245

Asp Glu Asp Gln Met Leu Gln Glu Thr Gly Asn Pro Ala Thr Arg Glu
    1250                1255                1260

Glu Val Tyr Gln Gln Asp Trp Ser Gln Asn Asn Ala Leu Gln Phe Gln
1265                1270                1275                1280

Lys Asn Lys Leu Arg Ile Asn Arg Gln His Ser Tyr Asp Asn Ile Leu
                1285                1290                1295

Asp Lys Pro Arg Glu Ile Asp Leu Ser Arg Pro Ser Arg Ser Ile Ser
            1300                1305                1310

Leu Lys Asp Arg Glu Arg Leu Leu Glu Gly Asn Leu Tyr Gly Ser Leu
        1315                1320                1325

Phe Ser Val Pro Ser Ser Lys Leu Leu Gly Asn Lys Ser Ser Leu Phe
    1330                1335                1340

Pro Gln Gly Leu Glu Asp Ser Lys Arg Ser Lys Ser Leu Leu Pro Asp
1345                1350                1355                1360
```

```
His Ala Ser Asp Asn Pro Phe Leu His Thr Tyr Gly Asp Asp Gln Arg
                1365                1370                1375

Leu Val Ile Gly Arg Cys Pro Ser Asp Pro Tyr Lys His Ser Leu Pro
            1380                1385                1390

Ser Gln Ala Val Asn Asp Ser Tyr Leu Arg Ser Ser Leu Arg Ser Thr
        1395                1400                1405

Ala Ser Tyr Cys Ser Arg Asp Ser Arg Gly His Ser Asp Val Tyr Ile
    1410                1415                1420

Ser Glu His Val Met Pro Tyr Ala Ala Asn Lys Asn Thr Met Tyr Ser
1425                1430                1435                1440

Thr Pro Arg Val Leu Asn Ser Cys Ser Asn Arg Arg Val Tyr Lys Lys
                1445                1450                1455

Met Pro Ser Ile Glu Ser Asp Val
            1460


<210> SEQ ID NO 16
<211> LENGTH: 1115
<212> TYPE: PRT
<213> ORGANISM: Rattus sp.

<400> SEQUENCE: 16

Met Arg Arg Leu Ser Leu Trp Trp Leu Leu Ser Arg Val Cys Leu Leu
 1               5                  10                  15

Leu Pro Pro Pro Cys Ala Leu Val Leu Ala Gly Val Pro Ser Ser Ser
            20                  25                  30

Ser His Pro Gln Pro Cys Gln Ile Leu Lys Arg Ile Gly His Ala Val
        35                  40                  45

Arg Val Gly Ala Val His Leu Gln Pro Trp Thr Thr Ala Pro Arg Ala
    50                  55                  60

Ala Ser Arg Ala Gln Glu Gly Gly Arg Ala Gly Ala Gln Arg Asp Asp
65                  70                  75                  80

Pro Glu Ser Gly Thr Trp Arg Pro Pro Ala Pro Ser Gln Gly Ala Arg
                85                  90                  95

Trp Leu Gly Ser Ala Leu His Gly Arg Gly Pro Pro Gly Ser Arg Lys
            100                 105                 110

Leu Gly Glu Gly Ala Gly Ala Glu Thr Leu Trp Pro Arg Asp Ala Leu
        115                 120                 125

Leu Phe Ala Val Glu Asn Leu Asn Arg Val Glu Gly Leu Leu Pro Tyr
    130                 135                 140

Asn Leu Ser Leu Glu Val Val Met Ala Ile Glu Ala Gly Leu Gly Asp
145                 150                 155                 160

Leu Pro Leu Met Pro Phe Ser Ser Pro Ser Ser Pro Trp Ser Ser Asp
                165                 170                 175

Pro Phe Ser Phe Leu Gln Ser Val Cys His Thr Val Val Val Gln Gly
            180                 185                 190

Val Ser Ala Leu Leu Ala Phe Pro Gln Ser Gln Gly Glu Met Met Glu
        195                 200                 205

Leu Asp Leu Val Ser Ser Val Leu His Ile Pro Val Leu Ser Ile Val
    210                 215                 220

Arg His Glu Phe Pro Arg Glu Ser Gln Asn Pro Leu His Leu Gln Leu
225                 230                 235                 240

Ser Leu Glu Asn Ser Leu Ser Ser Asp Ala Asp Val Thr Val Ser Ile
                245                 250                 255

Leu Thr Met Asn Asn Trp Tyr Asn Phe Ser Leu Leu Leu Cys Gln Glu
            260                 265                 270
```

```
Asp Trp Asn Ile Thr Asp Phe Leu Leu Leu Thr Glu Asn Asn Ser Lys
        275                 280                 285

Phe His Leu Glu Ser Val Ile Asn Ile Thr Ala Asn Leu Ser Ser Thr
    290                 295                 300

Lys Asp Leu Leu Ser Phe Leu Gln Val Gln Met Asp Asn Ile Arg Asn
305                 310                 315                 320

Ser Thr Pro Thr Met Val Met Phe Gly Cys Asp Met Asp Ser Ile Arg
                325                 330                 335

Gln Ile Phe Glu Met Ser Thr Gln Phe Gly Leu Ser Pro Pro Glu Leu
            340                 345                 350

His Trp Val Leu Gly Asp Ser Gln Asn Val Glu Glu Leu Arg Thr Glu
        355                 360                 365

Gly Leu Pro Leu Gly Leu Ile Ala His Gly Lys Thr Thr Gln Ser Val
    370                 375                 380

Phe Glu Tyr Tyr Val Gln Asp Ala Met Glu Leu Val Ala Arg Ala Val
385                 390                 395                 400

Ala Thr Ala Thr Met Ile Gln Pro Glu Leu Ala Leu Leu Pro Ser Thr
                405                 410                 415

Met Asn Cys Met Asp Val Lys Thr Thr Asn Leu Thr Ser Gly Gln Tyr
            420                 425                 430

Leu Ser Arg Phe Leu Ala Asn Thr Thr Phe Arg Gly Leu Ser Gly Ser
        435                 440                 445

Ile Lys Val Lys Gly Ser Thr Ile Ile Ser Ser Glu Asn Asn Phe Phe
    450                 455                 460

Ile Trp Asn Leu Gln His Asp Pro Met Gly Lys Pro Met Trp Thr Arg
465                 470                 475                 480

Leu Gly Ser Trp Gln Gly Gly Arg Ile Val Met Asp Ser Gly Ile Trp
                485                 490                 495

Pro Glu Gln Ala Gln Arg His Lys Thr His Phe Gln His Pro Asn Lys
            500                 505                 510

Leu His Leu Arg Val Val Thr Leu Ile Glu His Pro Phe Val Phe Thr
        515                 520                 525

Arg Glu Val Asp Asp Glu Gly Leu Cys Pro Ala Gly Gln Leu Cys Leu
    530                 535                 540

Asp Pro Met Thr Asn Asp Ser Ser Met Leu Asp Arg Leu Phe Ser Ser
545                 550                 555                 560

Leu His Ser Ser Asn Asp Thr Val Pro Ile Lys Phe Lys Lys Cys Cys
                565                 570                 575

Tyr Gly Tyr Cys Ile Asp Leu Leu Glu Gln Leu Ala Glu Asp Met Asn
            580                 585                 590

Phe Asp Phe Asp Leu Tyr Ile Val Gly Asp Gly Lys Tyr Gly Ala Trp
        595                 600                 605

Lys Asn Gly His Trp Thr Gly Leu Val Gly Asp Leu Leu Ser Gly Thr
    610                 615                 620

Ala Asn Met Ala Val Thr Ser Phe Ser Ile Asn Thr Ala Arg Ser Gln
625                 630                 635                 640

Val Ile Asp Phe Thr Ser Pro Phe Phe Ser Thr Ser Leu Gly Ile Leu
                645                 650                 655

Val Arg Thr Arg Asp Thr Ala Ala Pro Ile Gly Ala Phe Met Trp Pro
            660                 665                 670

Leu His Trp Thr Met Trp Leu Gly Ile Phe Val Ala Leu His Ile Thr
        675                 680                 685

Ala Ile Phe Leu Thr Leu Tyr Glu Trp Lys Ser Pro Phe Gly Met Thr
```

-continued

```
    690                 695                 700

Pro Lys Gly Arg Asn Arg Asn Lys Val Phe Ser Phe Ser Ser Ala Leu
705                 710                 715                 720

Asn Val Cys Tyr Ala Leu Leu Phe Gly Arg Thr Ala Ala Ile Lys Pro
                725                 730                 735

Pro Lys Cys Trp Thr Gly Arg Phe Leu Met Asn Leu Trp Ala Ile Phe
            740                 745                 750

Cys Met Phe Cys Leu Ser Thr Tyr Thr Ala Asn Leu Ala Ala Val Met
        755                 760                 765

Val Gly Glu Lys Ile Tyr Glu Glu Leu Ser Gly Ile His Asp Pro Lys
    770                 775                 780

Leu His His Pro Ser Gln Gly Phe Arg Phe Gly Thr Val Arg Glu Ser
785                 790                 795                 800

Ser Ala Glu Asp Tyr Val Arg Gln Ser Phe Pro Glu Met His Glu Tyr
                805                 810                 815

Met Arg Arg Tyr Asn Val Pro Ala Thr Pro Asp Gly Val Gln Tyr Leu
            820                 825                 830

Lys Asn Asp Pro Glu Lys Leu Asp Ala Phe Ile Met Asp Lys Ala Leu
        835                 840                 845

Leu Asp Tyr Glu Val Ser Ile Asp Ala Asp Cys Lys Leu Leu Thr Val
    850                 855                 860

Gly Lys Pro Phe Ala Ile Glu Gly Tyr Gly Ile Gly Leu Pro Pro Asn
865                 870                 875                 880

Ser Pro Leu Thr Ser Asn Ile Ser Glu Leu Ile Ser Gln Tyr Lys Ser
                885                 890                 895

His Gly Phe Met Asp Val Leu His Asp Lys Trp Tyr Lys Val Val Pro
            900                 905                 910

Cys Gly Lys Arg Ser Phe Ala Val Thr Glu Thr Leu Gln Met Gly Ile
        915                 920                 925

Lys His Phe Ser Gly Leu Phe Val Leu Leu Cys Ile Gly Phe Gly Leu
    930                 935                 940

Ser Ile Leu Thr Thr Ile Gly Glu His Ile Val His Arg Leu Leu Leu
945                 950                 955                 960

Pro Arg Ile Lys Asn Lys Ser Lys Leu Gln Tyr Trp Leu His Thr Ser
                965                 970                 975

Gln Arg Phe His Arg Ala Leu Asn Thr Ser Phe Val Glu Glu Lys Gln
            980                 985                 990

Pro Arg Ser Lys Thr Lys Arg Val Glu Lys Arg Ser Asn Leu Gly Pro
        995                 1000                1005

Gln Gln Leu Met Val Trp Asn Thr Ser Asn Leu Ser His Asp Asn Gln
    1010                1015                1020

Arg Lys Tyr Ile Phe Asn Asp Glu Glu Gly Gln Asn Gln Leu Gly Thr
1025                1030                1035                1040

Gln Ala His Gln Asp Ile Pro Leu Pro Gln Arg Arg Arg Glu Leu Pro
                1045                1050                1055

Ala Ser Leu Thr Thr Asn Gly Lys Ala Asp Ser Leu Asn Val Thr Arg
            1060                1065                1070

Ser Ser Val Ile Gln Glu Leu Ser Glu Leu Glu Lys Gln Ile Gln Val
        1075                1080                1085

Ile Arg Gln Glu Leu Gln Leu Ala Val Ser Arg Lys Thr Glu Leu Glu
    1090                1095                1100

Glu Tyr Gln Lys Thr Asn Arg Thr Cys Glu Ser
1105                1110                1115
```

<210> SEQ ID NO 17
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 17
tgctgctatg gctactgcat c 21

<210> SEQ ID NO 18
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 18
atgacagcag ccaggttggc cgt 23

<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 19
cacacatggc tgtgaccagc 20

<210> SEQ ID NO 20
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 20
agaatggcat agcacaggtt g 21

<210> SEQ ID NO 21
<211> LENGTH: 6
<212> TYPE: PRT
<213> ORGANISM: Rattus sp.

<400> SEQUENCE: 21

Ala Asp Gly Lys Phe Gly
1 5

<210> SEQ ID NO 22
<211> LENGTH: 6
<212> TYPE: PRT
<213> ORGANISM: Rattus sp.

<400> SEQUENCE: 22

Thr Asn Gly Lys His Gly
1 5

<210> SEQ ID NO 23
<211> LENGTH: 6
<212> TYPE: PRT
<213> ORGANISM: Rattus sp.

<400> SEQUENCE: 23

Thr Asn Gly Lys His Gly
1 5

<210> SEQ ID NO 24
<211> LENGTH: 6
<212> TYPE: PRT
<213> ORGANISM: Rattus sp.

<400> SEQUENCE: 24

Thr Asn Gly Lys His Gly
1 5

<210> SEQ ID NO 25
<211> LENGTH: 6
<212> TYPE: PRT
<213> ORGANISM: Rattus sp.

<400> SEQUENCE: 25

Thr Asn Gly Lys His Gly
1 5

<210> SEQ ID NO 26
<211> LENGTH: 6
<212> TYPE: PRT
<213> ORGANISM: Rattus sp.

<400> SEQUENCE: 26

Gly Asp Gly Lys Tyr Gly
1 5

<210> SEQ ID NO 27
<211> LENGTH: 6
<212> TYPE: PRT
<213> ORGANISM: Rattus sp.

<400> SEQUENCE: 27

Gly Asp Gly Lys Tyr Gly
1 5

<210> SEQ ID NO 28
<211> LENGTH: 6
<212> TYPE: PRT
<213> ORGANISM: Rattus sp.

<400> SEQUENCE: 28

Gly Asp Gly Lys Tyr Gly
1 5

<210> SEQ ID NO 29
<211> LENGTH: 11
<212> TYPE: PRT
<213> ORGANISM: Rattus sp.

<400> SEQUENCE: 29

Ala Pro Leu Thr Ile Asn Asn Glu Arg Ala Gln
1 5 10

<210> SEQ ID NO 30
<211> LENGTH: 11
<212> TYPE: PRT
<213> ORGANISM: Rattus sp.

<400> SEQUENCE: 30

Gly Ser Leu Thr Ile Asn Glu Glu Arg Ser Glu
1 5 10

<210> SEQ ID NO 31

-continued

<211> LENGTH: 11
<212> TYPE: PRT
<213> ORGANISM: Rattus sp.

<400> SEQUENCE: 31

Gly Ser Leu Thr Ile Asn Glu Glu Arg Ser Glu
1 5 10

<210> SEQ ID NO 32
<211> LENGTH: 11
<212> TYPE: PRT
<213> ORGANISM: Rattus sp.

<400> SEQUENCE: 32

Gly Ser Leu Thr Ile Asn Glu Glu Arg Ser Glu
1 5 10

<210> SEQ ID NO 33
<211> LENGTH: 11
<212> TYPE: PRT
<213> ORGANISM: Rattus sp.

<400> SEQUENCE: 33

Gly Ser Leu Thr Ile Asn Glu Glu Arg Ser Glu
1 5 10

<210> SEQ ID NO 34
<211> LENGTH: 11
<212> TYPE: PRT
<213> ORGANISM: Rattus sp.

<400> SEQUENCE: 34

Thr Ser Phe Ser Ile Asn Thr Ala Arg Ser Gln
1 5 10

<210> SEQ ID NO 35
<211> LENGTH: 11
<212> TYPE: PRT
<213> ORGANISM: Rattus sp.

<400> SEQUENCE: 35

Thr Ser Phe Ser Ile Asn Ser Ala Arg Ser Gln
1 5 10

<210> SEQ ID NO 36
<211> LENGTH: 11
<212> TYPE: PRT
<213> ORGANISM: Rattus sp.

<400> SEQUENCE: 36

Ala Pro Leu Thr Ile Thr Leu Val Arg Glu Glu
1 5 10

<210> SEQ ID NO 37
<211> LENGTH: 9
<212> TYPE: PRT
<213> ORGANISM: Rattus sp.

<400> SEQUENCE: 37

Ala Thr Val Lys Gln Ser Ser Val Asp
1 5

<210> SEQ ID NO 38
<211> LENGTH: 9
<212> TYPE: PRT
<213> ORGANISM: Rattus sp.

<400> SEQUENCE: 38

Gly Thr Val Pro Asn Gly Ser Thr Glu
1 5

<210> SEQ ID NO 39
<211> LENGTH: 9
<212> TYPE: PRT
<213> ORGANISM: Rattus sp.

<400> SEQUENCE: 39

Gly Thr Val Pro Asn Gly Ser Thr Glu
1 5

<210> SEQ ID NO 40
<211> LENGTH: 9
<212> TYPE: PRT
<213> ORGANISM: Rattus sp.

<400> SEQUENCE: 40

Gly Thr Val Pro Asn Gly Ser Thr Glu
1 5

<210> SEQ ID NO 41
<211> LENGTH: 9
<212> TYPE: PRT
<213> ORGANISM: Rattus sp.

<400> SEQUENCE: 41

Gly Thr Val Pro Asn Gly Ser Thr Glu
1 5

<210> SEQ ID NO 42
<211> LENGTH: 9
<212> TYPE: PRT
<213> ORGANISM: Rattus sp.

<400> SEQUENCE: 42

Gly Thr Val Arg Glu Ser Ser Ala Glu
1 5

<210> SEQ ID NO 43
<211> LENGTH: 9
<212> TYPE: PRT
<213> ORGANISM: Rattus sp.

<400> SEQUENCE: 43

Gly Thr Val Trp Glu Ser Ser Ala Glu
1 5

<210> SEQ ID NO 44
<211> LENGTH: 9
<212> TYPE: PRT
<213> ORGANISM: Rattus sp.

<400> SEQUENCE: 44

Gly Thr Leu Asp Ser Gly Ser Thr Lys
1 5

<210> SEQ ID NO 45
<211> LENGTH: 25
<212> TYPE: PRT
<213> ORGANISM: Rattus sp.

<400> SEQUENCE: 45

```
Asp Ala Leu Thr Leu Ser Ser Ala Met Trp Phe Ser Trp Gly Val Leu
 1               5                  10                  15

Leu Asn Ser Gly Ile Gly Glu Gly Ala
            20                  25


<210> SEQ ID NO 46
<211> LENGTH: 25
<212> TYPE: PRT
<213> ORGANISM: Rattus sp.

<400> SEQUENCE: 46

Pro Ser Phe Thr Ile Gly Lys Ala Ile Trp Leu Leu Trp Gly Leu Val
 1               5                  10                  15

Phe Asn Asn Ser Val Pro Val Gln Asn
            20                  25


<210> SEQ ID NO 47
<211> LENGTH: 25
<212> TYPE: PRT
<213> ORGANISM: Rattus sp.

<400> SEQUENCE: 47

Pro Ser Phe Thr Ile Gly Lys Ala Ile Trp Leu Leu Trp Gly Leu Val
 1               5                  10                  15

Phe Asn Asn Ser Val Pro Val Gln Asn
            20                  25


<210> SEQ ID NO 48
<211> LENGTH: 25
<212> TYPE: PRT
<213> ORGANISM: Rattus sp.

<400> SEQUENCE: 48

Pro Ser Phe Thr Ile Gly Lys Ser Val Trp Leu Leu Trp Ala Leu Val
 1               5                  10                  15

Phe Asn Asn Ser Val Pro Ile Glu Asn
            20                  25


<210> SEQ ID NO 49
<211> LENGTH: 25
<212> TYPE: PRT
<213> ORGANISM: Rattus sp.

<400> SEQUENCE: 49

Ser Thr Phe Thr Ile Gly Lys Ser Ile Trp Leu Leu Trp Ala Leu Val
 1               5                  10                  15

Phe Asn Asn Ser Val Pro Val Glu Asn
            20                  25


<210> SEQ ID NO 50
<211> LENGTH: 25
<212> TYPE: PRT
<213> ORGANISM: Rattus sp.

<400> SEQUENCE: 50

Lys Val Phe Ser Phe Ser Ser Ala Leu Asn Val Cys Tyr Ala Leu Leu
 1               5                  10                  15

Phe Gly Arg Thr Ala Ala Ile Lys Pro
            20                  25


<210> SEQ ID NO 51
<211> LENGTH: 25
<212> TYPE: PRT
```

<213> ORGANISM: Rattus sp.

<400> SEQUENCE: 51

```
Thr Val Phe Ser Tyr Ser Ser Ala Leu Asn Leu Cys Tyr Ala Ile Leu
 1               5                  10                  15

Phe Gly Arg Thr Val Ser Ser Lys Thr
            20                  25
```

<210> SEQ ID NO 52
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 52

```
ctagcggcgc gccttaatta agtttaaacg                                        30
```

<210> SEQ ID NO 53
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 53

```
ctagcgttta aacttaatta aggcgcgccg                                        30
```

<210> SEQ ID NO 54

<400> SEQUENCE: 54

000

<210> SEQ ID NO 55
<211> LENGTH: 3571
<212> TYPE: DNA
<213> ORGANISM: Homo sapiens
<220> FEATURE:
<221> NAME/KEY: CDS
<222> LOCATION: (224)...(3568)

<400> SEQUENCE: 55

```
cagaggatgc caggcggagg gacctgggag cgggatctga gactgccgga ggcgcgctac      60

gctccaactt gcatggccta gagaccgctc cagctcctgg gaccgcttca ccgagtggag     120

tgaagctgcg cgcgggacct ggaggcggag acctcaggca gcggctgcag aggggcgagc     180

cgggcgcagg agggggcgcg ctttctccct gcgggtctca gta atg agg aga ctg       235
                                                Met Arg Arg Leu
                                                 1

agt ttg tgg tgg ctg ctg agc agg gtc tgt ctg ctg ttg ccg ccg ccc       283
Ser Leu Trp Trp Leu Leu Ser Arg Val Cys Leu Leu Leu Pro Pro Pro
 5                  10                  15                  20

tgc gca ctg gtg ctg gcc ggg gtg ccc agc tcc tcc tcg cac ccg cag       331
Cys Ala Leu Val Leu Ala Gly Val Pro Ser Ser Ser Ser His Pro Gln
                25                  30                  35

ccc tgc cag atc ctc aag cgc atc ggg cac gcg gtg agg gtg ggc gcg       379
Pro Cys Gln Ile Leu Lys Arg Ile Gly His Ala Val Arg Val Gly Ala
            40                  45                  50

gtg cac ttg cag ccc tgg acc acc gcc ccc cgc gcg gcc agc cgc gct       427
Val His Leu Gln Pro Trp Thr Thr Ala Pro Arg Ala Ala Ser Arg Ala
        55                  60                  65

ccg gac gac agc cga gca gga gcc cag agg gat gag ccg gag cca ggg       475
Pro Asp Asp Ser Arg Ala Gly Ala Gln Arg Asp Glu Pro Glu Pro Gly
```

-continued

```
     70                  75                  80

act agg cgg tcc ccg gcg ccc tcg ccg ggc gca cgc tgg ttg ggg agc      523
Thr Arg Arg Ser Pro Ala Pro Ser Pro Gly Ala Arg Trp Leu Gly Ser
 85                  90                  95                 100

acc ctg cat ggc cgg ggg ccg ccg ggc tcc cgt aag ccc ggg gag ggc      571
Thr Leu His Gly Arg Gly Pro Pro Gly Ser Arg Lys Pro Gly Glu Gly
                105                 110                 115

gcc agg gcg gag gcc ctg tgg cca cgg gac gcc ctc cta ttt gcc gtg      619
Ala Arg Ala Glu Ala Leu Trp Pro Arg Asp Ala Leu Leu Phe Ala Val
            120                 125                 130

gac aac ctg aac cgc gtg gaa ggg ctg cta ccc tac aac ctg tct ttg      667
Asp Asn Leu Asn Arg Val Glu Gly Leu Leu Pro Tyr Asn Leu Ser Leu
        135                 140                 145

gaa gta gtg atg gcc atc gag gca ggc ctg ggc gat ctg cca ctt ttg      715
Glu Val Val Met Ala Ile Glu Ala Gly Leu Gly Asp Leu Pro Leu Leu
    150                 155                 160

ccc ttc tcc tcc cct agt tcg cca tgg agc agt gac cct ttc tcc ttc      763
Pro Phe Ser Ser Pro Ser Ser Pro Trp Ser Ser Asp Pro Phe Ser Phe
165                 170                 175                 180

ctg caa agt gtg tgc cat acc gtg gtg gtg caa ggg gtg tcg gcg ctg      811
Leu Gln Ser Val Cys His Thr Val Val Val Gln Gly Val Ser Ala Leu
                185                 190                 195

ctc gcc ttc ccc cag agc cag ggc gaa atg atg gag ctc gac ttg gtc      859
Leu Ala Phe Pro Gln Ser Gln Gly Glu Met Met Glu Leu Asp Leu Val
            200                 205                 210

agc tta gtc ctg cac att cca gtg atc agc atc gtg cgc cac gag ttt      907
Ser Leu Val Leu His Ile Pro Val Ile Ser Ile Val Arg His Glu Phe
        215                 220                 225

cca cgg gag agt cag aat ccc ctt cac cta caa ctg agt tta gaa aat      955
Pro Arg Glu Ser Gln Asn Pro Leu His Leu Gln Leu Ser Leu Glu Asn
    230                 235                 240

tca tta agt tct gat gct gat gtc act gtc tca atc ctg acc atg aac     1003
Ser Leu Ser Ser Asp Ala Asp Val Thr Val Ser Ile Leu Thr Met Asn
245                 250                 255                 260

aac tgg tac aat ttt agc ttg ttg ctg tgc cag gaa gac tgg aac atc     1051
Asn Trp Tyr Asn Phe Ser Leu Leu Leu Cys Gln Glu Asp Trp Asn Ile
                265                 270                 275

acc gac ttc ctc ctc ctt acc cag aat aat tcc aag ttc cac ctt ggt     1099
Thr Asp Phe Leu Leu Leu Thr Gln Asn Asn Ser Lys Phe His Leu Gly
            280                 285                 290

tct atc atc aac atc acc gct aac ctc ccc tcc acc cag gac ctc ttg     1147
Ser Ile Ile Asn Ile Thr Ala Asn Leu Pro Ser Thr Gln Asp Leu Leu
        295                 300                 305

agc ttc cta cag atc cag ctt gag agt att aag aac agc aca ccc aca     1195
Ser Phe Leu Gln Ile Gln Leu Glu Ser Ile Lys Asn Ser Thr Pro Thr
    310                 315                 320

gtg gtg atg ttt ggc tgc gac atg gaa agt atc cgg cgg att ttc gaa     1243
Val Val Met Phe Gly Cys Asp Met Glu Ser Ile Arg Arg Ile Phe Glu
325                 330                 335                 340

att aca acc cag ttt ggg gtc atg ccc cct gaa ctt cgt tgg gtg ctg     1291
Ile Thr Thr Gln Phe Gly Val Met Pro Pro Glu Leu Arg Trp Val Leu
                345                 350                 355

gga gat tcc cag aat gtg gag gaa ctg agg aca gag ggt ctg ccc tta     1339
Gly Asp Ser Gln Asn Val Glu Glu Leu Arg Thr Glu Gly Leu Pro Leu
            360                 365                 370

ggg ctc att gct cat gga aaa aca aca cag tct gtc ttt gag cac tac     1387
Gly Leu Ile Ala His Gly Lys Thr Thr Gln Ser Val Phe Glu His Tyr
        375                 380                 385

gta caa gat gct atg gag ctg gtc gca aga gct gta gcc aca gcc acc     1435
Val Gln Asp Ala Met Glu Leu Val Ala Arg Ala Val Ala Thr Ala Thr
```

-continued

```
    390                 395                 400

atg atc caa cca gaa ctt gct ctc att ccc agc acg atg aac tgc atg     1483
Met Ile Gln Pro Glu Leu Ala Leu Ile Pro Ser Thr Met Asn Cys Met
405                 410                 415                 420

gag gtg gaa act aca aat ctc act tca gga caa tat tta tca agg ttt     1531
Glu Val Glu Thr Thr Asn Leu Thr Ser Gly Gln Tyr Leu Ser Arg Phe
                425                 430                 435

cta gcc aat acc act ttc aga ggc ctc agt ggt tcc atc aga gta aaa     1579
Leu Ala Asn Thr Thr Phe Arg Gly Leu Ser Gly Ser Ile Arg Val Lys
            440                 445                 450

ggt tcc acc atc gtc agc tca gaa aac aac ttt ttc atc tgg aat ctt     1627
Gly Ser Thr Ile Val Ser Ser Glu Asn Asn Phe Phe Ile Trp Asn Leu
        455                 460                 465

caa cat gac ccc atg gga aag cca atg tgg acc cgc ttg ggc agc tgg     1675
Gln His Asp Pro Met Gly Lys Pro Met Trp Thr Arg Leu Gly Ser Trp
    470                 475                 480

cag ggg gga aag att gtc atg gac tat gga ata tgg cca gag cag gcc     1723
Gln Gly Gly Lys Ile Val Met Asp Tyr Gly Ile Trp Pro Glu Gln Ala
485                 490                 495                 500

cag aga cac aaa acc cac ttc caa cat cca agt aag cta cac ttg aga     1771
Gln Arg His Lys Thr His Phe Gln His Pro Ser Lys Leu His Leu Arg
                505                 510                 515

gtg gtt acc ctg att gag cat cct ttt gtc ttc aca agg gag gta gat     1819
Val Val Thr Leu Ile Glu His Pro Phe Val Phe Thr Arg Glu Val Asp
            520                 525                 530

gat gaa ggc ttg tgc cct gct ggc caa ctc tgt cta gac ccc atg act     1867
Asp Glu Gly Leu Cys Pro Ala Gly Gln Leu Cys Leu Asp Pro Met Thr
        535                 540                 545

aat gac tct tcc aca ttg gac agc ctt ttt agc agc ctc cat agc agt     1915
Asn Asp Ser Ser Thr Leu Asp Ser Leu Phe Ser Ser Leu His Ser Ser
    550                 555                 560

aat gat aca gtg ccc att aaa ttc aag aag tgc tgc tat gga tat tgc     1963
Asn Asp Thr Val Pro Ile Lys Phe Lys Lys Cys Cys Tyr Gly Tyr Cys
565                 570                 575                 580

att gat ctg ctg gaa aag ata gca gaa gac atg aac ttt gac ttc gac     2011
Ile Asp Leu Leu Glu Lys Ile Ala Glu Asp Met Asn Phe Asp Phe Asp
                585                 590                 595

ctc tat att gta ggg gat gga aag tat gga gca tgg aaa aat ggg cac     2059
Leu Tyr Ile Val Gly Asp Gly Lys Tyr Gly Ala Trp Lys Asn Gly His
            600                 605                 610

tgg act ggg cta gtg ggt gat ctc ctg aga ggg act gcc cac atg gca     2107
Trp Thr Gly Leu Val Gly Asp Leu Leu Arg Gly Thr Ala His Met Ala
        615                 620                 625

gtc act tcc ttt agc atc aat act gca cgg agc cag gtg ata gat ttc     2155
Val Thr Ser Phe Ser Ile Asn Thr Ala Arg Ser Gln Val Ile Asp Phe
    630                 635                 640

acc agc cct ttc ttc tcc acc agc ttg ggc atc tta gtg agg acc cga     2203
Thr Ser Pro Phe Phe Ser Thr Ser Leu Gly Ile Leu Val Arg Thr Arg
645                 650                 655                 660

gat aca gca gct ccc att gga gcc ttc atg tgg cca ctc cac tgg aca     2251
Asp Thr Ala Ala Pro Ile Gly Ala Phe Met Trp Pro Leu His Trp Thr
                665                 670                 675

atg tgg ctg ggg att ttt gtg gct ctg cac atc act gcc gtc ttc ctc     2299
Met Trp Leu Gly Ile Phe Val Ala Leu His Ile Thr Ala Val Phe Leu
            680                 685                 690

act ctg tat gaa tgg aag agt cca ttt ggt ttg act ccc aag ggg cga     2347
Thr Leu Tyr Glu Trp Lys Ser Pro Phe Gly Leu Thr Pro Lys Gly Arg
        695                 700                 705

aat aga agt aaa gtc ttc tcc ttt tct tca gcc ttg aac atc tgt tat     2395
Asn Arg Ser Lys Val Phe Ser Phe Ser Ser Ala Leu Asn Ile Cys Tyr
```

```
    710                 715                 720

gcc ctc ttg ttt ggc aga aca gtg gcc atc aaa cct cca aaa tgt tgg     2443
Ala Leu Leu Phe Gly Arg Thr Val Ala Ile Lys Pro Pro Lys Cys Trp
725                 730                 735                 740

act gga agg ttt cta atg aac ctt tgg gcc att ttc tgt atg ttt tgc     2491
Thr Gly Arg Phe Leu Met Asn Leu Trp Ala Ile Phe Cys Met Phe Cys
                745                 750                 755

ctt tcc aca tac acg gca aac ttg gct gct gtc atg gta ggt gag aag     2539
Leu Ser Thr Tyr Thr Ala Asn Leu Ala Ala Val Met Val Gly Glu Lys
            760                 765                 770

atc tat gaa gag ctt tct gga ata cat gac ccc aag tta cat cat cct     2587
Ile Tyr Glu Glu Leu Ser Gly Ile His Asp Pro Lys Leu His His Pro
        775                 780                 785

tcc caa gga ttc cgc ttt gga act gtc cga gaa agc agt gct gaa gat     2635
Ser Gln Gly Phe Arg Phe Gly Thr Val Arg Glu Ser Ser Ala Glu Asp
    790                 795                 800

tat gtg aga caa agt ttc cca gag atg cat gaa tat atg aga agg tac     2683
Tyr Val Arg Gln Ser Phe Pro Glu Met His Glu Tyr Met Arg Arg Tyr
805                 810                 815                 820

aat gtt cca gcc acc cct gat gga gtg gag tat ctg aag aat gat cca     2731
Asn Val Pro Ala Thr Pro Asp Gly Val Glu Tyr Leu Lys Asn Asp Pro
                825                 830                 835

gag aaa cta gac gcc ttc atc atg gac aaa gcc ctt ctg gat tat gaa     2779
Glu Lys Leu Asp Ala Phe Ile Met Asp Lys Ala Leu Leu Asp Tyr Glu
            840                 845                 850

gtg tca ata gat gct gac tgc aaa ctt ctc act gtg ggg aag cca ttt     2827
Val Ser Ile Asp Ala Asp Cys Lys Leu Leu Thr Val Gly Lys Pro Phe
        855                 860                 865

gcc ata gaa gga tac ggc att ggc ctc cca ccc aac tct cca ttg acc     2875
Ala Ile Glu Gly Tyr Gly Ile Gly Leu Pro Pro Asn Ser Pro Leu Thr
    870                 875                 880

gcc aac ata tcc gag cta atc agt caa tac aag tca cat ggg ttt atg     2923
Ala Asn Ile Ser Glu Leu Ile Ser Gln Tyr Lys Ser His Gly Phe Met
885                 890                 895                 900

gat atg ctc cat gac aag tgg tac agg gtg gtt ccc tgt ggc aag aga     2971
Asp Met Leu His Asp Lys Trp Tyr Arg Val Val Pro Cys Gly Lys Arg
                905                 910                 915

agt ttt gct gtc acg gag act ttg caa atg ggc atc aaa cac ttc tct     3019
Ser Phe Ala Val Thr Glu Thr Leu Gln Met Gly Ile Lys His Phe Ser
            920                 925                 930

ggg ctc ttt gtg ctg ctg tgc att gga ttt ggt ctg tcc att ttg acc     3067
Gly Leu Phe Val Leu Leu Cys Ile Gly Phe Gly Leu Ser Ile Leu Thr
        935                 940                 945

acc att ggt gag cac ata gta tac agg ctg ctg cta cca cga atc aaa     3115
Thr Ile Gly Glu His Ile Val Tyr Arg Leu Leu Leu Pro Arg Ile Lys
    950                 955                 960

aac aaa tcc aag ctg caa tac tgg ctc cac acc agc cag aga tta cac     3163
Asn Lys Ser Lys Leu Gln Tyr Trp Leu His Thr Ser Gln Arg Leu His
965                 970                 975                 980

aga gca ata aat aca tca ttt ata gag gaa aag cag cag cat ttc aag     3211
Arg Ala Ile Asn Thr Ser Phe Ile Glu Glu Lys Gln Gln His Phe Lys
                985                 990                 995

acc aaa cgt gtg gaa aag agg tct aat gtg gga ccc cgt cag ctt acc     3259
Thr Lys Arg Val Glu Lys Arg Ser Asn Val Gly Pro Arg Gln Leu Thr
            1000                1005                1010

gta tgg aat act tcc aat ctg agt cat gac aac cga cgg aaa tac atc     3307
Val Trp Asn Thr Ser Asn Leu Ser His Asp Asn Arg Arg Lys Tyr Ile
        1015                1020                1025

ttt agt gat gag gaa gga caa aac cag ctg ggc atc cgg atc cac cag     3355
Phe Ser Asp Glu Glu Gly Gln Asn Gln Leu Gly Ile Arg Ile His Gln
```

-continued

```
    1030                1035                1040

gac atc ccc ctc cct cca agg aga aga gag ctc cct gcc ttg cgg acc      3403
Asp Ile Pro Leu Pro Pro Arg Arg Arg Glu Leu Pro Ala Leu Arg Thr
1045                1050                1055                1060

acc aat ggg aaa gca gac tcc cta aat gta tct cgg aac tca gtg atg      3451
Thr Asn Gly Lys Ala Asp Ser Leu Asn Val Ser Arg Asn Ser Val Met
                1065                1070                1075

cag gaa ctc tca gag ctc gag aag cag att cag gtg atc cgt cag gag      3499
Gln Glu Leu Ser Glu Leu Glu Lys Gln Ile Gln Val Ile Arg Gln Glu
            1080                1085                1090

ctg cag ctg gct gtg agc agg aaa acg gag ctg gag gag tat caa agg      3547
Leu Gln Leu Ala Val Ser Arg Lys Thr Glu Leu Glu Glu Tyr Gln Arg
        1095                1100                1105

aca agt cgg act tgt gag tcc tag                                      3571
Thr Ser Arg Thr Cys Glu Ser
    1110                1115


<210> SEQ ID NO 56
<211> LENGTH: 1115
<212> TYPE: PRT
<213> ORGANISM: Homo sapiens

<400> SEQUENCE: 56

Met Arg Arg Leu Ser Leu Trp Trp Leu Leu Ser Arg Val Cys Leu Leu
 1               5                  10                  15

Leu Pro Pro Pro Cys Ala Leu Val Leu Ala Gly Val Pro Ser Ser Ser
            20                  25                  30

Ser His Pro Gln Pro Cys Gln Ile Leu Lys Arg Ile Gly His Ala Val
        35                  40                  45

Arg Val Gly Ala Val His Leu Gln Pro Trp Thr Thr Ala Pro Arg Ala
    50                  55                  60

Ala Ser Arg Ala Pro Asp Asp Ser Arg Ala Gly Ala Gln Arg Asp Glu
65                  70                  75                  80

Pro Glu Pro Gly Thr Arg Arg Ser Pro Ala Pro Ser Pro Gly Ala Arg
                85                  90                  95

Trp Leu Gly Ser Thr Leu His Gly Arg Gly Pro Pro Gly Ser Arg Lys
            100                 105                 110

Pro Gly Glu Gly Ala Arg Ala Glu Ala Leu Trp Pro Arg Asp Ala Leu
        115                 120                 125

Leu Phe Ala Val Asp Asn Leu Asn Arg Val Glu Gly Leu Leu Pro Tyr
    130                 135                 140

Asn Leu Ser Leu Glu Val Val Met Ala Ile Glu Ala Gly Leu Gly Asp
145                 150                 155                 160

Leu Pro Leu Leu Pro Phe Ser Ser Pro Ser Ser Pro Trp Ser Ser Asp
                165                 170                 175

Pro Phe Ser Phe Leu Gln Ser Val Cys His Thr Val Val Val Gln Gly
            180                 185                 190

Val Ser Ala Leu Leu Ala Phe Pro Gln Ser Gln Gly Glu Met Met Glu
        195                 200                 205

Leu Asp Leu Val Ser Leu Val Leu His Ile Pro Val Ile Ser Ile Val
    210                 215                 220

Arg His Glu Phe Pro Arg Glu Ser Gln Asn Pro Leu His Leu Gln Leu
225                 230                 235                 240

Ser Leu Glu Asn Ser Leu Ser Ser Asp Ala Asp Val Thr Val Ser Ile
                245                 250                 255

Leu Thr Met Asn Asn Trp Tyr Asn Phe Ser Leu Leu Leu Cys Gln Glu
            260                 265                 270
```

```
Asp Trp Asn Ile Thr Asp Phe Leu Leu Leu Thr Gln Asn Asn Ser Lys
        275                 280                 285

Phe His Leu Gly Ser Ile Ile Asn Ile Thr Ala Asn Leu Pro Ser Thr
    290                 295                 300

Gln Asp Leu Leu Ser Phe Leu Gln Ile Gln Leu Glu Ser Ile Lys Asn
305                 310                 315                 320

Ser Thr Pro Thr Val Val Met Phe Gly Cys Asp Met Glu Ser Ile Arg
                325                 330                 335

Arg Ile Phe Glu Ile Thr Thr Gln Phe Gly Val Met Pro Pro Glu Leu
            340                 345                 350

Arg Trp Val Leu Gly Asp Ser Gln Asn Val Glu Glu Leu Arg Thr Glu
        355                 360                 365

Gly Leu Pro Leu Gly Leu Ile Ala His Gly Lys Thr Thr Gln Ser Val
    370                 375                 380

Phe Glu His Tyr Val Gln Asp Ala Met Glu Leu Val Ala Arg Ala Val
385                 390                 395                 400

Ala Thr Ala Thr Met Ile Gln Pro Glu Leu Ala Leu Ile Pro Ser Thr
                405                 410                 415

Met Asn Cys Met Glu Val Glu Thr Thr Asn Leu Thr Ser Gly Gln Tyr
            420                 425                 430

Leu Ser Arg Phe Leu Ala Asn Thr Thr Phe Arg Gly Leu Ser Gly Ser
        435                 440                 445

Ile Arg Val Lys Gly Ser Thr Ile Val Ser Ser Glu Asn Asn Phe Phe
    450                 455                 460

Ile Trp Asn Leu Gln His Asp Pro Met Gly Lys Pro Met Trp Thr Arg
465                 470                 475                 480

Leu Gly Ser Trp Gln Gly Gly Lys Ile Val Met Asp Tyr Gly Ile Trp
                485                 490                 495

Pro Glu Gln Ala Gln Arg His Lys Thr His Phe Gln His Pro Ser Lys
            500                 505                 510

Leu His Leu Arg Val Val Thr Leu Ile Glu His Pro Phe Val Phe Thr
        515                 520                 525

Arg Glu Val Asp Asp Glu Gly Leu Cys Pro Ala Gly Gln Leu Cys Leu
    530                 535                 540

Asp Pro Met Thr Asn Asp Ser Ser Thr Leu Asp Ser Leu Phe Ser Ser
545                 550                 555                 560

Leu His Ser Ser Asn Asp Thr Val Pro Ile Lys Phe Lys Lys Cys Cys
                565                 570                 575

Tyr Gly Tyr Cys Ile Asp Leu Leu Glu Lys Ile Ala Glu Asp Met Asn
            580                 585                 590

Phe Asp Phe Asp Leu Tyr Ile Val Gly Asp Gly Lys Tyr Gly Ala Trp
        595                 600                 605

Lys Asn Gly His Trp Thr Gly Leu Val Gly Asp Leu Leu Arg Gly Thr
    610                 615                 620

Ala His Met Ala Val Thr Ser Phe Ser Ile Asn Thr Ala Arg Ser Gln
625                 630                 635                 640

Val Ile Asp Phe Thr Ser Pro Phe Phe Ser Thr Ser Leu Gly Ile Leu
                645                 650                 655

Val Arg Thr Arg Asp Thr Ala Ala Pro Ile Gly Ala Phe Met Trp Pro
            660                 665                 670

Leu His Trp Thr Met Trp Leu Gly Ile Phe Val Ala Leu His Ile Thr
        675                 680                 685

Ala Val Phe Leu Thr Leu Tyr Glu Trp Lys Ser Pro Phe Gly Leu Thr
```

```
    690                 695                 700

Pro Lys Gly Arg Asn Arg Ser Lys Val Phe Ser Phe Ser Ser Ala Leu
705                 710                 715                 720

Asn Ile Cys Tyr Ala Leu Leu Phe Gly Arg Thr Val Ala Ile Lys Pro
                725                 730                 735

Pro Lys Cys Trp Thr Gly Arg Phe Leu Met Asn Leu Trp Ala Ile Phe
            740                 745                 750

Cys Met Phe Cys Leu Ser Thr Tyr Thr Ala Asn Leu Ala Ala Val Met
        755                 760                 765

Val Gly Glu Lys Ile Tyr Glu Glu Leu Ser Gly Ile His Asp Pro Lys
    770                 775                 780

Leu His His Pro Ser Gln Gly Phe Arg Phe Gly Thr Val Arg Glu Ser
785                 790                 795                 800

Ser Ala Glu Asp Tyr Val Arg Gln Ser Phe Pro Glu Met His Glu Tyr
                805                 810                 815

Met Arg Arg Tyr Asn Val Pro Ala Thr Pro Asp Gly Val Glu Tyr Leu
            820                 825                 830

Lys Asn Asp Pro Glu Lys Leu Asp Ala Phe Ile Met Asp Lys Ala Leu
        835                 840                 845

Leu Asp Tyr Glu Val Ser Ile Asp Ala Asp Cys Lys Leu Leu Thr Val
    850                 855                 860

Gly Lys Pro Phe Ala Ile Glu Gly Tyr Gly Ile Gly Leu Pro Pro Asn
865                 870                 875                 880

Ser Pro Leu Thr Ala Asn Ile Ser Glu Leu Ile Ser Gln Tyr Lys Ser
                885                 890                 895

His Gly Phe Met Asp Met Leu His Asp Lys Trp Tyr Arg Val Val Pro
            900                 905                 910

Cys Gly Lys Arg Ser Phe Ala Val Thr Glu Thr Leu Gln Met Gly Ile
        915                 920                 925

Lys His Phe Ser Gly Leu Phe Val Leu Leu Cys Ile Gly Phe Gly Leu
    930                 935                 940

Ser Ile Leu Thr Thr Ile Gly Glu His Ile Val Tyr Arg Leu Leu Leu
945                 950                 955                 960

Pro Arg Ile Lys Asn Lys Ser Lys Leu Gln Tyr Trp Leu His Thr Ser
                965                 970                 975

Gln Arg Leu His Arg Ala Ile Asn Thr Ser Phe Ile Glu Glu Lys Gln
            980                 985                 990

Gln His Phe Lys Thr Lys Arg Val Glu Lys Arg Ser Asn Val Gly Pro
        995                 1000                1005

Arg Gln Leu Thr Val Trp Asn Thr Ser Asn Leu Ser His Asp Asn Arg
    1010                1015                1020

Arg Lys Tyr Ile Phe Ser Asp Glu Glu Gly Gln Asn Gln Leu Gly Ile
1025                1030                1035                1040

Arg Ile His Gln Asp Ile Pro Leu Pro Pro Arg Arg Arg Glu Leu Pro
                1045                1050                1055

Ala Leu Arg Thr Thr Asn Gly Lys Ala Asp Ser Leu Asn Val Ser Arg
            1060                1065                1070

Asn Ser Val Met Gln Glu Leu Ser Glu Leu Glu Lys Gln Ile Gln Val
        1075                1080                1085

Ile Arg Gln Glu Leu Gln Leu Ala Val Ser Arg Lys Thr Glu Leu Glu
    1090                1095                1100

Glu Tyr Gln Arg Thr Ser Arg Thr Cys Glu Ser
1105                1110                1115
```

-continued

<210> SEQ ID NO 57
<211> LENGTH: 3178
<212> TYPE: DNA
<213> ORGANISM: Rattus sp
<220> FEATURE:
<221> NAME/KEY: CDS
<222> LOCATION: (76)...(3084)

<400> SEQUENCE: 57
gcacgagggg acaagagcgg gtctggctgg ggtgtctcct tcccttcgca cagcacagtg 60
gtaacttctt tcggg atg gag agt gtg cgg acg ctg tgg ctc agc gtg gcc 111
Met Glu Ser Val Arg Thr Leu Trp Leu Ser Val Ala
1 5 10 ctg gcg ctg gcg gtg ggg tcc cga gtg gtg cgc ggt cac cct cag ccc 159
Leu Ala Leu Ala Val Gly Ser Arg Val Val Arg Gly His Pro Gln Pro
15 20 25 tgc cgg gtt ccc acg cgc gct ggg gcc tcc gtg cgc ctg gcg gcg ctc 207
Cys Arg Val Pro Thr Arg Ala Gly Ala Ser Val Arg Leu Ala Ala Leu
30 35 40 ctg ccc cgg gcg ccc gcc gcc cgc gcc cgc gtc cta gct gcc ctg gcc 255
Leu Pro Arg Ala Pro Ala Ala Arg Ala Arg Val Leu Ala Ala Leu Ala
45 50 55 60 acc cct gcg ccg cgg ctg ccg cac aac ctg agt ctg gaa ctg gtg gcc 303
Thr Pro Ala Pro Arg Leu Pro His Asn Leu Ser Leu Glu Leu Val Ala
65 70 75 gtc gcg tcc ccg acc cgg gac ccc gcg tcg cta gct cga ggt ctg tgc 351
Val Ala Ser Pro Thr Arg Asp Pro Ala Ser Leu Ala Arg Gly Leu Cys
80 85 90 cag gtt ctg gca ccg cct ggc gtg gtg gcc tct ata gcc ttt ccc gag 399
Gln Val Leu Ala Pro Pro Gly Val Val Ala Ser Ile Ala Phe Pro Glu
95 100 105 gcg cgg ccc gag ctg cgg cta ctg cag ttc ctg gca gcc gcc aca gag 447
Ala Arg Pro Glu Leu Arg Leu Leu Gln Phe Leu Ala Ala Ala Thr Glu
110 115 120 acc cca gtg gtg agc gtc ctg cgg agg gag gtg cgc acg gcc ctc gga 495
Thr Pro Val Val Ser Val Leu Arg Arg Glu Val Arg Thr Ala Leu Gly
125 130 135 140 gcc ccg act ccg ttc cat ctg cag ctg gac tgg gct agt ccc ctg gag 543
Ala Pro Thr Pro Phe His Leu Gln Leu Asp Trp Ala Ser Pro Leu Glu
145 150 155 acc ata ctg gat gtg ctg gtg tcc ctg gta cgg gca cat gcc tgg gag 591
Thr Ile Leu Asp Val Leu Val Ser Leu Val Arg Ala His Ala Trp Glu
160 165 170 gac att gct cta gta ctc tgc cgt gtc cgg gac cct ggc agc ctg gtg 639
Asp Ile Ala Leu Val Leu Cys Arg Val Arg Asp Pro Gly Ser Leu Val
175 180 185 aca ctc tgg act aac cat gct agc cag gct cca aag ttt gtg ctg gac 687
Thr Leu Trp Thr Asn His Ala Ser Gln Ala Pro Lys Phe Val Leu Asp
190 195 200 ctg agc cgg ctg gac agc agg aat gac agc ctt cgg gct gga ctg gcc 735
Leu Ser Arg Leu Asp Ser Arg Asn Asp Ser Leu Arg Ala Gly Leu Ala
205 210 215 220 ctg ttg ggg gcg ctg gaa gga ggg gga acc cca gtg cct gca gca gtc 783
Leu Leu Gly Ala Leu Glu Gly Gly Gly Thr Pro Val Pro Ala Ala Val
225 230 235 ctc cta ggc tgc agc act gcc cgt gca cat gag gtc cta gag gct gca 831
Leu Leu Gly Cys Ser Thr Ala Arg Ala His Glu Val Leu Glu Ala Ala
240 245 250 cca ccg ggt ccc cag tgg ttg ctg ggc aca cca ttg ccc gct gag gca 879
Pro Pro Gly Pro Gln Trp Leu Leu Gly Thr Pro Leu Pro Ala Glu Ala
255 260 265

```
ctg ccc acg act ggt ctg cca cct ggc gtg ctg gcg ctg ggg gaa acc      927
Leu Pro Thr Thr Gly Leu Pro Pro Gly Val Leu Ala Leu Gly Glu Thr
    270                 275                 280

gaa caa cac tct ctg gaa gct gtc gtc cac gac atg gtg gag ctt gtg      975
Glu Gln His Ser Leu Glu Ala Val Val His Asp Met Val Glu Leu Val
285                 290                 295                 300

gct cag gca ctc agt agc atg gcc ctt gta cac cca gag cgg gca ctg     1023
Ala Gln Ala Leu Ser Ser Met Ala Leu Val His Pro Glu Arg Ala Leu
                305                 310                 315

ctt cca gct gtg gtg aac tgt gat gac ctg aaa aca ggc gga tct gag     1071
Leu Pro Ala Val Val Asn Cys Asp Asp Leu Lys Thr Gly Gly Ser Glu
            320                 325                 330

gca aca ggg cgc acc ttg gct cgg ttt ctc ggc aac acc tca ttt cag     1119
Ala Thr Gly Arg Thr Leu Ala Arg Phe Leu Gly Asn Thr Ser Phe Gln
        335                 340                 345

ggc cga aca ggg gcc gtg tgg gtg aca ggc tcc tct cag gtg cat gtg     1167
Gly Arg Thr Gly Ala Val Trp Val Thr Gly Ser Ser Gln Val His Val
    350                 355                 360

tct cgg cat ttc aag gta tgg agc ctg cgc cgg gat ccg ctg ggt gcc     1215
Ser Arg His Phe Lys Val Trp Ser Leu Arg Arg Asp Pro Leu Gly Ala
365                 370                 375                 380

cca gcc tgg gca acc gtg ggc agc tgg cag gat gga cag ctg gac ttc     1263
Pro Ala Trp Ala Thr Val Gly Ser Trp Gln Asp Gly Gln Leu Asp Phe
                385                 390                 395

cag cca ggg gca gcc gct ctc cga gtc cca tct ccg tct ggc acc cag     1311
Gln Pro Gly Ala Ala Ala Leu Arg Val Pro Ser Pro Ser Gly Thr Gln
            400                 405                 410

gcc cga cca aag ctg cgt gtg gta acc ctg gtg gaa cac ccg ttt gtg     1359
Ala Arg Pro Lys Leu Arg Val Val Thr Leu Val Glu His Pro Phe Val
        415                 420                 425

ttc acc agg gaa tct gat gaa gac gga cag tgc cca gct ggg cag ctg     1407
Phe Thr Arg Glu Ser Asp Glu Asp Gly Gln Cys Pro Ala Gly Gln Leu
    430                 435                 440

tgt ctg gac cca ggc acc aat gac tca gcc agg ctg gat gcc ctc ttt     1455
Cys Leu Asp Pro Gly Thr Asn Asp Ser Ala Arg Leu Asp Ala Leu Phe
445                 450                 455                 460

gct gca ctg gtg aat ggc tca gta cct cga acg ctg aga aga tgc tgc     1503
Ala Ala Leu Val Asn Gly Ser Val Pro Arg Thr Leu Arg Arg Cys Cys
                465                 470                 475

tat ggc tac tgc atc gac ctg ctg gag cgg ctg gcc gag gac ctg gcc     1551
Tyr Gly Tyr Cys Ile Asp Leu Leu Glu Arg Leu Ala Glu Asp Leu Ala
            480                 485                 490

ttt gac ttt gag ctc tat att gtg ggg gat ggc aag tac ggg gcc ctg     1599
Phe Asp Phe Glu Leu Tyr Ile Val Gly Asp Gly Lys Tyr Gly Ala Leu
        495                 500                 505

cgt gat ggg cgc tgg acg ggc ctg gtg ggt gac ctg ctg gct ggc cgg     1647
Arg Asp Gly Arg Trp Thr Gly Leu Val Gly Asp Leu Leu Ala Gly Arg
    510                 515                 520

gca cac atg gct gtg acc agc ttc agc atc aac tca gct cgc tct cag     1695
Ala His Met Ala Val Thr Ser Phe Ser Ile Asn Ser Ala Arg Ser Gln
525                 530                 535                 540

gtg gtg gat ttc acc agc cct ttc ttc tcc acc agc ctg ggg att atg     1743
Val Val Asp Phe Thr Ser Pro Phe Phe Ser Thr Ser Leu Gly Ile Met
                545                 550                 555

gtg cgc acg aga gac acg gcc tcg ccc atc ggg gct ttc atg tgg ccc     1791
Val Arg Thr Arg Asp Thr Ala Ser Pro Ile Gly Ala Phe Met Trp Pro
            560                 565                 570

ctg cac tgg tcc atg tgg gtg ggc gtg ttt gct gct ctg cac ctc aca     1839
Leu His Trp Ser Met Trp Val Gly Val Phe Ala Ala Leu His Leu Thr
        575                 580                 585
```

-continued

```
gcg ctc ttt ctc acc ctg tac gaa tgg cga agt ccc tac ggg ctc acg     1887
Ala Leu Phe Leu Thr Leu Tyr Glu Trp Arg Ser Pro Tyr Gly Leu Thr
    590                 595                 600

ccg cgc ggc cgc aac cgt ggc act gtc ttc tct tac tcc tcc gcg ctc     1935
Pro Arg Gly Arg Asn Arg Gly Thr Val Phe Ser Tyr Ser Ser Ala Leu
605                 610                 615                 620

aac ctg tgc tat gcc att ctc ttt gga cgc act gtc tcc agt aag acg     1983
Asn Leu Cys Tyr Ala Ile Leu Phe Gly Arg Thr Val Ser Ser Lys Thr
                625                 630                 635

ccc aag tgc cct act gga cgc ttc ctc atg aac ctc tgg gca atc ttc     2031
Pro Lys Cys Pro Thr Gly Arg Phe Leu Met Asn Leu Trp Ala Ile Phe
            640                 645                 650

tgc ctg ctg gtg ctt tcc agt tac acg gcc aac ctg gct gct gtc atg     2079
Cys Leu Leu Val Leu Ser Ser Tyr Thr Ala Asn Leu Ala Ala Val Met
        655                 660                 665

gtt ggg gac aaa acc ttt gag gag ctg tct gga atc cat gat ccc aag     2127
Val Gly Asp Lys Thr Phe Glu Glu Leu Ser Gly Ile His Asp Pro Lys
    670                 675                 680

ctg cac cac cct tcc caa ggc ttt cgc ttt ggc acc gta tgg gag agc     2175
Leu His His Pro Ser Gln Gly Phe Arg Phe Gly Thr Val Trp Glu Ser
685                 690                 695                 700

agc gcg gag gcc tac atc aag gca agc ttc cct gag atg cac gca cac     2223
Ser Ala Glu Ala Tyr Ile Lys Ala Ser Phe Pro Glu Met His Ala His
                705                 710                 715

atg cgt cgg cac agc gca ccc acc act cca cat ggg gtg gcc atg ctc     2271
Met Arg Arg His Ser Ala Pro Thr Thr Pro His Gly Val Ala Met Leu
            720                 725                 730

acg agc gac ccg ccc aag ctc aac gcc ttc atc atg gat aaa tca cta     2319
Thr Ser Asp Pro Pro Lys Leu Asn Ala Phe Ile Met Asp Lys Ser Leu
        735                 740                 745

ctg gac tat gag gtg tcc ata gat gcg gac tgc aag ctg ctc acc gtt     2367
Leu Asp Tyr Glu Val Ser Ile Asp Ala Asp Cys Lys Leu Leu Thr Val
    750                 755                 760

ggc aaa ccc ttt gct atc gag ggc tac ggc ata ggg cta ccc caa aac     2415
Gly Lys Pro Phe Ala Ile Glu Gly Tyr Gly Ile Gly Leu Pro Gln Asn
765                 770                 775                 780

tcg ccg ctc acc tcc aac ctg tcg gag ttc atc agt agg tac aag tct     2463
Ser Pro Leu Thr Ser Asn Leu Ser Glu Phe Ile Ser Arg Tyr Lys Ser
                785                 790                 795

tca ggc ttc att gat ctg ctc cat gac aag tgg tac aag atg gtg cct     2511
Ser Gly Phe Ile Asp Leu Leu His Asp Lys Trp Tyr Lys Met Val Pro
            800                 805                 810

tgc ggg aag cgg gtg ttc gcc gtg acg gag acg ctg cag atg ggg gtc     2559
Cys Gly Lys Arg Val Phe Ala Val Thr Glu Thr Leu Gln Met Gly Val
        815                 820                 825

tac cac ttc tca gga ttg ttt gtc ctg ctg tgc ctc ggg ctg ggc agc     2607
Tyr His Phe Ser Gly Leu Phe Val Leu Leu Cys Leu Gly Leu Gly Ser
    830                 835                 840

gcg ctt ctc acc tct ctg ggt gag cat gtc ttc tac cgc ctg gtg ctg     2655
Ala Leu Leu Thr Ser Leu Gly Glu His Val Phe Tyr Arg Leu Val Leu
845                 850                 855                 860

ccg cgc atc cgc agg ggt aat aag ctg cag tat tgg ctt cac acg agc     2703
Pro Arg Ile Arg Arg Gly Asn Lys Leu Gln Tyr Trp Leu His Thr Ser
                865                 870                 875

cag aag atc cac cga gcc ctc aat aca gga cca ccc gag ggg caa cag     2751
Gln Lys Ile His Arg Ala Leu Asn Thr Gly Pro Pro Glu Gly Gln Gln
            880                 885                 890

gag agg gca gag cag gag cgc agc ggc ccc aag gac gag ctg cct gcc     2799
Glu Arg Ala Glu Gln Glu Arg Ser Gly Pro Lys Asp Glu Leu Pro Ala
        895                 900                 905
```

```
acc gat ggt gca ggg cgc tgg agg cgg gtg cgc cgg gct gtg gaa cgg      2847
Thr Asp Gly Ala Gly Arg Trp Arg Arg Val Arg Arg Ala Val Glu Arg
    910                 915                 920

gag cga cgc gtg cgt ttc ctg ctg gaa cct ggg gag gct ggc gga gac      2895
Glu Arg Arg Val Arg Phe Leu Leu Glu Pro Gly Glu Ala Gly Gly Asp
925                 930                 935                 940

cgc ccg tgg ctc tgc tcc aac ggg ccc ggg ctg caa gcg gag ctg cgg      2943
Arg Pro Trp Leu Cys Ser Asn Gly Pro Gly Leu Gln Ala Glu Leu Arg
                945                 950                 955

gag ctg gag ctg cgc att gag gct gca cgg gag cgg ctg cgc agt gcg      2991
Glu Leu Glu Leu Arg Ile Glu Ala Ala Arg Glu Arg Leu Arg Ser Ala
            960                 965                 970

ctg ttg cgg cgc ggg gag ctg cgg gcc ctg ctt ggg gat ggc acc cgg      3039
Leu Leu Arg Arg Gly Glu Leu Arg Ala Leu Leu Gly Asp Gly Thr Arg
        975                 980                 985

ctc agg cca ctg cgc ctg ttg cat gcg gcg cct gct gag agc tga          3084
Leu Arg Pro Leu Arg Leu Leu His Ala Ala Pro Ala Glu Ser  *
     990                 995                 1000

ggaaccacaa ggccgcactg tccacgacag tttattctat atacaaacac gactctgtac   3144

actgcaatta aatagcgtgg aacgtgaaaa aaaa                               3178


<210> SEQ ID NO 58
<211> LENGTH: 1002
<212> TYPE: PRT
<213> ORGANISM: Rattus sp

<400> SEQUENCE: 58

Met Glu Ser Val Arg Thr Leu Trp Leu Ser Val Ala Leu Ala Leu Ala
 1               5                  10                  15

Val Gly Ser Arg Val Val Arg Gly His Pro Gln Pro Cys Arg Val Pro
            20                  25                  30

Thr Arg Ala Gly Ala Ser Val Arg Leu Ala Ala Leu Leu Pro Arg Ala
        35                  40                  45

Pro Ala Ala Arg Ala Arg Val Leu Ala Ala Leu Ala Thr Pro Ala Pro
     50                  55                  60

Arg Leu Pro His Asn Leu Ser Leu Glu Leu Val Ala Val Ala Ser Pro
 65                  70                  75                  80

Thr Arg Asp Pro Ala Ser Leu Ala Arg Gly Leu Cys Gln Val Leu Ala
                85                  90                  95

Pro Pro Gly Val Val Ala Ser Ile Ala Phe Pro Glu Ala Arg Pro Glu
            100                 105                 110

Leu Arg Leu Leu Gln Phe Leu Ala Ala Ala Thr Glu Thr Pro Val Val
        115                 120                 125

Ser Val Leu Arg Arg Glu Val Arg Thr Ala Leu Gly Ala Pro Thr Pro
    130                 135                 140

Phe His Leu Gln Leu Asp Trp Ala Ser Pro Leu Glu Thr Ile Leu Asp
145                 150                 155                 160

Val Leu Val Ser Leu Val Arg Ala His Ala Trp Glu Asp Ile Ala Leu
                165                 170                 175

Val Leu Cys Arg Val Arg Asp Pro Gly Ser Leu Val Thr Leu Trp Thr
            180                 185                 190

Asn His Ala Ser Gln Ala Pro Lys Phe Val Leu Asp Leu Ser Arg Leu
        195                 200                 205

Asp Ser Arg Asn Asp Ser Leu Arg Ala Gly Leu Ala Leu Leu Gly Ala
    210                 215                 220

Leu Glu Gly Gly Gly Thr Pro Val Pro Ala Ala Val Leu Leu Gly Cys
```

-continued

```
225                 230                 235                 240

Ser Thr Ala Arg Ala His Glu Val Leu Glu Ala Ala Pro Pro Gly Pro
                245                 250                 255

Gln Trp Leu Leu Gly Thr Pro Leu Pro Ala Glu Ala Leu Pro Thr Thr
            260                 265                 270

Gly Leu Pro Pro Gly Val Leu Ala Leu Gly Glu Thr Glu Gln His Ser
        275                 280                 285

Leu Glu Ala Val Val His Asp Met Val Glu Leu Val Ala Gln Ala Leu
    290                 295                 300

Ser Ser Met Ala Leu Val His Pro Glu Arg Ala Leu Leu Pro Ala Val
305                 310                 315                 320

Val Asn Cys Asp Asp Leu Lys Thr Gly Gly Ser Glu Ala Thr Gly Arg
                325                 330                 335

Thr Leu Ala Arg Phe Leu Gly Asn Thr Ser Phe Gln Gly Arg Thr Gly
            340                 345                 350

Ala Val Trp Val Thr Gly Ser Ser Gln Val His Val Ser Arg His Phe
        355                 360                 365

Lys Val Trp Ser Leu Arg Arg Asp Pro Leu Gly Ala Pro Ala Trp Ala
    370                 375                 380

Thr Val Gly Ser Trp Gln Asp Gly Gln Leu Asp Phe Gln Pro Gly Ala
385                 390                 395                 400

Ala Ala Leu Arg Val Pro Ser Pro Ser Gly Thr Gln Ala Arg Pro Lys
                405                 410                 415

Leu Arg Val Val Thr Leu Val Glu His Pro Phe Val Phe Thr Arg Glu
            420                 425                 430

Ser Asp Glu Asp Gly Gln Cys Pro Ala Gly Gln Leu Cys Leu Asp Pro
        435                 440                 445

Gly Thr Asn Asp Ser Ala Arg Leu Asp Ala Leu Phe Ala Ala Leu Val
    450                 455                 460

Asn Gly Ser Val Pro Arg Thr Leu Arg Arg Cys Cys Tyr Gly Tyr Cys
465                 470                 475                 480

Ile Asp Leu Leu Glu Arg Leu Ala Glu Asp Leu Ala Phe Asp Phe Glu
                485                 490                 495

Leu Tyr Ile Val Gly Asp Gly Lys Tyr Gly Ala Leu Arg Asp Gly Arg
            500                 505                 510

Trp Thr Gly Leu Val Gly Asp Leu Leu Ala Gly Arg Ala His Met Ala
        515                 520                 525

Val Thr Ser Phe Ser Ile Asn Ser Ala Arg Ser Gln Val Val Asp Phe
    530                 535                 540

Thr Ser Pro Phe Phe Ser Thr Ser Leu Gly Ile Met Val Arg Thr Arg
545                 550                 555                 560

Asp Thr Ala Ser Pro Ile Gly Ala Phe Met Trp Pro Leu His Trp Ser
                565                 570                 575

Met Trp Val Gly Val Phe Ala Ala Leu His Leu Thr Ala Leu Phe Leu
            580                 585                 590

Thr Leu Tyr Glu Trp Arg Ser Pro Tyr Gly Leu Thr Pro Arg Gly Arg
        595                 600                 605

Asn Arg Gly Thr Val Phe Ser Tyr Ser Ser Ala Leu Asn Leu Cys Tyr
    610                 615                 620

Ala Ile Leu Phe Gly Arg Thr Val Ser Ser Lys Thr Pro Lys Cys Pro
625                 630                 635                 640

Thr Gly Arg Phe Leu Met Asn Leu Trp Ala Ile Phe Cys Leu Leu Val
                645                 650                 655
```

```
Leu Ser Ser Tyr Thr Ala Asn Leu Ala Ala Val Met Val Gly Asp Lys
            660                 665                 670

Thr Phe Glu Glu Leu Ser Gly Ile His Asp Pro Lys Leu His His Pro
        675                 680                 685

Ser Gln Gly Phe Arg Phe Gly Thr Val Trp Glu Ser Ser Ala Glu Ala
    690                 695                 700

Tyr Ile Lys Ala Ser Phe Pro Glu Met His Ala His Met Arg Arg His
705                 710                 715                 720

Ser Ala Pro Thr Thr Pro His Gly Val Ala Met Leu Thr Ser Asp Pro
                725                 730                 735

Pro Lys Leu Asn Ala Phe Ile Met Asp Lys Ser Leu Leu Asp Tyr Glu
            740                 745                 750

Val Ser Ile Asp Ala Asp Cys Lys Leu Leu Thr Val Gly Lys Pro Phe
        755                 760                 765

Ala Ile Glu Gly Tyr Gly Ile Gly Leu Pro Gln Asn Ser Pro Leu Thr
    770                 775                 780

Ser Asn Leu Ser Glu Phe Ile Ser Arg Tyr Lys Ser Ser Gly Phe Ile
785                 790                 795                 800

Asp Leu Leu His Asp Lys Trp Tyr Lys Met Val Pro Cys Gly Lys Arg
                805                 810                 815

Val Phe Ala Val Thr Glu Thr Leu Gln Met Gly Val Tyr His Phe Ser
            820                 825                 830

Gly Leu Phe Val Leu Leu Cys Leu Gly Leu Gly Ser Ala Leu Leu Thr
        835                 840                 845

Ser Leu Gly Glu His Val Phe Tyr Arg Leu Val Leu Pro Arg Ile Arg
    850                 855                 860

Arg Gly Asn Lys Leu Gln Tyr Trp Leu His Thr Ser Gln Lys Ile His
865                 870                 875                 880

Arg Ala Leu Asn Thr Gly Pro Pro Glu Gly Gln Gln Glu Arg Ala Glu
                885                 890                 895

Gln Glu Arg Ser Gly Pro Lys Asp Glu Leu Pro Ala Thr Asp Gly Ala
            900                 905                 910

Gly Arg Trp Arg Arg Val Arg Arg Ala Val Glu Arg Glu Arg Arg Val
        915                 920                 925

Arg Phe Leu Leu Glu Pro Gly Glu Ala Gly Gly Asp Arg Pro Trp Leu
    930                 935                 940

Cys Ser Asn Gly Pro Gly Leu Gln Ala Glu Leu Arg Glu Leu Glu Leu
945                 950                 955                 960

Arg Ile Glu Ala Ala Arg Glu Arg Leu Arg Ser Ala Leu Leu Arg Arg
                965                 970                 975

Gly Glu Leu Arg Ala Leu Leu Gly Asp Gly Thr Arg Leu Arg Pro Leu
            980                 985                 990

Arg Leu Leu His Ala Ala Pro Ala Glu Ser
        995                 1000


<210> SEQ ID NO 59
<211> LENGTH: 3133
<212> TYPE: DNA
<213> ORGANISM: Rattus sp.
<220> FEATURE:
<221> NAME/KEY: CDS
<222> LOCATION: (76)...(3036)

<400> SEQUENCE: 59

gcacgagggg acaagagcgg gtctggctgg ggtgtctcct tcccttcgca cagcacagtg      60

gtaacttctt tcggg atg gag agt gtg cgg acg ctg tgg ctc agc gtg gcc      111
```

-continued

Met Glu Ser Val Arg Thr Leu Trp Leu Ser Val Ala
1 5 10 ctg gcg ctg gcg gtg ggg tcc cga gtg gtg cgc ggt cac cct cag ccc 159
Leu Ala Leu Ala Val Gly Ser Arg Val Val Arg Gly His Pro Gln Pro
15 20 25 tgc cgg gtt ccc acg cgc gct ggg gcc tcc gtg cgc ctg gcg gcg ctc 207
Cys Arg Val Pro Thr Arg Ala Gly Ala Ser Val Arg Leu Ala Ala Leu
30 35 40 ctg ccc cgg gcg ccc gcc gcc cgc gcc cgc gtc cta gct gcc ctg gcc 255
Leu Pro Arg Ala Pro Ala Ala Arg Ala Arg Val Leu Ala Ala Leu Ala
45 50 55 60 acc cct gcg ccg cgg ctg ccg cac aac ctg agt ctg gaa ctg gtg gcc 303
Thr Pro Ala Pro Arg Leu Pro His Asn Leu Ser Leu Glu Leu Val Ala
65 70 75 gtc gcg tcc ccg acc cgg gac ccc gcg tcg cta gct cga ggt ctg tgc 351
Val Ala Ser Pro Thr Arg Asp Pro Ala Ser Leu Ala Arg Gly Leu Cys
80 85 90 cag gtt ctg gca ccg cct ggc gtg gtg gcc tct ata gcc ttt ccc gag 399
Gln Val Leu Ala Pro Pro Gly Val Val Ala Ser Ile Ala Phe Pro Glu
95 100 105 gcg cgg ccc gag ctg cgg cta ctg cag ttc ctg gca gcc gcc aca gag 447
Ala Arg Pro Glu Leu Arg Leu Leu Gln Phe Leu Ala Ala Ala Thr Glu
110 115 120 acc cca gtg act ccg ttc cat ctg cag ctg gac tgg gct agt ccc ctg 495
Thr Pro Val Thr Pro Phe His Leu Gln Leu Asp Trp Ala Ser Pro Leu
125 130 135 140 gag acc ata ctg gat gtg ctg gtg tcc ctg gta cgg gca cat gcc tgg 543
Glu Thr Ile Leu Asp Val Leu Val Ser Leu Val Arg Ala His Ala Trp
145 150 155 gag gac att gct cta gta ctc tgc cgt gtc cgg gac cct ggc agc ctg 591
Glu Asp Ile Ala Leu Val Leu Cys Arg Val Arg Asp Pro Gly Ser Leu
160 165 170 gtg aca ctc tgg act aac cat gct agc cag gct cca aag ttt gtg ctg 639
Val Thr Leu Trp Thr Asn His Ala Ser Gln Ala Pro Lys Phe Val Leu
175 180 185 gac ctg agc cgg ctg gac agc agg aat gac agc ctt cgg gct gga ctg 687
Asp Leu Ser Arg Leu Asp Ser Arg Asn Asp Ser Leu Arg Ala Gly Leu
190 195 200 gcc ctg ttg ggg gcg ctg gaa gga ggg gga acc cca gtg cct gca gca 735
Ala Leu Leu Gly Ala Leu Glu Gly Gly Gly Thr Pro Val Pro Ala Ala
205 210 215 220 gtc ctc cta ggc tgc agc act gcc cgt gca cat gag gtc cta gag gct 783
Val Leu Leu Gly Cys Ser Thr Ala Arg Ala His Glu Val Leu Glu Ala
225 230 235 gca cca ccg ggt ccc cag tgg ttg ctg ggc aca cca ttg ccc gct gag 831
Ala Pro Pro Gly Pro Gln Trp Leu Leu Gly Thr Pro Leu Pro Ala Glu
240 245 250 gca ctg ccc acg act ggt ctg cca cct ggc gtg ctg gcg ctg ggg gaa 879
Ala Leu Pro Thr Thr Gly Leu Pro Pro Gly Val Leu Ala Leu Gly Glu
255 260 265 acc gaa caa cac tct ctg gaa gct gtc gtc cac gac atg gtg gag ctt 927
Thr Glu Gln His Ser Leu Glu Ala Val Val His Asp Met Val Glu Leu
270 275 280 gtg gct cag gca ctc agt agc atg gcc ctt gta cac cca gag cgg gca 975
Val Ala Gln Ala Leu Ser Ser Met Ala Leu Val His Pro Glu Arg Ala
285 290 295 300 ctg ctt cca gct gtg gtg aac tgt gat gac ctg aaa aca ggc gga tct 1023
Leu Leu Pro Ala Val Val Asn Cys Asp Asp Leu Lys Thr Gly Gly Ser
305 310 315 gag gca aca ggg cgc acc ttg gct cgg ttt ctc ggc aac acc tca ttt 1071

-continued

```
Glu Ala Thr Gly Arg Thr Leu Ala Arg Phe Leu Gly Asn Thr Ser Phe
                320                 325                 330

cag ggc cga aca ggg gcc gtg tgg gtg aca ggc tcc tct cag gtg cat      1119
Gln Gly Arg Thr Gly Ala Val Trp Val Thr Gly Ser Ser Gln Val His
            335                 340                 345

gtg tct cgg cat ttc aag gta tgg agc ctg cgc cgg gat ccg ctg ggt      1167
Val Ser Arg His Phe Lys Val Trp Ser Leu Arg Arg Asp Pro Leu Gly
        350                 355                 360

gcc cca gcc tgg gca acc gtg ggc agc tgg cag gat gga cag ctg gac      1215
Ala Pro Ala Trp Ala Thr Val Gly Ser Trp Gln Asp Gly Gln Leu Asp
365                 370                 375                 380

ttc cag cca ggg gca gcc gct ctc cga gtc cca tct ccg tct ggc acc      1263
Phe Gln Pro Gly Ala Ala Ala Leu Arg Val Pro Ser Pro Ser Gly Thr
                385                 390                 395

cag gcc cga cca aag ctg cgt gtg gta acc ctg gtg gaa cac ccg ttt      1311
Gln Ala Arg Pro Lys Leu Arg Val Val Thr Leu Val Glu His Pro Phe
                400                 405                 410

gtg ttc acc agg gaa tct gat gaa gac gga cag tgc cca gct ggg cag      1359
Val Phe Thr Arg Glu Ser Asp Glu Asp Gly Gln Cys Pro Ala Gly Gln
            415                 420                 425

ctg tgt ctg gac cca ggc acc aat gac tca gcc agg ctg gat gcc ctc      1407
Leu Cys Leu Asp Pro Gly Thr Asn Asp Ser Ala Arg Leu Asp Ala Leu
        430                 435                 440

ttt gct gca ctg gtg aat ggc tca gta cct cga acg ctg aga aga tgc      1455
Phe Ala Ala Leu Val Asn Gly Ser Val Pro Arg Thr Leu Arg Arg Cys
445                 450                 455                 460

tgc tat ggc tac tgc atc gac ctg ctg gag cgg ctg gcc gag gac ctg      1503
Cys Tyr Gly Tyr Cys Ile Asp Leu Leu Glu Arg Leu Ala Glu Asp Leu
                465                 470                 475

gcc ttt gac ttt gag ctc tat att gtg ggg gat ggc aag tac ggg gcc      1551
Ala Phe Asp Phe Glu Leu Tyr Ile Val Gly Asp Gly Lys Tyr Gly Ala
                480                 485                 490

ctg cgt gat ggg cgc tgg acg ggc ctg gtg ggt gac ctg ctg gct ggc      1599
Leu Arg Asp Gly Arg Trp Thr Gly Leu Val Gly Asp Leu Leu Ala Gly
            495                 500                 505

cgg gca cac atg gct gtg acc agc ttc agc atc aac tca gct cgc tct      1647
Arg Ala His Met Ala Val Thr Ser Phe Ser Ile Asn Ser Ala Arg Ser
        510                 515                 520

cag gtg gtg gat ttc acc agc cct ttc ttc tcc acc agc ctg ggg att      1695
Gln Val Val Asp Phe Thr Ser Pro Phe Phe Ser Thr Ser Leu Gly Ile
525                 530                 535                 540

atg gtg cgc acg aga gac acg gcc tcg ccc atc ggg gct ttc atg tgg      1743
Met Val Arg Thr Arg Asp Thr Ala Ser Pro Ile Gly Ala Phe Met Trp
                545                 550                 555

ccc ctg cac tgg tcc atg tgg gtg ggc gtg ttt gct gct ctg cac ctc      1791
Pro Leu His Trp Ser Met Trp Val Gly Val Phe Ala Ala Leu His Leu
                560                 565                 570

aca gcg ctc ttt ctc acc ctg tac gaa tgg cga agt ccc tac ggg ctc      1839
Thr Ala Leu Phe Leu Thr Leu Tyr Glu Trp Arg Ser Pro Tyr Gly Leu
            575                 580                 585

acg ccg cgc ggc cgc aac cgt ggc act gtc ttc tct tac tcc tcc gcg      1887
Thr Pro Arg Gly Arg Asn Arg Gly Thr Val Phe Ser Tyr Ser Ser Ala
        590                 595                 600

ctc aac ctg tgc tat gcc att ctc ttt gga cgc act gtc tcc agt aag      1935
Leu Asn Leu Cys Tyr Ala Ile Leu Phe Gly Arg Thr Val Ser Ser Lys
605                 610                 615                 620

acg ccc aag tgc cct act gga cgc ttc ctc atg aac ctc tgg gca atc      1983
Thr Pro Lys Cys Pro Thr Gly Arg Phe Leu Met Asn Leu Trp Ala Ile
                625                 630                 635

ttc tgc ctg ctg gtg ctt tcc agt tac acg gcc aac ctg gct gct gtc      2031
```

```
Phe Cys Leu Leu Val Leu Ser Ser Tyr Thr Ala Asn Leu Ala Ala Val
            640                 645                 650

atg gtt ggg gac aaa acc ttt gag gag ctg tct gga atc cat gat ccc     2079
Met Val Gly Asp Lys Thr Phe Glu Glu Leu Ser Gly Ile His Asp Pro
        655                 660                 665

aag ctg cac cac cct tcc caa ggc ttt cgc ttt ggc acc gta tgg gag     2127
Lys Leu His His Pro Ser Gln Gly Phe Arg Phe Gly Thr Val Trp Glu
    670                 675                 680

agc agc gcg gag gcc tac atc aag gca agc ttc cct gag atg cac gca     2175
Ser Ser Ala Glu Ala Tyr Ile Lys Ala Ser Phe Pro Glu Met His Ala
685                 690                 695                 700

cac atg cgt cgg cac agc gca ccc acc act cca cat ggg gtg gcc atg     2223
His Met Arg Arg His Ser Ala Pro Thr Thr Pro His Gly Val Ala Met
                705                 710                 715

ctc acg agc gac ccg ccc aag ctc aac gcc ttc atc atg gat aaa tca     2271
Leu Thr Ser Asp Pro Pro Lys Leu Asn Ala Phe Ile Met Asp Lys Ser
            720                 725                 730

cta ctg gac tat gag gtg tcc ata gat gcg gac tgc aag ctg ctc acc     2319
Leu Leu Asp Tyr Glu Val Ser Ile Asp Ala Asp Cys Lys Leu Leu Thr
        735                 740                 745

gtt ggc aaa ccc ttt gct atc gag ggc tac ggc ata ggg cta ccc caa     2367
Val Gly Lys Pro Phe Ala Ile Glu Gly Tyr Gly Ile Gly Leu Pro Gln
    750                 755                 760

aac tcg ccg ctc acc tcc aac ctg tcg gag ttc atc agt agg tac aag     2415
Asn Ser Pro Leu Thr Ser Asn Leu Ser Glu Phe Ile Ser Arg Tyr Lys
765                 770                 775                 780

tct tca ggc ttc att gat ctg ctc cat gac aag tgg tac aag atg gtg     2463
Ser Ser Gly Phe Ile Asp Leu Leu His Asp Lys Trp Tyr Lys Met Val
                785                 790                 795

cct tgc ggg aag cgg gtg ttc gcc gtg acg gag acg ctg cag atg ggg     2511
Pro Cys Gly Lys Arg Val Phe Ala Val Thr Glu Thr Leu Gln Met Gly
            800                 805                 810

gtc tac cac ttc tca gga ttg ttt gtc ctg ctg tgc ctc ggg ctg ggc     2559
Val Tyr His Phe Ser Gly Leu Phe Val Leu Leu Cys Leu Gly Leu Gly
        815                 820                 825

agc gcg ctt ctc acc tct ctg ggt gag cat gtc ttc tac cgc ctg gtg     2607
Ser Ala Leu Leu Thr Ser Leu Gly Glu His Val Phe Tyr Arg Leu Val
    830                 835                 840

ctg ccg cgc atc cgc agg ggt aat aag ctg cag tat tgg ctt cac acg     2655
Leu Pro Arg Ile Arg Arg Gly Asn Lys Leu Gln Tyr Trp Leu His Thr
845                 850                 855                 860

agc cag aag atc cac cga gcc ctc aat aca gga cca ccc gag ggg caa     2703
Ser Gln Lys Ile His Arg Ala Leu Asn Thr Gly Pro Pro Glu Gly Gln
                865                 870                 875

cag gag agg gca gag cag gag cgc agc ggc ccc aag gac gag ctg cct     2751
Gln Glu Arg Ala Glu Gln Glu Arg Ser Gly Pro Lys Asp Glu Leu Pro
            880                 885                 890

gcc acc gat ggt gca ggg cgc tgg agg cgg gtg cgc cgg gct gtg gaa     2799
Ala Thr Asp Gly Ala Gly Arg Trp Arg Arg Val Arg Arg Ala Val Glu
        895                 900                 905

cgg gag cga cgc gtg cgt ttc ctg ctg gaa cct ggg gag gct ggc gga     2847
Arg Glu Arg Arg Val Arg Phe Leu Leu Glu Pro Gly Glu Ala Gly Gly
    910                 915                 920

gac cgc ccg tgg ctc tgc tcc aac ggg ccc ggg ctg caa gcg gag ctg     2895
Asp Arg Pro Trp Leu Cys Ser Asn Gly Pro Gly Leu Gln Ala Glu Leu
925                 930                 935                 940

cgg gag ctg gag ctg cgc att gag gct gca cgg gag cgg ctg cgc agt     2943
Arg Glu Leu Glu Leu Arg Ile Glu Ala Ala Arg Glu Arg Leu Arg Ser
                945                 950                 955

gcg ctg ttg cgg cgc ggg gag ctg cgg gcc ctg ctt ggg gat ggc acc     2991
```

-continued

```
Ala Leu Leu Arg Arg Gly Glu Leu Arg Ala Leu Leu Gly Asp Gly Thr
            960                 965                 970

cgg ctc agg cca ctg cgc ctg ttg cat gcg gcg cct gct gag agc         3036
Arg Leu Arg Pro Leu Arg Leu Leu His Ala Ala Pro Ala Glu Ser
        975                 980                 985

tgaggaacca caaggccgca ctgtccacga cagtttattc tatatacaaa cacgactctg   3096

tacactgcaa ttaaatagcg tggaacgtga aaaaaaa                            3133


<210> SEQ ID NO 60
<211> LENGTH: 987
<212> TYPE: PRT
<213> ORGANISM: Rattus sp.

<400> SEQUENCE: 60

Met Glu Ser Val Arg Thr Leu Trp Leu Ser Val Ala Leu Ala Leu Ala
 1               5                  10                  15

Val Gly Ser Arg Val Val Arg Gly His Pro Gln Pro Cys Arg Val Pro
            20                  25                  30

Thr Arg Ala Gly Ala Ser Val Arg Leu Ala Ala Leu Leu Pro Arg Ala
        35                  40                  45

Pro Ala Ala Arg Ala Arg Val Leu Ala Ala Leu Ala Thr Pro Ala Pro
    50                  55                  60

Arg Leu Pro His Asn Leu Ser Leu Glu Leu Val Ala Val Ala Ser Pro
65                  70                  75                  80

Thr Arg Asp Pro Ala Ser Leu Ala Arg Gly Leu Cys Gln Val Leu Ala
                85                  90                  95

Pro Pro Gly Val Val Ala Ser Ile Ala Phe Pro Glu Ala Arg Pro Glu
            100                 105                 110

Leu Arg Leu Leu Gln Phe Leu Ala Ala Ala Thr Glu Thr Pro Val Thr
        115                 120                 125

Pro Phe His Leu Gln Leu Asp Trp Ala Ser Pro Leu Glu Thr Ile Leu
    130                 135                 140

Asp Val Leu Val Ser Leu Val Arg Ala His Ala Trp Glu Asp Ile Ala
145                 150                 155                 160

Leu Val Leu Cys Arg Val Arg Asp Pro Gly Ser Leu Val Thr Leu Trp
                165                 170                 175

Thr Asn His Ala Ser Gln Ala Pro Lys Phe Val Leu Asp Leu Ser Arg
            180                 185                 190

Leu Asp Ser Arg Asn Asp Ser Leu Arg Ala Gly Leu Ala Leu Leu Gly
        195                 200                 205

Ala Leu Glu Gly Gly Gly Thr Pro Val Pro Ala Ala Val Leu Leu Gly
    210                 215                 220

Cys Ser Thr Ala Arg Ala His Glu Val Leu Glu Ala Ala Pro Pro Gly
225                 230                 235                 240

Pro Gln Trp Leu Leu Gly Thr Pro Leu Pro Ala Glu Ala Leu Pro Thr
                245                 250                 255

Thr Gly Leu Pro Pro Gly Val Leu Ala Leu Gly Glu Thr Glu Gln His
            260                 265                 270

Ser Leu Glu Ala Val Val His Asp Met Val Glu Leu Val Ala Gln Ala
        275                 280                 285

Leu Ser Ser Met Ala Leu Val His Pro Glu Arg Ala Leu Leu Pro Ala
    290                 295                 300

Val Val Asn Cys Asp Asp Leu Lys Thr Gly Gly Ser Glu Ala Thr Gly
305                 310                 315                 320

Arg Thr Leu Ala Arg Phe Leu Gly Asn Thr Ser Phe Gln Gly Arg Thr
```

-continued

```
            325                 330                 335

Gly Ala Val Trp Val Thr Gly Ser Ser Gln Val His Val Ser Arg His
            340                 345                 350

Phe Lys Val Trp Ser Leu Arg Arg Asp Pro Leu Gly Ala Pro Ala Trp
        355                 360                 365

Ala Thr Val Gly Ser Trp Gln Asp Gly Gln Leu Asp Phe Gln Pro Gly
    370                 375                 380

Ala Ala Ala Leu Arg Val Pro Ser Pro Ser Gly Thr Gln Ala Arg Pro
385                 390                 395                 400

Lys Leu Arg Val Val Thr Leu Val Glu His Pro Phe Val Phe Thr Arg
                405                 410                 415

Glu Ser Asp Glu Asp Gly Gln Cys Pro Ala Gly Gln Leu Cys Leu Asp
            420                 425                 430

Pro Gly Thr Asn Asp Ser Ala Arg Leu Asp Ala Leu Phe Ala Ala Leu
        435                 440                 445

Val Asn Gly Ser Val Pro Arg Thr Leu Arg Arg Cys Cys Tyr Gly Tyr
    450                 455                 460

Cys Ile Asp Leu Leu Glu Arg Leu Ala Glu Asp Leu Ala Phe Asp Phe
465                 470                 475                 480

Glu Leu Tyr Ile Val Gly Asp Gly Lys Tyr Gly Ala Leu Arg Asp Gly
                485                 490                 495

Arg Trp Thr Gly Leu Val Gly Asp Leu Leu Ala Gly Arg Ala His Met
            500                 505                 510

Ala Val Thr Ser Phe Ser Ile Asn Ser Ala Arg Ser Gln Val Val Asp
        515                 520                 525

Phe Thr Ser Pro Phe Phe Ser Thr Ser Leu Gly Ile Met Val Arg Thr
    530                 535                 540

Arg Asp Thr Ala Ser Pro Ile Gly Ala Phe Met Trp Pro Leu His Trp
545                 550                 555                 560

Ser Met Trp Val Gly Val Phe Ala Ala Leu His Leu Thr Ala Leu Phe
                565                 570                 575

Leu Thr Leu Tyr Glu Trp Arg Ser Pro Tyr Gly Leu Thr Pro Arg Gly
            580                 585                 590

Arg Asn Arg Gly Thr Val Phe Ser Tyr Ser Ser Ala Leu Asn Leu Cys
        595                 600                 605

Tyr Ala Ile Leu Phe Gly Arg Thr Val Ser Ser Lys Thr Pro Lys Cys
    610                 615                 620

Pro Thr Gly Arg Phe Leu Met Asn Leu Trp Ala Ile Phe Cys Leu Leu
625                 630                 635                 640

Val Leu Ser Ser Tyr Thr Ala Asn Leu Ala Ala Val Met Val Gly Asp
                645                 650                 655

Lys Thr Phe Glu Glu Leu Ser Gly Ile His Asp Pro Lys Leu His His
            660                 665                 670

Pro Ser Gln Gly Phe Arg Phe Gly Thr Val Trp Glu Ser Ser Ala Glu
        675                 680                 685

Ala Tyr Ile Lys Ala Ser Phe Pro Glu Met His Ala His Met Arg Arg
    690                 695                 700

His Ser Ala Pro Thr Thr Pro His Gly Val Ala Met Leu Thr Ser Asp
705                 710                 715                 720

Pro Pro Lys Leu Asn Ala Phe Ile Met Asp Lys Ser Leu Leu Asp Tyr
                725                 730                 735

Glu Val Ser Ile Asp Ala Asp Cys Lys Leu Leu Thr Val Gly Lys Pro
            740                 745                 750
```

```
Phe Ala Ile Glu Gly Tyr Gly Ile Gly Leu Pro Gln Asn Ser Pro Leu
        755                 760                 765

Thr Ser Asn Leu Ser Glu Phe Ile Ser Arg Tyr Lys Ser Ser Gly Phe
    770                 775                 780

Ile Asp Leu Leu His Asp Lys Trp Tyr Lys Met Val Pro Cys Gly Lys
785                 790                 795                 800

Arg Val Phe Ala Val Thr Glu Thr Leu Gln Met Gly Val Tyr His Phe
                805                 810                 815

Ser Gly Leu Phe Val Leu Leu Cys Leu Gly Leu Gly Ser Ala Leu Leu
            820                 825                 830

Thr Ser Leu Gly Glu His Val Phe Tyr Arg Leu Val Leu Pro Arg Ile
        835                 840                 845

Arg Arg Gly Asn Lys Leu Gln Tyr Trp Leu His Thr Ser Gln Lys Ile
    850                 855                 860

His Arg Ala Leu Asn Thr Gly Pro Pro Glu Gly Gln Gln Glu Arg Ala
865                 870                 875                 880

Glu Gln Glu Arg Ser Gly Pro Lys Asp Glu Leu Pro Ala Thr Asp Gly
                885                 890                 895

Ala Gly Arg Trp Arg Arg Val Arg Arg Ala Val Glu Arg Glu Arg Arg
            900                 905                 910

Val Arg Phe Leu Leu Glu Pro Gly Glu Ala Gly Gly Asp Arg Pro Trp
        915                 920                 925

Leu Cys Ser Asn Gly Pro Gly Leu Gln Ala Glu Leu Arg Glu Leu Glu
    930                 935                 940

Leu Arg Ile Glu Ala Ala Arg Glu Arg Leu Arg Ser Ala Leu Leu Arg
945                 950                 955                 960

Arg Gly Glu Leu Arg Ala Leu Leu Gly Asp Gly Thr Arg Leu Arg Pro
                965                 970                 975

Leu Arg Leu Leu His Ala Ala Pro Ala Glu Ser
            980                 985


<210> SEQ ID NO 61
<211> LENGTH: 3097
<212> TYPE: DNA
<213> ORGANISM: Homo sapiens
<220> FEATURE:
<221> NAME/KEY: CDS
<222> LOCATION: (1)...(3024)

<400> SEQUENCE: 61

atg gag ttt gtg cgg gcg ctg tgg ctg ggc ctg gcg ctg gcg ctg ggg       48
Met Glu Phe Val Arg Ala Leu Trp Leu Gly Leu Ala Leu Ala Leu Gly
 1               5                  10                  15

ccg ggg tcc gcg ggg ggc cac cct cag ccg tgc ggc gtc ctg gcg cgc       96
Pro Gly Ser Ala Gly Gly His Pro Gln Pro Cys Gly Val Leu Ala Arg
            20                  25                  30

ctc ggg ggc tcc gtg cgc ctg ggc gcc ctc ctg ccc cgc gcg cct ctc      144
Leu Gly Gly Ser Val Arg Leu Gly Ala Leu Leu Pro Arg Ala Pro Leu
        35                  40                  45

gcc cgc gcc cgc gcc cgc gcc gcc ctg gcc cgg gcc gcc ctg gcg ccg      192
Ala Arg Ala Arg Ala Arg Ala Ala Leu Ala Arg Ala Ala Leu Ala Pro
     50                  55                  60

cgg ctg ccg cac aac ctg agc ttg gag ctg gtg gtc gcc gcg ccc ccc      240
Arg Leu Pro His Asn Leu Ser Leu Glu Leu Val Val Ala Ala Pro Pro
 65                  70                  75                  80

gcc cgc gac ccc gcc tcg ctg acc cgc ggc ctg tgc cag gcg ctg gtg      288
Ala Arg Asp Pro Ala Ser Leu Thr Arg Gly Leu Cys Gln Ala Leu Val
                85                  90                  95
```

-continued

```
cct ccg ggc gtg gcg gcc ctg ctc gcc ttt ccc gag gct cgg ccc gag       336
Pro Pro Gly Val Ala Ala Leu Leu Ala Phe Pro Glu Ala Arg Pro Glu
            100                 105                 110

ctg ctg cag ctg cac ttc ctg gcg gcg gcc acc gag acc ccc gtg ctc       384
Leu Leu Gln Leu His Phe Leu Ala Ala Ala Thr Glu Thr Pro Val Leu
        115                 120                 125

agc ctg ctg cgg cgg gag gcg cgc gcg ccc ctc gga gcc ccg aac cca       432
Ser Leu Leu Arg Arg Glu Ala Arg Ala Pro Leu Gly Ala Pro Asn Pro
    130                 135                 140

ttc cac ctg cag ctg cac tgg gcc agc ccc ctg gag acg ctg ctg gat       480
Phe His Leu Gln Leu His Trp Ala Ser Pro Leu Glu Thr Leu Leu Asp
145                 150                 155                 160

gtg ctg gtg gcg gtg ctg cag gcg cac gcc tgg gaa gac gtc ggc ctg       528
Val Leu Val Ala Val Leu Gln Ala His Ala Trp Glu Asp Val Gly Leu
                165                 170                 175

gcc ctg tgc cgc act cag gac ccc ggc ggc ctg gtg gcc ctc tgg aca       576
Ala Leu Cys Arg Thr Gln Asp Pro Gly Gly Leu Val Ala Leu Trp Thr
            180                 185                 190

agc cgg gct ggc cgg ccc cca cag ctg gtc ctg gac cta agc cgg cgg       624
Ser Arg Ala Gly Arg Pro Pro Gln Leu Val Leu Asp Leu Ser Arg Arg
        195                 200                 205

gac acg gga gat gca gga ctg cgg gca cgc ctg gcc ccg atg gcg gcg       672
Asp Thr Gly Asp Ala Gly Leu Arg Ala Arg Leu Ala Pro Met Ala Ala
    210                 215                 220

cca gtg ggg ggt gaa gca ccg gta ccc gcg gcg gtc ctc ctc ggc tgt       720
Pro Val Gly Gly Glu Ala Pro Val Pro Ala Ala Val Leu Leu Gly Cys
225                 230                 235                 240

gac atc gcc cgt gcc cgt cgg gtg ctg gag gcc gta cct ccc ggc ccc       768
Asp Ile Ala Arg Ala Arg Arg Val Leu Glu Ala Val Pro Pro Gly Pro
                245                 250                 255

cac tgg ctg ttg ggg aca cca ctg ccg ccc aag gcc ctg ccc acc gcg       816
His Trp Leu Leu Gly Thr Pro Leu Pro Pro Lys Ala Leu Pro Thr Ala
            260                 265                 270

ggg ctg cca cca ggg ctg ctg gcg ctg ggc gag gtg gca cga ccc ccg       864
Gly Leu Pro Pro Gly Leu Leu Ala Leu Gly Glu Val Ala Arg Pro Pro
        275                 280                 285

ctg gag gcc gcc atc cat gac att gtg caa ctg gtg gcc cgg gcg ctg       912
Leu Glu Ala Ala Ile His Asp Ile Val Gln Leu Val Ala Arg Ala Leu
    290                 295                 300

ggc agt gcg gcc cag gtg cag ccg aag cga gcc ctc ctc ccc gcc ccg       960
Gly Ser Ala Ala Gln Val Gln Pro Lys Arg Ala Leu Leu Pro Ala Pro
305                 310                 315                 320

gtc aac tgc ggg gac ctg cag ccg gcc ggg ccc gag tcc ccg ggg cgc      1008
Val Asn Cys Gly Asp Leu Gln Pro Ala Gly Pro Glu Ser Pro Gly Arg
                325                 330                 335

ttc ttg gca cgg ttc ctg gcc aac acg tcc ttc cag ggc cgc acg ggc      1056
Phe Leu Ala Arg Phe Leu Ala Asn Thr Ser Phe Gln Gly Arg Thr Gly
            340                 345                 350

ccc gtg tgg gtg aca ggc agc tcc cag gta cac atg tct cgg cac ttt      1104
Pro Val Trp Val Thr Gly Ser Ser Gln Val His Met Ser Arg His Phe
        355                 360                 365

aag gtg tgg agc ctt cgc cgg gac cca cgg ggc gcc ccg gcc tgg gcc      1152
Lys Val Trp Ser Leu Arg Arg Asp Pro Arg Gly Ala Pro Ala Trp Ala
    370                 375                 380

acg gtg ggc agc tgg cgg gac ggc cag ctg gac ttg gaa ccg gga ggt      1200
Thr Val Gly Ser Trp Arg Asp Gly Gln Leu Asp Leu Glu Pro Gly Gly
385                 390                 395                 400

gcc tct gca cgg ccc ccg ccc cca cag ggt gcc cag gtc tgg ccc aag      1248
Ala Ser Ala Arg Pro Pro Pro Pro Gln Gly Ala Gln Val Trp Pro Lys
                405                 410                 415
```

```
ctg cgt gtg gta acg ctg ttg gaa cac cca ttt gtg ttt gcc cgt gat      1296
Leu Arg Val Val Thr Leu Leu Glu His Pro Phe Val Phe Ala Arg Asp
            420                 425                 430

cca gac gaa gac ggg cag tgc cca gcg ggg cag ctg tgc ctg gac cct      1344
Pro Asp Glu Asp Gly Gln Cys Pro Ala Gly Gln Leu Cys Leu Asp Pro
        435                 440                 445

ggc acc aac gac tcg gcc acc ctg gac gca ctg ttc gcc gcg ctg gcc      1392
Gly Thr Asn Asp Ser Ala Thr Leu Asp Ala Leu Phe Ala Ala Leu Ala
    450                 455                 460

aac ggc tca gcg ccc cgt gcc ctg cgc aag tgc tgc tac ggc tac tgc      1440
Asn Gly Ser Ala Pro Arg Ala Leu Arg Lys Cys Cys Tyr Gly Tyr Cys
465                 470                 475                 480

att gac ctg ctg gag cgg ctg gcg gag gac acg ccc ttc gac ttc gag      1488
Ile Asp Leu Leu Glu Arg Leu Ala Glu Asp Thr Pro Phe Asp Phe Glu
                485                 490                 495

ctg tac ctc gtg ggt gac ggc aag tac ggc gcc ctg cgg gac ggc cgc      1536
Leu Tyr Leu Val Gly Asp Gly Lys Tyr Gly Ala Leu Arg Asp Gly Arg
            500                 505                 510

tgg acc ggc ctg gtc ggg gac ctg ctg gcc ggc cgg gcc cac atg gcg      1584
Trp Thr Gly Leu Val Gly Asp Leu Leu Ala Gly Arg Ala His Met Ala
        515                 520                 525

gtc acc agc ttc agt atc aac tcc gcc cgc tca cag gtg gtg gac ttc      1632
Val Thr Ser Phe Ser Ile Asn Ser Ala Arg Ser Gln Val Val Asp Phe
    530                 535                 540

acc agc ccc ttc ttc tcc acc agc ctg ggc atc atg gtg cgg gca cgg      1680
Thr Ser Pro Phe Phe Ser Thr Ser Leu Gly Ile Met Val Arg Ala Arg
545                 550                 555                 560

gac acg gcc tca ccc atc ggt gcc ttt atg tgg ccc ctg cac tgg tcc      1728
Asp Thr Ala Ser Pro Ile Gly Ala Phe Met Trp Pro Leu His Trp Ser
                565                 570                 575

acg tgg ctg ggc gtc ttt gcg gcc ctg cac ctc acc gcg ctc ttc ctc      1776
Thr Trp Leu Gly Val Phe Ala Ala Leu His Leu Thr Ala Leu Phe Leu
            580                 585                 590

acc gtg tac gag tgg cgt agc ccc tac ggc ctc acg cca cgt ggc cgc      1824
Thr Val Tyr Glu Trp Arg Ser Pro Tyr Gly Leu Thr Pro Arg Gly Arg
        595                 600                 605

aac cgc agc acc gtc ttc tcc tac tcc tca gcc ctc aac ctg tgc tac      1872
Asn Arg Ser Thr Val Phe Ser Tyr Ser Ser Ala Leu Asn Leu Cys Tyr
    610                 615                 620

gcc atc ctc ttc aga cgc acc gtg tcc agc aag acg ccc aag tgc ccc      1920
Ala Ile Leu Phe Arg Arg Thr Val Ser Ser Lys Thr Pro Lys Cys Pro
625                 630                 635                 640

acg ggc cgc ctg ctc atg aac ctc tgg gcc atc ttc tgc ctg ctg gtg      1968
Thr Gly Arg Leu Leu Met Asn Leu Trp Ala Ile Phe Cys Leu Leu Val
                645                 650                 655

ctg tcc agc tac acg gcc aac ctg gct gcc gtc atg gtc ggg gac aag      2016
Leu Ser Ser Tyr Thr Ala Asn Leu Ala Ala Val Met Val Gly Asp Lys
            660                 665                 670

acc ttc gag gag ctg tcg ggg atc cac gac ccc aag ctg cac cac ccg      2064
Thr Phe Glu Glu Leu Ser Gly Ile His Asp Pro Lys Leu His His Pro
        675                 680                 685

gcg cag ggc ttc cgc ttc ggc acc gtg tgg gag agc agc gcc gag gcg      2112
Ala Gln Gly Phe Arg Phe Gly Thr Val Trp Glu Ser Ser Ala Glu Ala
    690                 695                 700

tac atc aag aag agc ttc ccc gac atg cac gca cac atg cgg cgc cac      2160
Tyr Ile Lys Lys Ser Phe Pro Asp Met His Ala His Met Arg Arg His
705                 710                 715                 720

agc gcg ccc acc acg ccc cgc ggc gtc gcc atg ctc acg agc gac ccc      2208
Ser Ala Pro Thr Thr Pro Arg Gly Val Ala Met Leu Thr Ser Asp Pro
                725                 730                 735
```

```
ccc aag ctc aac gcc ttc atc atg gac aag tcg ctc ctg gac tac gag      2256
Pro Lys Leu Asn Ala Phe Ile Met Asp Lys Ser Leu Leu Asp Tyr Glu
            740                 745                 750

gtc tcc atc gac gcc gac tgc aaa ctg ctg acc gtg gga aag ccc ttc      2304
Val Ser Ile Asp Ala Asp Cys Lys Leu Leu Thr Val Gly Lys Pro Phe
        755                 760                 765

gcc att gag ggc tat ggg atc gga ctg ccc cag aac tcg ccg ctc acc      2352
Ala Ile Glu Gly Tyr Gly Ile Gly Leu Pro Gln Asn Ser Pro Leu Thr
    770                 775                 780

tcc aac ctg tcc gag ttc atc agc cgc tac aag tcc tcc ggc ttc atc      2400
Ser Asn Leu Ser Glu Phe Ile Ser Arg Tyr Lys Ser Ser Gly Phe Ile
785                 790                 795                 800

gac ctg ctc cac gac aag tgg tac aag atg gtg cct tgc ggc aag cgg      2448
Asp Leu Leu His Asp Lys Trp Tyr Lys Met Val Pro Cys Gly Lys Arg
                805                 810                 815

gtc ttt gcg gtt aca gag acc ctg cag atg agc atc tac cac ttc gcg      2496
Val Phe Ala Val Thr Glu Thr Leu Gln Met Ser Ile Tyr His Phe Ala
            820                 825                 830

ggc ctc ttc gtg ttg ctg tgc ctg ggc ctg ggc agc gct ctg ctc agc      2544
Gly Leu Phe Val Leu Leu Cys Leu Gly Leu Gly Ser Ala Leu Leu Ser
        835                 840                 845

tcg ctg ggc gag cac gcc ttc ttc cgc ctg gcg ctg ccg cgc atc cgc      2592
Ser Leu Gly Glu His Ala Phe Phe Arg Leu Ala Leu Pro Arg Ile Arg
    850                 855                 860

aag ggg agc agg ctg cag tac tgg ctg cac acc agc cag aaa atc cac      2640
Lys Gly Ser Arg Leu Gln Tyr Trp Leu His Thr Ser Gln Lys Ile His
865                 870                 875                 880

cgc gcc ctc aac acg gag cca cca gag ggg tcg aag gag gag acg gca      2688
Arg Ala Leu Asn Thr Glu Pro Pro Glu Gly Ser Lys Glu Glu Thr Ala
                885                 890                 895

gag gcg gag ccc agg gag cag cag cag cag cag cag gac cag cca acg      2736
Glu Ala Glu Pro Arg Glu Gln Gln Gln Gln Gln Gln Asp Gln Pro Thr
            900                 905                 910

gct ccg gag ggc tgg aaa cgg gcg cgc cgg gcc gtg gac aag gag cgc      2784
Ala Pro Glu Gly Trp Lys Arg Ala Arg Arg Ala Val Asp Lys Glu Arg
        915                 920                 925

cgc gtg cgc ttc ctg ctg gag ccc gcc ggc tcc tac ggc cgc ccg ccc      2832
Arg Val Arg Phe Leu Leu Glu Pro Ala Gly Ser Tyr Gly Arg Pro Pro
    930                 935                 940

gcc gca agg ccc acg ggg gcc ccc cag ccc ggg gag ctg cag gag ctg      2880
Ala Ala Arg Pro Thr Gly Ala Pro Gln Pro Gly Glu Leu Gln Glu Leu
945                 950                 955                 960

gag cgc cgc atc gaa gtc gcg cgt gag cgg ctc cgc cag gcc ctg gtg      2928
Glu Arg Arg Ile Glu Val Ala Arg Glu Arg Leu Arg Gln Ala Leu Val
                965                 970                 975

cgg cgc ggc cag ctc ctg gca cag ctc ggg gac agc gca cgt cac cgg      2976
Arg Arg Gly Gln Leu Leu Ala Gln Leu Gly Asp Ser Ala Arg His Arg
            980                 985                 990

cct cgg cgc ttg ctt cag gcc aga gcg gcc ccc gcg gag gcc cca cag      3024
Pro Arg Arg Leu Leu Gln Ala Arg Ala Ala Pro Ala Glu Ala Pro Gln
        995                 1000                1005

tgagccgctg tcaacagaca gtttattcta tatacaaaca caattttgta cactgcaatt    3084

aaatagaatg gaa                                                       3097
```

<210> SEQ ID NO 62
<211> LENGTH: 1008
<212> TYPE: PRT
<213> ORGANISM: Homo sapiens

<400> SEQUENCE: 62

-continued

```
Met Glu Phe Val Arg Ala Leu Trp Leu Gly Leu Ala Leu Ala Leu Gly
1               5                   10                  15

Pro Gly Ser Ala Gly Gly His Pro Gln Pro Cys Gly Val Leu Ala Arg
            20                  25                  30

Leu Gly Gly Ser Val Arg Leu Gly Ala Leu Leu Pro Arg Ala Pro Leu
        35                  40                  45

Ala Arg Ala Arg Ala Arg Ala Ala Leu Ala Arg Ala Ala Leu Ala Pro
    50                  55                  60

Arg Leu Pro His Asn Leu Ser Leu Glu Leu Val Val Ala Ala Pro Pro
65                  70                  75                  80

Ala Arg Asp Pro Ala Ser Leu Thr Arg Gly Leu Cys Gln Ala Leu Val
                85                  90                  95

Pro Pro Gly Val Ala Ala Leu Leu Ala Phe Pro Glu Ala Arg Pro Glu
            100                 105                 110

Leu Leu Gln Leu His Phe Leu Ala Ala Ala Thr Glu Thr Pro Val Leu
        115                 120                 125

Ser Leu Leu Arg Arg Glu Ala Arg Ala Pro Leu Gly Ala Pro Asn Pro
    130                 135                 140

Phe His Leu Gln Leu His Trp Ala Ser Pro Leu Glu Thr Leu Leu Asp
145                 150                 155                 160

Val Leu Val Ala Val Leu Gln Ala His Ala Trp Glu Asp Val Gly Leu
                165                 170                 175

Ala Leu Cys Arg Thr Gln Asp Pro Gly Gly Leu Val Ala Leu Trp Thr
            180                 185                 190

Ser Arg Ala Gly Arg Pro Pro Gln Leu Val Leu Asp Leu Ser Arg Arg
        195                 200                 205

Asp Thr Gly Asp Ala Gly Leu Arg Ala Arg Leu Ala Pro Met Ala Ala
    210                 215                 220

Pro Val Gly Gly Glu Ala Pro Val Pro Ala Ala Val Leu Leu Gly Cys
225                 230                 235                 240

Asp Ile Ala Arg Ala Arg Arg Val Leu Glu Ala Val Pro Pro Gly Pro
                245                 250                 255

His Trp Leu Leu Gly Thr Pro Leu Pro Pro Lys Ala Leu Pro Thr Ala
            260                 265                 270

Gly Leu Pro Pro Gly Leu Leu Ala Leu Gly Glu Val Ala Arg Pro Pro
        275                 280                 285

Leu Glu Ala Ala Ile His Asp Ile Val Gln Leu Val Ala Arg Ala Leu
    290                 295                 300

Gly Ser Ala Ala Gln Val Gln Pro Lys Arg Ala Leu Leu Pro Ala Pro
305                 310                 315                 320

Val Asn Cys Gly Asp Leu Gln Pro Ala Gly Pro Glu Ser Pro Gly Arg
                325                 330                 335

Phe Leu Ala Arg Phe Leu Ala Asn Thr Ser Phe Gln Gly Arg Thr Gly
            340                 345                 350

Pro Val Trp Val Thr Gly Ser Ser Gln Val His Met Ser Arg His Phe
        355                 360                 365

Lys Val Trp Ser Leu Arg Arg Asp Pro Arg Gly Ala Pro Ala Trp Ala
    370                 375                 380

Thr Val Gly Ser Trp Arg Asp Gly Gln Leu Asp Leu Glu Pro Gly Gly
385                 390                 395                 400

Ala Ser Ala Arg Pro Pro Pro Pro Gln Gly Ala Gln Val Trp Pro Lys
                405                 410                 415

Leu Arg Val Val Thr Leu Leu Glu His Pro Phe Val Phe Ala Arg Asp
            420                 425                 430
```

```
Pro Asp Glu Asp Gly Gln Cys Pro Ala Gly Gln Leu Cys Leu Asp Pro
        435                 440                 445

Gly Thr Asn Asp Ser Ala Thr Leu Asp Ala Leu Phe Ala Ala Leu Ala
    450                 455                 460

Asn Gly Ser Ala Pro Arg Ala Leu Arg Lys Cys Cys Tyr Gly Tyr Cys
465                 470                 475                 480

Ile Asp Leu Leu Glu Arg Leu Ala Glu Asp Thr Pro Phe Asp Phe Glu
                485                 490                 495

Leu Tyr Leu Val Gly Asp Gly Lys Tyr Gly Ala Leu Arg Asp Gly Arg
            500                 505                 510

Trp Thr Gly Leu Val Gly Asp Leu Leu Ala Gly Arg Ala His Met Ala
        515                 520                 525

Val Thr Ser Phe Ser Ile Asn Ser Ala Arg Ser Gln Val Val Asp Phe
    530                 535                 540

Thr Ser Pro Phe Phe Ser Thr Ser Leu Gly Ile Met Val Arg Ala Arg
545                 550                 555                 560

Asp Thr Ala Ser Pro Ile Gly Ala Phe Met Trp Pro Leu His Trp Ser
                565                 570                 575

Thr Trp Leu Gly Val Phe Ala Ala Leu His Leu Thr Ala Leu Phe Leu
            580                 585                 590

Thr Val Tyr Glu Trp Arg Ser Pro Tyr Gly Leu Thr Pro Arg Gly Arg
        595                 600                 605

Asn Arg Ser Thr Val Phe Ser Tyr Ser Ser Ala Leu Asn Leu Cys Tyr
    610                 615                 620

Ala Ile Leu Phe Arg Arg Thr Val Ser Ser Lys Thr Pro Lys Cys Pro
625                 630                 635                 640

Thr Gly Arg Leu Leu Met Asn Leu Trp Ala Ile Phe Cys Leu Leu Val
                645                 650                 655

Leu Ser Ser Tyr Thr Ala Asn Leu Ala Ala Val Met Val Gly Asp Lys
            660                 665                 670

Thr Phe Glu Glu Leu Ser Gly Ile His Asp Pro Lys Leu His His Pro
        675                 680                 685

Ala Gln Gly Phe Arg Phe Gly Thr Val Trp Glu Ser Ser Ala Glu Ala
    690                 695                 700

Tyr Ile Lys Lys Ser Phe Pro Asp Met His Ala His Met Arg Arg His
705                 710                 715                 720

Ser Ala Pro Thr Thr Pro Arg Gly Val Ala Met Leu Thr Ser Asp Pro
                725                 730                 735

Pro Lys Leu Asn Ala Phe Ile Met Asp Lys Ser Leu Leu Asp Tyr Glu
            740                 745                 750

Val Ser Ile Asp Ala Asp Cys Lys Leu Leu Thr Val Gly Lys Pro Phe
        755                 760                 765

Ala Ile Glu Gly Tyr Gly Ile Gly Leu Pro Gln Asn Ser Pro Leu Thr
    770                 775                 780

Ser Asn Leu Ser Glu Phe Ile Ser Arg Tyr Lys Ser Ser Gly Phe Ile
785                 790                 795                 800

Asp Leu Leu His Asp Lys Trp Tyr Lys Met Val Pro Cys Gly Lys Arg
                805                 810                 815

Val Phe Ala Val Thr Glu Thr Leu Gln Met Ser Ile Tyr His Phe Ala
            820                 825                 830

Gly Leu Phe Val Leu Leu Cys Leu Gly Leu Gly Ser Ala Leu Leu Ser
        835                 840                 845

Ser Leu Gly Glu His Ala Phe Phe Arg Leu Ala Leu Pro Arg Ile Arg
```

-continued

```
    850                 855                 860

Lys Gly Ser Arg Leu Gln Tyr Trp Leu His Thr Ser Gln Lys Ile His
865                 870                 875                 880

Arg Ala Leu Asn Thr Glu Pro Pro Glu Gly Ser Lys Glu Glu Thr Ala
                885                 890                 895

Glu Ala Glu Pro Arg Glu Gln Gln Gln Gln Gln Gln Asp Gln Pro Thr
            900                 905                 910

Ala Pro Glu Gly Trp Lys Arg Ala Arg Arg Ala Val Asp Lys Glu Arg
        915                 920                 925

Arg Val Arg Phe Leu Leu Glu Pro Ala Gly Ser Tyr Gly Arg Pro Pro
    930                 935                 940

Ala Ala Arg Pro Thr Gly Ala Pro Gln Pro Gly Glu Leu Gln Glu Leu
945                 950                 955                 960

Glu Arg Arg Ile Glu Val Ala Arg Glu Arg Leu Arg Gln Ala Leu Val
                965                 970                 975

Arg Arg Gly Gln Leu Leu Ala Gln Leu Gly Asp Ser Ala Arg His Arg
            980                 985                 990

Pro Arg Arg Leu Leu Gln Ala Arg Ala Ala Pro Ala Glu Ala Pro Gln
        995                 1000                1005


<210> SEQ ID NO 63
<211> LENGTH: 114
<212> TYPE: PRT
<213> ORGANISM: Artificial Sequence
<220> FEATURE:
<223> OTHER INFORMATION: Hypothetical human sequence which would be
      chemically synthesized.
<220> FEATURE:
<221> NAME/KEY: VARIANT
<222> LOCATION: (1)...(114)
<223> OTHER INFORMATION: Xaa= any amino acid

<400> SEQUENCE: 63

Xaa Xaa Xaa Xaa Xaa Xaa Xaa Xaa Xaa Xaa Xaa Xaa Xaa Trp Lys Arg
 1               5                  10                  15

Ala Arg Arg Ala Val Asp Lys Glu Arg Arg Val Arg Phe Leu Leu Glu
            20                  25                  30

Pro Xaa Xaa Xaa Xaa Xaa Xaa Xaa Xaa Trp Leu Cys Ser Xaa Xaa Xaa
        35                  40                  45

Xaa Xaa Xaa Xaa Glu Leu Gln Glu Leu Glu Arg Arg Ile Glu Val Ala
    50                  55                  60

Arg Glu Arg Leu Arg Gln Ala Leu Val Arg Arg Gly Gln Leu Leu Ala
 65                  70                  75                  80

Gln Leu Gly Asp Ser Ala Arg His Arg Pro Arg Arg Leu Leu Gln Ala
                85                  90                  95

Arg Ala Ala Pro Ala Glu Ala Pro Pro His Ser Gly Arg Pro Gly Ser
            100                 105                 110

Gln Glu
```

EXCITATORY GLYCINE RECEPTORS AND METHODS

This application is a continuation of U.S. application Ser. No. 10/222,772, filed Aug. 16, 2002, now U.S. Pat. No. 7,790,404, which claims the benefit of priority of U.S. Provisional Application Ser. No. 60/453,707, filed Aug. 20, 2001, which was converted from U.S. application Ser. No. 09/934,070, each of which the entire contents are incorporated herein by reference.

This invention was made with United States Government support under grant numbers PO1 HD29587 and RO1 EY05477 awarded by the National Institutes of Health. The U.S. Government has certain rights in this invention.

The instant application contains a Sequence Listing which has been submitted in ASCII format via EFS-Web and is hereby incorporated by reference in its entirety. Said ASCII copy, created on Jan. 27, 2012, is named 12968-062-999 SeqList.txt and is 332,161 bytes in size.

BACKGROUND OF THE INVENTION

1. Field of the Invention

This invention relates generally to the fields of neurobiology and medicine and, more specifically, to the field of ionotropic receptors.

2. Background Information

Ionotropic glutamate receptors activate ligand-gated cation channels that mediate the predominant component of excitatory neurotransmission in the central nervous system (CNS). These receptors have been classified based on their preference for the glutamate-like agonists (RS)-2-amino-3-(3-hydroxy-5-methyl-4-isoxazolyl)propionic acid (AMPA), kainate (KA), and N-methyl-D-aspartate (NMDA). All three glutamate receptor subtypes are heteromultimeric complexes, and many of the subunits that comprise them have been identified and characterized. To date, four AMPA receptor subunits (GluR1-4), five KA receptor subunits (GluR5-7, KA1, and KA2), and six NMDA receptor subunits (NR1, NR2A-2D and NR3A) have been reported.

The NMDA receptor (NMDAR) has unique properties that distinguish it from the other glutamate receptor subtypes. First, the activation of NMDAR requires the presence of dual agonists, glutamate (or NMDA) and glycine. In addition, activation of these receptors is regulated by $Mg^{2+}$ in a voltage-dependent manner (i.e., the NMDAR is blocked at resting membrane potential and activated when depolarized). Most importantly, the NMDAR is extremely permeable to $Ca^{2+}$, a key regulator of cell function. These unique properties allow NMDARs to play a critical role in development of the nervous system, synaptic plasticity, memory, and other physiological processes in the CNS. However, excessive stimulation of NMDARs has also been implicated in many pathological conditions including stroke, ischemia, head and spinal trauma, headache, epilepsy, neuropathic pain syndromes including diabetic neuropathy, glaucoma, depression and anxiety, drug addiction/withdrawal/tolerance, and in chronic neurodegenerative states, such as Alzheimer's disease, Huntington's disease, HIV-associated dementia, Parkinson's disease, multiple sclerosis, and amyotrophic lateral sclerosis (ALS).

The molecular cloning and functional analysis of expressed NR1, NR2A-D, and NR3A subunits, coupled with the examination of their temporal and spatial expression patterns in vivo, has led to significant advances in our understanding of NMDAR function at the molecular level. However, the identification of these six subunits alone has failed to explain the observed diversity in NMDAR function, particularly in motor neurons.

Thus, there exists a need to identify and characterize additional NMDAR subunits, and to characterize the function of additional NMDA receptors. There also exists a need to provide screening assays that identify compounds that modulate the function of additional NMDA receptors. Such compounds can be used to treat pathological conditions in which inappropriate NMDA receptor activation, or inappropriate responses to glycine or glutamate, are involved. The present invention satisfies these needs and provides related advantages as well.

SUMMARY OF THE INVENTION

The invention provides isolated nucleic acid molecules encoding N-methyl-D-aspartate (NMDA) receptor type 3B (NR3B) polypeptides, including human, rat and mouse NR3B polypeptides.

Also provided are vectors and cells containing isolated nucleic acid molecules encoding NR3B polypeptides.

The invention also provides a method of producing an NR3B polypeptide by expressing a nucleic acid molecule encoding an NR3B polypeptide in vitro or in a cell under conditions suitable for expression of the polypeptide.

Further provided are isolated NR3B nucleic acid molecules encoding functional fragments of an NR3B polypeptide, including functional fragments that bind glycine.

The invention also provides an isolated NR3B polynucleotide containing at least 17 contiguous nucleotides from a human, rat or mouse NR3B nucleic acid molecule.

Also provided is a method for detecting a nucleic acid molecule encoding a NR3B polypeptide in a sample, by contacting the sample with one or more NR3B polynucleotides, and detecting specific hybridization to the polynucleotide, thereby detecting a nucleic acid molecule encoding an NR3B polypeptide in said sample.

The invention further provides isolated NR3B polypeptides, including human, rat and mouse NR3B polypeptides.

Also provided are functional fragments of NR3B polypeptides, including functional fragments that bind glycine.

The invention also provides isolated NR3B peptides, containing at least 8 contiguous residues of an NR3B polypeptide.

Further provided is an isolated antibody or antigen binding fragment thereof, which specifically binds an isolated NR3B polypeptide.

Also provided is a method of detecting an NR3B polypeptide in a sample, by contacting the sample with an antibody which specifically binds an NR3B polypeptide, and detecting the presence of specific binding of the antibody to the sample, thereby detecting an NR3B polypeptide in the sample.

The invention also provides methods of detecting an NR3B ligand, by contacting an NR3B polypeptide or functional fragment with one or more candidate compounds under conditions suitable for detecting binding to the polypeptide, and detecting a candidate compound that binds the polypeptide, wherein such a compound is characterized as an NR3B ligand.

Further provided is a composition containing an isolated excitatory glycine receptor. In one embodiment, the excitatory glycine receptor contains and NR3B polypeptide and an NR1 polypeptide. In another embodiment, the excitatory glycine receptor contains and NR3A polypeptide and an NR1 polypeptide. Optionally, the receptor further contains an NR2A, NR2B, NR2c or NR2D polypeptide.

The invention also provides a method of detecting an excitatory glycine receptor ligand, by contacting an excitatory glycine receptor with one or more candidate compounds under conditions suitable for detecting binding to said receptor, and detecting a candidate compound that binds said receptor, wherein such a compound is characterized as an excitatory glycine receptor ligand.

Also provided is a method of detecting an excitatory glycine receptor agonist or antagonist, by contacting an excitatory glycine receptor with one or more candidate compounds under conditions suitable for detecting receptor activation, and detecting a candidate compound that alters receptor activation, wherein such a compound is characterized as an excitatory glycine receptor agonist or antagonist.

Further provided is a method of modulating a cellular response to glycine or glutamate, by introducing a nucleic acid molecule encoding an NR3B polypeptide or functional fragment into a cell, and expressing the NR3B polypeptide or functional fragment encoded by said nucleic acid molecule in said cell, whereby expression of the polypeptide or functional fragment modulates a cellular response to glycine or glutamate.

The invention further provides a method of modulating a cellular response to glycine or glutamate, by introducing an antisense nucleic acid molecule, a ribozyme molecule or a small interfering RNA (siRNA) molecule into the cell, wherein the molecule hybridizes to an NR3B nucleic acid molecule and prevents translation of the encoded NR3B polypeptide.

BRIEF DESCRIPTION OF THE DRAWINGS

FIGS. 2*a* and 2*b* show that positive signals (arrows) were detected only by probes derived from antisense (AS) sequences, but not with sense (S) probes in adult rat tissue. Strong NR3B signals were observed in facial and trigeminal nuclei of the brainstem and in the ventral horn of the spinal cord.

FIG. 2*c* shows NR3B-positive cells viewed under high magnification (400×, top panel). These cells resemble motor neurons retrogradely labeled by injection of a fluorescent dye (granular blue) into leg muscles (bottom panel).

FIG. 2*d* shows the distribution of the NR3B subunit in the lumbar spinal cord of rats at different ages. NR3B signals developed postnatally, appearing as early as P2, reached a peak around P14, and remained elevated in the adult. The positive cells are large and are located in layer VIII and IX, suggesting that they are motor neurons. Arrows pointing to the labeled motor neurons are placed only on the right side of the spinal cord.

FIG. 3*a* shows a dose-response of glycine-evoked NR1/NR3B currents.

FIG. 3*b* shows that NMDA and L-glutamate did not potentiate glycine-evoked currents, and did not evoke a glycine-independent response.

FIG. 3*c*1 shows that D-serine evoked small currents alone but inhibited the glycine response. FIG. 3*c*2 shows inhibition (mean±SEM) of glycine-evoked currents by D-serine, D-alanine (30 μM), D-cycloserine (30 μM), or ACPC (1 μM).

FIGS. 3*d*1 and *d*2 show inhibition by AP5, strychnine (10 μM), and 5,7-DCKA (100 μM).

FIGS. 3*e*1 and 3*e*2 show inhibition by $Mg^{2+}$, MK-801 (10 μM), and memantine (12 μM). Data are representative of recordings from 3-9 oocytes in each case.

FIG. 4*a* shows inhibition of glycine (10 μM)-evoked NR1/NR3B currents by addition of $Mg^{2+}$ (0.5 mM) or replacement of cations in the bath solution with 90 mM NMDG.

FIG. 4*b* shows glycine-evoked NR1/NR3B currents during voltage ramps (20 mV/s) in normal bath solution containing 0.5 mM $Mg^{2+}$ (thin solid line) or no added $Mg^{2+}$ (dashed line), and in isosmotic solution containing 90 mM NMDG (with 1 mM $Ba^{2+}$; thick solid line) or 10 mM $Mg^{2+}$ (with 2 mM $Na^+$, balance NMDG; dotted line).

FIGS. 4*c* and 4*d* show glycine-evoked NR1/NR3B currents (c) and NMDA (100 μM)/glycine-evoked NR1/NR2A currents (d) during voltage ramps in 1 mM $Ba^{2+}$ (with 20 mM $Na^+$, balance NMDG; dashed line) versus 10 mM $Ba^{2+}$ (with 2 mM $Na^+$, balance NMDG; solid line).

FIG. 5*a* shows current recordings at a holding potential of −60 mV. Application of glycine (10 μM) activated single-channel currents, and $Mg^{2+}$ (0.5 mM) had no significant effect on these currents. Single-channel currents are shown at higher time resolution below. The single-channel currents display a main conductance state (2.3 pA) and a sub conductance state (0.7 pA) in the presence of 2 mM $Ba^{2+}$ (the zero current level is shown as a dotted line).

FIG. 5*b* shows all point amplitude histograms of single channel currents of NR1/NR3B receptors activated by glycine.

FIG. 5*c* shows single-channel currents recorded at different membrane potentials.

FIG. 5*d* shows single channel current-voltage relationship of the main conductance (squares) and sub conductance (circle) states.

FIG. 6*a* shows dose-response of glycine-evoked NR1/NR3A currents.

FIG. 6*b* shows that NMDA and L-glutamate did not potentiate glycine-evoked currents.

FIG. 6*c* shows inhibition of glycine (2 μM)-evoked currents by D-serine (10 μM), AP5 (100 μM), $Mg^{2+}$ (1 mM), MK-801 (10 μM), and memantine (12 μM).

DETAILED DESCRIPTION OF THE INVENTION

Figure 1A:
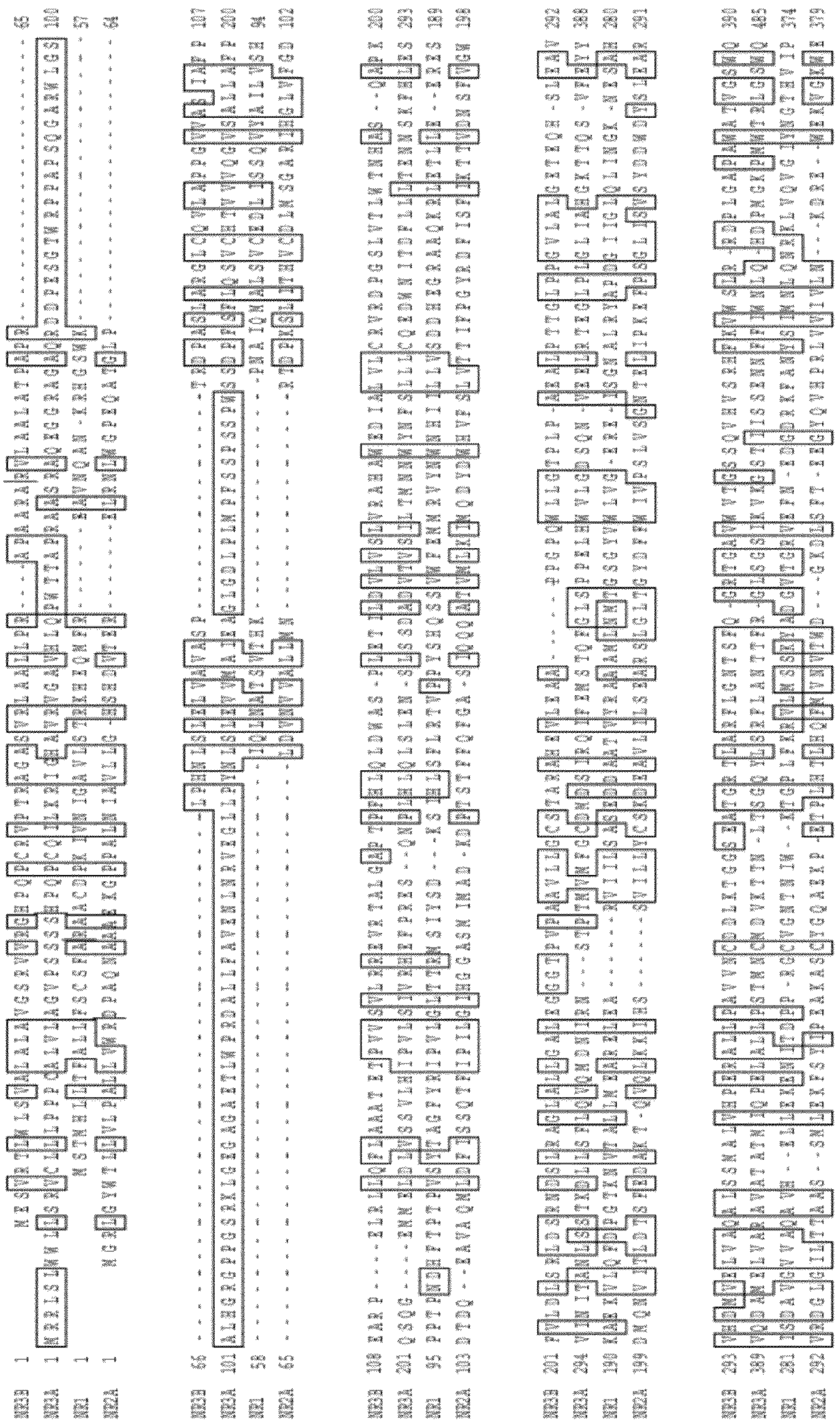
FIGS. 1A-1D show an alignment of the deduced amino acid sequence of ionotropic glutamate receptor subunits from rat, designated NR1 (SEQ ID NO:14), NR2A (SEQ ID NO:15), NR3B B4 (SEQ ID NO:4) and NR3A (SEQ ID NO:16; sequence shown in FIGS. 1A-1D corresponds to SEQ ID NO: 91). Sequences were aligned using ClustalW and the BLOSUM series protein scoring matrix. Exact matches are boxed and shaded; conservative substitutions are boxed (no shading). Predicted signal peptide cleavage sites are indicated by vertical lines. Membrane regions (M1-M4) are indicated by horizontal lines. Asterisks indicate the positions of amino acid residues in NR1 and NR2A which have been shown to be required for glycine and glutamate binding, respectively. An arrow marks the position of the conserved asparagine residue in NR1 and NR2A-D.
Figure 1B:
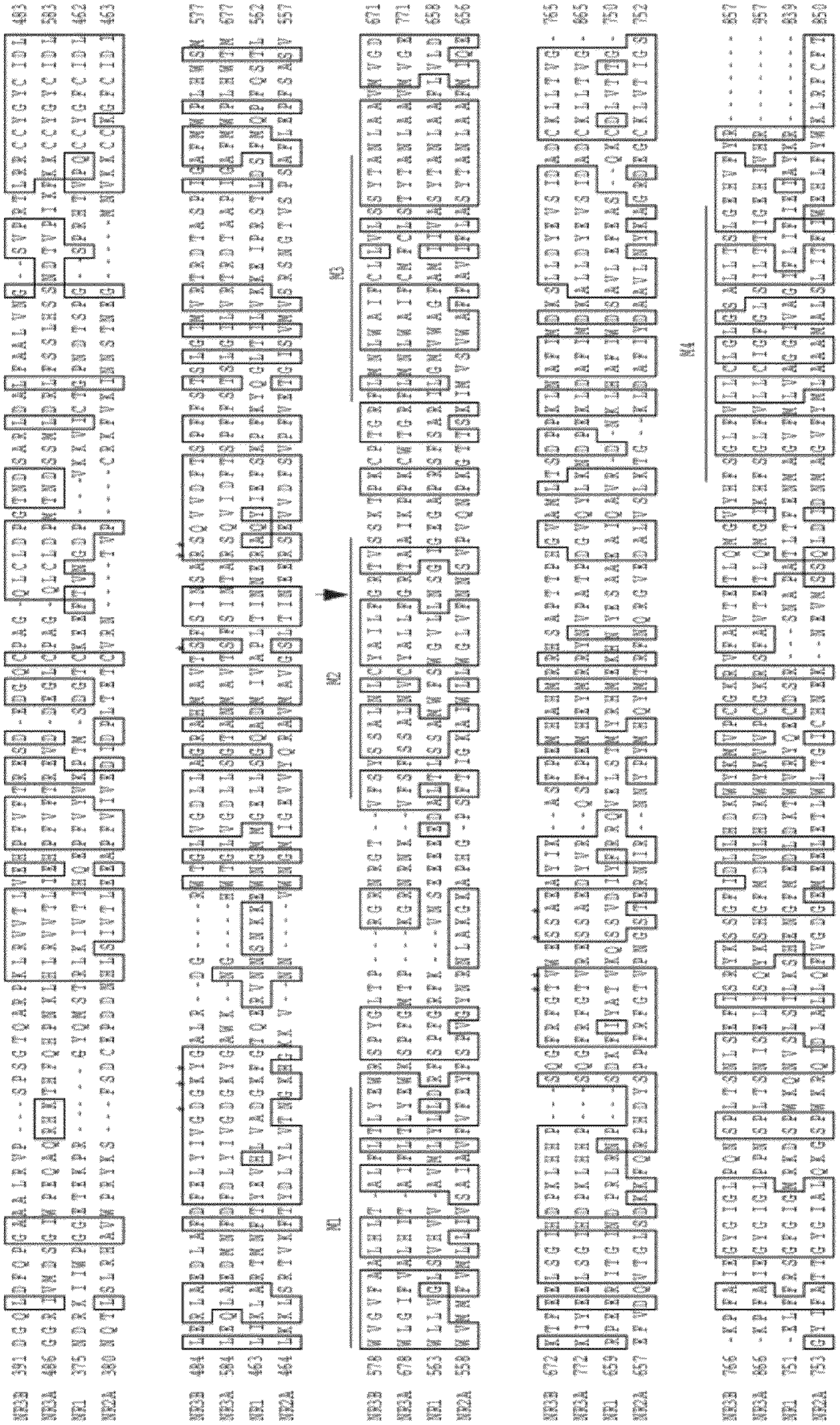
Figure 1C:
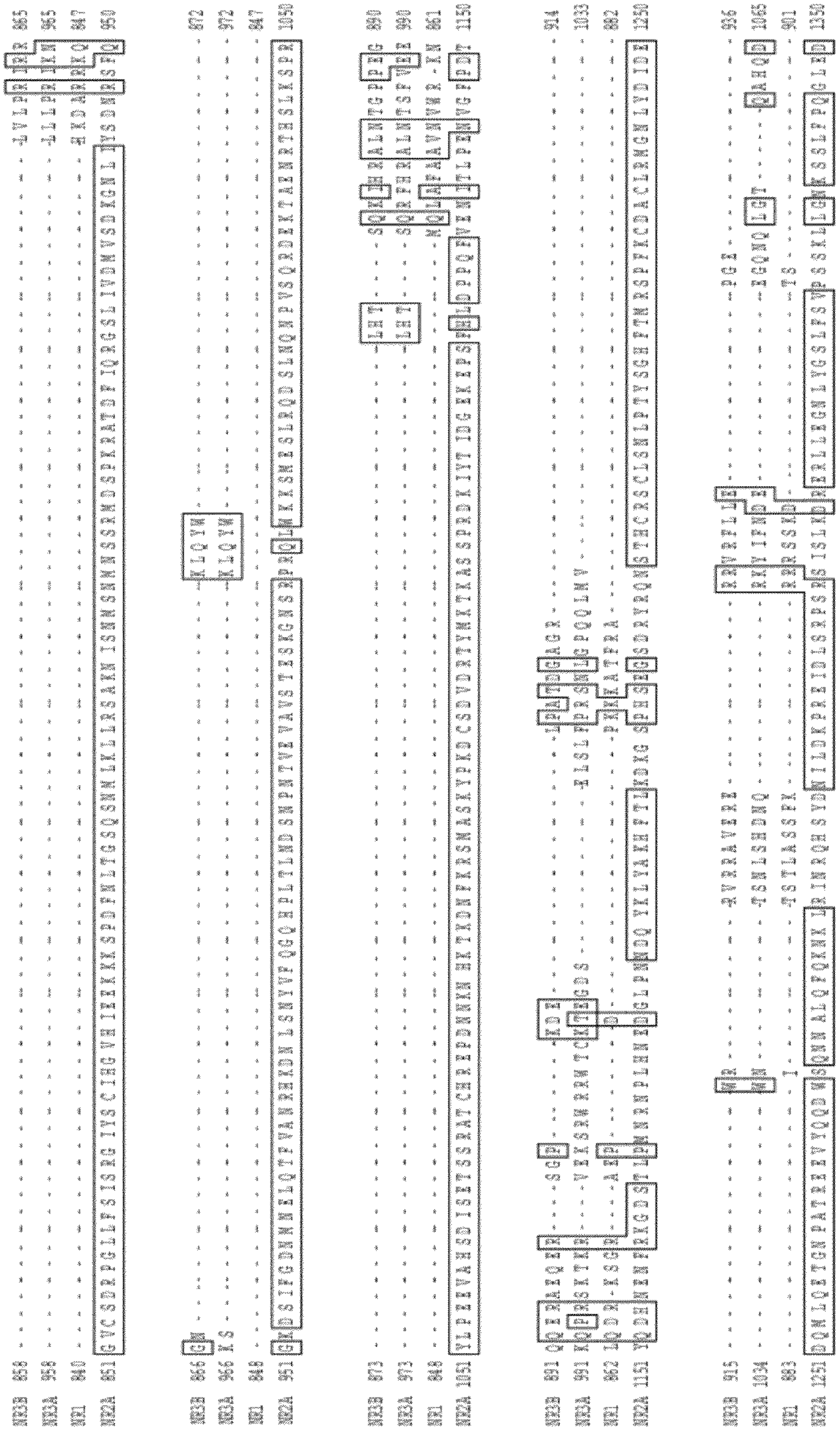
Figure 1D:
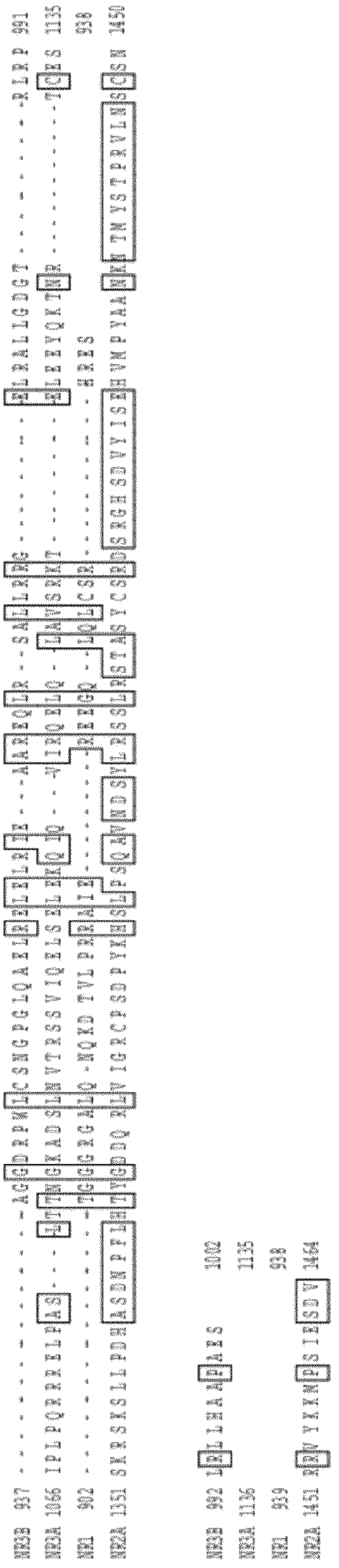

The present invention relates to the cloning and characterization of a seventh NMDAR subunit, designated herein NR3B. The present invention also relates to the determination that receptors containing NR3B, or receptors containing the previously identified NMDAR subunit NR3A, display strikingly distinctive properties from all previously characterized NMDARs. The invention provides molecules and methods that can be used to prevent or ameliorate conditions in which inappropriate NMDA receptor activation, or inappropriate responses to glycine or glutamate, are involved.

The invention provides an isolated nucleic acid molecule encoding a NR3B polypeptide. As used herein, the term "NR3B polypeptide" refers to a polypeptide that retains at least one biological activity characteristic of the naturally occurring mammalian NR3B polypeptides designated herein SEQ ID NOS:2, 4, 58, 60, 6, 62 or 8. As disclosed herein, an exemplary biological activity characteristic of NR3B is the ability to form a subunit of an excitatory glycine receptor. An "excitatory glycine receptor" can be characterized as a receptor that responds to micromolar concentrations of glycine with a cation current. An excitatory glycine receptor can further be characterized by exhibiting any or all of the following properties: little or no response to NMDA or glutamate; little or no response to certain NR1 glycine site agonists, such as D-alanine, ACPC or D-cycloserine; inhibition of current in response to D-serine; inhibition of current in response to 5,7-dichlorokynuric acid; lack of inhibition of current in response to L-strychnine; lack of substantial inhibitory response to $Mg^{2+}$, MK801 or memantine; enhancement of glycine-invoked current by ≧40 μM APV; relatively $Ca^{2+}$-impermeable.

A further exemplary biological activity characteristic of NR3B is the ability to oligomerize with an NR1 subunit, and possibly further with both an NR1 and an NR2 subunit.

Yet another exemplary biological activity characteristic of NR3B is the ability to bind glycine with high affinity. The skilled person can determine other biological activities characteristic of an NR3B polypeptide designated herein SEQ ID NOS:2, 4, 58, 60, 6, 62 or 8.

Isolated nucleic acid molecules encoding NR3B polypeptides can be used, for example, as templates for the recombinant expression of NR3B subunits (the uses of which are described in more detail below); as probes to detect NR3B-encoding nucleic acid molecules in samples; in in vivo and ex vivo gene therapy applications in which modulation of NR3B expression is desired; and in other therapeutic, diagnostic, screening and research applications known to those skilled in the art.

The term "isolated," in reference to an invention nucleic acid molecule or polypeptide is intended to mean that the molecule is substantially removed or separated from components with which it is naturally associated, or is otherwise modified by the hand of man, thereby excluding nucleic acid and polypeptide molecules as they exist in nature. An isolated molecule can be in any form, such as in a buffered solution, a suspension, a lyophilized powder, attached to a solid support (e.g. as a component of an array, or on a filter or column), or in a cell or cell extract.

The term "nucleic acid molecule," as used herein, refers to a polynucleotide of natural or synthetic origin. A nucleic acid molecule can be single- or double-stranded genomic DNA, cDNA or RNA, and can represent a sense strand, an antisense strand, or both. Accordingly, a designated sequence identifier, unless specified otherwise, is intended to refer to the single-stranded molecule having the recited sequence, the single-stranded complement of the recited sequence, or a double stranded (or partially double-stranded) molecule in which one strand has the recited sequence.

A nucleic acid molecule can optionally include one or more non-native nucleotides, having, for example, modifications to the base, the sugar, or the phosphate portion, or having a modified phosphodiester linkage. Such modifications can be advantageous in increasing the stability of the nucleic acid molecule. Furthermore, a nucleic acid molecule can include, for example, a detectable moiety, such as a radiolabel, a fluorochrome, a ferromagnetic substance, a luminescent tag or a detectable binding agent such as biotin. Such modifications can be advantageous in applications where detection of a hybridizing nucleic acid molecule is desired.

An isolated nucleic acid molecule encoding a NR3B polypeptide can encode SEQ ID NO:6, or encode a polypeptide having at least 60% identity to SEQ ID NO:6, such as at least 70%, 80%, 85%, 90%, 95%, 97%, 99% or greater identity to SEQ ID NO:6. Identity of any two nucleic acid or amino acid sequences can be determined by those skilled in the art based, for example, on known computer alignments such as BLAST 2.0, ClustalW and the like, which can be adjusted manually, if appropriate, to insert gaps to optimize the alignment according to standard practice in the art.

An isolated nucleic acid molecule encoding a NR3B polypeptide with at least 60% identity to SEQ ID NO:6 can encode a naturally occurring or a non-naturally occurring amino acid sequence. SEQ ID NO:6 represents the predicted amino acid sequence of a naturally occurring human NR3B polypeptide.

Figure 8A:
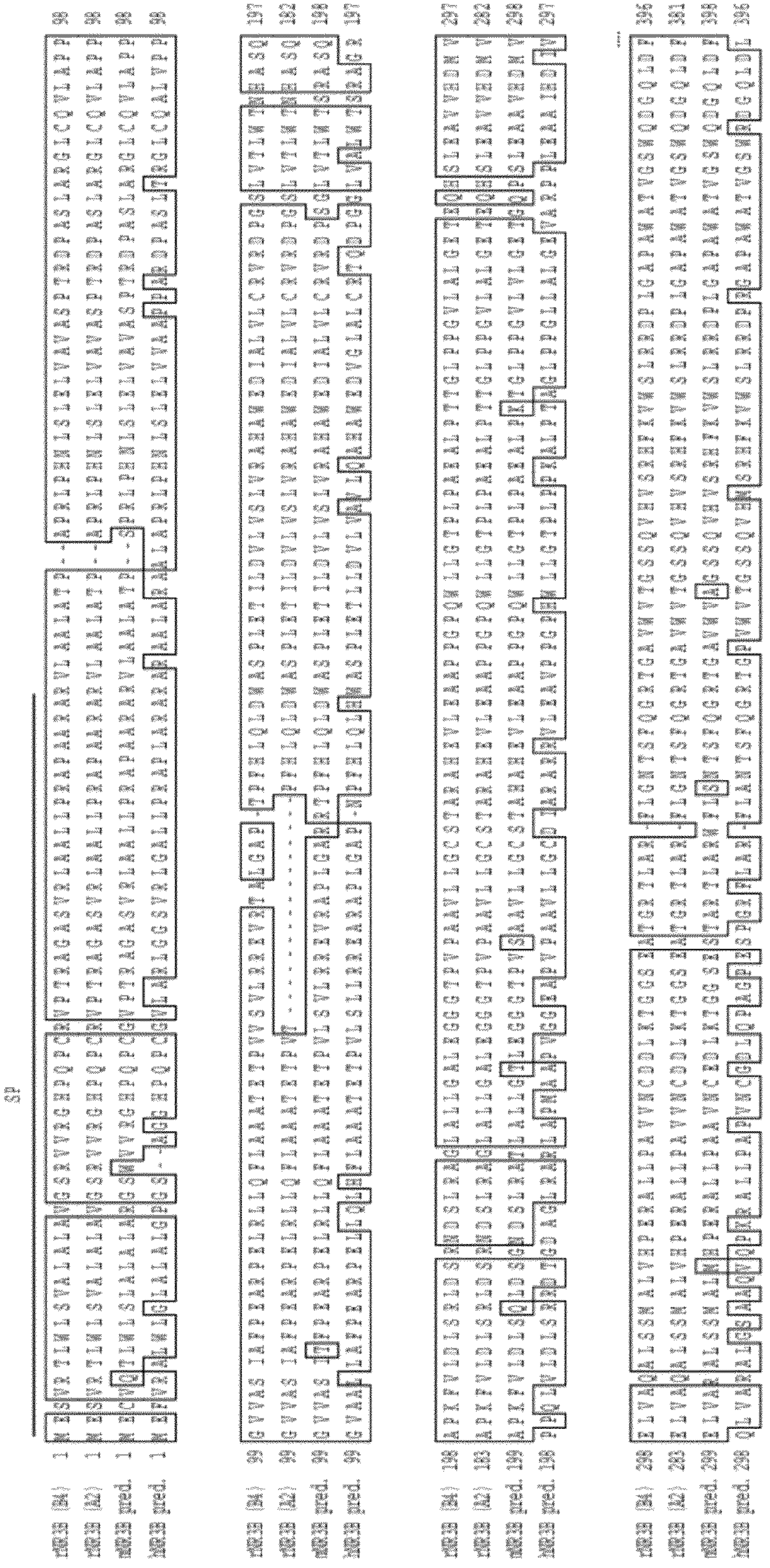
FIGS. 8A-8C show the deduced amino acid sequences of a rat NR3B B4 (SEQ ID NO:4) and a rat NR3B A2 (SEQ ID NO:2) and their alignment with the predicted sequences of a mouse NR3B (SEQ ID NO:8; sequence shown in FIGS. 8A-8C corresponds to SEQ ID NO: 92) and a human NR3B (SEQ ID NO:6; sequence shown in FIGS. 8A-8C corresponds to SEQ ID NO: 93). Sequences were aligned using ClustalW and the BLOSUM series protein scoring matrix. Exact matches are boxed and shaded; conservative substitutions are boxed (no shading). Gaps (−) were inserted to maximize homology. Thick horizontal lines indicate the positions of the predicted signal peptide and membrane regions (M1-M4). Dotted horizontal lines indicate the positions of the S1 and S2 ligand binding domains.
Figure 8B:
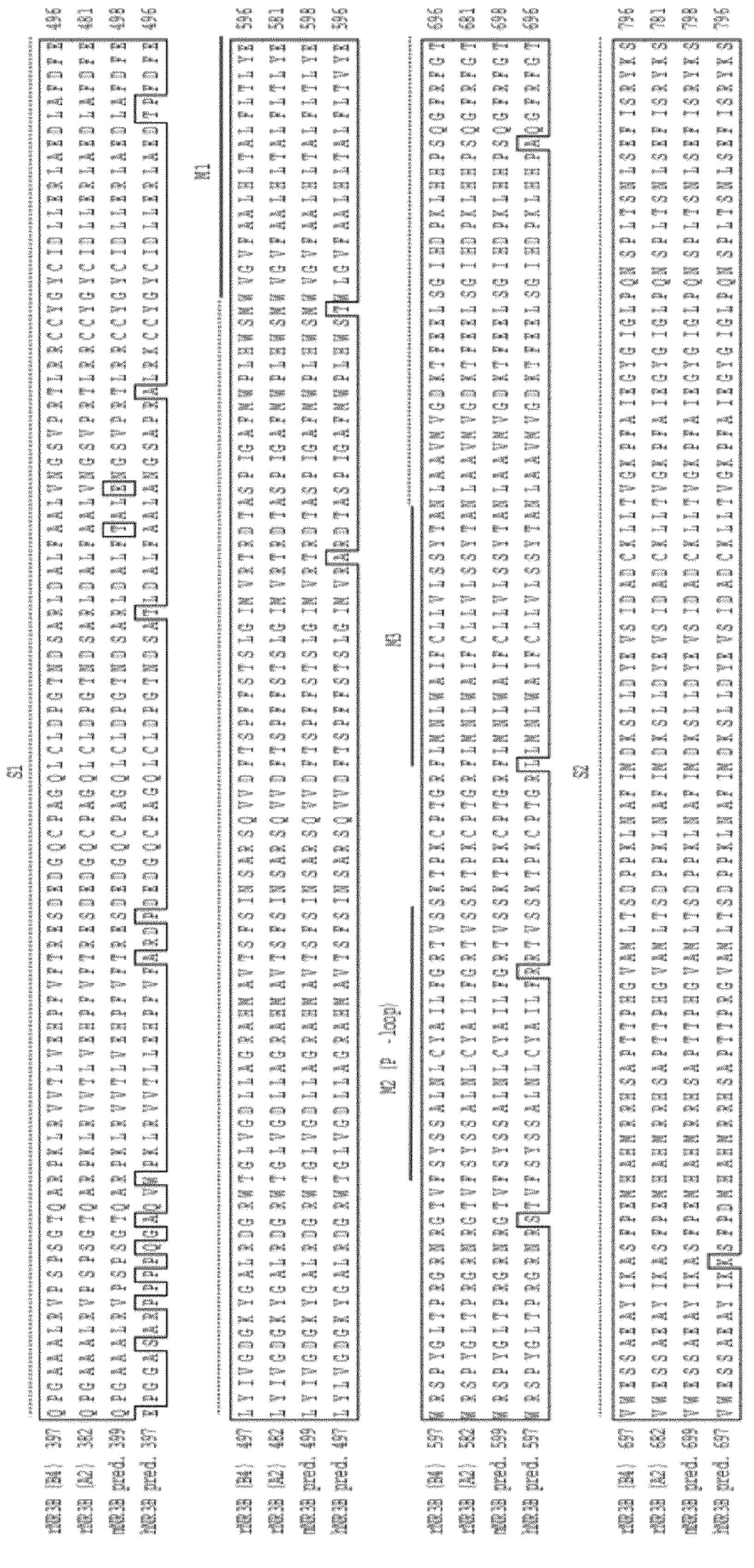
Figure 8C:
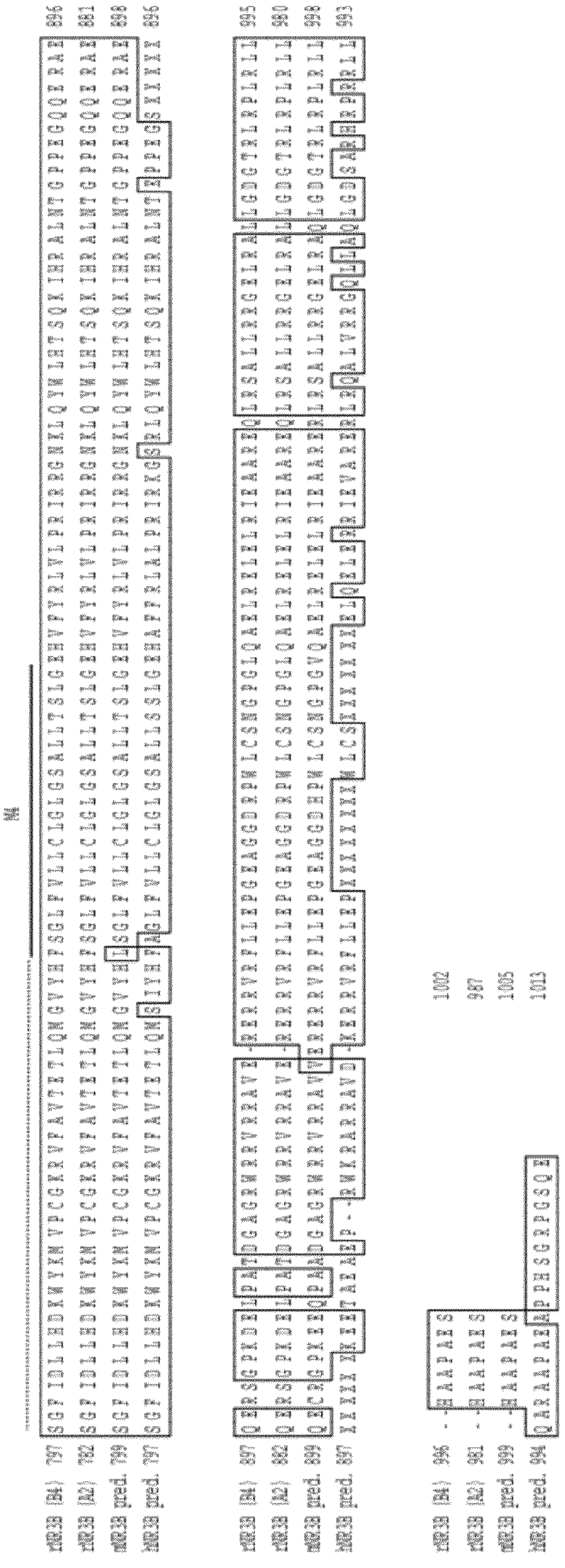

The skilled person will appreciate from the alignment shown in FIG. 8 that the C-terminus of SEQ ID NO:6 differs somewhat from the rat and mouse orthologs. Based on these observed differences, it is contemplated that a naturally occurring human NR3B polypeptide can contain additional sequence corresponding to one or more of the gaps where SEQ ID NO:6 does not apparently align with SEQ ID NOS: 2, 4 and 8, or no sequence in these positions.

For example, it is contemplated that a naturally occurring human NR3B polypeptide can contain several additional amino acids (e.g. 1-20 additional amino acids, such as 11 additional amino acids), or no amino acids, between the sequence "PPEGS" (SEQ ID NO:72) and "KEETA" (SEQ ID NO:73). Such additional sequence can be identical to, substantially similar to, or different from, the sequence QQERAEQERSGP (SEQ ID NO:74) or the sequence QQERAEQECRGP (SEQ ID NO:75). Likewise, it is contemplated that a naturally occurring human NR3B polypeptide can contain several additional amino acids (e.g. 1-20 additional amino acids, such as 8 additional amino acids), or no amino acids, between the sequence "FLLEP" (SEQ ID NO:76) and "WLCS" (SEQ ID NO:77). Such additional sequence can be identical to, substantially similar to, or different from, the sequence GEAGGDHP (SEQ ID NO:78) or the sequence GEAGGDHP (SEQ ID NO:79).

Likewise, it is contemplated that a naturally occurring human NR3B polypeptide can contain several additional amino acids (e.g. 1-20 additional amino acids, such as 7 additional amino acids), or no amino acids, between the sequence "WLCS" (SEQ ID NO:80) and "ELQEL" (SEQ ID NO:81). Such additional sequence can be identical to, substantially similar to, or different from, the sequence NGPGLQA (a SEQ ID NO:82) or the sequence NGPGVQA (SEQ ID NO:83). Furthermore, it is contemplated that a naturally occurring human NR3B polypeptide does not contain the residues in SEQ ID NO:6 that extend beyond the corresponding residues from the C-terminus of SEQ ID NO:4 and 8, such as the sequence PPHSGRPGSQE (SEQ ID NO:84).

A human NR3B polypeptide can contain C-terminal amino acid sequences that are not present in a sequence submitted to GenBank and annotated as a hypothetical protein most similar to rat ionotropic gluatmate receptor (L34938) with an ill-defined C-terminus (GenBank entry AC004528 and AAC12680; SEQ ID NOS:9 and 10). In particular, a human NR3B polypeptide can contain any or all of the C-terminal portion of SEQ ID NO:6 not also present in SEQ ID NO:10, such as the sequence (SEQ ID NO: 63)

XXXXXXXXXXXXXWKRARRAVDKERRVRFLLEPXXXXXXXXWLCSXXX

XXXXELQELERRIEVARERLRQALVRRGQLLAQLGDSARHRPRRLLQA

RAAPAEAPPHSGRPGSQE, where X can be any amino acid.

By further sequence analysis of nucleic acid molecules encoding human NR3B, the nucleotide sequence set forth as SEQ ID NO:61 was identified, which encodes SEQ ID NO:62. SEQ ID NO:62 contains identified amino acid residues in place of certain of the C-terminal residues designated by an "X" in SEQ ID NO:6, and several additional modifications relative to SEQ ID NO:6. This further amino acid sequence is an example of a sequence containing "minor modifications," as described herein, relative to SEQ ID NO:6.

Figure 11A:
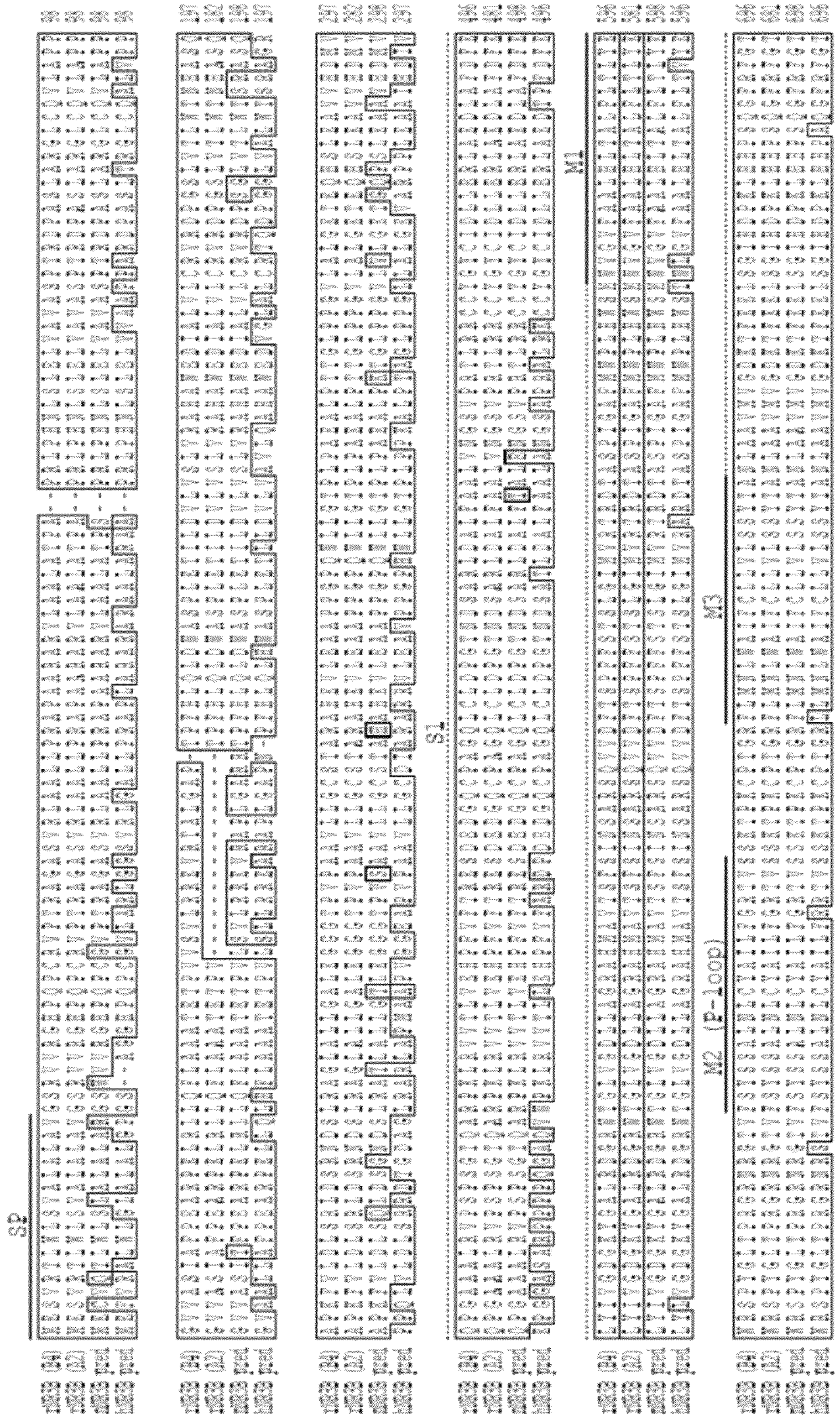
FIGS. 11A and 11B show the deduced amino acid sequences of a rat NR3B B4 (SEQ ID NO:58) and a rat NR3B A2 (SEQ ID NO:60) and their alignment with the predicted sequences of a mouse NR3B (SEQ ID NO:8) and a human NR3B (SEQ ID NO:62). The sequences shown in FIGS. 11A and 11B correspond as follows: rat NR3B B4, amino acids 1-297, SEQ ID NO: 105, amino acids 496-1,002, SEQ ID NO: 106; rat NR3B A2, amino acids 1-282, SEQ ID NO: 107, amino acids 481-987, SEQ ID NO: 108; mouse NR3B, amino acids 1-298, SEQ ID NO: 109, amino acids 498-1,005, SEQ ID NO: 110; human NR3B, amino acids 1 297, SEQ ID NO: 111, amino acids 496-1,008, SEQ ID NO: 112. Sequences were aligned using ClustalW and the BLOSUM series protein scoring matrix. Exact matches to NR3B B4 are boxed and shaded. Gaps (−) were inserted to maximize homology. Thick horizontal lines indicate the positions of the predicted signal peptide and membrane regions (M1-M4). Dotted horizontal lines indicate the positions of the 51 and S2 ligand binding domains.
Figure 11B:
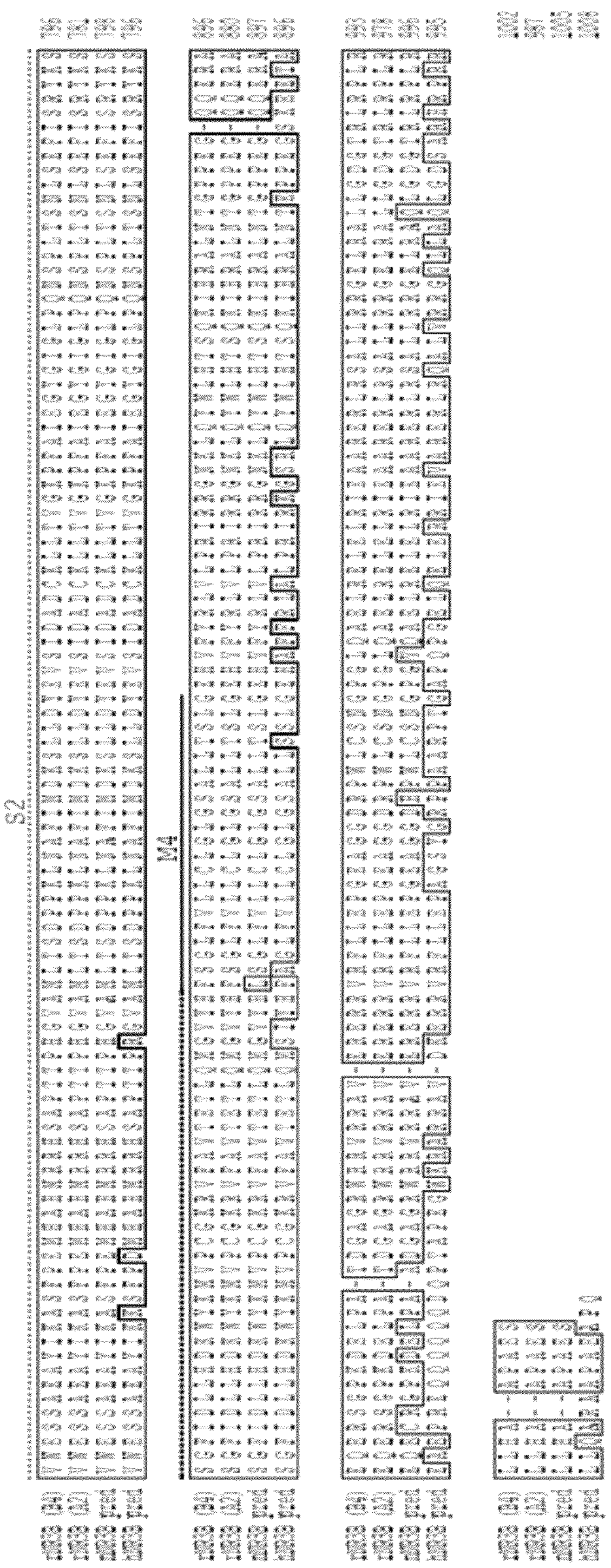

The skilled person will appreciate from the alignment shown in FIG. 11 that the C-terminus of SEQ ID NO:62 differs somewhat from the rat and mouse orthologs. Based on these observed differences, it is contemplated that a naturally occurring human NR3B polypeptide, or an NR3B polypeptide with minor modifications, can contain alternative sequences at one or more of the positions where SEQ ID NO:62 does not contain exact matches with residues of SEQ ID NOS:60, 58 and 8, such as any or all of the amino acids between 890 and 1008 of SEQ ID NO:62 that are unboxed in FIG. 11. Such alternative sequences can be additions, deletions or substitutions of amino acids. It is contemplated that substitutions at these positions can be identical to the corresponding residues in SEQ ID NOS: 60, 58 or 8, or can be conservative or non-conservative substitutions of these residues.

SEQ ID NOS:4 and 2 represent the predicted amino acid sequences of two naturally occurring rat NR3B polypeptides, NR3B B4 and NR3B A2, respectively.

By further sequence analysis of nucleic acid molecules encoding rat NR3B, the nucleotide sequences set forth as SEQ ID NO:57, which encodes SEQ ID NO:58 (B4 form) and SEQ ID NO: 59, which encodes SEQ ID NO:60 (A2 form), were identified. SEQ ID NO:58 differs from SEQ ID NO:4 by virtue of having an "Arg" at residue 968 instead of a "Gln" and, likewise, SEQ ID NO:60 differs from SEQ ID NO:2 by virtue of having an "Arg" at residue 953 instead of a "Gln."

These further amino acid sequences are examples of sequences containing "minor modifications," as described herein, relative to SEQ ID NOS:2 and 4.

SEQ ID NO:8 represents the predicted amino acid sequence of a naturally occurring mouse NR3B polypeptide.

An isolated nucleic acid molecule encoding SEQ ID NO:6 can have the nucleotide sequence designated SEQ ID NO:5, which represents a naturally occurring human NR3B cDNA sequence. The skilled person understands, however, that due to the degeneracy of the genetic code, SEQ ID NO:6 can also be encoded by a nucleotide sequence that differs from SEQ ID NO:5 at one or more codons.

Likewise, isolated nucleic acid molecules encoding SEQ ID NOS:4, 2 or 8 can have the nucleotide sequences designated SEQ ID NOS:3, 1 or 7, or be degenerate variants thereof, and isolated nucleic acid molecules encoding SEQ ID NOS:58, 60 and 62 can have the nucleotide sequences designated SEQ ID NOS:57, 59 and 61, or be degenerate variants thereof.

As shown in the alignments in FIG. 8 and FIG. 11, SEQ ID NOS:2, 4, 6 and 8, and likewise SEQ ID NOS:58, 60, 8 and 62, are highly homologous over their entire lengths. Because of this high degree of identity of NR3B polypeptides across these three mammalian species, it is expected that other naturally occurring mammalian NR3B polypeptides, such as NR3B polypeptides from non-human primates, mouse, rat, rabbit, bovine, porcine, ovine, canine or feline species, as well as naturally occurring NR3B polypeptides from other vertebrates, including fish, birds, reptiles and amphibians (e.g. *Xenopus*) will also exhibit a high degree of identity across their lengths with SEQ ID NO:6 or 62.

Using knowledge of the human, rat or mouse NR3B-encoding nucleic acid sequences and polypeptides disclosed herein, those skilled in the art can readily clone NR3B-encoding nucleic acids from other mammalian or vertebrate species using conventional cDNA or expression library screening methods, or using the polymerase chain reaction (PCR). Additionally, using knowledge of the human, rat or mouse NR3B-encoding nucleic acid sequences and polypeptides disclosed herein, those skilled in the art can readily determine cDNA and coding sequences form other species from an analysis of ESTs and genomic sequences present in available databases.

In contrast, SEQ ID NO:4 exhibits about 47% identity to rat NR3A, with much lower identity to other NMDA receptor subunits (i.e. 19.7% identity to rat NR1; 18.6% identity to rat NR2A). Therefore, the skilled person can readily distinguish an NR3B polypeptide from related receptor subunits based on sequence similarity.

For certain applications, an isolated nucleic acid molecule encoding an NR3B polypeptide need not encode the naturally occurring signal peptide sequence, which is cleaved in the mature polypeptide. The predicted signal peptide sequences of rat (SEQ ID NOS:2 and 4; also SEQ ID NOS:58 and 60), human (SEQ ID NO:6; also SEQ ID NO:62) and mouse (SEQ ID NO:8) NR3B polypeptides are shown by overlining and the designation "SP" in FIG. 8 and FIG. 11. Accordingly, in one embodiment, an isolated nucleic acid molecule can encode an NR3B polypeptide in which some or all or of amino acids 1-51 or 1-53 of SEQ ID NOS:2, 4, 58, 60, 6, 62 or 8 are not present. The skilled person can readily determine the boundaries of the signal peptide sequence from NR3B polypeptides and, if desired, replace these residues with another signal or sorting sequence.

An isolated nucleic acid molecule encoding an NR3B polypeptide can also be a splice variant form that differs from another form by one or more exons, thereby encoding a NR3B polypeptide that differs from another NR3B polypeptide by an insertion or deletion of one or more residues at one or more places in the polypeptide. NR3B splice variants can be expressed in a tissue or developmental stage-specific manner. Rat NR3B A2 (SEQ ID NOS:2 and 60) and rat NR3B B4 (SEQ ID NOS:4 and 58) are examples of splice variant forms that differ by containing (SEQ ID NOS:4 and 58) or not containing (SEQ ID NOS:2 and 60) the sequence VSVLRREVRTALGAP (SEQ ID NO:85). An exemplary splice variant of a human NR3B differs from SEQ ID NOS:6 or 62 by not containing the sequence LSLLRREARAPLGAP (SEQ ID NO:86) or by not containing the sequence LSLLRREARAPLGAPN (SEQ ID NO:87). An exemplary splice variant of a mouse NR3B differs from SEQ ID NO:8 by not containing the sequence LSVLRREVRAPLGAR (SEQ ID NO:8 SEQ ID NO:88) or by not containing the sequence LSVLRREVRAPLGARR (SEQ ID NO:89). The skilled person can readily determine additional splice variants of these and other NR3B polypeptides.

An isolated nucleic acid molecule encoding an NR3B polypeptide can also have one or more minor modifications to the naturally occurring sequence, such as one or more substitutions additions or deletions. Such modifications can be advantageous, for example, in enhancing the stability, bioavailability, bioactivity or immunogenicity of the polypeptide, or to facilitate its purification.

Substitutions to an NR3B amino acid sequence can either be conservative or non-conservative. Conservative amino acid substitutions include, but are not limited to, substitution of an apolar amino acid with another apolar amino acid (such as replacement of leucine with an isoleucine, valine, alanine, proline, tryptophan, phenylalanine or methionine); substitution of a charged amino acid with a similarly charged amino acid (such as replacement of a glutamic acid with an aspartic acid, or replacement of an arginine with a lysine or histidine); substitution of an uncharged polar amino acid with another uncharged polar amino acid (such as replacement of a serine with a glycine, threonine, tyrosine, cysteine, asparagine or glutamine); or substitution of a residue with a different functional group with a residue of similar size and shape (such as replacement of a serine with an alanine; an arginine with a methionine; or a tyrosine with a phenylalanine).

Additions to an NR3B amino acid sequence include, but are not limited to, the addition of "tag" sequences, which are conveniently added at the N- or C-termini, after the signal peptide, or within extracellular or intracellular loops. Such tag sequence include, for example, epitope tags, histidine tags, glutathione-S-transferase (GST), fluorescent proteins (e.g. Enhanced Green Fluorescent Protein (EGFP)) and the like. Such additional sequences can be used, for example, to facilitate expression, purification or characterization of an NR3B polypeptide.

Deletions to an NR3B amino acid sequence include, but are not limited to, deletion of signal peptide residues, and deletion of residues at the N- or C-termini that are not critical for function. Deleted sequences can optionally be replaced by tag sequences or fusion sequences, as described previously.

Modifications to an encoded NR3B amino acid sequence, such as modifications to any of SEQ ID NOS:2, 4, 58, 60, 6, 62 or 8, can be randomly generated, such as by random insertions, deletions or substitutions of nucleotides in a nucleic acid molecule encoding the polypeptide. Alternatively, modifications can be directed, such as by site-directed mutagenesis of a nucleic acid molecule encoding the polypeptide.

Guidance in modifying the sequence of an NR3B polypeptide while retaining biological activity can be provided by the alignment of the sequence of the NR3B orthologs from human, rat and mouse shown in FIG. 8 and FIG. 11. It is well known in the art that evolutionarily conserved amino acid residues are more likely to be important for maintaining biological activity than less well-conserved residues. Thus, it would be expected that substituting a residue that is highly conserved among NR3B polypeptides across species with a non-conserved residue may be deleterious, whereas making the same substitution at a residue which varies among species would likely not have a significant effect on biological activity.

Additionally, guidance in modifying amino acid residues of an NR3B polypeptide while retaining a desired biological activity can be provided by structure-function studies of known NMDA receptor subunits, which share an overall transmembrane topology and domain structure with NR3B. By analogy to other subunits, the ligand binding domain of NR3B is predicted to be formed by the extracellular S1 domain before the first membrane spanning region (M1) and by the extracellular S2 domain between membrane spanning regions M3 and M4 (FIG. 8 and FIG. 11). The second membrane domain (M2, or P-loop) is predicted to line the ion channel pore (see FIG. 8 and FIG. 11). Meddows et al., *J. Biol. Chem.* 276:18795-18803 (2001) have also determined that retention of the N-terminal residues of the NMDA receptor subunit NR1 (i.e. amino acids 1-380 of NR1) is important for subunit oligomerization, whereas the M4 domain and C-terminal residues (i.e. amino acids 811-938 of NR1) are dispensible for oligomerization but required for functional channel formation. The skilled person could apply this knowledge to predict the effect of various modifications within the above-described structural and functional domains on NR3B biological activity.

Computer programs well known in the art can also provide guidance in predicting which amino acid residues can be modified without abolishing a topological or functional feature of an NR3B polypeptide.

The invention also provides an isolated nucleic acid molecule that encodes a functional fragment of an NR3B polypeptide. As used herein, the term "functional fragment" refers to a portion of a full-length NR3B polypeptide that retains at least one biological activity characteristic of the full-length polypeptide. A functional fragment can contain, for example, at least about 6, 8, 10, 12, 15, 20, 25, 30, 35, 40, 50, 60, 70, 80, 90, 100, 110, 125, 150, 200, 250, 300, 400, 500, 600, 700, 800, 900, 950 or more amino acids of an NR3B polypeptide.

Figure 9:
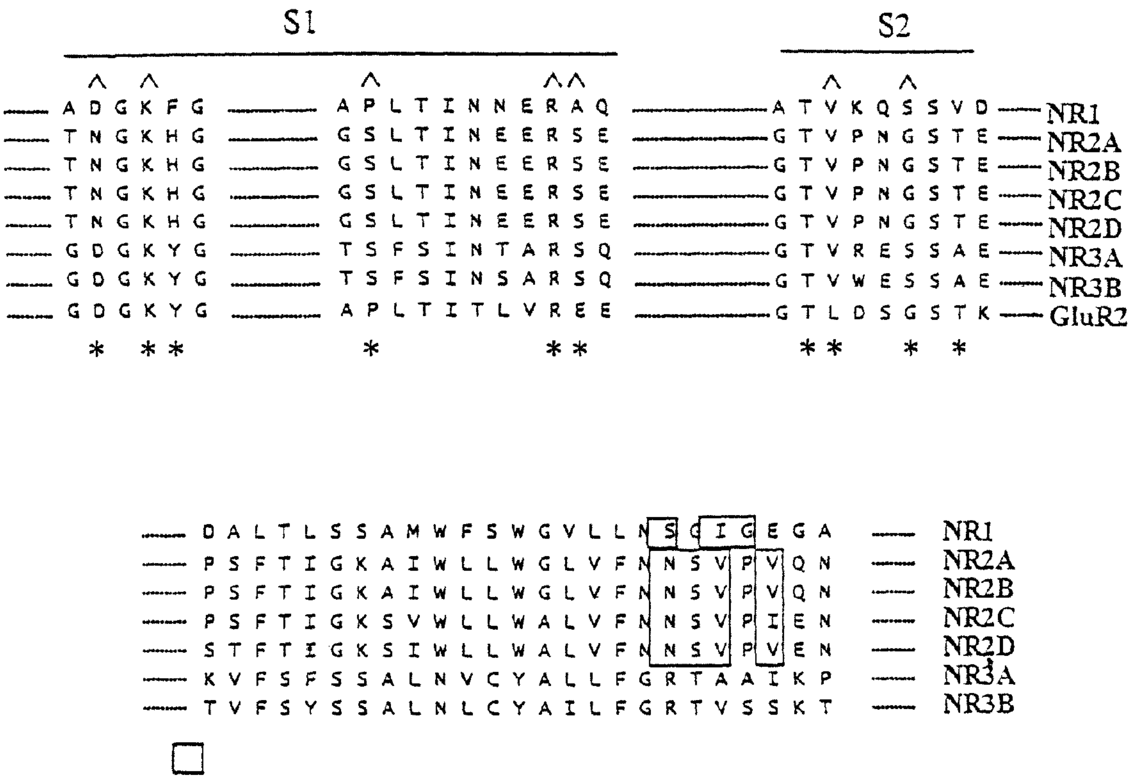
FIG. 9 shows an alignment of regions of ionotropic glutamate receptor subunits NR1 (SEQ ID NOS:64-67, respectively, in order of appearance), NR2A (SEQ ID NOS: 68-71, respectively, in order of appearance), NR2B (SEQ ID NOS:68-71, respectively, in order of appearance), NR2c (SEQ ID NOS:68-70 and 94, respectively, in order of appearance), NR2D (SEQ ID NOS:68-70 and 95, respectively, in order of appearance), NR3A (SEQ ID NOS:96-99, respectively, in order of appearance), NR3B (SEQ ID NOS:96 and 100-102, respectively, in order of appearance) and GluR2 (SEQ ID NOS:96 and 103-104, respectively, in order of appearance). Top: Residues of the 51 and S2 regions considered to be important for glutamate binding are indicated by *. Residues of the S1 and S2 regions considered to be important for glycine binding are indicated by ^. Bottom: Residues of the channel lumen that are accessible from either one or both sides of the channel are boxed.

For example, a functional fragment of an NR3B polypeptide can retain the ability to bind glycine. As shown in FIGS. 1 and 9, the residues of the S1 and S2 regions considered to be important in binding glycine are known. Thus, a functional fragment can contain all or part of the S1 and/or S2 domains of rat, human or mouse NR3B (see FIG. 8 and FIG. 11), and optionally further contain the naturally occurring NR3B intervening sequence, such as membrane regions M1-M3.

An exemplary NR3B functional fragment that binds glycine can contain SEQ ID NO:27 and/or SEQ ID NO:35 and/or SEQ ID NO:43. Advantageously, a chimeric polypeptide containing all or a portion of a different NMDA receptor subunit (e.g. NR1, NR2A-D or NR3A), with the glycine binding domain (e.g. the S1 and/or S2 regions; or SEQ ID NO:27 and/or SEQ ID NO:35 and/or SEQ ID NO:43) of NR3B replacing the corresponding region of the NMDA receptor subunit, can be constructed. Likewise, a chimeric polypeptide containing all or a portion of an NMDA receptor subunit (e.g. NR1, NR2A-D or NR3B), with the glycine binding domain (e.g. the S1 and/or S2 regions; or SEQ ID NO:26 and/or SEQ ID NO:34 and/or SEQ ID NO:42) of NR3A replacing the corresponding region of the NMDA receptor subunit, can be constructed. Such a functional fragment, or a chimeric polypeptide containing such a fragment, can be used, for example, in screening applications described further below to detect excitatory glycine receptor ligands, agonists and antagonists. Additionally, such a functional fragment can be used in therapeutic applications in which it is desirable to compete with an endogenous receptor for binding to agonist. Methods for making and testing chimeric glutamate receptor polypeptides are described, for example, in Villmann et al., *Eur. J. Neurosci.* 11:1765-1778 (1999).

A functional fragment of NR3B can also retain the ability to oligomerize with other NMDA receptor subunits, such as NR1, and optionally NR2. By analogy to NR1, such a fragment can retain all or most of the N-terminal region before the S1 domain, which is predicted to be important for oligomerization (see Meddows et al., supra (2001)).

A further exemplary functional fragment of NR3B can retain the ability to insert into the membrane or form a channel pore by retaining some or all of the membrane regions (M1-M4). Such fragments can be used, for example, to compete with or disrupt the structure of the naturally occurring NR3B.

Another exemplary functional fragment of NR3B can retain the ability to interact with intracellular proteins, such as effector proteins, by retaining some or all of the intracellular region C-terminal to M4. Such fragments can be used, for example, in binding assays to identify polypeptides that interact with NR3B, which can then themselves be used as targets in screening assays; and also can be used to compete with naturally occurring NR3B for binding to effector polypeptides.

Accordingly, the invention provides an isolated nucleic acid molecule that encodes an NR3B functional fragment that contains the extracellular domain of an NR3B polypeptide N-terminal to the S1 domain (with or without the signal peptide), and/or the S1 domain, and/or the M1 domain, and/or the M2 domain, and/or the and/or the M3 domain, and/or the S2 domain, and/or the M4 domain, and/or the intracellular domain C-terminal to the M4 domain. The boundaries of these domains for several mammalian NR3B polypeptides are shown in FIG. 8 and FIG. 11. The skilled person can determine appropriate functional fragments of an NR3B polypeptide for use in a particular application.

The biological activities of NR3B polypeptides and functional fragments can be determined or confirmed by methods known in the art and described further in the Examples. For example, the ability of an NR3B polypeptide or functional fragment to act as a subunit of an excitatory glycine receptor can be tested by recombinantly expressing an NR3B polypeptide in an appropriate cell (e.g. a *Xenopus* oocyte or mammalian cell) in the presence of a suitable amount of another endogenous or exogenous NMDAR subunit (e.g. an NR1 subunit, an NR2 subunit, or an NR3A subunit, or any combination thereof that includes an NR1 subunit), and detecting currents evoked in a dose-dependent fashion by addition of glycine. Other suitable methods for detecting the ability of an NR3B polypeptide to act as a subunit of an excitatory glycine receptor are known in the art and described further below with respect to screening assays.

The ability of an NR3B polypeptide or functional fragment to oligomerize with an NR1 and/or an NR2 and/or an NR3A polypeptide can be assayed, for example, by a functional assay to measure excitatory ionic responses of an NR3B/NR1 receptor to glycine, as described above, or alternatively by co-expressing the polypeptides and detecting NR3B/NR1 polypeptide association. Various assays for detecting polypeptide associations are well known in the art and include, for example, co-immunoprecipitation assays (see, for example, Meddows et al., supra (2001)), two-hybrid assays, GST pull-down assays, protein chip proteomic array analysis (e.g. ProteinChip™ System from Ciphergen Biosystems, which can be used in tandem with mass spectrometry analysis for sequence or structure determination) and the like, using an NR3B polypeptide or functional fragment.

The ability of an NR3B polypeptide or functional fragment to bind glycine can be also detected by a functional assay to measure excitatory ionic responses of an NR3B/NR1 receptor to glycine, as described above, or alternatively by a ligand binding assay. Various direct and competitive ligand binding assays, such as those described above with respect to oligomerization, and assays described below with respect to screening, are well known in the art and can be used to determine the ability of an NR3B polypeptide or functional fragment to bind glycine.

Further provided are isolated polynucleotides containing at least 17 contiguous nucleotides of an invention NR3B nucleic acid molecule or of its complement. An isolated polynucleotide can thus contain at least 18, 19, 20, 22, or at least 25 contiguous nucleotides, such as at least 30, 40, 50, 60, 70, 80, 90, 100, 125, 150, 175, 200, 225, 250, 275, 300, 350, 400, 500, 600, 700, 800, 1000, 1500, 2000, 2500, 3000, 3500 or more contiguous nucleotides from the reference nucleotide sequence, up to the full length sequence. An invention polynucleotide can be single or double stranded, represent the sense or antisense strand, and contain either coding or non-coding sequence or both. An invention polynucleotide can, but need not, encode a biologically active polypeptide and can, but need not, be inserted into a vector.

In one embodiment, the isolated polynucleotide comprises at least 17 contiguous nucleotides of any of SEQ ID NOS:1, 59, 3, 57, 5, 61 or 7 or the complement thereof. Such polynucleotides are of sufficient length and complexity to be able to specifically hybridize to an NR3B-encoding nucleic acid molecule under highly stringent hybridization conditions. Therefore, the invention polynucleotides can advantageously be used, for example, as probes to detect the presence, abundance or fidelity of NR3B-encoding nucleic acid molecules in a sample; as NR3B-specific sequencing or PCR primers; as antisense, RNA interference or ribozyme reagents for use in ex vivo or in vivo gene therapy applications to block expression of NR3B in a cell, as described in more detail below; or in other applications known to those skilled in the art in which hybridization to an NR3B-encoding nucleic acid molecule is desirable. In certain applications, polynucleotides that distinguish a splice variant form of an NR3B receptor are useful, such as polynucleotides containing the region of the rat NR3B B4 form not present in the NR3B A2 form.

Specific hybridization refers to the ability of a nucleic acid molecule to hybridize to the reference nucleic acid molecule without hybridization under the same conditions with nucleic acid molecules that are not the reference molecule, such as a nucleic acid molecule encoding another NMDA receptor subunit. Moderately stringent hybridization conditions are conditions equivalent to hybridization of filter-bound nucleic acid in 50% formamide, 5×Denhart's solution, 5×SSPE, 0.2% SDS at 42° C., followed by washing in 0.2×SSPE, 0.2% SDS, at 50°. Highly stringent conditions are conditions equivalent to hybridization of filter-bound nucleic acid in 50% formamide, 5×Denhart's solution, 5×SSPE, 0.2% SDS at 42° C., followed by washing in 0.2×SSPE, 0.2% SDS, at 65° C. Other suitable moderately stringent and highly stringent hybridization buffers and conditions are well known to those of skill in the art and are described, for example, in Sambrook et al., *Molecular Cloning: A Laboratory Manual,* 3rd ed., Cold Spring Harbor Press, Plainview, N.Y. (2001) and in Ausubel et al. (*Current Protocols in Molecular Biology* (Supplement 47), John Wiley & Sons, New York (1999)).

In one embodiment, the invention provides a primer pair containing two isolated polynucleotides as set forth above. The primer pair can be used, for example, to amplify an NR3B-encoding nucleic acid molecule by the polymerase chain reaction (PCR). A suitable primer pair can contain an isolated polynucleotide containing at least 17 contiguous nucleotides of the sense strand of an invention NR3B nucleic acid molecule, and an isolated polynucleotide containing at least 17 contiguous nucleotides of the antisense strand of an invention NR3B nucleic acid molecule. The skilled person can determine an appropriate primer length and sequence composition for the intended application.

NR3B nucleic acid molecules (including nucleic acid molecules encoding NR3B polypeptides, functional fragments thereof and polynucleotides, as described above) can optionally contain exogenous nucleotide sequences including, for example, sequences that facilitate identification or purification of the molecule, and sequences that facilitate cloning, such as restriction endonuclease recognition sites.

NR3B nucleic acid molecules can be produced or isolated by methods known in the art. The method chosen will depend on the type of nucleic acid molecule one intends to isolate. Those skilled in the art, based on knowledge of the nucleotide sequences disclosed herein, can readily isolate NR3B nucleic acid molecules as genomic DNA, as full-length cDNA or desired fragments therefrom, or as full-length mRNA or cRNA or desired fragments therefrom, by methods known in the art.

It will be appreciated that an invention NR3B polypeptide, functional fragment or peptide does not consist of the exact sequence of an amino acid sequence set forth in a publically available database, or of the exact amino acid sequence of a translated product of a nucleic acid molecule set forth in a publically available database Likewise, an invention nucleic acid molecule encoding a NR3B polypeptide or functional fragment, or an NR3B polynucleotide, does not consist of the exact sequence of a nucleotide sequence set forth in publically available databases, including but not limited to Expressed Sequence Tags (ESTs), Sequence Tagged Sites (STSs) and genomic fragments deposited in public databases such as the GenBank nr, dbest, dbsts and gss databases.

Specifically excluded from the invention polypeptides and nucleic acid molecules are molecules having the exact sequence of any of the following: the human EST sequence designated SEQ ID NO:13 (GenBank Accession No. AL359933); fragments of human chromosome 19 genomic sequences (e.g. GenBank Accession No. AC004528), such as the predicted cDNA sequence designated SEQ ID NO:9 which encodes a protein designated as a hypothetical human protein most similar to rat ionotropic gluatmate receptor, and the encoded polypeptide, SEQ ID NO:10 (GenBank Accession No. AAC12680); the mouse EST sequence designated SEQ ID NO:11 (GenBank Accession No. BC005494) and its predicted encoded polypeptide designated SEQ ID NO:12 (GenBank Accession No. AAH05494.1); and deposited fragments of mouse chromosome 10 genomic sequences (e.g. GenBank Accession No. AC087114).

Since one of skill in the art will realize that the above-recited excluded sequences may be revised in the database at a later date, it is intended that the above-recited sequences are excluded as they stand on the priority date of this application.

Isolated NR3B nucleic acid molecules can be prepared or isolated by methods well known in the art. The method chosen will depend on factors such as the type and size of the nucleic acid molecule; whether or not it encodes a biologically active polypeptide; and the source of the nucleic acid molecule. Such methods are described, for example, in Sambrook et al., supra (2001) and in Ausubel et al., supra (1999).

One useful method for producing an isolated NR3B nucleic acid molecule involves amplification of the nucleic acid molecule using the polymerase chain reaction (PCR) and specific primers and, optionally, purification of the resulting product by gel electrophoresis. Either PCR or reverse-transcription PCR(RT-PCR) can be used to produce a nucleic acid molecule having any desired nucleotide boundaries. Desired modifications to the nucleic acid sequence can also be conveniently introduced by choosing an appropriate primer with one or more additions, deletions or substitutions. Such nucleic acid molecules can be amplified exponentially starting from as little as a single gene or mRNA copy, from any cell, tissue or species of interest.

An isolated NR3B nucleic acid molecule can also be prepared by screening a library, such as a genomic library, cDNA library or expression library, with a detectable NR3B nucleic acid molecule or antibody. Human libraries, and libraries from a large variety of other species, are commercially available or can be produced from species or cells of interest. The library clones identified as containing NR3B nucleic acid molecules can be isolated, subcloned or sequenced by routine methods. From an initially identified fragment, nucleic acid molecules encoding full-length polypeptides can be obtained, if desired, by a variety of methods well-known in the art, such as 5' or 3' RACE.

Furthermore, an isolated NR3B nucleic acid molecule can be produced by synthetic means. For example, a single strand of a nucleic acid molecule can be chemically synthesized in one piece, or in several pieces, by automated synthesis methods known in the art. The complementary strand can likewise be synthesized in one or more pieces, and a double-stranded molecule made by annealing the complementary strands. Direct synthesis is particularly advantageous for producing relatively short molecules, such as probes and primers, and nucleic acid molecules containing modified nucleotides or linkages.

The invention also provides a vector containing an isolated NR3B nucleic acid molecule. The vectors of the invention are useful, for example, for subcloning and amplifying NR3B nucleic acid molecules, and for recombinantly expressing NR3B polypeptides and functional fragments thereof. A vector of the invention can include a variety of elements useful for cloning and/or expression of the encoded nucleic acid molecule in the desired host cell, such as promoter and/or enhancer sequences, which can provide for constitutive, inducible or cell-specific RNA transcription; transcription termination and RNA processing signals, including polyadenylation signals, which provide for stability of a transcribed mRNA sequence; an origin of replication, which allows for proper episomal replication; selectable marker genes, such as a neomycin or hygromycin resistance gene, useful for selecting stable or transient transfectants in mammalian cells, or an ampicillin resistance gene, useful for selecting transformants in prokaryotic cells; and versatile multiple cloning sites for inserting nucleic acid molecules of interest.

Cloning vectors of the invention include, for example, viral vectors such as a bacteriophage, a baculovirus or a retrovirus; cosmids or plasmids; and, particularly for cloning large nucleic acid molecules, bacterial artificial chromosome vectors (BACs) and yeast artificial chromosome vectors (YACs). Such vectors are commercially available, and their uses are well known in the art.

If it is desired to express NR3B RNA transcripts or polypeptides, an invention nucleic acid molecule can be operatively linked to a promoter of RNA transcription. The term "operatively linked," as used herein, is intended to mean that the nucleic acid molecule is positioned with respect to the endogenous promoter, or heterologous promoter, in such a manner that the promoter will direct the transcription of RNA using the nucleic acid molecule as a template. Methods for operatively linking a nucleic acid to a desired promoter are well known in the art and include, for example, cloning the nucleic acid into a vector containing the desired promoter, or appending the promoter to a nucleic acid sequence using PCR.

Thus, an invention nucleic acid molecule operatively linked to a promoter of RNA transcription can be used to express NR3B transcripts and polypeptides in a desired host cell, or in an in vitro system, such as an extract or lysate that supports transcription and translation.

Contemplated promoters and expression vectors provide for expression in bacterial cells, yeast cells, insect cells, amphibian cells, mammalian cells (including human, non-human primate and rodent cells) and other vertebrate cells. A variety of promoters and expression vectors suitable for such purposes are commercially available, and can be further modified, if desired, to include appropriate regulatory elements to provide for the desired level of expression or replication in the host cell.

For use in the gene therapy applications described further below, an invention nucleic acid molecule can be incorporated into suitable gene therapy vector, such as a viral vector or plasmid. Viral based vectors are advantageous in being able to introduce relatively high levels of a heterologous nucleic acid into a variety of cells, including nondividing cells.

Suitable viral vectors for gene therapy applications are well known in the art, and include, for example, Herpes simplex virus vectors (U.S. Pat. No. 5,501,979), Vaccinia virus vectors (U.S. Pat. No. 5,506,138), Cytomegalovirus vectors (U.S. Pat. No. 5,561,063), Modified Moloney murine leukemia virus vectors (U.S. Pat. No. 5,693,508), adenovirus vectors (U.S. Pat. Nos. 5,700,470 and 5,731,172), adeno-associated virus vectors (U.S. Pat. No. 5,604,090), constitutive and regulatable retrovirus vectors (U.S. Pat. Nos. 4,405,712; 4,650,764 and 5,739,018, 5,646,013, 5,624,820, 5,693,508 and 5,674,703), papilloma virus vectors (U.S. Pat. Nos. 5,674,703 and 5,719,054), lentiviral vectors (Kafri et al., Mol. Ther. 1:516-521 (2000), and the like. For targeting neural cells in the treatment of neuronal diseases, adenoviral vectors, Herpes simplex virus vectors and lentiviral vectors are particularly useful.

The invention also provides a cell containing an isolated NR3B nucleic acid molecule. Such a cell need not express a recombinant NR3B polypeptide or fragment for use in cloning procedures. However, a cell can optionally express an NR3B polypeptide or functional fragment encoded by the nucleic acid molecule. Such cells can be used in a variety of applications including, for example, screening for agonists, antagonists and ligands of excitatory glycine receptors, as described further below; as a source to isolate recombinantly expressed NR3B polypeptides; for identifying additional cellular molecules, such as additional receptor subunits or intracellular proteins that associate with NR3B; and in other applications known to those skilled in the art.

Optionally, a cell that recombinantly expresses an NR3B polypeptide can further endogenously or recombinantly express at least one other NMDA subunit, such as an NR1 subunit. As disclosed herein, co-expression of an NR3B and an NR1 polypeptide results in the formation of excitatory glycine receptors. NR1 polypeptides and encoding nucleic acid molecules from various species are known in the art, and include the naturally occurring NR1 polypeptides from human, rat, mouse, duck, fish and *Xenopus* having the nucleotide and predicted amino acid sequences set forth in Table 1:

TABLE 1

| SUBUNIT | ACCESSION NUMBER |
|---|---|
| Human NR1 | D13515 |
| Human NR1-1 | L13266 |
| Human NR1-2 | L13267 |
| Human NR1-3 | L13268 |
| Human NR1-3b | AF015730 |
| Human NR1-4b | AF015731 |
| Rat NR1 | U11418 |
| Rat NR1 | X63255 |
| Rat NR1-2b | U08264 |
| Rat NR1-3a | U08265 |
| Rat NR1-3b | U08266 |
| Rat NR1-4a | U08267 |
| Rat NR1-4b | U08268 |
| Mouse NR1 | D10028 |
| Duck NR1 | D83352 |
| Fish NR1 | AF060557 |
| Rat NR1-1a | U08261 |
| Rat NR1-2a | U08262 |
| Rat NR1-1b | U08263 |
| *Xenopus* NR1 | X94081 |

The skilled person will appreciate that for use in the methods described herein, a co-expressed NR1 polypeptide can have modifications to the naturally occurring sequence, or be a functional fragment of the naturally occurring sequence, so long as the desired NR1 biological activity is retained. An exemplary modification of a naturally occurring NR1 polypeptide that does not affect biological activity is the addition of an epitope tag to facilitate identification in procedures such as immunolocalization and immunoprecipitation. NR1 biological activities include, for example, the ability to oligomerize with other NMDA subunits, including NR2A-D, NR3B and NR3A; the ability to bind glycine; the ability to form excitatory glycine receptors in association with either NR3B or NR3A; and the ability to form NMDA- and glycine-responsive receptors in association with NR2 subunits. As described above with respect to NR3B polypeptides and functional fragments, the skilled person can readily make NR1 molecules with sequences that differ from the naturally occurring sequence and test such molecules to confirm that a desired NR1 biological activity is retained.

Exemplary host cells that can be used to recombinantly express receptor polypeptides and fragments include mammalian primary cells; established mammalian cell lines, such as COS, CHO, HeLa, NIH3T3, HEK 293-T and PC12 cells; amphibian cells, such as *Xenopus* embryos and oocytes; and other vertebrate cells. Exemplary host cells also include insect cells (e.g. *Drosophila*), yeast cells (e.g. *S. cerevisiae, S. pombe*, or *Pichia pastoris*) and prokaryotic cells (e.g. *E. coli*).

Also provided are extracts of recombinant cells that express NR3B at the cell membrane, wherein the extract contains the cell membrane. Advantageously, NR3B is expected to retain a biologically active conformation in a membrane extract, but is partially purified away from other cellular components that may be undesirable for certain applications. Cell membrane extracts can be prepared by methods known in the art (see, for example Das et al., *Nature* 393:377-381 (1998)) and can be used in many of the screening assays described herein.

Methods for introducing a recombinant nucleic acid molecule into a host cell are well known in the art. The choice of method will depend on the host cell, the type of nucleic acid molecule, and the intended application of the host cell. Suitable methods include, for example, various methods of transfection such as calcium phosphate, DEAE-dextran and lipofection methods; viral transduction; electroporation; and microinjection.

Animal model systems can be useful for elucidating normal and pathological functions of NR3B polypeptides, and for determining the efficacy and safety of potential therapeutic compounds that target excitatory glycine receptors. Accordingly, the invention also provides a transgenic non-human animal that contains an NR3B nucleic acid molecule. Such transgenic animals can express a nucleic acid molecule encoding an invention NR3B polypeptide or functional fragment, including a functional fragment that competes with or inhibits the function of the naturally occurring NR3B, as described previously. Alternatively, transgenic animals can express an invention NR3B polynucleotide that prevents effective translation of the naturally occurring NR3B polypeptide, such as an antisense, ribozyme, RNAi or similar construct. By employing suitable inducible and/or tissue specific regulatory elements, NR3B expression or activity in the transgenic animal can be restricted to specific cell types, developmental stages, or induction conditions.

Any of a variety of methods known in the art can be used to introduce a desired transgene into animals to produce the founder lines of transgenic animals (see, for example, Hogan et al., *Manipulating the Mouse Embryo: A Laboratory Manual*, second ed., Cold Spring Harbor Laboratory (1994), U.S. Pat. Nos. 5,602,299; 5,175,384; 6,066,778; and 6,037,521). Such techniques include, but are not limited to, pronuclear microinjection (U.S. Pat. No. 4,873,191); retrovirus mediated gene transfer into germ lines (Van der Putten et al., *Proc. Natl. Acad. Sci. USA* 82:6148-6152 (1985)); gene targeting in embryonic stem cells (Thompson et al., *Cell* 56:313-321 (1989)); electroporation of embryos (Lo, *Mol. Cell. Biol.* 3:1803-1814 (1983)); and sperm-mediated gene transfer (Lavitrano et al., *Cell* 57:717-723 (1989)). Once the founder animals are produced, they can be bred to produce colonies of the particular animal by methods known in the art.

Figure 10:
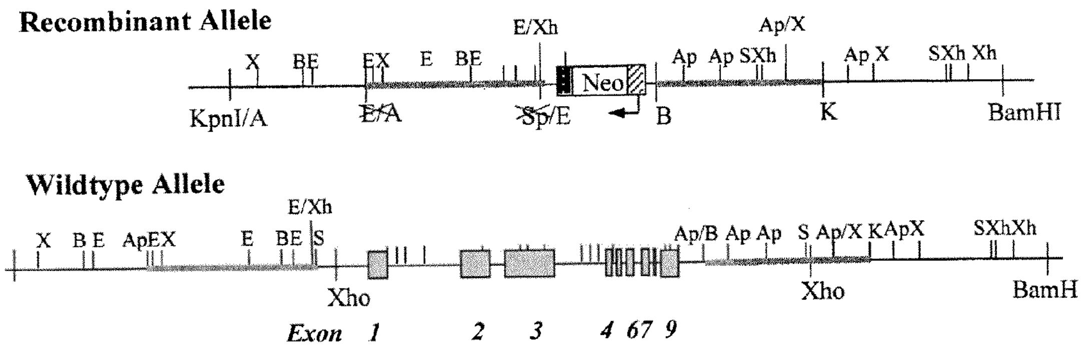
FIG. 10 shows the design of an NR3B targeting vector. The DNA fragment containing mouse NR3B exons 2-10 (−7.6 kb) was replaced by a fragment containing the neomycin resistant (Ned) gene-(~2 kb). The 5'-(~3.6 kb) and 3'-(~3.2 kb) arms used for homologous recombination are indicated by the thicker lines. The targeting DNA fragment was inserted into a pGTN29 vector.

In another embodiment, the invention provides NR3B-deficient non-human animals, or NR3B “knock-out” animals. Methods of deleting all or a portion of a gene so as to alter or prevent expression of the naturally occurring polypeptide are well known in the art. Gene knockout by homologous recombination is described, for example, in Capecchi et al., Science 244:1288 (1989), and in U.S. Pat. Nos. 5,616,491, 5,750,826, and 5,981,830. Methods of making and using an NR3A knockout mouse are described in Das et al., *Nature* 393:377-381 (1998). Analogous targeting vectors and methods are expected to be useful in generating NR3B knockout animals. FIG. 10 describes a targeting construct suitable for use in generating an NR3B knockout mouse.

The invention also provides a method for detecting a nucleic acid molecule encoding an NR3B polypeptide in a sample. Because of the critical role NMDA receptors play in neurologic disorders, the method can be used, for example, to diagnose or prognose a pathological condition mediated, in part, by altered expression, abundance or integrity of an NR3B nucleic acid molecule. Such conditions include, for example, acute neurologic conditions and chronic neurodegenerative diseases described further below. The detection method can also be used to identify additional regions of the nervous system in which NR3B is normally or pathologically expressed. Such information can be valuable in determining additional diagnostic and therapeutic applications for the invention molecules and methods described herein. Furthermore, the detection method can also be used to identify additional naturally occurring splice variants of NR3B receptors, and NR3B-encoding nucleic acid molecules from other species of interest, such as veterinary and laboratory animals.

In one embodiment, the detection method is practiced by contacting a sample with one or more NR3B polynucleotides and detecting specific hybridization to the polynucleotide. Suitable hybridization conditions for detecting specific hybridization will depend on the detection format, and are well known in the art. Exemplary conditions useful for filter-based assays have been described previously. Example II provides exemplary conditions suitable for in situ hybridization assays. Suitable conditions for PCR-based detection methods are also well known in the art and described, for example, in Sambrook et al., supra (2001) and in Ausubel et al., supra (1999).

As used herein, the term "sample" is intended to mean any biological fluid, cell, tissue, organ or portion thereof that contains or potentially contains an NR3B nucleic acid molecule or polypeptide. For example, a sample can be a histologic section of a specimen obtained by biopsy, or cells that are placed in or adapted to tissue culture. A sample further can be a subcellular fraction or extract, or a crude or substantially pure nucleic acid or protein preparation. A sample can be prepared by methods known in the art suitable for the particular format of the detection method employed.

The methods of detecting an NR3B nucleic acid molecule in a sample can be either qualitative or quantitative, and can detect the presence, abundance, integrity or structure of the nucleic acid molecule, as desired for a particular application. Suitable hybridization-based assay methods include, for example, in situ hybridization, which can be used to detect altered chromosomal location of the nucleic acid molecule, altered gene copy number, and RNA abundance, depending on the assay format used. Other hybridization methods include, for example, Northern blots and RNase protection assays, which can be used to determine the abundance and integrity of different RNA splice variants, and Southern blots, which can be used to determine the copy number and integrity of DNA. A hybridization probe can be labeled with any suitable detectable moiety, such as a radioisotope, fluorochrome, chemiluminescent marker, biotin, or other detectable moiety known in the art that is detectable by analytical methods.

Suitable amplification-based detection methods are also well known in the art, and include, for example, qualitative or quantitative polymerase chain reaction (PCR); reverse-transcription PCR(RT-PCR); single strand conformational polymorphism (SSCP) analysis, which can readily identify a single point mutation in DNA based on differences in the secondary structure of single-strand DNA that produce an altered electrophoretic mobility upon non-denaturing gel electrophoresis; and coupled PCR, transcription and translation assays, such as a protein truncation test, in which a mutation in DNA is determined by an altered protein product on an electrophoresis gel. The amplified nucleic acid molecule can be sequenced to detect mutations and mutational hot-spots, and specific PCR-based assays for large-scale screening of samples to identify such mutations can be developed.

The invention also provides isolated NR3B polypeptides and functional fragments therefrom, having amino acid sequences as described above with respect to polypeptides encoded by invention nucleic acid molecules. NR3B polypeptides and functional fragments can be used, for example, in therapeutic applications in which such polypeptides and fragments are administered onto or into cells; in screening assays to identify ligands, agonists and antagonists of excitatory glycine receptors; in research applications to identify additional NR3B-associating polypeptides; to raise antibodies for use in diagnostic and prognostic methods; to affinity purify antibodies and ligands; and in other applications known to those skilled in the art.

An isolated NR3B polypeptide of the invention can optionally contain amino acids with various chemical or enzymatic modifications with respect to naturally occurring amino acids. Such modifications can enhance the stability, bioactivity, immunogenicity or other advantageous property of an invention polypeptide. Thus, a polypeptide can contain an amino acid modified by replacement of hydrogen by an alkyl, acyl, or amino group; by esterification of a carboxyl group with a suitable alkyl or aryl moiety; by alkylation of a hydroxyl group to form an ether derivative; by phosphorylation or dephosphorylation of a serine, threonine or tyrosine residue; by N- or O-linked glycosylation; by iodination; by radiolabeling; or the like. A polypeptide can also include a modified amino acids such as hydroxyproline or carboxyglutamate, or a D-amino acid in place of its corresponding L-amino acid. Those skilled in the art can determine an appropriate amino acid modification for a given application.

In another embodiment, the invention provides an isolated NR3B peptide. An exemplary NR3B peptide contains at least 8 contiguous amino acids of a naturally occurring NR3B polypeptide, such as at least 8 contiguous amino acids of SEQ ID NOS:2, 4, 58, 60, 6, 62 or 8. Such a peptide can contain, for example, at least about 10, 12, 15, 20, 25, 30, 35, 40, 50, 60, 70, 80, 90, 100, 110, 125, 150, 200, 250, 300, 400, 500, 600, 700, 800, 900, 950 or more amino acids, up to the full length of the reference polypeptide. A peptide of at least about 8 amino acids can be used, for example, as an immunogen to raise antibodies specific for an NR3B polypeptide, or as an antigen to purify antibodies specific for an NR3B polypeptide. When used as an antigen, an invention peptide can be attached to a carrier molecule such as bovine serum albumin (BSA) or keyhole limpet hemocyanin (KLH).

Peptides that are likely to be antigenic or immunogenic can be predicted using methods and algorithms known in the art and described, for example, by Irnaten et al., *Protein Eng.* 11:949-955 (1998), and Savoie et al., *Pac. Symp. Biocomput.* 1999:182-189 (1999). Immunogenicity of the peptides of the invention can be determined by methods known in the art, such as assay of a delayed-type hypersensitivity response in an animal sensitized to a NR3B polypeptide, or by elicitation of antibodies specific for NR3B polypeptides. Likewise, antigenicity of the peptides of the invention can be determined by methods known in the art, such as by ELISA analysis, as described, for example, in Harlow and Lane, *Antibodies: A Laboratory Manual*, Cold Spring Harbor Laboratory Press (1988).

The isolated NR3B polypeptides, functional fragments and peptides of the invention can be prepared by methods known in the art, including biochemical, recombinant and synthetic methods. For example, polypeptides can be purified by routine biochemical methods from cells or tissues that express the polypeptide. The detection methods disclosed herein can be adapted for determining which cells or tissues are appropriate starting materials. Biochemical purification can include, for example, steps such as solubilization of the appropriate cells, size or affinity chromatography, electrophoresis, and immunoaffinity procedures. The methods and conditions for biochemical purification of a polypeptide of the invention can be chosen by those skilled in the art, and purification monitored, for example, by an ELISA assay or a functional assay.

An NR3B polypeptide, functional fragment or peptide having any desired boundaries can also be produced by recombinant methods. Recombinant methods involve expressing a nucleic acid molecule encoding the desired polypeptide or fragment in a host cell or cell extract, and isolating the recombinant polypeptide or fragment, such as by routine biochemical purification methods described above. To facilitate identification and purification of the recombinant polypeptide, it is often desirable to insert or add, in-frame with the coding sequence, nucleic acid sequences that encode epitope tags, polyhistidine tags, glutathione-S-transferase (GST) domains, fluorescent proteins (e.g. EGFP) and the like. Methods for producing and expressing recombinant polypeptides in vitro and in prokaryotic and eukaryotic host cells are well known in the art.

Thus, the invention provides a method of producing an NR3B polypeptide or functional fragment either in vitro or in a cell, by expressing a nucleic acid molecule encoding the polypeptide or fragment under appropriate conditions. Optionally, the polypeptide or fragment so produced can be partially purified, such as obtained as a membrane extract.

The invention NR3B polypeptide fragments and peptides can also be produced, for example, by enzymatic or chemical cleavage of the full-length polypeptide. Methods for enzymatic and chemical cleavage and for purification of the resultant peptide fragments are well known in the art (see, for example, Deutscher, *Methods in Enzymology*, Vol. 182, "Guide to Protein Purification," San Diego: Academic Press, Inc. (1990)).

Depending on the intended application, the isolated NR3B polypeptide or functional fragment can optionally be isolated in, or reconstituted into, a natural or artificial lipid bilayer, such as a cell membrane or liposome, with or without other cellular components. Thus, in one embodiment, the invention provides an isolated NR3B polypeptide, further comprising a membrane, and optionally further comprising an NMDA receptor subunit, such as an NR1 subunit. Membrane-associated NR3B polypeptides and functional fragments are useful in applications in which structural integrity of the subunit and/or excitatory glycine receptor are important, such as in the screening assays described herein.

The invention also provides an antibody or antigen binding fragment thereof which specifically binds an NR3B polypeptide. Such antibodies, which include polyclonal, monoclonal, chimeric, bifunctional, and humanized antibodies, can be used, for example, to affinity purify an NR3B polypeptide or functional fragment; to detect cellular polypeptides, including NMDA receptor subunits, that associate with NR3B; and in therapeutic, diagnostic and research applications known to those skilled in the art and described further below. An antibody that "specifically binds" and NR3B polypeptide binds with high affinity to a NR3B polypeptide in a binding assay, such as an immunoblot or ELISA assay, without substantial cross-reactivity with other polypeptides such as other NMDA receptor subunits.

An "antigen binding fragment" of an antibody of the invention includes, for example, individual heavy or light chains and fragments thereof, such as VL, VH and Fd; monovalent fragments, such as Fv, Fab, and Fab'; bivalent fragments such as $F(ab')_2$; single chain Fv (scFv); and Fc fragments. Antigen binding fragments include, for example, fragments produced by protease digestion or reduction of an antibody, as well as fragments produced by recombinant DNA methods known to those skilled in the art.

In one embodiment, the invention provides antibodies and antigen binding fragments thereof that specifically bind an NR3B polypeptide containing an amino acid sequence designated SEQ ID NO:2, 4, 6 or 8. For certain applications, such as to antagonize receptor activity, antibodies that bind an extracellular portion of NR3B are desirable, including antibodies that bind the region N-terminal to the S1 domain, the S1 domain, the S2 domain, or the region between the M3 and M4 domains. For other applications, antibodies that distinguish a splice variant form of an NR3B receptor are useful, such as antibodies that bind the 15 amino acid portion of rat NR3B B4 not present in the NR3B A2 form.

The antibodies of the invention can be produced by any suitable method known in the art. For example, a NR3B polypeptide or immunogenic peptide of the invention, or a nucleic acid expressing such a polypeptide or peptide, can be administered to an animal, using standard methods, and polyclonal antibodies isolated therefrom. Such polypeptides or peptides, if desired, can be conjugated to a carrier, such as KLH, serum albumin, tetanus toxoid and the like, using standard linking techniques, to increase their immunogenicity. Additionally, such peptides can be formulated together with an adjuvant known in the art, such as Freund's complete or incomplete adjuvant. The antibodies so generated can be used in the form of serum isolated from an immunized animal, or the antibody can be affinity purified from the serum using the invention peptides or polypeptides.

Additionally, the antibodies of the invention can be monoclonal antibodies produced by a hybridoma cell line, by chemical synthesis, or by recombinant methods. Modified antibodies, such as chimeric antibodies, single chain antibodies, humanized antibodies and CDR-grafted or bifunctional antibodies, can also be produced by methods well known to those skilled in the art.

Methods of preparing and using antibodies and antigen-binding fragments, including detectably labeled antibodies, are described, for example, in Harlow and Lane, *Antibodies: A Laboratory Manual*, Cold Spring Harbor Laboratory, New York (1989); in Day, E. D., *Advanced Immunochemistry*, Second Ed., Wiley-Liss, Inc., New York, N.Y. (1990); and in Borrebaeck (Ed.), *Antibody Engineering*, Second Ed., Oxford University Press, New York (1995). Example V describes a method for producing NR3B-specific antibodies.

The invention also provides a method for detecting an NR3B polypeptide in a sample. The method is practiced by contacting a sample with an antibody specific for an NR3B polypeptide and detecting specific binding of the antibody to the sample. As described above with respect to encoding nucleic acid molecules, altered expression, abundance or integrity of an NR3B polypeptide in a sample can thus be indicative of a pathological condition, including any of the acute or chronic neurological and neurodegenerative conditions described herein.

The methods of detecting an NR3B polypeptide in a sample can be either qualitative or quantitative, and can detect the presence, abundance, integrity or localization of the polypeptide, as desired for a particular application. Contemplated assays to detect a polypeptide in a sample include in situ histochemistry, immunoblotting, immunoprecipitation, FACS analysis, radioligand binding, and ELISA analysis. Such assays can be direct, using a detectably labeled ligand, or indirect, using a labeled secondary reagent, such as an anti-ligand antibody. Exemplary labels include fluorescent labels, enzymes, radioisotopes, and biotin. Detection can be by any convenient analytical means, including by spectrophotometric, radiographic or chemiluminescent means, depending on the assay.

The invention also provides a method of detecting an NR3B ligand. In one embodiment, the method is practiced by contacting an NR3B polypeptide with one or more compounds under conditions suitable for detecting binding to the polypeptide, and detecting a candidate compound that binds the polypeptide. In another embodiment, the invention is practiced by contacting an NR3B functional fragment with one or more compounds under conditions suitable for detecting binding to the fragment, and detecting a candidate compound that binds the fragment. For use in such an application, the NR3B functional fragment desirably contains at least one extracellular domain of the NR3B polypeptide, such as the region N-terminal to the S1 domain, the S1 domain, the S2 domain, or the region between the M3 and M4 domains (see FIG. 8 and FIG. 11).

The invention further provides a method of detecting an excitatory glycine receptor ligand. The method is practiced by contacting an excitatory glycine receptor with one or more compounds under conditions suitable for detecting binding to the receptor, and detecting a candidate compound that binds the receptor.

In one embodiment, the excitatory glycine receptor contains an NR3B polypeptide and an NR1 polypeptide. In another embodiment, the excitatory glycine receptor contains an NR3A polypeptide and an NR1 polypeptide. In a further embodiment, the excitatory glycine receptor contains an NR3B polypeptide, an NR3A polypeptide and an NR1 polypeptide. In yet another embodiment, the excitatory glycine receptor contains an NR3B and/or an NR3A polypeptide, an NR1 polypeptide and an NR2 polypeptide (i.e. an NR2A, 2B, 2C or 2D polypeptide).

As disclosed herein, co-expression of an NR3A and an NR1 polypeptide also results in the formation of excitatory glycine receptors. Rat NR3A polypeptides and encoding nucleic acid molecules are known in the art, and exemplary molecules have the nucleotide and predicted amino acid sequences set forth in Table 2:

TABLE 2

| SUBUNIT | ACCESSION NUMBER |
|---|---|
| Rat NR3A (NMDAR-L) | U29873 |
| Rat NR3A (x-1) | L34938 |
| Rat NR3A (splicing variant) | AF061945 |
| Rat NR3A (splicing variant) | AF073379 |

Disclosed herein as SEQ ID NO:55 is the predicted human NR3A cDNA sequence and its encoding amino acid sequence (SEQ ID NO:56). These sequence were predicted from the human NR3A genomic sequences in the database (GenBank Accession Nos. NT_025809, AL35616, XM042803.1 and AL359651.1) based on the rat NR3A cDNA and amino acid sequences. The skilled person can likewise determine additional NR3A sequences from other species.

NR2 polypeptides and encoding nucleic acid molecules are also known in the art, and exemplary molecules have the nucleotide and predicted amino acid sequences set forth in Table 3:

TABLE 3

| SUBUNIT | ACCESSION NUMBER |
|---|---|
| Human NR2A cDNA | NM_000833, U09002, U90277, XM_030214, XM_030215, XM_007911, XM_016282 |
| Human NR2A genomic | AC007218, AC006531 |
| Rat NR2A cDNA | NM_012573, M91561, AF001423, D13211 |
| Mouse NR2A (epsilon 1) | NM_008170, D10217 |
| Human NR2B cDNA | XM_006636, XM_042404, XM_042405, XM_042406, NM_000834, U88963, U11287, U90278 |
| Human NR2B genomic | AC007535 |
| Rat NR2B cDNA | NM_012574, U11419, M91562 |
| Mouse NR2B (epsilon 2) | NM_008171, D10651 |
| Human NR2C cDNA | NM_000835, U77782, XM_046949, L76224, XM_012596 |
| Rat NR2C | NM_012575, D13212, M91563, U08259 |
| Mouse NR2C (epsilon 3) | NM_010350, D10694 |
| Human NR2D cDNA | XM_009108, NM_000836, U77783 |
| Human NR2D genomic | AC011527, AC008403 |
| Rat NR2D | U08260, NM_022797, L31612, L31611, D13213 |
| Mouse NR2D (epsilon 4) | NM_008172, D12822 |

The skilled person will appreciate that for use in the methods described herein, an NR3A or NR2 polypeptide can have modifications to a naturally occurring sequence, or be a functional fragment of the naturally occurring sequence, so long as the desired biological activity is retained. An exemplary modification of a naturally occurring NR3A or NR2 polypeptide that does not affect biological activity is the addition of an epitope tag to facilitate identification in procedures such as immunolocalization and immunoprecipitation.

NR3A biological activities include, for example, the ability to oligomerize with other NMDA subunits, including NR1; the ability to bind glycine; and the ability to form excitatory glycine receptors in association with NR1. NR2 biological activities include, for example, the ability to oligomerize with other NMDA subunits, including NR1; the ability to bind glutamate; and the ability to form excitatory glutamate receptors in association with NR1.

As described above with respect to NR3B and NR1 polypeptides and functional fragments, the skilled person can readily make NR3A and NR2 molecules with sequences that differ from the naturally occurring sequence and test such molecules to confirm that a desired NR3A or NR2 biological activity is retained.

As used herein, the term “ligand” refers to any biological or chemical compound that binds the recited polypeptide, fragment or receptor with high affinity. High affinity binding refers to binding with a Kd of less than about $10^{-3}$ M, such as less than $10^{-5}$ M, and often less than $10^{-7}$ M. Glycine and NR3B antibodies are examples of ligands of NR3B.

An “NR3B ligand” or “excitatory glycine receptor ligand” can further be an agonist or antagonist of an excitatory glycine receptor, as described below, or can be a compound having little or no effect on excitatory glycine receptor biological activity. For example, a ligand without agonistic or antagonistic activity can be used to specifically target a diagnostic or therapeutic moiety to cells and tissues that express an excitatory glycine receptor. Thus, an identified ligand can be labeled with a detectable moiety, such as a radiolabel, fluorochrome, ferromagnetic substance, or luminescent substance, and used to detect normal or abnormal expression of an excitatory glycine receptor in an isolated sample or in in vivo diagnostic imaging procedures. Likewise, an identified ligand can be labeled with a therapeutic moiety, such as a cytotoxic or cytostatic agent or radioisotope, and administered in an effective amount to arrest proliferation or kill a cell or tissue that aberrantly expresses an excitatory glycine receptor for use in therapeutic applications described further below.

Binding assays, including high-throughput automated binding assays, are well known in the art and can be used in the invention methods. The assay format can employ a cell, cell membrane, artificial membrane system, or purified polypeptide, fragment or receptor, either in solution or attached to a solid phase. If desired, the binding assay can be performed in the presence of a known ligand of NR3B or of an excitatory glycine receptor, such as glycine.

Suitable assays that can be used for detecting ligand binding include, for example, scintillation proximity assays (SPA) (Alouani, *Methods Mol. Biol.* 138:135-41 (2000)), UV or chemical cross-linking (Fancy, *Curr. Opin. Chem. Biol.* 4:28-33 (2000)), competition binding assays (Yamamura et al., *Methods in Neurotransmitter Receptor Analysis*, Raven Press, New York, 1990), biomolecular interaction analysis (BIA) (Weinberger et al., *Pharmacogenomics* 1:395-416 (2000)), mass spectrometry (MS) (McLafferty et al., *Science* 284:1289-1290 (1999) and Degterev, et al., *Nature Cell Biology* 3:173-182 (2001)), nuclear magnetic resonance (NMR) (Shuker et al., *Science* 274:1531-1534 (1996), Hajduk et al., *J. Med. Chem.* 42:2315-2317 (1999), and Chen and Shapiro, *Anal. Chem.* 71:669A-675A (1999)), fluorescence polarization assays (FPA) (Degterev et al., supra, 2001); surface plasmon resonance (SPR)(Liparoto et al., *J. Mol. Recognit.* 12:316-321 (1999)); and protein chip proteomic array analysis (e.g. ProteinChip™ System from Ciphergen Biosystems, which can be used in tandem with mass spectrometry analysis for sequence or structure determination).

An exemplary assay that has been used successfully to identify ligands of an NMDA receptor is phage display (see Li et al., *Nature Biotech.* 14:986-991 (1996), which describes contacting an N-terminal fragment of an NR1 polypeptide with a phage display library). A similar phage display approach can be applied to determine NR3B ligands and excitatory glycine receptor ligands.

Exemplary high-throughput receptor binding assays are described, for example, in Mellentin-Micelotti et al., *Anal. Biochem.* 272:P182-190 (1999); Zuck et al., *Proc. Natl. Acad. Sci. USA* 96:11122-11127 (1999); and Zhang et al., *Anal. Biochem.* 268; 134-142 (1999). Other suitable methods are known in the art.

The invention also provides methods of detecting an excitatory glycine receptor agonist or antagonist The method is practiced by contacting an excitatory glycine receptor under conditions suitable for detecting excitatory glycine receptor activation, and detecting a candidate compound that alters excitatory glycine receptor activation. As described herein, excitatory glycine receptor activation can be evidenced by elicitation of a monovalent cation current, with little or no channel permeability to $Ca^{2+}$ and little or no inhibition by $Mg^{2+}$.

In one embodiment, the excitatory glycine receptor contains an NR3B polypeptide and an NR1 polypeptide. In another embodiment, the excitatory glycine receptor contains an NR3A polypeptide and an NR1 polypeptide. In a further embodiment, the excitatory glycine receptor contains an NR3B polypeptide, an NR3A polypeptide and an NR1 polypeptide. In yet another embodiment, the excitatory glycine receptor contains an NR3B polypeptide, an NR1 polypeptide and an NR2 polypeptide (i.e. an NR2A, 2B, 2C or 2D polypeptide). In another embodiment, the excitatory glycine receptor contains an NR3A polypeptide, an NR1 polypeptide and an NR2 polypeptide (i.e. an NR2A, 2B, 2C or 2D polypeptide).

The agonists and antagonists identified by the methods of the invention are useful in therapeutic applications, described further below, in which it is desirable to increase or decrease ion flow through the excitatory glycine receptor.

As used herein, the term "excitatory glycine receptor agonist" refers to a compound that increases or activates excitatory glycine receptor cation currents. An agonist can act by any mechanism, such as by binding the receptor at the normal glycine binding site, thereby mimicking glycine and promoting receptor activation. An agonist can also act, for example, by potentiating the activity of glycine, or by favorably altering the conformation of the receptor. The methods of the invention can be used to detect agonists that act through any agonistic mechanism.

As used herein, the term "excitatory glycine receptor antagonist" refers to a compound that decreases or inhibits excitatory glycine receptor cation currents. Typically, the effect of an antagonist is observed as a blocking of activation by an agonist. For example, 5,7-di-Cl-Kynurenate blocks glycine activated currents through the NR3B/NR1 receptor.

Figure 3:
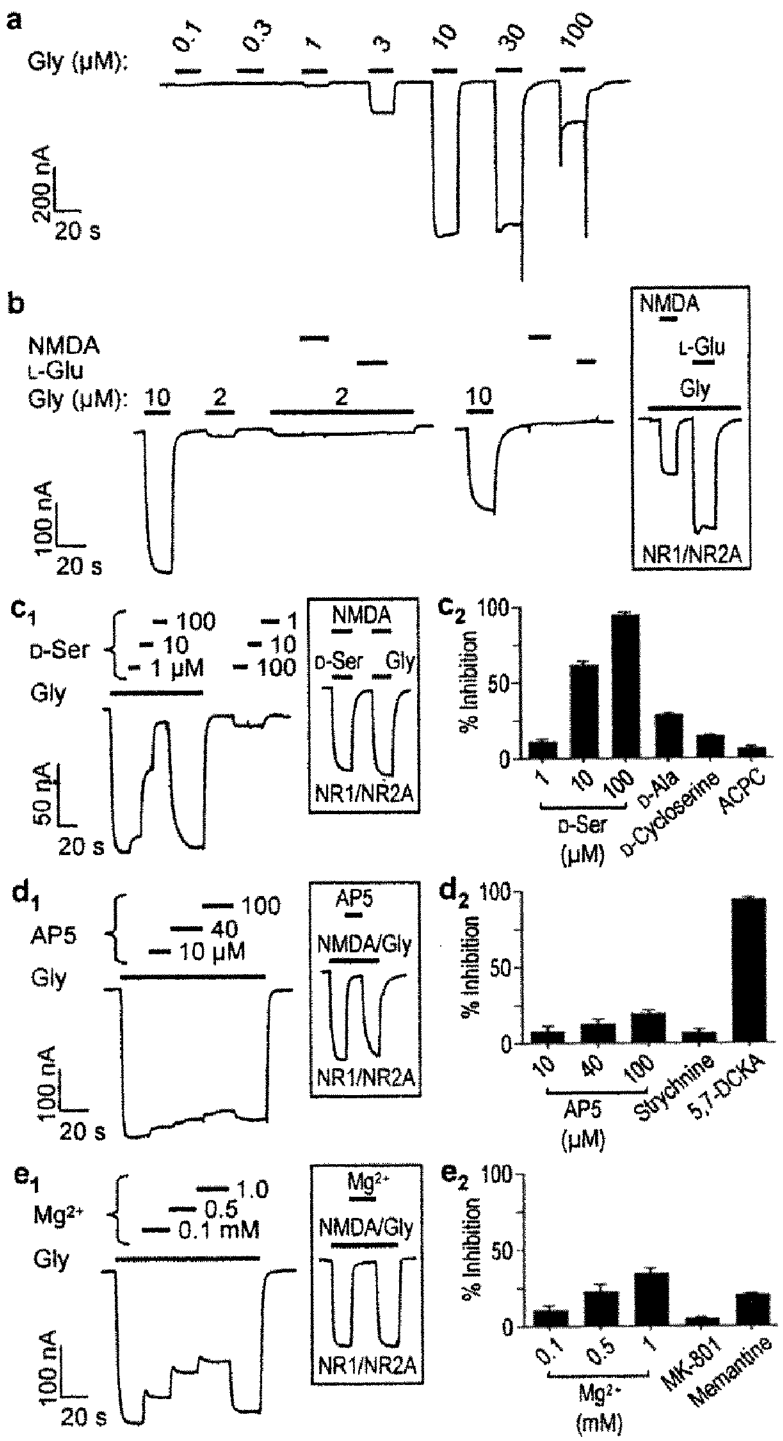
FIG. 3(*a-e*) shows pharmacological characterization of NR1/NR3B receptors in *Xenopus* oocytes. Glycine-evoked currents were recorded from oocytes injected with NR1/NR3B. The insets show NMDA/glycine-evoked NR1/NR2A currents for comparison. Glycine and NMDA (or L-glutamate) concentrations were 10 and 100 μM, respectively, unless otherwise indicated. Data are representative of recordings from 3-9 oocytes in each case.

Antagonists include, for example, partial antagonists, partial agonists, competitive antagonists, non-competitive antagonists and uncompetitive antagonists. A competitive antagonist interacts with or near the site specific for the agonist. A non-competitive antagonist inactivates the function of the receptor by interacting with a site other than the site that interacts with the agonist. Partial agonists have both agonistic and antagonistic activity. For example, as shown in FIG. 3, D-serine evokes small NR1/NR3B currents alone, but dose-dependently inhibits currents in the presence of glycine. The methods of the invention can be used to detect antagonists that act through any antagonistic mechanism.

Methods of detecting excitatory glycine receptor agonists and antagonists can advantageously be performed either in the presence or absence of a physiologically relevant excitatory glycine receptor agonist such as glycine. Compounds that demonstrate agonistic and antagonistic effects in the presence of glycine are particularly useful for use in therapeutic applications, in which physiological concentrations of circulatory glycine are present. In such methods, concentrations of glycine of about 1 to about 100 μM, such as about 5-10 μM, are suitable.

Electrophysiological methods for detecting monovalent cation currents through an excitatory glycine receptor are well known in the art. Exemplary methods for recording whole-cell and single-channel currents in *Xenopus* oocytes, brain slices, mammalian cells and cell-free membrane patches are described in Das et al., *Nature* 393:377-381 (1998); Sakmann and Neherand, in *Single-Channel Recording,* 2nd ed., Ch. 15, pp. 341-355, (1995), edited by Bert Sakmann and Erwin Neher, Plenum Press, New York; Penner, in *Single-Channel Recording,* 2nd ed., Ch. 1, pp. 3-28; Hamill et al., Pflugers Arch. 391:85-100 (1981); Ilers et al., in *Single-Channel Recording,* 2nd ed., Ch. 9, pp. 213-229, (1995), edited by Bert Sakmann and Erwin Neher, Plenum Press, New York; and in the Examples, below.

Ionic currents can also be detected using suitable detectably labeled ion indicators. Ion indicators and methods for their use are known in the art. For example, monovalent cation currents through the excitatory glycine receptor can be detected using $Na^+$ or $K^+$ ion indicators, which can be fluorescently labeled or radiolabeled (see, for example, Moore et al., *Proc. Natl. Acad. Sci. USA* 90:8058-8062 (1993); Paucek et al., *J. Biol. Chem.* 267:26062-26069 (1992); Xu et al., *J. Biol. Chem.* 270: 19606-19612 (1995)). Exemplary ion indicators include: SBFI sodium indicator, Sodium Green sodium indicator; CoroNa Red sodium indicator; PBFI potassium indicator; 6-Methoxy-N-(3-sulfopropyl)quinolinium (SPQ) chloride indicator; N-(Ethoxycarbonylmethyl)-6-methoxyquinolinium bromide (MQAE) chloride indicator; 6-Methoxy-N-ethylquinolinium iodide (MEQ) chloride indicator; Lucigenin chloride indicator, which are available from Molecular Probes, Inc.

Subsequent to excitatory glycine receptor activation and membrane depolarization, an influx of $Ca^{2+}$ ions occurs if voltage-dependent $Ca^{2+}$ channels are present in the cell being studied. If the cell of interest does not endogenously express voltage-dependent $Ca^{2+}$ channels, the cell can be recombinantly engineered to express such channels, using voltage-dependent $Ca^{2+}$ channel subunit gene sequences and molecular biology methods known in the art. Accordingly, ionic currents through the excitatory glycine receptor can also be detected, indirectly, using detectably labeled $Ca^{2+}$ ion indicators, which can be fluorescently labeled or radiolabeled. Exemplary $Ca^{2+}$ ion indicators include FLUO-3 AM, FLUO-4 AM, FURA-2, INDO-1, FURA RED, CALCIUM GREEN, CALCIUM ORANGE, CALCIUM CRIMSON, BTC, and OREGON GREEN BAPTA (see, for example, Grynkiewitz et al., *J. Biol. Chem.* 260:3440-3450 (1985); Sullivan et al., in *Calcium Signal Protocol, Methods in Molecular Biology* 114: 125-133, Edited by David G. Lambert, Human Press, Totowa, N.J. (1999); Miyawaki et al., *Proc. Natl. Acad. Sci. USA* 96:2135-2140 (1999); and Coward et al., *Analyt. Biochem.* 270:242-248 (1999)).

Assay methods for identifying compounds that bind to or modulate excitatory glycine receptor activity (e.g. ligands, agonists and antagonists) generally involve comparison to a control. One type of a "control" is a NR3B polypeptide or excitatory glycine receptor that is treated substantially the same as the polypeptide or receptor exposed to the candidate compound, except the control is not exposed to the candidate compound. For example, the same recombinant cell can be tested in the presence and absence of candidate compound, by merely changing the solution contacting the cell. Another type of "control" is a cell that is essentially identical to the NR3B polypeptide- or excitatory glycine receptor-expressing recombinant cell, except the control cell does not express the polypeptide or receptor. In this situation, the response of the test cell to a candidate compound is compared to the response (or lack of response) of the control cell to the same compound under substantially the same reaction conditions.

The term "candidate compound" refers to any molecule that potentially acts as a ligand, agonist or antagonist or ligand in the screening methods disclosed herein. A candidate compound can be a naturally occurring macromolecule, such as a polypeptide, amino acid, nucleic acid, carbohydrate, lipid, or any combination thereof. A candidate compound also can be a partially or completely synthetic derivative, analog or mimetic of such a macromolecule, or a small organic molecule prepared by combinatorial chemistry methods. If desired in a particular assay format, a candidate compound can be detectably labeled or attached to a solid support.

Methods for preparing large libraries of compounds, including simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422-428 (1998); Tietze et al., *Curr. Biol.,* 2:363-371 (1998); Sofia, *Mol. Divers.* 3:75-94 (1998); Eichler et al., *Med. Res. Rev.* 15:481-496 (1995); and the like. Libraries containing large numbers of natural and synthetic compounds also can be obtained from commercial sources.

The number of different candidate compounds to test in the methods of the invention will depend on the application of the method. For example, one or a small number of candidate compounds can be advantageous in manual screening procedures, or when it is desired to compare efficacy among several predicted ligands, agonists or antagonists. However, it is generally understood that the larger the number of candidate compounds, the greater the likelihood of identifying a compound having the desired activity in a screening assay. Additionally, large numbers of compounds can be processed in high-throughput automated screening assays. Therefore, "one or more candidate compounds" can be, for example, 2 or more, such as 5, 10, 15, 20, 50 or 100 or more different compounds, such as greater than about $10^3$, $10^5$ or $10^7$ different compounds, which can be assayed simultaneously or sequentially.

The function of the NR3A polypeptide has remained elusive, despite years of investigation (see Ciaberra et al., *J. Neuroscience* 15:6498-6508 (1995); Sucher et al., *J. Neuroscience* 15:6509-6520 (1995); Das et al. supra (1998); Perez-Otano et al., *J. Neuroscience* 21:1228-1237 (2001)). As disclosed herein, when expressed in combination with NR1 and optionally also NR2 subunits, the NR3A polypeptide, like the NR3B polypeptide, forms an excitatory glycine receptor (see Example IV). The invention thus provides isolated excitatory glycine receptors containing either an NR3A polypeptide or an NR3B polypeptide, or both. Such receptors are suitable use in the methods described herein of detecting excitatory glycine receptors agonists, antagonists and ligands. As described previously, depending on the particular assay, the isolated receptors can optionally be present at the surface of an intact cell, present in a cell membrane with or without other cellular components, or reconstituted into a natural or artificial lipid bilayer.

In one embodiment, the excitatory glycine receptor contains an NR3B polypeptide and an NR1 polypeptide. In another embodiment, the excitatory glycine receptor contains an NR3A polypeptide and an NR1 polypeptide. In a further embodiment, the excitatory glycine receptor contains an NR3B polypeptide, an NR3A polypeptide and an NR1 polypeptide. In yet another embodiment, the excitatory glycine receptor contains an NR3B polypeptide, an NR1 polypeptide and an NR2 polypeptide (i.e. an NR2A, 2B, 2C or 2D polypeptide). In another embodiment, the excitatory glycine receptor contains an NR3A polypeptide, an NR1 polypeptide and an NR2 polypeptide (i.e. an NR2A, 2B, 2C or 2D polypeptide).

Suitable NR3B, NR3A, NR2A-D and NR1 polypeptides that can be used as subunits of excitatory glycine receptors, including both naturally occurring polypeptides, and modifications and functional fragments of such polypeptides, have been described previously.

The invention also provides therapeutic methods for the prevention and amelioration of conditions in which inappropriate NMDA receptor activation, or inappropriate responses to glycine or glutamate, are implicated. Such conditions include, for example, acute neurologic condition, such as cerebral ischemia; stroke; hypoxia; anoxia; poisoning by carbon monoxide, manganese, cyanide or domoic acid; hypoglycemia; mechanical trauma to the nervous system such as trauma to the head or spinal cord; or epileptic seizure. Other conditions include, for example, chronic neurodegenerative disease, such as Huntington's disease; a disorder of photoreceptor degeneration such as retinitis pigmentosa; acquired immunodeficiency syndrome (AIDS) dementia complex (HIV-associated dementia); a neuropathic pain syndrome such as causalgia or a painful peripheral neuropathy; olivopontocerebellar atrophy; Parkinsonism; amyotrophic lateral sclerosis; a mitochondrial abnormality or other biochemical disorder such as MELAS syndrome, MERRF, Leber's disease, Wernicke's encephalopathy, Rett syndrome, homocysteinuria, hyperhomocysteinemia, hyperprolinemia, nonketotic hyperglycinemia, hydroxybutyric aminoaciduria, sulfite oxidase deficiency, combined systems disease, lead encephalopathy, Alzheimer's disease, hepatic encephalopathy, Tourette's syndrome, drug addiction/tolerance/dependency, glaucoma, depression, anxiety, multiple sclerosis and other demyelinating disorders. Other conditions are known in the art and reviewed, for example, in Lipton et al., New Engl. J. Med. 330:613-622 (1994) and Cull-Candy et al., *Curr. Opin. Neurobiol.* 11:327-335 (2001).

Thus, the invention provides methods for increasing or decreasing signaling through an excitatory glycine receptor by administering an excitatory glycine receptor agonist, antagonist or ligand, or an NR3B ligand, to an individual. Methods of identifying such agonist, antagonist and ligands have been described previously.

The invention also provides gene therapy methods for modulating a cellular response to glycine or glutamate. By overexpressing a full-length NR3B polypeptide, the NR1 subunit can form NR1/NR3B receptors, which are insensitive to glutamate, rather than NR1/NR2 receptors. Therefore, detrimental glutamate responses can be reduced. In contrast, by expressing a dominant negative NR3B polypeptide, or a construct that prevents translation of endogenous NR3B, fewer functional NR1/NR3B receptors will be formed. Therefore, detrimental glycine responses can be reduced. Therapeutic applications in which it is desirable to modulate cellular responses to glutamate and glycine are described above.

In one embodiment, the invention provides a method of modulating a cellular response to glycine or glutamate by introducing a nucleic acid molecule encoding an NR3B polypeptide or functional fragment into a cell, and expressing the NR3B functional fragment encoded by the nucleic acid molecule in the cell. In another embodiment, the invention provides a method of modulating a cellular response to glycine or glutamate by introducing an antisense nucleic acid molecule, a ribozyme molecule or a small interfering RNA (siRNA) molecule into the cell, wherein the molecule hybridizes to an NR3B nucleic acid molecule and prevents translation of the encoded NR3B polypeptide.

Suitable gene therapy vectors have been described previously. For gene therapy applications, the nucleic acid molecule can be administered to a subject by various routes. For example, local administration at the site of a pathology can be advantageous because there is no dilution effect and, therefore, the likelihood that a majority of the targeted cells will be contacted with the nucleic acid molecule is increased. This is particularly true in the eye, where either intravitreal or intraretinal administration is possible. In addition, administration can be systemic, such as via intravenous or subcutaneous injection into the subject. For example, following injection, viral vectors will circulate until they recognize host cells with the appropriate target specificity for infection.

Receptor-mediated DNA delivery approaches also can be used to deliver a nucleic acid molecule into cells in a tissue-specific manner using a tissue-specific ligand or an antibody that is non-covalently complexed with the nucleic acid molecule via a bridging molecule. Direct injection of a naked nucleic acid molecule or a nucleic acid molecule encapsulated, for example, in cationic liposomes also can be used for stable gene transfer into non-dividing or dividing cells. In addition, a nucleic acid molecule can be transferred into a variety of tissues using the particle bombardment method.

Antisense nucleotide sequences that are complementary to a nucleic acid molecule encoding an NR3B polypeptide can be used to prevent or reduce NR3B expression. Therefore, the method can be practiced with an antisense nucleic acid molecule complementary to at least a portion of the nucleotide sequence of SEQ ID NOS:1, 59, 3, 57, 5, 61 or 7 For example, the antisense nucleic acid molecule can be complementary to a region within the N-terminus of SEQ ID NOS:1, 59, 3, 57, 5, 61 or 7, such as within nucleotides 1-1000, 1-500, 1-100 or 1-18, and can optionally include sequences 5' to the start codon. Methods of preparing antisense nucleic acids molecules and using them therapeutically are known in the art and described, for example, in Galderisi et al., *J. Cell Physiol.* 181:251-257 (1999).

Likewise, ribozymes that bind to and cleave SEQ ID NOS: 1, 59, 3, 57, 5, 61 or 7 can also be effective in preventing or reducing NR3B expression. Methods of preparing ribozymes and DNA encoding ribozymes, including hairpin and hammerhead ribozymes, and using them therapeutically are known in the art and described, for example, in Lewin et al., *Trends Mol. Med.* 7:221-228 (2001).

Additionally, small interfering RNAs (siRNAs), which are short duplex RNAs with overhanging 3' ends, directed against SEQ ID NOS:1, 59, 3, 57, 5, 61 or 7, can also be effective in preventing or reducing NR3B expression. Methods of preparing and using siRNAs are known in the art and described, for example, in Elbashir et al., *Nature* 411:494-498 (2001).

The therapeutic compounds of the invention, including agonists, antagonists, ligands and nucleic acid molecules, can be formulated and administered in a manner and in an amount appropriate for the condition to be treated; the weight, gender, age and health of the individual; the biochemical nature, bioactivity, bioavailability and side effects of the particular compound; and in a manner compatible with concurrent treatment regimens. An appropriate amount and formulation for a particular therapeutic application in humans can be extrapolated based on the activity of the compound in the in vitro binding and signaling assays described herein, or from recognized animal models of the particular disorder.

The total amount of therapeutic compound can be administered as a single dose or by infusion over a relatively short period of time, or can be administered in multiple doses administered over a more prolonged period of time. Additionally, the compound can be administered in a slow-release matrice, which can be implanted for systemic delivery at or near the site of the target tissue. Contemplated matrices useful for controlled release of therapeutic compounds are well known in the art, and include materials such as DepoFoam™, biopolymers, micropumps, and the like.

The therapeutic compounds can be administered to an individual by routes known in the art including, for example, intravenously, intramuscularly, subcutaneously, intraorbitally, intracapsularly, intraperitoneally, intracisternally, intraarticularly, intracerebrally, orally, intravaginally, rectally, topically, intranasally, transdermally or intravitreally.

Preferably, the therapeutic compounds are administered to a subject as a pharmaceutical composition comprising the compound and a pharmaceutically acceptable carrier. The choice of pharmaceutically acceptable carrier depends on the route of administration of the compound and on its particular physical and chemical characteristics. Pharmaceutically acceptable carriers are well known in the art and include sterile aqueous solvents such as physiologically buffered saline, and other solvents or vehicles such as glycols, glycerol, oils such as olive oil and injectable organic esters. A pharmaceutically acceptable carrier can further contain physiologically acceptable compounds that stabilize the compound, increase its solubility, or increase its absorption. Such physiologically acceptable compounds include carbohydrates such as glucose, sucrose or dextrans; antioxidants, such as ascorbic acid or glutathione; chelating agents; and low molecular weight proteins.

For applications that require the compounds and compositions to cross the blood-brain barrier, or to cross the cell membrane, formulations that increase the lipophilicity of the compound are particularly desirable. For example, the compounds of the invention can be incorporated into liposomes (Gregoriadis, *Liposome Technology*, Vols. I to III, 2nd ed. (CRC Press, Boca Raton Fla. (1993)). Liposomes, which consist of phospholipids or other lipids, are nontoxic, physiologically acceptable and metabolizable carriers that are relatively simple to make and administer. Additionally, the therapeutic compound can be conjugated to a peptide that facilitates cell entry, such as penetratin (also known as Antennapedia peptide), other homeodomain sequences, or the HIV protein Tat.

It is contemplated that administration of the therapeutic compounds and compositions of the invention will result in some beneficial effect to the individual, such as improved overall neurological function or a specific neurological function; an improvement in the quality of life; a reduction in the severity of the symptoms of the disease; a reduction in the number of diseased cells; prolonged survival, and the like. Indicators of beneficial effect are well known in the art, and an appropriate indicator for a particular application can be determined by the skilled person.

The following examples are intended to illustrate but not limit the present invention.

EXAMPLE I

This example shows cloning and sequence analysis of NR3B.

Degenerate primers were designed based on the sequences of NR3A and other NMDAR family members. Using degenerate PCR in concert with homology screening of a rat brain cDNA library, two novel cDNA fragments (called 5-2 clone 1 and 5-2 clone 2) were obtained which exhibited significant sequence identity with NR3A, but clearly corresponded to a distinct and previously unidentified gene. The novel gene was therefore designated NR3B.

Based on the sequences of 5-2 clone 1 and 5-2 clone 2, two pairs of more specific, nested primers (f4, TGCTGCTATGGCTACTGCATC (SEQ ID NO:17); r4, ATGACAGCAGCCAGGTTGGCCGT (SEQ ID NO:18); f5, CACACATGGCTGTGACCAGC (SEQ ID NO:19); and r5, AGAATGGCATAGCACAGGTTG (SEQ ID NO:20)) were designed and used to PCR screen a Rapid-Screen rat brain cDNA library panel (OriGene Technologies, Inc., Rockville, Md.). Four independent partial NR3B cDNA clones were thus obtained. The coding regions of three of the clones were identical (one of these was designated clone B4), but the fourth clone (clone A2) had a 45-nucleotide deletion in the 5' coding region, which may, therefore, represent a splice variant of NR3B. A comparison of the sequences of clones B4, A2, 5-2 clone 1, and 5-2 clone 2 revealed that all overlap, e.g., 5-2 clone 2 spans 49% of the 5' end, and clones B4 and A2 span 92% of the 3' end of the full-length NR3B cDNA. Full-length NR3B cDNAs were assembled by ligating the EcoRI-XhoI fragment of 5-2 clone 2 (345 bp) to the XhoI-XbaI fragment of either clone B4 (2847 bp) or clone A2 (2802 bp).

The NR3B (B4 form) cDNA has an open reading frame encoding a peptide of 1002 amino acid (aa) residues. Multiple alignments of the predicted amino acid sequence of NR3B with other glutamate receptor subunits indicated that NR3B is closely related to NR3A (47% identity), but shares less identity with the NR1 and NR2 subfamilies (17 to 21%) (FIG. 1). To a lesser degree, NR3B also shares sequence identity (13 to 16%) with other GluR subunits representing non-NMDAR subunits.

The major structural features of NR3A are highly conserved in NR3B, including the S1 and S2 agonist binding domains, and the membrane spanning regions (FIG. 1). A detailed comparison of the critical residues involved in ligand binding to the NR1 and NR2 subunits revealed that NR3B could potentially share ligand specificity with either or both of these classes of NMDA receptor subunits. Five of the seven amino acid residues required for glycine binding to NR1 and six of the ten amino acid residues required for glutamate binding to NR2A are conserved in NR3B. Furthermore, the M2 region of NR3B is similar to that of NR3A, but strikingly different from those of the NR1 and NR2 subunits. The M2 region forms the re-entrant P-loop which lines the ion channel pore of fully assembled NMDA receptors. These molecular features suggest that the NR3B subunit may confer novel ligand binding and channel gating properties to the NMDA receptor complexes into which it is assembled.

The first ~500 aa residues in the extracellular N-terminus and intracellular C-terminus are the most divergent regions between NR3B and other NMDA receptor subunits, including the NR3A subunit. These regions are important for intra-subunit assembly of glutamate receptors and for interaction of the receptor complex with associated proteins. Thus, these differences may uniquely specify the selection of partner subunits, subcellular localization and CNS distribution of the NR3B subunit.

A rat NR3B nucleotide sequence (SEQ ID NO:57) with a single nucleotide difference with respect to SEQ ID NO:3 was identified by further sequence analysis. SEQ ID NO:57 has a "G" at position 2978, whereas SEQ ID NO:3 has an "A" at the corresponding position. The rat NR3B amino acid sequence encoded by SEQ ID NO:57 (designated SEQ ID NO:58) differs from SEQ ID NO:4 by virtue of having an "Arg" at amino acid 968 instead of a "Gln."

Based on the rat NR3B sequence, the corresponding mouse (SEQ ID NOS:7 and 8) and human (SEQ ID NOS:5 and 6; SEQ ID NOS:61 and 62) NR3B sequences were identified from an analysis of homologous genomic sequences in the database (Accession numbers AC087114 and AC004528, respectively).

EXAMPLE II

This example shows analysis of the expression and localization of the NR3B subunit.

Figure 2:
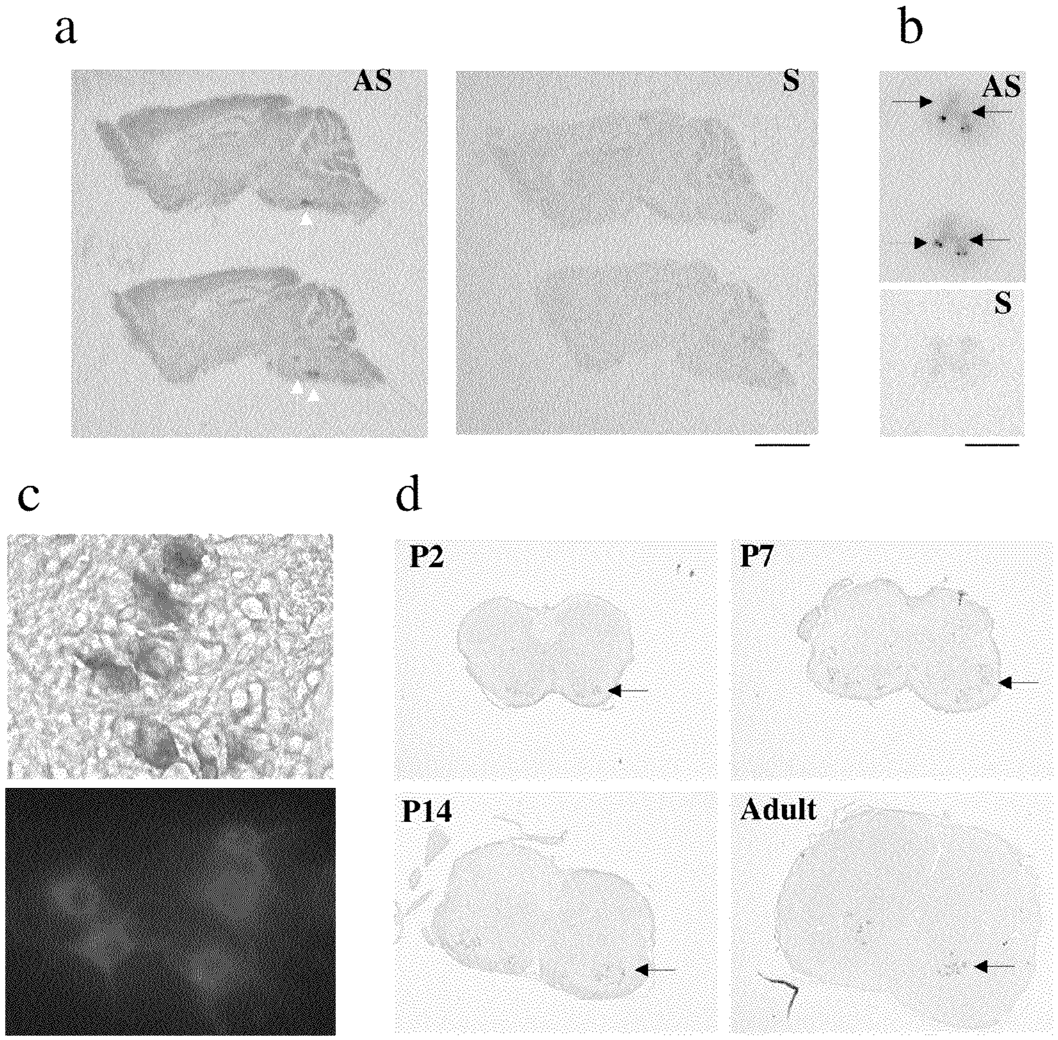
FIG. 2(*a-d*) shows the distribution of the NR3B subunit in the CNS by in situ hybridization. NR3B probes were labeled using isotopic ($^{33}P$)—(a, b) and non-isotopic (digoxigenin) (c, d) methods. Bar represents 6 mm for panel a, 3 mm for b, 50 mm for c, and 1 mm for d.

Initially, in situ hybridization was used to detect NR3B mRNA in adult rat brain. Three probes of approximately 400 bp were generated from different N-terminal and C-terminal regions of NR3B. These regions shared little sequence identity with other NMDAR subunits, including NR3A. All three probes detected NR3B signals in the initial experiment. The probe in the N-terminal region giving the strongest signal was chosen for subsequent experiments. $^{33}P$-labeled antisense probes detected "hot spots" in the facial and trigeminal nuclei of the brainstem, and in the ventral horn of the spinal cord (FIGS. 2*a, b*). Subsequent use of non-isotopic (digoxigenin) labeled probes yielded signals of much higher resolution at the cellular level. NR3B was not detectable in most brain areas, including the cerebrocortex, thalamus, basal ganglia, and hippocampus. In contrast, the spinal cord and the brainstem displayed very strong NR3B signals. In the spinal cord, the NR3B signal was found in motor neurons of the anterior horn at all levels in both layers VIII and IX, which innervate proximal and distal muscle groups, respectively (FIG. 2*c, d*).

However, an NR3B signal was detected only in specific motor nuclei of the brainstem, specifically the facial and trigeminal nuclei. In addition, some large cells in the vestibular nucleus and reticular formation were also positive for NR3B mRNA.

Further analysis using rats at different ages (P2, P7, P14 and adult) confirmed that NR3B mRNA expression begins at an early postnatal stage (FIG. 2*d*). A weak NR3B signal was detectable at P2 but increased substantially by P7. The level of NR3B mRNA expression increased postnatally, reaching a peak at P14, and remained elevated into adulthood, consistent with a specific role of NR3B in developing and maintaining motor neuron functions. Based upon these data, it was concluded that NR3B mRNA is localized mainly in motor neurons of the spinal cord and in some motor nuclei of the brainstem. Expression of NR3B protein in these regions has been confirmed by immunocytochemistry.

EXAMPLE III

This example shows characterization of biological activities of NR3B-containing and NR3A-containing excitatory glycine receptors.

NR3B cRNA for oocyte expression was produced as follows. The full-length NR3B cDNA was constructed in the pCMV6-XL4 vector (OriGene Technologies, Inc., Rockville, Md.), which contains a T7 promoter upstream of the cDNA insert. Initial attempts to generate an NR3B cRNA using T7 RNA polymerase resulted in the formation of both full-length and truncated species. The truncated cRNA could potentially encode a dominant negative form of NR3B. Therefore, a new vector was constructed to facilitate production of exclusively full-length NR3B cRNA. Construction of this vector proceeded as follows. NR1 cDNA was excised from the pGEM-HE/NR1 vector (a gift from S. F. Heinemann) by digestion with EcoRI and the two ends of the truncated pGEM-HE vector were re-ligated. The truncated pGEM-HE vector retained the 5' and 3' UTRs of the *X. laevis* β-globin gene for high level protein expression in frog oocytes. The SfoI-KpnI fragment of truncated pGEM-HE, which contains the T7 promoter, was replaced with the PvuII-KpnI fragment of pBluescript II KS, which contains the T3 promoter, to generate pJC32. The abbreviated multiple cloning site of pJC32 was then replaced with the multiple cloning site from pcDNA3.1(+) (Invitrogen, Carlsbad, Calif.) by ligating the 102 bp PmeI fragment of pcDNA3.1(+) into the 3 kb SmaI-EcoRV fragment of pJC32 to generate pJC34. Oligos encoding restriction sites for AscI, Pad, and PmeI (ctagcG-GCGCGCCTTAATTAAGTTTAAACg (SEQ ID NO:52) and ctagcGTTTAAACTTAATTAAGGCGCGCCg (SEQ ID NO:53)) were annealed and ligated into the NheI site of pJC34. The resulting vector, pJC39, contains three rare restriction sites downstream of the multiple cloning site to facilitate linearization prior to in vitro transcription using T3 RNA polymerase.

The full-length NR3B (B4 form) cDNA was then excised from pCMV6-XL4 by digestion with EcoRI and XbaI, and the 3.2 kb fragment was ligated into EcoRI/XbaI-digested pJC39. The resulting vector, pJC42, was linearized with PmeI, and in vitro transcription was performed using the mMessage mMachine T3 kit (Ambion, Inc., Austin, Tex.) according to the manufacturer's instructions. The cRNA product consisted of a single species with a molecular weight of approximately 1.5 kb.

Microinjection of oocytes and electrophysiological recordings were performed as follows. Physiological and pharmacological properties of NMDA receptor subunits were characterized in the *X. laevis* oocyte expression system. Full-length cDNAs encoding NMDA receptor subunits were linearized and used as templates for synthesis of cRNA by in vitro transcription using T3 or T7 RNA polymerase (Ambion, Inc., Austin, Tex.). The DNA template was removed by DNase I digestion, and the RNA was purified by phenol/chloroform extraction and ethanol precipitation. The RNA was resuspended in water at 1 μg/μl and stored in −80° C. freezer until use. *X. laevis* oocytes were harvested and defolliculated by digestion with collagenase (2 mg/ml) for 2 hrs. Twenty to 40 ng of cRNA were injected into each oocyte using glass pipettes with a tip size of 20-40 μm in diameter. Electrophysiological recordings were performed from whole oocytes 2-7 days after injection using a dual-electrode voltage-clamp amplifier (Model OC-725A, Warner Instrument, Hamden, Conn.). Micropipettes were filled with 3 M KCl. The bath solution contained 115 mM NaCl, 2.5 mM KCl, 1.5 mM $BaCl_2$, and 10 mM Hepes at pH 7.4. Drugs were applied to oocytes via a rapid perfusion system. Data were collected at 2.2 to 11.1 Hz at room temperature using the MacLab/4e A/D converter (AD Instruments, Mountain View, Calif.). Data analysis was performed using the programs Chart (AD Instruments, Mountain View, Calif.) and Microsoft Excel.

Additionally, using the patch-clamp technique, outside-out patches were pulled from oocytes previously injected with NMDAR cRNAs. This method allowed the recording of NMDA-evoked or glycine-evoked single-channel currents, as described previously (Das et al., supra (1998)).

Several novel properties of the NR3B subunit were identified by functional expression of the B4 form in *Xenopus* oocytes. First, functional receptors (defined by the presence of glycine-evoked current) were assembled in oocytes after co-injection of cRNAs for the NR3B and NR1 subunits. Functional receptors were also observed after co-injection of NR3B cRNA with both NR1 and NR2A subunit cRNAs. However, oocytes expressing NR1/NR2A/NR3B receptors exhibited ligand-evoked currents that were 5 to 10 times larger than those expressing NR1/NR3B receptors. In contrast, no functional receptors were detected when NR3B cRNA was co-injected with either NR2A or NR3A alone in the absence of NR1. These results suggest that assembly of the NR3B subunit into a functional receptor complex requires association with the NR1 subunit.

Unlike conventional (that is, NR1/NR2) NMDARs, it was found that the NR1/NR3B receptor was activated by glycine alone, in the absence of glutamate or NMDA (FIG. 3*a*). NMDA and L-glutamate, agonists that activate conventional NMDARs through NR2 subunits, displayed little or no effect on the glycine-induced current of NR1/NR3B receptors and did not evoke glycine-independent responses (FIG. 3*b*).

Figure 6:
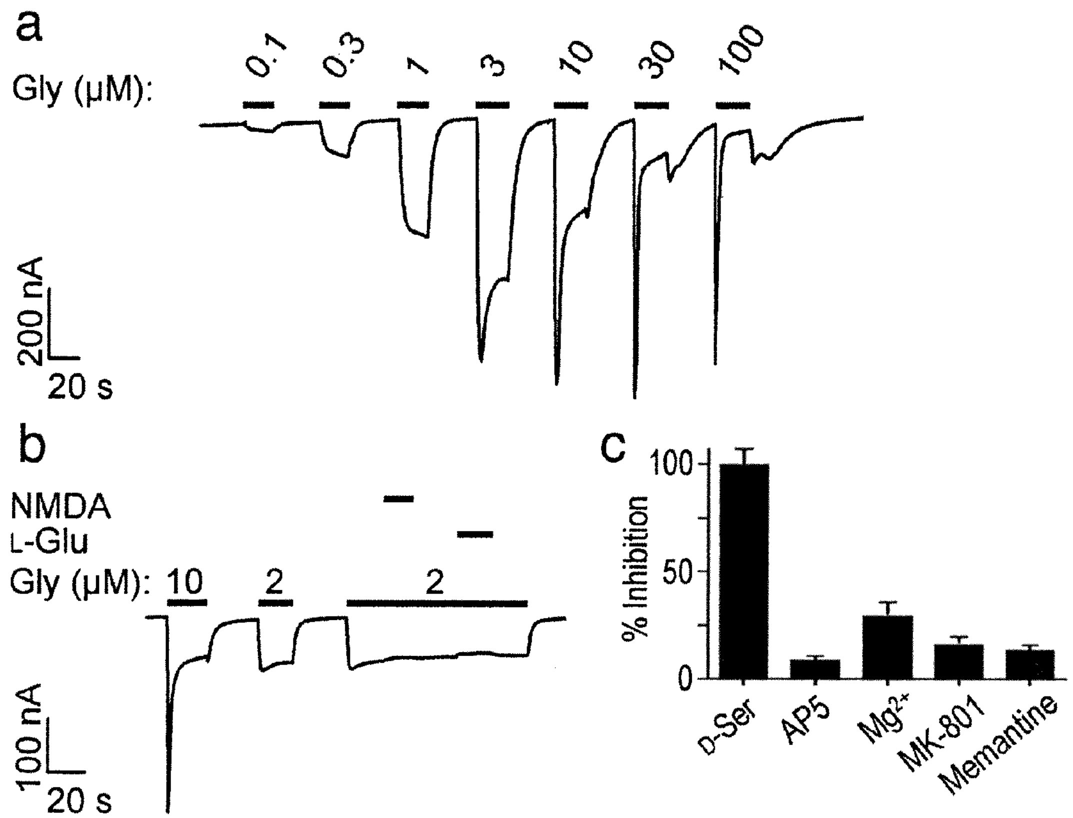
FIG. 6 (*a-c*) shows pharmacological characterization of NR1/NR3A receptors in *Xenopus* oocytes. Glycine-evoked currents were recorded from oocytes injected with NR1/NR3A. Glycine and NMDA (or L-glutamate) concentrations were 10 and 100 μM, respectively, unless otherwise indicated. Data are representative of recordings from 3-9 oocytes in each case.

Because of the high degree of sequence similarity between NR3B and NR3A subunits, the ability of the NR3A subunit to form functional receptors when co-expressed with NR1 was re-examined. Reminiscent of NR1/NR3B receptors, it was found that under specific conditions during two-electrode voltage recordings from oocytes, NR1/NR3A receptors could be activated by glycine alone (FIG. 6*a*). However, rapid desensitization of the current from NR1/NR3A receptors at micromolar concentrations of ligand rendered the observation of glycine-evoked currents extremely difficult (FIG. 6*a*), which may explain why they had not been reported previously (Ciabarra et al., *J. Neurosci.* 15:6498-6508 (1995); Sucher et al., *J. Neuroscience* 15:6509-6520 (1995); Das et al., *Nature* 393:377-381 (1998).

Of note, glycine alone activated NR1/NR3B receptors with high efficacy despite the fact that by itself glycine fails to excite the previously studied NMDARs or any other type of glutamate receptors. For NR1/NR3B receptors, the $EC_{50}$ for glycine was estimated to be approximately 5 μM. A more precise calculation of $EC_{50}$ was precluded by the desensitization that occurs at high glycine concentrations (FIG. 3*a*). For NR1/NR3A receptors the $EC_{50}$ was even lower (about 1 μM glycine), with detectable responses at 0.1 μM, and rapid desensitization at 3 μM and above (FIG. 6*a*).

D-serine, D-alanine, D-cycloserine and 1-aminocyclopropanecarboxylic acid (ACPC), all co-agonists of traditional NMDARs via activation of the glycine site on the NR1 subunit, each inhibited glycine-induced currents of NR1/NR3B receptors (FIG. 3*c*). Among these, only D-serine activated NR1/NR3B receptors in the absence of glycine (FIG. 3*c*). At NR1/NR3A receptors, D-serine was an even more potent antagonist (FIG. 6*c*) and did not independently manifest any agonist activity.

The effect of traditional NMDAR antagonists and channel blockers further demonstrated the altered pharmacological properties conferred by the NR3 family of subunits. A competitive antagonist at the glutamate site of NR2 subunits, D-(−)-2-amino-5-phosphonopentanoate (AP5), had little or no effect at 10 μM on glycine-evoked currents of NR1/NR3B receptors (FIG. 3*d*) or NR1/NR3A receptors (FIG. 6*c*). In contrast, 5,7-dichlorokynurenate (5,7-DCKA), a noncompetitive antagonist of the NR1 subunit glycine binding site, virtually abolished glycine-evoked currents of NR1/NR3B receptors (FIG. 3*d*). Strychnine, an antagonist of the inhibitory, chloride permeable glycine receptors, had minimal effect (FIG. 3*d*).

Properties linked to the channel region were also altered by the presence of an NR3 subunit. Compared to NR1/NR2A receptors, NR1/NR3B receptors (FIG. 3*e*) and NR1/NR3A receptors (FIG. 6*c*) were drastically less sensitive to the open-channel blockers $Mg^{2+}$, MK-801, and memantine.

Figure 4:
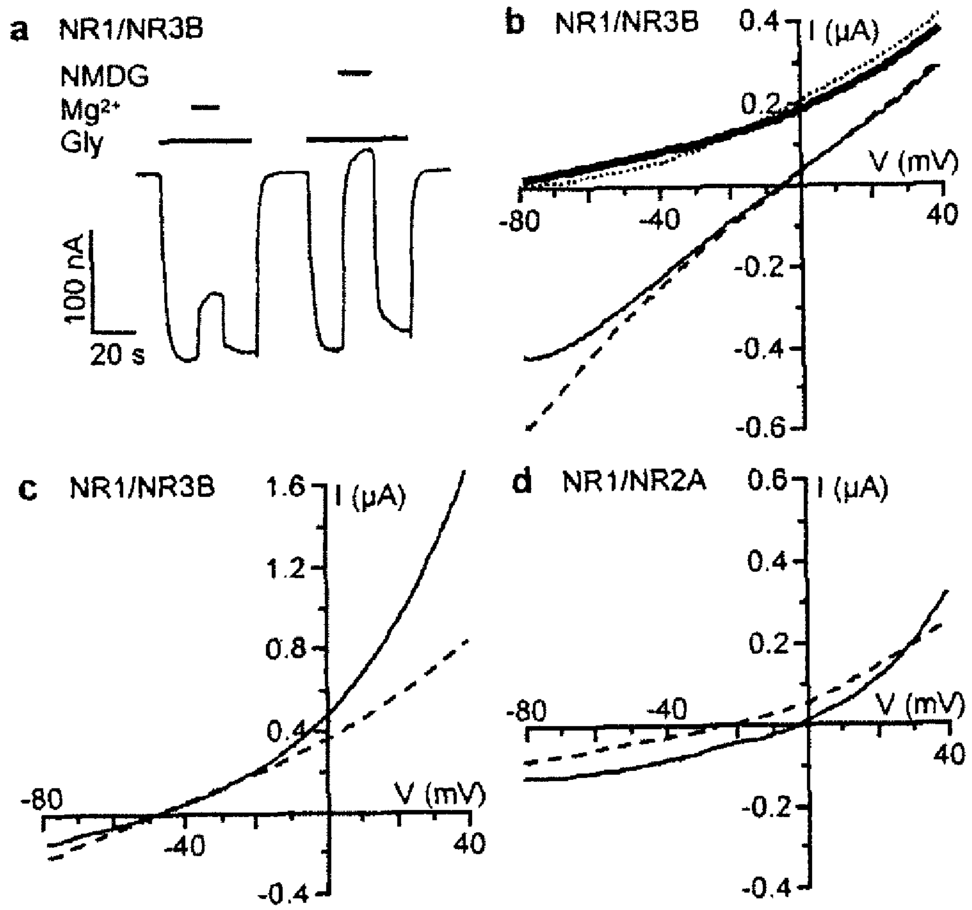
FIG. 4(*a-d*) shows ion-selectivity of NR1/NR3B receptors in *Xenopus* oocytes.

The voltage dependence and permeation of channels operated by NR1/NR3B receptors was examined. I-V curves remained nearly linear between −80 and +40 mV in the presence of 0.5 mM $Mg^{2+}$ (FIG. 4*a*, b), reflecting relative $Mg^{2+}$ insensitivity at physiologically relevant voltages and further distinguishing NR1/NR3B receptors from conventional NMDARs. However, between −80 and −120 mV, the channel became outwardly rectifying, indicating a shift in the voltage-dependent $Mg^{2+}$ block towards more negative potentials compared with NR1/NR2 receptors (data not shown). Replacement of cations in the external bath with the large cation N-methyl-D-glutamine (NMDG) completely abolished the glycine-induced inward current (FIG. 4*a, b*), suggesting that NR1/NR3B channels are impermeable to large cations and anions ($Cl^-$) but permeable to small cations such as $Na^+$. Similarly, $Mg^{2+}$ did not permeate NR1/NR3B channels at potentials positive to −80 mV (FIG. 4*b*). Increasing the $Ba^{2+}$ concentration from 1 to 10 mM caused virtually no change in reversal potential for NR1/NR3B receptors, whereas NR1/NR2A receptors underwent a rightward shift of about 20 mV (FIG. 4*c*, d). Furthermore, with $Ca^{2+}$ in the external bath, activation of NR1/NR3B receptors evoked far less $Ca^{2+}$-triggered $Cl^-$ current than NR1/NR2 receptors. These results suggest that NR1/NR3B channels are less permeable to divalent cations such as $Ca^{2+}$ and $Ba^{2+}$ than are conventional NMDARs. Similar results were obtained for channels containing NR3A instead of NR3B.

Figure 5:
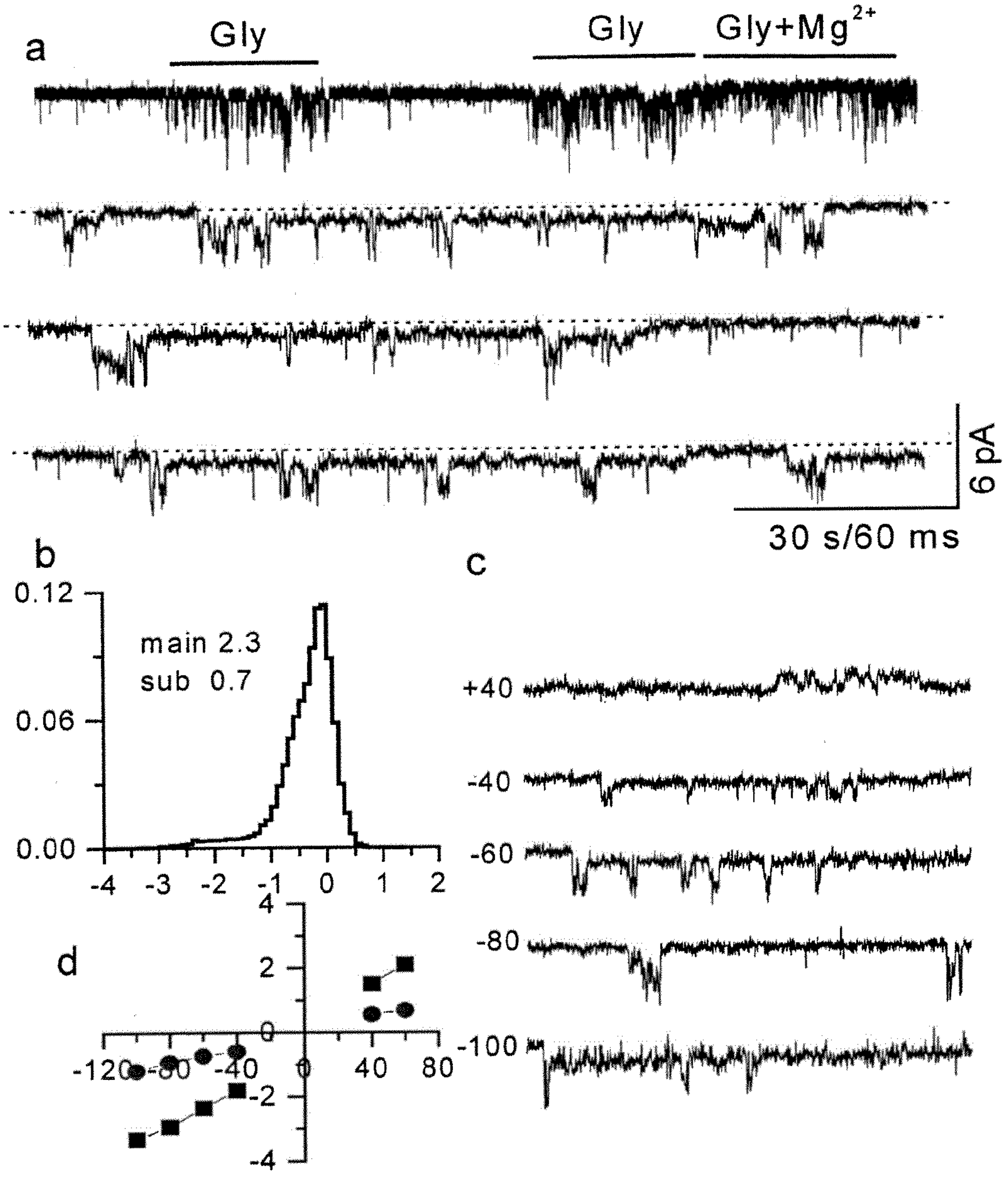
FIG. 5(*a-d*) shows single-channel recordings from outside-out patches obtained from oocytes injected with NR1/NR3B (1:12) cRNA.

Single-channel recording of NR1/NR3B receptors confirmed many of the aforementioned unique properties of these receptors, including activation by glycine alone and reduced sensitivity to $Mg^{2+}$ (FIG. 5*a*). Recorded from outside-out patches of oocyte membrane, NR1/NR3B receptor-operated channels manifest a unitary conductance of −38 pS and a subconductance of 12 pS in the presence of 2 mM external $Ba^{2+}$ (FIG. 5*a*, c). When all anions in the patch electrode were replaced by impermeant gluconate, the conductance states remained unaffected at both positive and negative holding potentials (FIG. 5*c*), confirming that the channels were permeable to cations.

EXAMPLE IV

This example shows the production of NR3B-specific antibodies using NR3B peptides.

In order to produce NR3B-specific antibodies, the XhoI-AvrII and MluI-XbaI fragments of rat NR3B cDNA (B4 form), which encode amino acids 89-238 and 927-1002, respectively, were subcloned into pET28 to facilitate expression of 6×His-tagged NR3B fragments ("6×His" disclosed as SEQ ID NO: 90) in bacteria. These regions of NR3B exhibit relatively poor homology with NR3A and other NMDA receptor subunits. The 6×His-tagged proteins ("6×His" disclosed as SEQ ID NO: 90) were expressed in BL21(DE3) cells and purified by metal affinity chromatography (Talon Purification Kit, Clontech, Palo Alto, Calif.). The purified proteins are used to immunize chickens (Ayes Labs, Tigard, Oreg.) and rabbits (Covance, Princeton, N.J.) for the production of anti-NR3B polyclonal antibodies.

EXAMPLE V

This example shows physiological effects of glycine in cerebrocortical neurons containing NR3 family members.

To investigate the physiological relevance of the NR3 family, whole-cell and single-channel recordings were performed as described in Das et al., *Nature* 393:377-381 (1998) and Chen et al., *J. Neurosci.* 12:4427-4436 (1992), except that 5-10 μM strychnine was generally added to the bathing medium.

Figure 7:
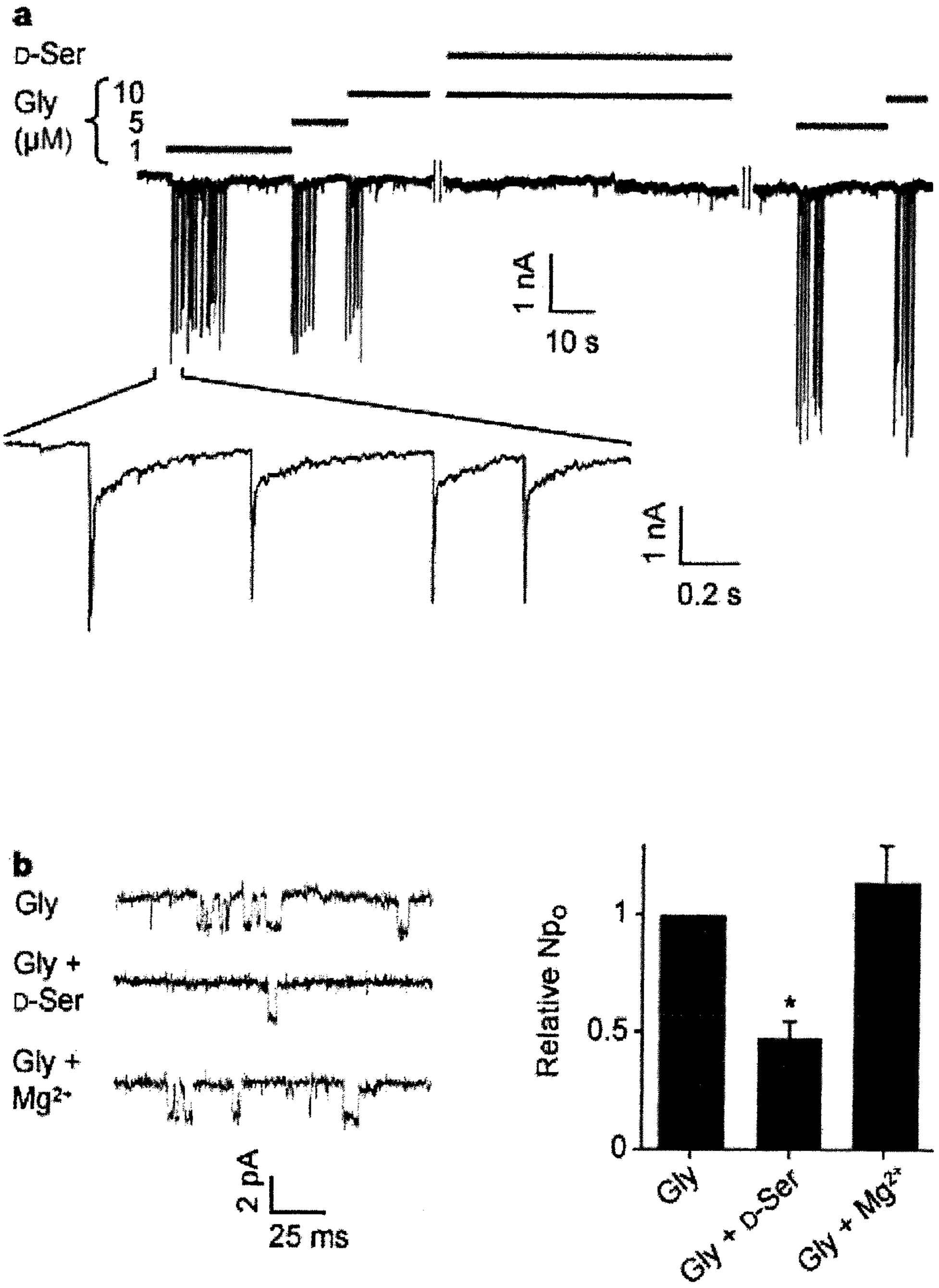
FIG. 7*a* shows whole-cell recording from cultured neurons in the presence of strychnine (10 μM), which revealed glycine-evoked bursts of action currents. The glycine-evoked response was inhibited by D-serine (10 μM).
FIG. 7*b* shows that single-channel currents from outside-out patches of cerebrocortical neurons in response to 2.5 μM glycine at −60 mV manifested a main conductance state of 38±1.0 pS (in n=3 of 12 patches recorded for 5-30 min). Channel activity was decreased by D-serine (100 μM) (asterisk, P<0.01, Student's t-test), but 1 mM $Mg^2$ had little effect. $NP_o$ represents the product of the number (N) of channels in the patch and the single-channel open probability ($P_o$).

Whole-cell currents were monitored from cultured cerebrocortical neurons dissociated on P0 (recorded at days 8-13 in vitro) or E16 (recorded at day 19 in vitro), at which times NR3A is maximally expressed and NR3B may also be present (Das et al., supra (1998)). In 22 of 26 recordings performed in the presence of strychnine, glycine (1-10 μM) triggered neuronal bursting, accompanied by little inward current monitored at the cell body; D-serine inhibited this effect in 5 of 22 glycine-responsive cells (FIG. 7*a*). Thus, the pharmacological profile matched that of NR1/NR3A or -3B receptors in about one-quarter of the recordings. If conventional NMDARs had been involved (for example, if submaximal glycine were present in conjunction with endogenous glutamate), then D-serine would have enhanced the responses rather than inhibiting them, as observed in other recordings. This glycine-triggered bursting phenomenon was ascribed to a presynaptic or network effect, as it was inhibited by tetrodotoxin. Whatever the mechanism, these glycine-mediated responses seem to affect the threshold for bursts of action potentials within a network, and a substantial number of these responses displayed the pharmacology of NR1/NR3A or -3B receptors. Additionally, application of glycine to outside-out patches formed from the cell body of cerebrocortical neneurons evoked single channels of appropriate size (38 pS) and with appropriate pharmacology for the described receptors: in the presence of strychnine, D-serine inhibited the glycine-activated channels and $Mg^{2+}$ had little effect (FIG. 7*b*). The easily desensitized nature of these extrasynaptic currents, similar to those of recombinant NR1/NR3A channels, may have obscured them from previous workers.

In vivo, co-assembly of NR3A or NR3B with NR1 and possibly NR2 subunits may impart to heteromeric NMDARs some or all of the unique properties described here, and may account for the observed diversity in NMDAR function (von Euler et al., *J. Neurotrauma* 14:53-61 (1997); Paleček et al., *Eur. J. Neurosci* 11:827-836 (1999); and Souverbie et al., *Eur. J. Pharmacol* 307:347-353 (1996)). NR3 may also be physiologically important during synapse formation and long-term potentiation when NMDARs are thought to be functionally silent in the absence of AMPA (α-amino-3-hydroxy-5-methyl-4-isoxazole propionic acid) receptors. In this case, insensitivity of NR3-containing channels to $Mg^{2+}$ may obviate the need for AMPAR-mediated depolarization. Rather, NR1/NR3-mediated depolarization may activate conventional NMDARs at the synapse. For these reasons, standard pharmacological methods that have been used to study NMDAR activity in culture and in vivo must be re-evaluated in light of NR3A or NR3B expression.

All journal article, reference, sequence and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention.

What is claimed is:

1. An isolated NR3B polypeptide, comprising the amino acid sequence SEQ ID NO:6.

2. The isolated NR3B polypeptide of claim 1, wherein the amino acid sequence consists of SEQ ID NO:6.

3. A composition, comprising an isolated excitatory glycine receptor, wherein said excitatory glycine receptor comprises the NR3B polypeptide of claim 1 and an NR1 polypeptide.

4. The composition of claim 3, further comprising a cell membrane.

5. The composition of claim 3, wherein said excitatory glycine receptor further comprises an NR2 polypeptide.

6. The composition of claim 5, further comprising a cell membrane.

7. The isolated NR3B polypeptide of claim 3, wherein the amino acid sequence consists of SEQ ID NO:6.

* * * * *